(12) United States Patent  
Nakamura et al.

(10) Patent No.: US 9,187,450 B2  
(45) Date of Patent: Nov. 17, 2015

(54) SUBSTITUTED PYRIDINE COMPOUND

(75) Inventors: Tsuyoshi Nakamura, Tokyo (JP); Hidenori Namiki, Tokyo (JP); Naoki Terasaka, Tokyo (JP); Akiko Shima, Tokyo (JP); Masahiko Hagihara, Yamaguchi (JP); Noriaki Iwase, Yamaguchi (JP); Katsunori Takata, Yamaguchi (JP); Osamu Kikuchi, Yamaguchi (JP); Kazunari Tsuboike, Yamaguchi (JP); Hiroyuki Setoguchi, Yamaguchi (JP); Kenji Yoneda, Yamaguchi (JP); Hidetoshi Sunamoto, Yamaguchi (JP); Koji Ito, Yamaguchi (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 185 days.

(21) Appl. No.: 13/809,115

(22) PCT Filed: Jul. 8, 2011

(86) PCT No.: PCT/JP2011/065651  
§ 371 (c)(1),  
(2), (4) Date: Jan. 8, 2013

(87) PCT Pub. No.: WO2012/005343  
PCT Pub. Date: Jan. 12, 2012

(65) Prior Publication Data  
US 2013/0109653 A1    May 2, 2013  
US 2014/0005143 A2    Jan. 2, 2014  
US 2014/0213549 A9    Jul. 31, 2014

(30) Foreign Application Priority Data  
Jul. 9, 2010  (JP) .................................. 2010-156590

(51) Int. Cl.  
A01N 55/00      (2006.01)  
A61K 31/695     (2006.01)  
C07D 401/14     (2006.01)  
C07D 413/14     (2006.01)  
C07D 417/14     (2006.01)  
C07F 7/18       (2006.01)

(52) U.S. Cl.  
CPC ............ C07D 401/14 (2013.01); C07D 413/14 (2013.01); C07D 417/14 (2013.01); C07F 7/1804 (2013.01)

(58) Field of Classification Search  
CPC .. C07D 401/14; C07D 413/14; C07D 417/14; C07F 7/1804  
USPC ............... 514/63, 228.2, 235.2, 252.18, 275; 544/122, 229, 295, 331, 58.2, 61  
See application file for complete search history.

(56) References Cited

U.S. PATENT DOCUMENTS

| 5,932,587 A | 8/1999 | Schmeck et al. |
| 6,069,148 A | 5/2000 | Schmidt et al. |
| 6,207,671 B1 | 3/2001 | Schmidt et al. |

(Continued)

FOREIGN PATENT DOCUMENTS

| JP | 10-067746    | 3/1998 |
| JP | 10-167967    | 6/1998 |
| JP | 2001-516757  | 10/2001 |
| JP | 2001-517655  | 10/2001 |
| JP | 2005-508341  | 3/2005 |
| JP | 2008-524137  | 7/2008 |
| JP | 2008-524145  | 7/2008 |
| JP | 2009-516649  | 4/2009 |

(Continued)

OTHER PUBLICATIONS

Briand et al , Clinical and Translational Science, vol. 4, Issue 6, pp. 414-420, Dec. 2011.*

(Continued)

*Primary Examiner* — Wu-Cheng Winston Shen  
*Assistant Examiner* — Jean Cornet  
(74) *Attorney, Agent, or Firm* — Dorsey and Whitney LLP

(57) ABSTRACT

The present invention provides a substituted pyridine compound or a pharmacologically acceptable salt thereof which has excellent CETP inhibition activity and is useful as a medicament. The present invention provides a compound represented by a general formula (I),

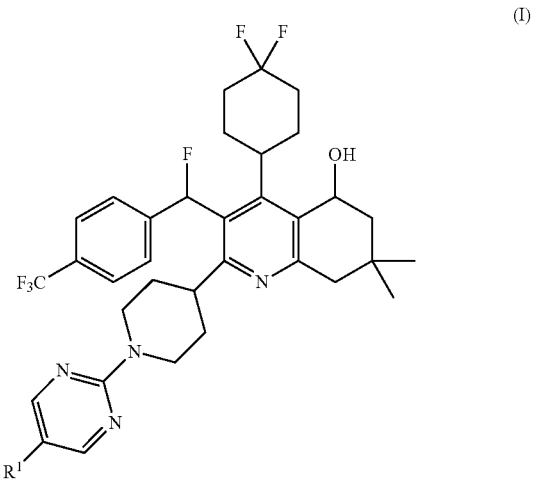

(I)

wherein $R^1$ is H, optionally substituted alkyl, OH, optionally substituted alkoxy, alkylsulfonyl, optionally substituted amino, carboxy, optionally substituted carbonyl, CN, halogeno, optionally substituted phenyl, optionally substituted aromatic heterocyclyl, optionally substituted saturated heterocyclyl, optionally substituted saturated heterocyclyloxy or optionally substituted saturated heterocyclylcarbonyl, etc., and the like.

35 Claims, No Drawings

(56) References Cited

U.S. PATENT DOCUMENTS

| | | |
|---|---|---|
| 6,291,477 B1 | 9/2001 | Schmidt et al. |
| 6,387,929 B1 | 5/2002 | Stoltefuss et al. |
| 6,562,976 B2 | 5/2003 | Schmidt et al. |
| 6,897,317 B2 | 5/2005 | Schmidt et al. |
| 2005/0043341 A1 | 2/2005 | Gielen et al. |
| 2008/0194609 A1 | 8/2008 | Bischoff et al. |
| 2008/0255068 A1 | 10/2008 | Bischoff et al. |
| 2009/0023729 A1 | 1/2009 | Nakamura et al. |
| 2009/0264405 A1 | 10/2009 | Ali et al. |
| 2009/0286790 A1 | 11/2009 | Imase et al. |

FOREIGN PATENT DOCUMENTS

| | | |
|---|---|---|
| JP | 2009-524579 | 7/2009 |
| WO | WO 2007/088999 A1 | 8/2007 |
| WO | WO 2008/009435 A1 | 1/2008 |
| WO | WO 2008/156715 A1 | 12/2008 |
| WO | WO 2009/071509 A1 | 6/2009 |
| WO | WO 2009/109549 A1 | 9/2009 |

OTHER PUBLICATIONS

Park Diabetes Research and Clinical Practice 66S (2004) S33-S35.*

Friedman et al, Nature, vol. 395, Oct. 22, 1998, 763-770.*

Mantlo et al, J. Med. Chem. 2014, 57, 1-17.*

Barter et al, N Engl J Med 2007; 357:2109-2122Nov. 22, 2007.*

International Preliminary Report on Patentability, PCT Application No. PCT/JP2011/065651, Feb. 12, 2013, 6 pages (English translation).

International Search Report, PCT Application No. PCT/JP2011/065651, Sep. 6, 2011, 3 pages (English translation).

Written Opinion of the International Searching Authority, PCT Application No. PCT/JP2011/065651, Sep. 6, 2011, 5 pages (English translation).

Barter, "Lessons Learned from the Investigation of Lipid Level Management to Understand its Impact in Atherosclerotic Events (Illuminate) Trial," *The American Journal of Cardiology*, 104(10A):10E-15E.

Nicholls, et al., "Coronary Heart Disease: Cholesteryl Ester Transfer Protein Inhibition, High-Density Lipoprotein Raising, and Progression of Coronary Atherosclerosis—Insights from Illustrate (Investigation of Lipid Level Management Using Coronary Ultrasound to Assess Reduction of Atherosclerosis by CETP Inhibition and HDL Elevation)," *Circulation*, Dec. 9, 2008, 118:2506-2514 and 4 supplemental pages.

* cited by examiner

SUBSTITUTED PYRIDINE COMPOUND

This application is a national stage application under 35 U.S.C. §371 of International Application No. PCT/JP2011/065651, filed Jul. 8, 2011, entitled "Substituted Pyridine Compound," which claims priority to Japanese Patent Application No. 2010-156590, filed Jul. 9, 2010, the contents of all of which are hereby incorporated in their entirety by reference.

TECHNICAL FIELD

The present invention relates to a novel substituted pyridine compound or a pharmacologically acceptable salt thereof, which has excellent CETP inhibition activity and is useful as a medicament (particularly, a medicament for treatment or prophylaxis of dyslipidemia, low HDL cholesterolemia, arteriosclerosis or coronary heart disease).

BACKGROUND ART

It has been shown from the results of many epidemiological surveys that the concentration of serum lipoprotein is related to diseases such as dyslipidemia and arteriosclerosis (for example, Badimon, J. Clin. Invest., 1990, Vol. 85, pp. 1234-1241). Both an increase in the blood concentration of low density lipoprotein (hereinafter, referred to as LDL) cholesterol and a decrease in the blood concentration of high density lipoprotein (hereinafter, referred to as HDL) cholesterol are risk factors for coronary disease.

Cholesterol in the peripheral tissue is extracted by HDL and esterified in HDL to become cholesteryl ester (hereinafter, referred to as CE). Cholesteryl ester transfer protein (hereinafter, referred to as CETP) transfers the CE in HDL to LDL. Therefore, inhibition of CETP action increases the concentration of the CE in HDL and decreases the concentration of the CE in LDL. As described above, it is considered that a medicine which inhibits CETP activity is useful as a medicament for treatment or prophylaxis of diseases such as dyslipidemia and arteriosclerosis (for example, N. Engl. J. Med., 2004, Vol. 350, pp. 1505-1515).

Certain pyridine compounds that have CETP inhibition activity are known (for example, see Patent references 1 to 8). In addition, certain pyrimidinyl piperidine compounds that have CETP inhibition activity are known (for example, see Patent references 9 to 13).

PRIOR ART REFERENCES

Patent References

Patent reference 1: Japanese Patent Application Laid-Open (JP-A) No. Hei 10-067746 (corresponding U.S. Pat. No. 6,069,148 and U.S. Pat. No. 6,207,671)

Patent reference 2: Japanese Patent Application National Publication No. 2001-516757 (corresponding U.S. Pat. No. 6,387,929)

Patent reference 3: Japanese Patent Application National Publication No. 2001-517655 (corresponding U.S. Pat. No. 6,291,477, U.S. Pat. No. 6,562,976 and U.S. Pat. No. 6,897,317)

Patent reference 4: Japanese Patent Application National Publication No. 2005-508341 (corresponding US patent application: U.S. Application Publication No. 2005/0043341)

Patent reference 5: Japanese Patent Application Laid-Open (JP-A) No. Hei 10-167967 (corresponding U.S. Pat. No. 5,932,587)

Patent reference 6: Japanese Patent Application National Publication No. 2008-524145 (corresponding US application: U.S. Application Publication No. 2008/0255068)

Patent reference 7: Japanese Patent Application National Publication No. 2008-524137 (corresponding US application: U.S. Application Publication No. 2008/0194609)

Patent reference 8: International Publication WO2009/109549

Patent reference 9: Japanese Patent Application National Publication No. 2009-516649 (corresponding US application: U.S. Application Publication No. 2009/0264405)

Patent reference 10: International Publication WO2008/156715

Patent reference 11: Japanese Patent Application National Publication No. 2009-524579 (corresponding US application: U.S. Application Publication No. 2009/0023729)

Patent reference 12: International Publication WO2008/009435 (corresponding US application: U.S. Application Publication No. 2009/0286790)

Patent reference 13: International Publication WO2009/071509

DISCLOSURE OF THE INVENTION

Object of the Invention

The inventors have researched novel substituted pyridine compounds with the aim of developing an excellent CETP inhibitor and found that a substituted pyridine compound having a specific structure or a pharmacologically acceptable salt thereof has excellent CETP inhibition activity and is useful as a medicament (particularly, a medicament for treatment or prophylaxis of dyslipidemia, low HDL cholesterolemia, arteriosclerosis or coronary heart disease). The invention has been accomplished on the basis of the findings described above.

Means for Achieving the Object

The present invention provides a novel substituted pyridine compound which has excellent CETP inhibition activity or a pharmacologically acceptable salt thereof;

a pharmaceutical composition comprising a substituted pyridine compound or a pharmacologically acceptable salt thereof as an active ingredient, and a pharmaceutical composition for treatment or prophylaxis of, preferably, dyslipidemia, hypercholesterolemia, low HDL cholesterolemia, high LDL cholesterolemia, hypertriglyceridemia, arteriosclerosis, arteriosclerotic heart disease, coronary heart disease (including heart failure, myocardial infarction, angina pectoris, cardiac ischemia, cardiovascular disorder and angioplasty-related restenosis), cerebrovascular disease (including stroke and cerebral infarction), peripheral vascular disease (including diabetic vascular complications) or obesity, more preferably dyslipidemia, low HDL cholesterolemia, high LDL cholesterolemia, arteriosclerosis, arteriosclerotic heart disease or coronary heart disease, further preferably dyslipidemia, low HDL cholesterolemia, arteriosclerosis or coronary heart disease, and even more preferably low HDL cholesterolemia or arteriosclerosis;

use of a substituted pyridine compound or a pharmacologically acceptable salt thereof for preparing a pharmaceutical composition for treatment or prophylaxis (preferably treatment) of diseases (preferably the above-described diseases);

a method of treatment or prophylaxis (preferably treating) of diseases (preferably the above-described diseases) comprising administering to a warm-blooded animal (preferably human) a pharmaceutically effective amount of a substituted pyridine compound or a pharmacologically acceptable salt thereof; and a method of preparing a substituted pyridine compound or a pharmacologically acceptable salt thereof or an intermediate thereof.

In one aspect, the present invention provides the following.

(1A) A compound represented by general formula (I) or a pharmacologically acceptable salt thereof:

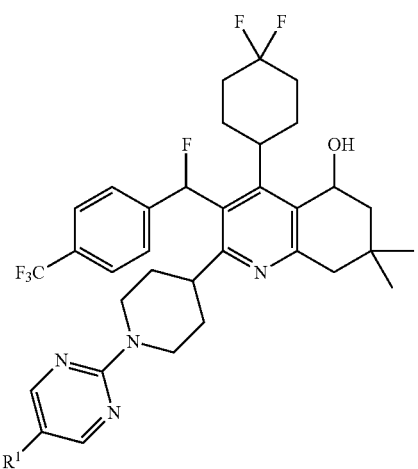

(I)

wherein $R^1$ represents a hydrogen atom, a $C_1$-$C_6$ alkyl group, a hydroxy($C_1$-$C_6$ alkyl) group, a ($C_1$-$C_6$ alkoxy)-($C_1$-$C_6$ alkyl) group, a hydroxy($C_1$-$C_6$ alkoxy)-($C_1$-$C_6$ alkyl) group, a ($C_1$-$C_6$ alkyl)amino-($C_1$-$C_6$ alkyl) group, a hydroxy($C_1$-$C_6$ alkyl)amino-($C_1$-$C_6$ alkyl) group, a [N—($C_1$-$C_6$ alkyl)-N-hydroxy($C_1$-$C_6$ alkyl)amino]-($C_1$-$C_6$ alkyl) group, a ($C_1$-$C_6$ alkyl)sulfonylamino-($C_1$-$C_6$ alkyl) group, a [N—($C_1$-$C_6$ alkyl)-N—($C_1$-$C_6$ alkyl)sulfonylamino]-($C_1$-$C_6$ alkyl) group, a carboxy($C_1$-$C_6$ alkyl) group, a halogeno($C_1$-$C_6$ alkyl) group, a ($C_3$-$C_8$ cycloalkyl)-($C_1$-$C_6$ alkyl) group, a $C_2$-$C_6$ alkenyl group, a $C_2$-$C_6$ alkynyl group, a $C_3$-$C_8$ cycloalkyl group, a $C_3$-$C_8$ cycloalkenyl group, a hydroxy group, a $C_1$-$C_6$ alkoxy group, a hydroxy($C_1$-$C_6$ alkoxy) group, a ($C_1$-$C_6$ alkoxy)-($C_1$-$C_6$ alkoxy) group, a ($C_1$-$C_6$ alkyl)sulfonyl-($C_1$-$C_6$ alkoxy) group, a carboxy($C_1$-$C_6$ alkoxy) group, a halogeno($C_1$-$C_6$ alkoxy) group, a $C_1$-$C_6$ alkylthio group, a $C_1$-$C_6$ alkylsulfinyl group, a $C_1$-$C_6$ alkylsulfonyl group, an amino group, a $C_1$-$C_6$ alkylamino group, a di($C_1$-$C_6$ alkyl)amino group, a hydroxy($C_1$-$C_6$ alkyl)amino group, a N—($C_1$-$C_6$ alkyl)-N-hydroxy($C_1$-$C_6$ alkyl)amino group, a formylamino group, a ($C_1$-$C_6$ alkyl)carbonylamino group, a carboxy group, a ($C_1$-$C_6$ alkoxy)carbonyl group, a carbamoyl group, a ($C_1$-$C_6$ alkylamino)carbonyl group, a di($C_1$-$C_6$ alkyl)aminocarbonyl group, a cyano group, a halogeno group, a phenyl group, a substituted phenyl group in which the substituent(s) represent 1 to 4 groups independently selected from the substituent group α, a 5- or 6-membered aromatic heterocyclyl group, a substituted 5- or 6-membered aromatic heterocyclyl group in which the substituent(s) represent 1 to 4 groups independently selected from the substituent group α, a 5- or 6-membered saturated heterocyclyl group, a substituted 5- or 6-membered saturated heterocyclyl group in which the substituent(s) represent 1 to 4 groups independently selected from the substituent group α, a 5- or 6-membered saturated heterocyclyl-($C_1$-$C_6$ alkyl) group, a substituted 5- or 6-membered saturated heterocyclyl-($C_1$-$C_6$ alkyl) group in which the substituent(s) represent 1 to 4 groups independently selected from the substituent group α, a 5- or 6-membered saturated heterocyclyloxy group, a substituted 5- or 6-membered saturated heterocyclyloxy group in which the substituent(s) represent 1 to 4 groups independently selected from the substituent group α, a 5- or 6-membered saturated heterocyclylcarbonyl group or a substituted 5- or 6-membered saturated heterocyclylcarbonyl group in which the substituent(s) represent 1 to 4 groups independently selected from the substituent group α, and the substituent group α represents the group consisting of a $C_1$-$C_6$ alkyl group, a hydroxy($C_1$-$C_6$ alkyl) group, a halogeno($C_1$-$C_6$ alkyl) group, a ($C_3$-$C_8$ cycloalkyl)-($C_1$-$C_6$ alkyl) group, a $C_3$-$C_8$ cycloalkyl group, a hydroxy group, a $C_1$-$C_6$ alkoxy group, a halogeno($C_1$-$C_6$ alkoxy) group, a $C_1$-$C_6$ alkylamino group, a di($C_1$-$C_6$ alkyl)amino group, a carboxy group, a ($C_1$-$C_6$ alkoxy)carbonyl group, a carbamoyl group, a ($C_1$-$C_6$ alkylamino)carbonyl group, a di($C_1$-$C_6$ alkyl)aminocarbonyl group, a cyano group, a halogeno group and an oxo group.

(2A) The compound represented by general formula (I-1) according to (1A) or a pharmacologically acceptable salt thereof:

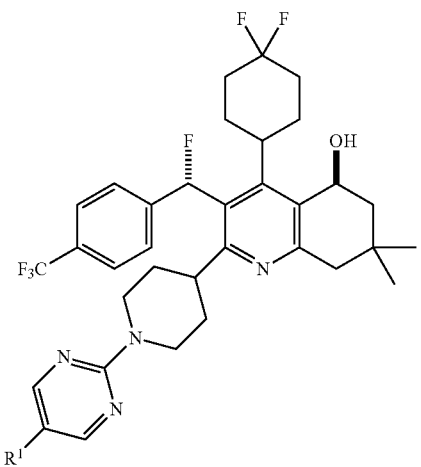

(I-1)

(3A) The compound according to (2A) or a pharmacologically acceptable salt thereof, wherein $R^1$ is a hydrogen atom, a $C_1$-$C_6$ alkyl group, a hydroxy($C_1$-$C_6$ alkyl) group, a ($C_1$-$C_6$ alkoxy)-($C_1$-$C_6$ alkyl) group, a ($C_1$-$C_6$ alkyl)amino-($C_1$-$C_6$ alkyl) group, a [N—($C_1$-$C_6$ alkyl)-N-hydroxy($C_1$-$C_6$ alkyl)amino]-($C_1$-$C_6$ alkyl) group, a [N—($C_1$-$C_6$ alkyl)-N—($C_1$-$C_6$ alkyl)sulfonylamino]-($C_1$-$C_6$ alkyl) group, a carboxy($C_1$-$C_6$ alkyl) group, a halogeno($C_1$-$C_6$ alkyl) group, a $C_2$-$C_6$ alkenyl group, a $C_3$-$C_8$ cycloalkyl group, a $C_3$-$C_8$ cycloalkenyl group, a hydroxy group, a $C_1$-$C_6$ alkoxy group, a hydroxy($C_1$-$C_6$ alkoxy) group, a ($C_1$-$C_6$ alkyl)sulfonyl-($C_1$-$C_6$ alkoxy) group, a carboxy($C_1$-$C_6$ alkoxy) group, a halogeno($C_1$-$C_6$ alkoxy) group, a $C_1$-$C_6$ alkylthio group, a $C_1$-$C_6$ alkylsulfonyl group, a N—($C_1$-$C_6$ alkyl)-N-hydroxy($C_1$-$C_6$ alkyl)amino group, a ($C_1$-$C_6$ alkylamino)carbonyl group, a di($C_1$-$C_6$ alkyl)aminocarbonyl group, a cyano group or a halogeno group.

(4A) The compound according to (2A) or a pharmacologically acceptable salt thereof, wherein $R^1$ is a hydrogen atom, a $C_1$-$C_4$ alkyl group, a hydroxy($C_1$-$C_4$ alkyl) group, a ($C_1$-$C_4$ alkoxy)-(C₁-C₄ alkyl) group, a halogeno(C₁-C₄ alkyl) group, a C₁-C₄ alkoxy group, a hydroxy(C₁-C₆ alkoxy) group or a (C₁-C₄ alkyl)sulfonyl-(C₁-C₄ alkoxy) group.

(5A) The compound according to (2A) or a pharmacologically acceptable salt thereof, wherein R¹ is a C₁-C₄ alkyl group, a halogeno(C₁-C₄ alkyl) group, a C₁-C₄ alkoxy group or a hydroxy(C₁-C₆ alkoxy) group.

(6A) The compound according to (2A) or a pharmacologically acceptable salt thereof, wherein R¹ is a C₁-C₄ alkyl group.

(7A) The compound according to (2A) or a pharmacologically acceptable salt thereof, wherein R¹ is a halogeno(C₁-C₄ alkyl) group.

(8A) The compound according to (2A) or a pharmacologically acceptable salt thereof, wherein R¹ is a C₁-C₄ alkoxy group.

(9A) The compound according to (2A) or a pharmacologically acceptable salt thereof, wherein R¹ is a hydroxy(C₁-C₆ alkoxy) group.

(10A) The compound according to (2A) or a pharmacologically acceptable salt thereof, wherein R¹ is a (C₁-C₄ alkyl) sulfonyl-(C₁-C₄ alkoxy) group.

(11A) The compound according to (2A) or a pharmacologically acceptable salt thereof, wherein
R¹ is a substituted phenyl group in which the substituent(s) represent 1 to 4 groups independently selected from the substituent group α1, a substituted 5- or 6-membered aromatic heterocyclyl group in which the substituent(s) represent 1 to 4 groups independently selected from the substituent group α1, a 5- or 6-membered saturated heterocyclyl group, a substituted 5- or 6-membered saturated heterocyclyl group in which the substituent(s) represent 1 to 4 groups independently selected from the substituent group α1, a substituted 5- or 6-membered saturated heterocyclyloxy group in which the substituent(s) represent 1 to 4 groups independently selected from the substituent group α1 or a 5- or 6-membered saturated heterocyclylcarbonyl group, and
the substituent group α1 represents the group consisting of a C₁-C₆ alkyl group, a hydroxy group, a carboxy group and an oxo group.

(12A) The compound according to (2A) or a pharmacologically acceptable salt thereof, wherein
R¹ is a 5- or 6-membered nitrogen-containing saturated heterocyclyl group, a substituted 5- or 6-membered nitrogen-containing saturated heterocyclyl group in which the substituent(s) represent 1 to 4 groups independently selected from the substituent group α2, a substituted 5- or 6-membered nitrogen-containing saturated heterocyclyloxy group in which the substituent(s) represent 1 to 4 groups independently selected from the substituent group α2 or a 5- or 6-membered nitrogen-containing saturated heterocyclylcarbonyl group, and
the substituent group α2 represents the group consisting of a C₁-C₄ alkyl group and a hydroxy group.

(13A) The compound according to (2A) or a pharmacologically acceptable salt thereof, wherein
R¹ is a substituted pyrrolidinyl group, a substituted piperazyl group, a substituted pyrrolidinyloxy group or a substituted piperidyloxy group in which the substituent(s) of the pyrrolidinyl group, piperazyl group, pyrrolidinyloxy group and piperidyloxy group represent 1 to 2 groups independently selected from the substituent group α3, or a morpholinylcarbonyl group, and
the substituent group α3 represents the group consisting of a methyl group and a hydroxy group.

(14A) The compound according to (2A) or a pharmacologically acceptable salt thereof, wherein R¹ is a substituted phenyl group in which the substituent(s) represent 1 to 2 groups independently selected from the substituent group α1.

(15A) The compound according to (2A) or a pharmacologically acceptable salt thereof, which is selected from the group consisting of (5S)-4-(4,4-Difluorocyclohexyl)-3-{(S)-fluoro[4-(trifluoromethyl)phenyl]methyl}-7,7-dimethyl-2-{1-[5-(4-methylpiperazin-1-yl)pyrimidin-2-yl]piperidin-4-yl}-5,6,7,8-tetrahydroquinolin-5-ol, (5S)-4-(4,4-Difluorocyclohexyl)-3-{(S)-fluoro[4-(trifluoromethyl)phenyl]methyl}-2-{1-[5-(2-hydroxyethoxyl)pyrimidin-2-yl]piperidin-4-yl}-7,7-dimethyl-5,6,7,8-tetrahydroquinolin-5-ol, (5S)-2-{1-[5-(4-Carboxybutoxyl)pyrimidin-2-yl]piperidin-4-yl}-4-(4,4-difluorocyclohexyl)-3-{(S)-fluoro[4-(trifluoromethyl)phenyl]methyl}-7,7-dimethyl-5,6,7,8-tetrahydroquinolin-5-ol, (5S)-2-{1-[5-(4-Carboxybutyl)pyrimidin-2-yl]piperidin-4-yl}-4-(4,4-difluorocyclohexyl)-3-{(S)-fluoro[4-(trifluoromethyl)phenyl]methyl}-7,7-dimethyl-5,6,7,8-tetrahydroquinolin-5-ol, (5S)-4-(4,4-Difluorocyclohexyl)-3-{(S)-fluoro[4-(trifluoromethyl)phenyl]methyl}-7,7-dimethyl-2-{1-[5-(methylcarbamoyl)pyrimidin-2-yl]piperidin-4-yl}-5,6,7,8-tetrahydroquinolin-5-ol, (5S)-4-(4,4-Difluorocyclohexyl)-2-{1-[5-(dimethylcarbamoyl)pyrimidin-2-yl]piperidin-4-yl}-3-{(S)-fluoro[4-(trifluoromethyl)phenyl]methyl}-7,7-dimethyl-5,6,7,8-tetrahydroquinolin-5-ol, (5S)-4-(4,4-Difluorocyclohexyl)-3-{(S)-fluoro[4-(trifluoromethyl)phenyl]methyl}-7,7-dimethyl-2-{1-[5-(morpholin-4-ylcarbonyl)pyrimidin-2-yl]piperidin-4-yl}-5,6,7,8-tetrahydroquinolin-5-ol, (5S)-4-(4,4-Difluorocyclohexyl)-3-{(S)-fluoro[4-(trifluoromethyl)phenyl]methyl}-2-{1-(5-{[(2-hydroxyethyl)(methyl)amino]methyl}pyrimidin-2-yl)piperidin-4-yl}-7,7-dimethyl-5,6,7,8-tetrahydroquinolin-5-ol, (5S)-4-(4,4-Difluorocyclohexyl)-3-{(S)-fluoro[4-(trifluoromethyl)phenyl]methyl}-2-[1-(5-{[(2S)-2-hydroxypropyl]oxy}pyrimidin-2-yl)piperidin-4-yl]-7,7-dimethyl-5,6,7,8-tetrahydroquinolin-5-ol, (5S)-4-(4,4-Difluorocyclohexyl)-3-{(S)-fluoro[4-(trifluoromethyl)phenyl]methyl}-7,7-dimethyl-2-(1-{5-[(1-methylpiperidin-4-yl)oxy]pyrimidin-2-yl}piperidin-4-yl)-5,6,7,8-tetrahydroquinolin-5-ol, (5S)-4-(4,4-Difluorocyclohexyl)-2-[1-(5-{[(2S)-2,3-dihydroxypropyl]oxy}pyrimidin-2-yl)piperidin-4-yl]-3-{(S)-fluoro[4-(trifluoromethyl)phenyl]methyl}-7,7-dimethyl-5,6,7,8-tetrahydroquinolin-5-ol, (5S)-4-(4,4-Difluorocyclohexyl)-2-[1-(5-{[(2R)-2,3-dihydroxypropyl]oxy}pyrimidin-2-yl)piperidin-4-yl]-3-{(S)-fluoro[4-(trifluoromethyl)phenyl]methyl}-7,7-dimethyl-5,6,7,8-tetrahydroquinolin-5-ol, (5S)-4-(4,4-Difluorocyclohexyl)-3-{(S)-fluoro[4-(trifluoromethyl)phenyl]methyl}-7,7-dimethyl-2-[1-(5-{[(3R)-1-methylpyrrolidin-3-yl]oxy}pyrimidin-2-yl)piperidin-4-yl]-5,6,7,8-tetrahydroquinolin-5-ol, (5S)-4-(4,4-Difluorocyclohexyl)-3-{(S)-fluoro[4-(trifluoromethyl)phenyl]methyl}-2-[1-(5-{[(2R)-2-hydroxypropyl]oxy}pyrimidin-2-yl)piperidin-4-yl]-7,7-dimethyl-5,6,7,8-tetrahydroquinolin-5-ol, (5S)-4-(4,4-Difluorocyclohexyl)-3-{(S)-fluoro[4-(trifluoromethyl)phenyl]methyl}-2-{1-[5-(3-hydroxy-3-methylbutoxy)pyrimidin-2-yl]piperidin-4-yl}-7,7-dimethyl-5,6,7,8-tetrahydroquinolin-5-ol, (5S)-4-(4,4-Difluorocyclohexyl)-3-{(S)-fluoro[4-(trifluoromethyl)phenyl]methyl}-2-{1-[5-(2-hydroxy-2-methylpropoxy)pyrimidin-2-yl]piperidin-4-yl}-7,7-dimethyl-5, 6,7,8-tetrahydroquinolin-5-ol,
(5S)-4-(4,4-Difluorocyclohexyl)-3-{(S)-fluoro[4-(trifluoromethyl)phenyl]methyl}-7,7-dimethyl-2-(1-{5-[3-(methylsulphonyl)propoxy]pyrimidin-2-yl}piperidin-4-yl)-5, 6,7,8-tetrahydroquinolin-5-ol,
(5S)-4-(4,4-Difluorocyclohexyl)-3-{(S)-fluoro[4-(trifluoromethyl)phenyl]methyl}-2-{1-[5-(3-hydroxypropoxy) pyrimidin-2-yl]piperidin-4-yl}-7,7-dimethyl-5,6,7,8-tetrahydroquinolin-5-ol,
(5S)-4-(4,4-Difluorocyclohexyl)-3-{(S)-fluoro[4-(trifluoromethyl)phenyl]methyl}-7,7-dimethyl-2-{1-[5-(3,3,3-trifluoropropoxy)pyrimidin-2-yl]piperidin-4-yl}-5,6,7,8-tetrahydroquinolin-5-ol,
(5S)-4-(4,4-Difluorocyclohexyl)-3-{(S)-fluoro[4-(trifluoromethyl)phenyl]methyl}-2-(1-{5-[3-hydroxy-2-(hydroxymethyl)propoxy]pyrimidin-2-yl}piperidin-4-yl)-7, 7-dimethyl-5,6,7,8-tetrahydroquinolin-5-ol,
(5S)-4-(4,4-Difluorocyclohexyl)-3-{(S)-fluoro[4-(trifluoromethyl)phenyl]methyl}-2-(1-{5-[3-hydroxy-2-(hydroxymethyl)-2-methylpropoxy]pyrimidin-2-yl}piperidin-4-yl)-7,7-dimethyl-5,6,7,8-tetrahydroquinolin-5-ol,
(5S)-4-(4,4-Difluorocyclohexyl)-3-{(S)-fluoro[4-(trifluoromethyl)phenyl]methyl}-7,7-dimethyl-2-[1-(5-{[methyl (methylsulphonyl)amino]methyl}pyrimidin-2-yl)piperidin-4-yl]-5,6,7,8-tetrahydroquinolin-5-ol,
(5S)-4-(4,4-Difluorocyclohexyl)-3-{(S)-fluoro[4-(trifluoromethyl)phenyl]methyl}-7,7-dimethyl-2-[1-(5-{[methyl (propan-2-ylsulfonyl)amino]methyl}pyrimidin-2-yl)piperidin-4-yl]-5,6,7,8-tetrahydroquinolin-5-ol,
(5S)-4-(4,4-Difluorocyclohexyl)-3-{(S)-fluoro[4-(trifluoromethyl)phenyl]methyl}-7,7-dimethyl-2-[1-(5-methylthiopyrimidin-2-yl)piperidin-4-yl]-5,6,7,8-tetrahydroquinolin-5-ol,
(5S)-4-(4,4-Difluorocyclohexyl)-3-{(S)-fluoro[4-(trifluoromethyl)phenyl]methyl}-7,7-dimethyl-2-{1-[5-(methylsulphonyl)pyrimidin-2-yl]piperidin-4-yl}-5,6,7,8-tetrahydroquinolin-5-ol,
(5S)-2-{1-[5-(3-Carboxyphenyl)pyrimidin-2-yl]piperidin-4-yl}-4-(4,4-difluorocyclohexyl)-3-{(S)-fluoro[4-(trifluoromethyl)phenyl]methyl}-7,7-dimethyl-5,6,7,8-tetrahydroquinolin-5-ol,
(5S)-4-(4,4-Difluorocyclohexyl)-3-{(S)-fluoro[4-(trifluoromethyl)phenyl]methyl}-2-(1-{5-[(2-hydroxyethyl)(methyl)amino]pyrimidin-2-yl}piperidin-4-yl)-7,7-dimethyl-5,6,7,8-tetrahydroquinolin-5-ol, and
(5S)-4-(4,4-Difluorocyclohexyl)-3-{(S)-fluoro[4-(trifluoromethyl)phenyl]methyl}-2-(1-{5-[(3S)-3-hydroxypyrrolidin-1-yl]pyrimidin-2-yl}piperidin-4-yl)-7,7-dimethyl-5, 6,7,8-tetrahydroquinolin-5-ol.

(16A) A pharmaceutical composition comprising the compound according to any one of (1A) to (15A) or a pharmacologically acceptable salt thereof as an active ingredient.

(17A) The pharmaceutical composition according to (16A) for treatment or prophylaxis of dyslipidemia, hypercholesterolemia, low HDL cholesterolemia, high LDL cholesterolemia, hypertriglyceridemia, arteriosclerosis, arteriosclerotic heart disease, coronary heart disease, cerebrovascular disease, peripheral vascular disease or obesity.

(18A) The pharmaceutical composition according to (16A) for treatment or prophylaxis of dyslipidemia, low HDL cholesterolemia, arteriosclerosis or coronary heart disease.

(19A) The pharmaceutical composition according to (16A) for treatment or prophylaxis of low HDL cholesterolemia.

(20A) The pharmaceutical composition according to (16A) for treatment or prophylaxis of arteriosclerosis.

(21A) The pharmaceutical composition according to (16A) for treatment or prophylaxis of a disease caused by a decrease in the blood concentration of HDL cholesterol.

(22A) The pharmaceutical composition according to (16) for treatment or prophylaxis of a disease caused by an increase in the blood concentration of LDL cholesterol.

(23A) A medicament for inhibiting CETP comprising the compound according to any one of (1A) to (15A) or a pharmacologically acceptable salt thereof as an active ingredient.

(24A) A medicament for increasing the concentration of HDL cholesterol comprising the compound according to any one of (1A) to (15A) or a pharmacologically acceptable salt thereof as an active ingredient.

(25A) A medicament for decreasing the concentration of LDL cholesterol comprising the compound according to any one of (1A) to (15A) or a pharmacologically acceptable salt thereof as an active ingredient.

(26A) Use of the compound according to any one of (1A) to (15A) or a pharmacologically acceptable salt thereof for preparing a pharmaceutical composition.

(27A) The use according to (26A) for preparing a pharmaceutical composition for treatment or prophylaxis of dyslipidemia, hypercholesterolemia, low HDL cholesterolemia, high LDL cholesterolemia, hypertriglyceridemia, arteriosclerosis, arteriosclerotic heart disease, coronary heart disease, cerebrovascular disease, peripheral vascular disease or obesity.

(28A) The use according to (26A) for preparing a pharmaceutical composition for treatment or prophylaxis of dyslipidemia, low HDL cholesterolemia, arteriosclerosis or coronary heart disease.

(29A) The use according to (26A) for preparing a pharmaceutical composition for treatment or prophylaxis of low HDL cholesterolemia.

(30A) The use according to (26A) for preparing a pharmaceutical composition for treatment or prophylaxis of arteriosclerosis.

(31A) The compound according to any one of (1A) to (15A) or a pharmacologically acceptable salt thereof for use in a method of treatment or prophylaxis of a disease.

(32A) The compound according to (31A) or a pharmacologically acceptable salt thereof, wherein the disease is dyslipidemia, hypercholesterolemia, low HDL cholesterolemia, high LDL cholesterolemia, hypertriglyceridemia, arteriosclerosis, arteriosclerotic heart disease, coronary heart disease, cerebrovascular disease, peripheral vascular disease or obesity.

(33A) The compound according to (31A) or a pharmacologically acceptable salt thereof, wherein the disease is dyslipidemia, low HDL cholesterolemia, arteriosclerosis or coronary heart disease.

(34A) The compound according to (31A) or a pharmacologically acceptable salt thereof, wherein the disease is low HDL cholesterolemia.

(35A) The compound according to (31A) or a pharmacologically acceptable salt thereof, wherein the disease is arteriosclerosis.

(36A) A method of treatment or prophylaxis of a disease comprising administering to a warm-blooded animal a pharmacologically effective amount of the compound according to any one of (1A) to (15A) or a pharmacologically acceptable salt thereof.

(37A) The method according to (36A), wherein the disease is dyslipidemia, hypercholesterolemia, low HDL cholesterolemia, high LDL cholesterolemia, hypertriglyceridemia, arteriosclerosis, arteriosclerotic heart disease, coronary heart disease, cerebrovascular disease, peripheral vascular disease or obesity.

(38A) The method according to (36A), wherein the disease is dyslipidemia, low HDL cholesterolemia, arteriosclerosis or coronary heart disease.

(39A) The method according to (36A), wherein the disease is low HDL cholesterolemia.

(40A) The method according to (36A), wherein the disease is arteriosclerosis.

(41A) The method according to any one of (36A) to (40A), wherein the warm-blooded animal is a human.

Further, in one aspect, the present invention provides the following.

(1) A compound represented by general formula (I) or a pharmacologically acceptable salt thereof:

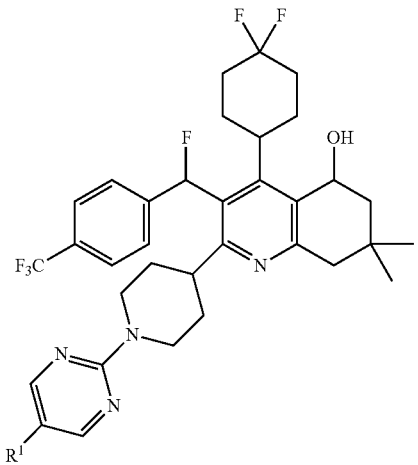

(I)

wherein $R^1$ represents a hydrogen atom, a $C_1$-$C_6$ alkyl group, a hydroxy($C_1$-$C_6$ alkyl) group, a ($C_1$-$C_6$ alkoxy)-($C_1$-$C_6$ alkyl) group, a hydroxy($C_1$-$C_6$ alkoxy)-($C_1$-$C_6$ alkyl) group, a ($C_1$-$C_6$ alkyl)amino-($C_1$-$C_6$ alkyl) group, a hydroxy($C_1$-$C_6$ alkyl)amino-($C_1$-$C_6$ alkyl) group, a [N—($C_1$-$C_6$ alkyl)-N-hydroxy($C_1$-$C_6$ alkyl)amino]-($C_1$-$C_6$ alkyl) group, a ($C_1$-$C_6$ alkyl)sulfonylamino-($C_1$-$C_6$ alkyl) group, a [N—($C_1$-$C_6$ alkyl)-N—($C_1$-$C_6$ alkyl)sulfonylamino]-($C_1$-$C_6$ alkyl) group, a carboxy($C_1$-$C_6$ alkyl) group, a halogeno($C_1$-$C_6$ alkyl) group, a ($C_3$-$C_8$ cycloalkyl)-($C_1$-$C_6$ alkyl) group, a $C_2$-$C_6$ alkenyl group, a $C_2$-$C_6$ alkynyl group, a $C_3$-$C_8$ cycloalkyl group, a $C_3$-$C_8$ cycloalkenyl group, a hydroxy group, a $C_1$-$C_6$ alkoxy group, a hydroxy($C_1$-$C_6$ alkoxy) group, a ($C_1$-$C_6$ alkoxy)-($C_1$-$C_6$ alkoxy) group, a ($C_1$-$C_6$ alkyl)sulfonyl-($C_1$-$C_6$ alkoxy) group, a carboxy($C_1$-$C_6$ alkoxy) group, a halogeno($C_1$-$C_6$ alkoxy) group, a $C_1$-$C_6$ alkylthio group, a $C_1$-$C_6$ alkylsulfinyl group, a $C_1$-$C_6$ alkylsulfonyl group, an amino group, a $C_1$-$C_6$ alkylamino group, a di($C_1$-$C_6$ alkyl)amino group, a hydroxy($C_1$-$C_6$ alkyl)amino group, a N—($C_1$-$C_6$ alkyl)-N-hydroxy($C_1$-$C_6$ alkyl)amino group, a formylamino group, a ($C_1$-$C_6$ alkyl)carbonylamino group, a carboxy group, a ($C_1$-$C_6$ alkoxy)carbonyl group, a carbamoyl group, a ($C_1$-$C_6$ alkylamino)carbonyl group, a di($C_1$-$C_6$ alkyl)aminocarbonyl group, a cyano group, a halogeno group, a phenyl group, a substituted phenyl group in which the substituent(s) represent 1 to 4 groups independently selected from the substituent group α, a 5- or 6-membered aromatic heterocyclyl group, a substituted 5- or 6-membered aromatic heterocyclyl group in which the substituent(s) represent 1 to 4 groups independently selected from the substituent group α, a 5- or 6-membered saturated heterocyclyl group, a substituted 5- or 6-membered saturated heterocyclyl group in which the substituent(s) represent 1 to 4 groups independently selected from the substituent group α, a 5- or 6-membered saturated heterocyclyl-($C_1$-$C_6$ alkyl) group, a substituted 5- or 6-membered saturated heterocyclyl-($C_1$-$C_6$ alkyl) group in which the substituent(s) represent 1 to 4 groups independently selected from the substituent group α, a 5- or 6-membered saturated heterocyclyloxy group, a substituted 5- or 6-membered saturated heterocyclyloxy group in which the substituent(s) represent 1 to 4 groups independently selected from the substituent group α, a 5- or 6-membered saturated heterocyclylcarbonyl group or a substituted 5- or 6-membered saturated heterocyclylcarbonyl group in which the substituent(s) represent 1 to 4 groups independently selected from the substituent group α, and the substituent group α represents the group consisting of a $C_1$-$C_6$ alkyl group, a hydroxy($C_1$-$C_6$ alkyl) group, a halogeno($C_1$-$C_6$ alkyl) group, a ($C_3$-$C_8$ cycloalkyl)-($C_1$-$C_6$ alkyl) group, a $C_3$-$C_8$ cycloalkyl group, a hydroxy group, a $C_1$-$C_6$ alkoxy group, a halogeno($C_1$-$C_6$ alkoxy) group, a $C_1$-$C_6$ alkylamino group, a di($C_1$-$C_6$ alkyl)amino group, a carboxy group, a ($C_1$-$C_6$ alkoxy)carbonyl group, a carbamoyl group, a ($C_1$-$C_6$ alkylamino)carbonyl group, a di($C_1$-$C_6$ alkyl)aminocarbonyl group, a cyano group, a halogeno group and an oxo group.

(2) The compound according to (1) or a pharmacologically acceptable salt thereof, wherein $R^1$ is a hydrogen atom, a $C_1$-$C_6$ alkyl group, a hydroxy($C_1$-$C_6$ alkyl) group, a ($C_1$-$C_6$ alkoxy)-($C_1$-$C_6$ alkyl) group, a [N—($C_1$-$C_6$ alkyl)-N-hydroxy($C_1$-$C_6$ alkyl)amino]-($C_1$-$C_6$ alkyl) group, a [N—($C_1$-$C_6$ alkyl)-N—($C_1$-$C_6$ alkyl)sulfonylamino]-($C_1$-$C_6$ alkyl) group, a carboxy($C_1$-$C_6$ alkyl) group, a halogeno($C_1$-$C_6$ alkyl) group, a $C_2$-$C_6$ alkenyl group, a $C_3$-$C_8$ cycloalkyl group, a $C_3$-$C_8$ cycloalkenyl group, a hydroxy group, a $C_1$-$C_6$ alkoxy group, a hydroxy($C_1$-$C_6$ alkoxy) group, a ($C_1$-$C_6$ alkyl)sulfonyl-($C_1$-$C_6$ alkoxy) group, a carboxy($C_1$-$C_6$ alkoxy) group, a halogeno($C_1$-$C_6$ alkoxy) group, a $C_1$-$C_6$ alkylthio group, a $C_1$-$C_6$ alkylsulfonyl group, a N—($C_1$-$C_6$ alkyl)-N-hydroxy($C_1$-$C_6$ alkyl)amino group, a ($C_1$-$C_6$ alkylamino)carbonyl group, a di($C_1$-$C_6$ alkyl)aminocarbonyl group, a cyano group or a halogeno group.

(3) The compound according to (1) or a pharmacologically acceptable salt thereof, wherein $R^1$ is a hydrogen atom, a $C_1$-$C_4$ alkyl group, a hydroxy($C_1$-$C_4$ alkyl) group, a ($C_1$-$C_4$ alkoxy)-($C_1$-$C_4$ alkyl) group, a halogeno($C_1$-$C_4$ alkyl) group, a $C_1$-$C_4$ alkoxy group, a hydroxy($C_1$-$C_6$ alkoxy) group or a ($C_1$-$C_4$ alkyl)sulfonyl-($C_1$-$C_4$ alkoxy) group.

(4) The compound according to (1) or a pharmacologically acceptable salt thereof, wherein $R^1$ is a $C_1$-$C_4$ alkyl group, a halogeno($C_1$-$C_4$ alkyl) group, a $C_1$-$C_4$ alkoxy group or a hydroxy($C_1$-$C_6$ alkoxy) group.

(5) The compound according to (1) or a pharmacologically acceptable salt thereof, wherein $R^1$ is a $C_1$-$C_4$ alkyl group.

(6) The compound according to (1) or a pharmacologically acceptable salt thereof, wherein $R^1$ is a halogeno($C_1$-$C_4$ alkyl) group.

(7) The compound according to (1) or a pharmacologically acceptable salt thereof, wherein $R^1$ is a $C_1$-$C_4$ alkoxy group.

(8) The compound according to (1) or a pharmacologically acceptable salt thereof, wherein $R^1$ is a hydroxy($C_1$-$C_6$ alkoxy) group.

(9) The compound according to (1) or a pharmacologically acceptable salt thereof, wherein $R^1$ is a substituted phenyl group in which the substituent(s) represent 1 to 4 groups independently selected from the substituent group α1, a substituted 5- or 6-membered aromatic heterocyclyl group in which the substituent(s) represent 1 to 4 groups independently selected from the substituent group α1, a 5- or 6-membered saturated heterocyclyl group, a substituted 5- or 6-membered saturated heterocyclyl group in which the substituent(s) represent 1 to 4 groups independently selected from the substituent group α1, a substituted 5- or 6-membered saturated heterocyclyloxy group in which the substituent(s) represent 1 to 4 groups independently selected from the substituent group α1 or a 5- or 6-membered saturated heterocyclylcarbonyl group, and the substituent group α1 represents the group consisting of a $C_1$-$C_6$ alkyl group, a hydroxy group, a carboxy group and an oxo group.

(10) The compound according to (1) or a pharmacologically acceptable salt thereof, wherein $R^1$ is a 5- or 6-membered nitrogen-containing saturated heterocyclyl group, a substituted 5- or 6-membered nitrogen-containing saturated heterocyclyl group in which the substituent(s) represent 1 to 4 groups independently selected from the substituent group α2 or a substituted 5- or 6-membered nitrogen-containing saturated heterocyclyloxy group in which the substituent(s) represent 1 to 4 groups independently selected from the substituent group α2, and the substituent group α2 represents the group consisting of a $C_1$-$C_4$ alkyl group and a hydroxy group.

(11) The compound according to (1) or a pharmacologically acceptable salt thereof, wherein $R^1$ is a substituted pyrrolidinyl group, a substituted piperidyl group, a substituted piperazyl group, a substituted thiomorpholinyl group, a substituted pyrrolidinyloxy group or a substituted piperidyloxy group in which the substituent(s) of the pyrrolidinyl group, piperidyl group, piperazyl group, thiomorpholinyl group, pyrrolidinyloxy group and piperidyloxy group represent 1 to 2 groups independently selected from the substituent group α3, and the substituent group α3 represents the group consisting of a methyl group and a hydroxy group.

(12) The compound according to (1) or a pharmacologically acceptable salt thereof, which is selected from the group consisting of, (−)-4-(4,4-Difluorocyclohexyl)-3-{fluoro[4-(trifluoromethyl)phenyl]methyl}-7,7-dimethyl-2-{1-[5-(4-methylpiperazin-1-yl)pyrimidin-2-yl]piperidin-4-yl}-5,6,7,8-tetrahydroquinolin-5-ol, (−)-4-(4,4-Difluorocyclohexyl)-3-{fluoro[4-(trifluoromethyl)phenyl]methyl}-7,7-dimethyl-2-{1-[5-(2-hydroxyethoxy)pyrimidin-2-yl]piperidin-4-yl}-5,6,7,8-tetrahydroquinolin-5-ol, (−)-2-{1-[5-(4-Carboxybutoxyl)pyrimidine-2-yl]piperidin-4-yl}-4-(4,4-difluorocyclohexyl)-3-{fluoro[4-(trifluoromethyl)phenyl]methyl}-7,7-dimethyl-5,6,7,8-tetrahydroquinolin-5-ol, (−)-2-{1-[5-(4-Carboxybutyl)pyrimidine-2-yl]piperidin-4-yl}-4-(4,4-difluorocyclohexyl)-3-{fluoro[4-(trifluoromethyl)phenyl]methyl}-7,7-dimethyl-5,6,7,8-tetrahydroquinolin-5-ol, 4-(4,4-Difluorocyclohexyl)-3-{fluoro[4-(trifluoromethyl)phenyl]methyl}-7,7-dimethyl-2-{1-[5-(methylcarbamoyl)pyrimidin-2-yl]piperidin-4-yl}-5,6,7,8-tetrahydroquinolin-5-ol, (−)-4-(4,4-Difluorocyclohexyl)-2-{1-[5-(dimethylcarbamoyl)pyrimidin-2-yl]piperidin-4-yl}-3-{fluoro[4-(trifluoromethyl)phenyl]methyl}-7,7-dimethyl-5,6,7,8-tetrahydroquinolin-5-ol, 4-(4,4-Difluorocyclohexyl)-3-{fluoro[4-(trifluoromethyl)phenyl]methyl}-7,7-dimethyl-2-{1-[5-(morpholin-4-ylcarbonyl)pyrimidin-2-yl]piperidin-4-yl}-5,6,7,8-tetrahydroquinolin-5-ol, (−)-4-(4,4-Difluorocyclohexyl)-3-{fluoro[4-(trifluoromethyl)phenyl]methyl}-2-{1-(5-{[(2-hydroxyethyl)(methyl)amino]methyl}pyrimidin-2-yl)piperidin-4-yl}-7,7-dimethyl-5,6,7,8-tetrahydroquinolin-5-ol, (−)-4-(4,4-Difluorocyclohexyl)-3-{fluoro[4-(trifluoromethyl)phenyl]methyl}-2-[1-(5-{[(2S)-2-hydroxypropyl]oxy}pyrimidin-2-yl)piperidin-4-yl]-7,7-dimethyl-5,6,7,8-tetrahydroquinolin-5-ol, 4-(4,4-Difluorocyclohexyl)-3-{fluoro[4-(trifluoromethyl)phenyl]methyl}-7,7-dimethyl-2-(1-{5-[(1-methylpiperidin-4-yl)oxy]pyrimidin-2-yl}piperidin-4-yl)-5,6,7,8-tetrahydroquinolin-5-ol, (−)-4-(4,4-Difluorocyclohexyl)-2-[1-(5-{[(2S)-2,3-dihydroxypropyl]oxy}pyrimidin-2-yl)piperidin-4-yl]-3-{fluoro[4-(trifluoromethyl)phenyl]methyl}-7,7-dimethyl-5,6,7,8-tetrahydroquinolin-5-ol, (−)-4-(4,4-Difluorocyclohexyl)-2-[1-(5-{[(2R)-2,3-dihydroxypropyl]oxy}pyrimidin-2-yl)piperidin-4-yl]-3-{fluoro[4-(trifluoromethyl)phenyl]methyl}-7,7-dimethyl-5,6,7,8-tetrahydroquinolin-5-ol, 4-(4,4-Difluorocyclohexyl)-3-{fluoro[4-(trifluoromethyl)phenyl]methyl}-7,7-dimethyl-2-[1-(5-{[(3R)-1-methylpyrrolidin-3-yl]oxy}pyrimidin-2-yl)piperidin-4-yl]-5,6,7,8-tetrahydroquinolin-5-ol, (−)-4-(4,4-Difluorocyclohexyl)-3-{fluoro[4-(trifluoromethyl)phenyl]methyl}-2-[1-(5-{[(2R)-2-hydroxypropyl]oxy}pyrimidin-2-yl)piperidin-4-yl]-7,7-dimethyl-5,6,7,8-tetrahydroquinolin-5-ol, (−)-4-(4,4-Difluorocyclohexyl)-3-{fluoro[4-(trifluoromethyl)phenyl]methyl}-2-{1-[5-(3-hydroxy-3-methylbutoxy)pyrimidin-2-yl]piperidin-4-yl}-7,7-dimethyl-5,6,7,8-tetrahydroquinolin-5-ol, 4-(4,4-Difluorocyclohexyl)-3-{fluoro[4-(trifluoromethyl)phenyl]methyl}-2-{1-[5-(2-hydroxy-2-methylpropoxy)pyrimidin-2-yl]piperidin-4-yl}-7,7-dimethyl-5,6,7,8-tetrahydroquinolin-5-ol, (−)-4-(4,4-Difluorocyclohexyl)-3-{fluoro[4-(trifluoromethyl)phenyl]methyl}-7,7-dimethyl-2-(1-{5-[3-(methylsulphonyl)propoxy]pyrimidin-2-yl}piperidin-4-yl)-5,6,7,8-tetrahydroquinolin-5-ol, (−)-4-(4,4-Difluorocyclohexyl)-3-{fluoro[4-(trifluoromethyl)phenyl]methyl}-2-{1-[5-(3-hydroxypropoxy)pyrimidin-2-yl]piperidin-4-yl}-7,7-dimethyl-5,6,7,8-tetrahydroquinolin-5-ol, (−)-4-(4,4-Difluorocyclohexyl)-3-{fluoro[4-(trifluoromethyl)phenyl]methyl}-7,7-dimethyl-2-{1-[5-(3,3,3-trifluoropropoxy)pyrimidin-2-yl]piperidin-4-yl}-5,6,7,8-tetrahydroquinolin-5-ol (−)-4-(4,4-Difluorocyclohexyl)-3-{fluoro[4-(trifluoromethyl)phenyl]methyl}-2-(1-{5-[3-hydroxy-2-(hydroxymethyl)propoxy]pyrimidin-2-yl}piperidin-4-yl)-7,7-dimethyl-5,6,7,8-tetrahydroquinolin-5-ol, (−)-4-(4,4-Difluorocyclohexyl)-3-{fluoro[4-(trifluoromethyl)phenyl]methyl}-2-(1-{5-[3-hydroxy-2-(hydroxymethyl)-2-methylpropoxy]pyrimidin-2-yl}piperidin-4-yl)-7,7-dimethyl-5,6,7,8-tetrahydroquinolin-5-ol, (−)-4-(4,4-Difluorocyclohexyl)-3-{fluoro[4-(trifluoromethyl)phenyl]methyl}-7,7-dimethyl-2-[1-(5-{[methyl(methylsulphonyl)amino]methyl}pyrimidin-2-yl)piperidin-4-yl]-5,6,7,8-tetrahydroquinolin-5-ol, 4-(4,4-Difluorocyclohexyl)-3-{fluoro[4-(trifluoromethyl)phenyl]methyl}-7,7-dimethyl-2-[1-(5-{[methyl(propan- 2-ylsulfonyl)amino]methyl}pyrimidin-2-yl)piperidin-4-yl]-5,6,7,8-tetrahydroquinolin-5-ol, (−)-4-(4,4-Difluorocyclohexyl)-3-{fluoro[4-(trifluoromethyl)phenyl]methyl}-7,7-dimethyl-2-[1-(5-methylthiopyrimidin-2-yl)piperidin-4-yl]-5,6,7,8-tetrahydroquinolin-5-ol, (−)-4-(4,4-Difluorocyclohexyl)-3-{fluoro[4-(trifluoromethyl)phenyl]methyl}-7,7-dimethyl-2-{1-[5-(methylsulphonyl)pyrimidin-2-yl]piperidin-4-yl}-5,6,7,8-tetrahydroquinolin-5-ol, 4-(4,4-Difluorocyclohexyl)-3-{fluoro[4-(trifluoromethyl)phenyl]methyl}-2-(1-{5-[(2-hydroxyethyl)(methyl)amino]pyrimidin-2-yl}piperidin-4-yl)-7,7-dimethyl-5,6,7,8-tetrahydroquinolin-5-ol, and (−)-4-(4,4-Difluorocyclohexyl)-3-{fluoro[4-(trifluoromethyl)phenyl]methyl}-2-(1-{5-[(3 S)-3-hydroxypyrrolidin-1-yl]pyrimidin-2-yl}piperidin-4-yl)-7,7-dimethyl-5,6,7,8-tetrahydroquinolin-5-ol.

(13) A pharmaceutical composition comprising the compound according to any one of (1) to (12) or a pharmacologically acceptable salt thereof as an active ingredient.

(14) The pharmaceutical composition according to (13) for treatment or prophylaxis of dyslipidemia, hypercholesterolemia, low HDL cholesterolemia, high LDL cholesterolemia, hypertriglyceridemia, arteriosclerosis, arteriosclerotic heart disease, coronary heart disease, cerebrovascular disease, peripheral vascular disease or obesity.

(15) The pharmaceutical composition according to (13) for treatment or prophylaxis of dyslipidemia, low HDL cholesterolemia, arteriosclerosis or coronary heart disease.

(16) The pharmaceutical composition according to (13) for treatment or prophylaxis of low HDL cholesterolemia.

(17) The pharmaceutical composition according to (13) for treatment or prophylaxis of arteriosclerosis.

(18) The pharmaceutical composition according to (13) for treatment or prophylaxis of a disease caused by a decrease in the blood concentration of HDL cholesterol.

(19) The pharmaceutical composition according to (13) for treatment or prophylaxis of a disease caused by an increase in the blood concentration of LDL cholesterol.

(20) A medicament for inhibiting CETP comprising the compound according to any one of (1) to (12) or a pharmacologically acceptable salt thereof as an active ingredient.

(21) A medicament for increasing the concentration of HDL cholesterol comprising the compound according to any one of (1) to (12) or a pharmacologically acceptable salt thereof as an active ingredient.

(22) A medicament for decreasing the concentration of LDL cholesterol comprising the compound according to any one of (1) to (12) or a pharmacologically acceptable salt thereof as an active ingredient.

Each group in general formula (I) of the present invention has the meanings described below.

The "$C_1$-$C_6$ alkyl" represents straight or branched alkyl which has 1 to 6 carbon atoms and may be, for example, methyl, ethyl, 1-propyl, 2-propyl, 1-butyl, 2-butyl, 2-methyl-1-propyl, 2-methyl-2-propyl, 1-pentyl, 2-pentyl, 3-pentyl, 2-methyl-2-butyl, 3-methyl-2-butyl, 1-hexyl, 2-hexyl, 3-hexyl, 2-methyl-1-pentyl, 3-methyl-1-pentyl, 2-ethyl-1-butyl, 2,2-dimethyl-1-butyl or 2,3-dimethyl-1-butyl. The $C_1$-$C_6$ alkyl in $R^1$ is preferably $C_2$-$C_5$ alkyl, and most preferably 2-propyl, 1-pentyl or 2-methyl-1-propyl. The $C_1$-$C_6$ alkyl in the substituent group α is preferably $C_1$-$C_4$ alkyl, more preferably $C_1$-$C_2$ alkyl, and most preferably methyl.

The "hydroxy($C_1$-$C_6$ alkyl)" represents the above-described $C_1$-$C_6$ alkyl substituted with 1 to 4 hydroxy groups and may be, for example, hydroxymethyl, hydroxyethyl, hydroxypropyl, hydroxybutyl, hydroxypentyl, hydroxyhexyl, dihydroxypropyl, dihydroxybutyl, dihydroxypentyl, dihydroxyhexyl, trihydroxybutyl, trihydroxypentyl, trihydroxyhexyl, tetrahydroxypentyl or tetrahydroxyhexyl, preferably hydroxy($C_1$-$C_4$ alkyl), more preferably hydroxy($C_1$-$C_2$ alkyl), and most preferably hydroxymethyl.

The "($C_1$-$C_6$ alkoxy)-($C_1$-$C_6$ alkyl)" represents the above-described $C_1$-$C_6$ alkyl substituted with one $C_1$-$C_6$ alkoxy described below and may be, for example, methoxymethyl, ethoxymethyl, propoxymethyl, butoxymethyl, pentyloxymethyl, hexyloxymethyl, methoxyethyl, methoxypropyl, methoxybutyl, methoxypentyl or methoxyhexyl, preferably ($C_1$-$C_4$ alkoxy)-($C_1$-$C_4$ alkyl), more preferably ($C_1$-$C_4$ alkoxy)-($C_1$-$C_2$ alkyl), and most preferably methoxymethyl, ethoxymethyl, 2-propoxymethyl or (2-methyl-1-propoxy)methyl.

The "hydroxy($C_1$-$C_6$ alkoxy)-($C_1$-$C_6$ alkyl)" represents the above-described $C_1$-$C_6$ alkyl substituted with one hydroxy ($C_1$-$C_6$ alkoxy) described below and may be, for example, hydroxymethoxymethyl, hydroxyethoxymethyl, hydroxypropoxymethyl, hydroxybutoxymethyl, hydroxypentyloxymethyl, hydroxyhexyloxymethyl, hydroxyethoxyethyl, hydroxyethoxypropyl, hydroxyethoxybutyl, hydroxyethoxypentyl or hydroxyethoxyhexyl, preferably hydroxy($C_1$-$C_4$ alkoxy)-($C_1$-$C_4$ alkyl), and more preferably hydroxy($C_1$-$C_2$ alkoxy)-($C_1$-$C_2$ alkyl).

The "($C_1$-$C_6$ alkyl)amino-($C_1$-$C_6$ alkyl)" represents the above-described $C_1$-$C_6$ alkyl substituted with one ($C_1$-$C_6$ alkyl)amino described below and may be, for example, methylaminomethyl, ethylaminomethyl, propylaminomethyl, butylaminomethyl, pentylaminomethyl, hexylaminomethyl, methylaminoethyl, methylaminopropyl, methylaminobutyl, methylaminopentyl or methylaminohexyl, preferably ($C_1$-$C_4$ alkyl)amino-($C_1$-$C_4$ alkyl), more preferably ($C_1$-$C_2$ alkyl)amino-($C_1$-$C_2$ alkyl), and most preferably methylaminomethyl.

The "hydroxy($C_1$-$C_6$ alkyl)amino-($C_1$-$C_6$ alkyl)" represents the above-described $C_1$-$C_6$ alkyl substituted with one hydroxy($C_1$-$C_6$ alkyl)amino described below and may be, for example, hydroxymethylaminomethyl, hydroxyethylaminomethyl, hydroxypropylaminomethyl, hydroxybutylaminomethyl, hydroxypentylaminomethyl, hydroxyhexylaminomethyl, hydroxyethylaminoethyl, hydroxyethylaminopropyl, hydroxyethylaminobutyl, hydroxyethylaminopentyl or hydroxyethylaminohexyl, preferably hydroxy($C_1$-$C_4$ alkyl)amino-($C_1$-$C_4$ alkyl), and more preferably hydroxy($C_1$-$C_2$ alkyl)amino-($C_1$-$C_2$ alkyl).

The "[N—($C_1$-$C_6$ alkyl)-N-hydroxy($C_1$-$C_6$ alkyl)amino]-($C_1$-$C_6$ alkyl)" represents the above-described $C_1$-$C_6$ alkyl substituted with one N—($C_1$-$C_6$ alkyl)-N-hydroxy($C_1$-$C_6$ alkyl)amino described below and may be, for example, (N-methyl-N-hydroxymethylamino)methyl, (N-methyl-N-hydroxyethylamino)methyl, (N-methyl-N-hydroxypropylamino)methyl, (N-methyl-N-hydroxybutylamino)methyl, (N-methyl-N-hydroxypentylamino)methyl, (N-methyl-N-hydroxyhexylamino)methyl, (N-methyl-N-hydroxyethylamino)ethyl, (N-methyl-N-hydroxyethylamino)propyl, (N-methyl-N-hydroxyethylamino)butyl, (N-methyl-N-hydroxyethylamino)pentyl or (N-methyl-N-hydroxyethylamino)hexyl, preferably [N—($C_1$-$C_4$ alkyl)-N-hydroxy($C_1$-$C_4$ alkyl)amino]-($C_1$-$C_4$ alkyl), more preferably [N—($C_1$-$C_2$ alkyl)-N-hydroxy($C_1$-$C_2$ alkyl)amino]-($C_1$-$C_2$ alkyl), and most preferably (N-methyl-N-hydroxyethylamino)methyl.

The "($C_1$-$C_6$ alkyl)sulfonylamino-($C_1$-$C_6$ alkyl)" represents a group in which the above-described $C_1$-$C_6$ alkyl is substituted with one amino and the amino is further substituted with one $C_1$-$C_6$ alkylsulfonyl described below and may be, for example, methanesulfonylaminomethyl, ethanesulfonylaminomethyl, propanesulfonylaminomethyl, butanesulfonylaminomethyl, pentanesulfonylaminomethyl, hexanesulfonylaminomethyl, methanesulfonylaminoethyl, methanesulfonylaminopropyl, methanesulfonylaminobutyl, methanesulfonylaminopentyl or methanesulfonylaminohexyl, preferably ($C_1$-$C_4$ alkyl)sulfonylamino-($C_1$-$C_4$ alkyl), and more preferably ($C_1$-$C_2$ alkyl)sulfonylamino-($C_1$-$C_2$ alkyl).

The "[N—($C_1$-$C_6$ alkyl)-N—($C_1$-$C_6$ alkyl)sulfonylamino]-($C_1$-$C_6$ alkyl)" represents a group in which the nitrogen atom of the above-described ($C_1$-$C_6$ alkyl)sulfonylamino-($C_1$-$C_6$ alkyl) is substituted with one $C_1$-$C_6$ alkyl described above and may be, for example, (N-methyl-N-methanesulfonylamino)methyl, (N-methyl-N-ethanesulfonylamino)methyl, (N-methyl-N-propanesulfonylamino)methyl, (N-methyl-N-butanesulfonylamino)methyl, (N-methyl-N-pentanesulfonylamino)methyl, (N-methyl-N-hexanesulfonylamino)methyl, (N-methyl-N-methanesulfonylamino)ethyl, (N-methyl-N-methanesulfonylamino)propyl, (N-methyl-N-methanesulfonylamino)butyl, (N-methyl-N-methanesulfonylamino)pentyl or (N-methyl-N-methanesulfonylamino)hexyl, preferably [N—($C_1$-$C_4$ alkyl)-N—($C_1$-$C_4$ alkyl)sulfonylamino]-($C_1$-$C_4$ alkyl), more preferably [N—($C_1$-$C_2$ alkyl)-N—($C_1$-$C_3$ alkyl)sulfonylamino]-($C_1$-$C_2$ alkyl), and most preferably (N-methyl-N-methanesulfonylamino)methyl or [N-methyl-N-(2-propyl)sulfonylamino]methyl.

The "carboxy($C_1$-$C_6$ alkyl)" represents the above-described $C_1$-$C_6$ alkyl which is substituted with 1 or 2 carboxy groups and may be, for example, carboxymethyl, carboxyethyl, carboxypropyl, carboxybutyl, carboxypentyl, carboxyhexyl, dicarboxypropyl, dicarboxybutyl, dicarboxypentyl or dicarboxyhexyl, preferably carboxy($C_1$-$C_4$ alkyl), more preferably carboxy($C_3$-$C_4$ alkyl), and most preferably 4-carboxy-1-butyl.

The "halogeno($C_1$-$C_6$ alkyl)" represents the above-described $C_1$-$C_6$ alkyl which is substituted with 1 to 7 halogeno groups described below that are independently selected, and may be, for example, fluoromethyl, difluoromethyl, dichloromethyl, dibromomethyl, trifluoromethyl, trichloromethyl, fluoroethyl, chloroethyl, bromoethyl, iodoethyl, difluoroethyl, trifluoroethyl, trichloroethyl, pentafluoroethyl, fluoropropyl, chloropropyl, fluorobutyl, trifluorobutyl, fluoropentyl or fluorohexyl. The halogeno($C_1$-$C_6$ alkyl) in $R^1$ is preferably halogeno($C_1$-$C_4$ alkyl) in which the halogeno is 1 to 5 groups selected from the group consisting of fluoro and chloro, more preferably halogeno($C_2$-$C_4$ alkyl) in which the halogeno is 1 to 5 fluoro groups, and most preferably 4,4,4-trifluoro-1-butyl. The halogeno($C_1$-$C_6$ alkyl) in the substituent group α is preferably halogeno($C_1$-$C_4$ alkyl) in which the halogeno is 1 to 5 groups selected from the group consisting of fluoro and chloro, and more preferably halogeno($C_1$-$C_2$ alkyl) in which the halogeno is 1 to 5 fluoro groups.

The "($C_3$-$C_8$ cycloalkyl)-($C_1$-$C_6$ alkyl)" represents the above-described $C_1$-$C_6$ alkyl which is substituted with one $C_3$-$C_8$ cycloalkyl described below and may be, for example, cyclopropylmethyl, cyclobutylmethyl, cyclopentylmethyl, cyclohexylmethyl, cycloheptylmethyl, cyclooctylmethyl, cyclopropylethyl, cyclopropylpropyl, cyclopropylbutyl, cyclopropylpentyl or cyclopropylhexyl, preferably ($C_3$-$C_6$ cycloalkyl)-($C_1$-$C_4$ alkyl), and more preferably ($C_3$-$C_4$ cycloalkyl)-($C_1$-$C_2$ alkyl).

The "$C_2$-$C_6$ alkenyl" represents straight or branched alkenyl which has 2 to 6 carbon atoms and has one or more carbon-carbon double bonds and may be, for example, vinyl, propenyl (for example, allyl), butenyl, pentenyl or hexenyl, preferably $C_2$-$C_5$ alkenyl, more preferably $C_3$-$C_5$ alkenyl, and most preferably 3-methyl-but-1-en-1-yl.

The "$C_2$-$C_6$ alkynyl" represents straight or branched alkynyl which has 2 to 6 carbon atoms and has one or more carbon-carbon triple bond and may be, for example, ethynyl, propynyl, butynyl, pentynyl or hexynyl, and preferably $C_3$-$C_5$ alkynyl.

The "$C_3$-$C_8$ cycloalkyl" represents cyclic alkyl which has 3 to 8 carbon atoms and may be, for example, cyclopropyl, cyclobutyl, cyclopentyl, cyclohexyl, cycloheptyl or cyclooctyl, preferably $C_3$-$C_6$ cycloalkyl, more preferably $C_3$-$C_4$ cycloalkyl, and most preferably cyclopropyl.

The "$C_3$-$C_8$ cycloalkenyl" represents cyclic alkenyl which has 3 to 8 carbon atoms and has one or more carbon-carbon double bond and may be, for example, cyclopropenyl, cyclobutenyl, cyclopentenyl, cyclohexenyl, cycloheptenyl or cyclooctenyl, preferably $C_4$-$C_6$ cycloalkenyl, and most preferably 1-cyclohexenyl.

The "$C_1$-$C_6$ alkoxy" represents hydroxy substituted with one $C_1$-$C_6$ alkyl described above and may be, for example, methoxy, ethoxy, propoxy, butoxy, pentyloxy or hexyloxy. The $C_1$-$C_6$ alkoxy in $R^1$ is preferably methoxy, ethoxy, 2-propoxy, 2-methyl-1-propoxy or 3-methyl-1-butoxy. The $C_1$-$C_6$ alkoxy in the substituent group α is preferably $C_1$-$C_4$ alkoxy, and more preferably $C_1$-$C_2$ alkoxy.

The "hydroxy($C_1$-$C_6$ alkoxy)" represents the above-described $C_1$-$C_6$ alkoxy which is substituted with 1 to 4 hydroxy groups and may be, for example, hydroxymethoxy, hydroxyethoxy, hydroxypropoxy, hydroxybutoxy, hydroxypentyloxy, hydroxyhexyloxy, dihydroxypropoxy, dihydroxybutoxy, dihydroxypentyloxy, dihydroxyhexyloxy, trihydroxybutoxy, trihydroxypentyloxy, trihydroxyhexyloxy, tetrahydroxypentyloxy or tetrahydroxyhexyloxy, preferably hydroxy($C_2$-$C_6$ alkoxy), and most preferably 2-hydroxyethoxy, 3-hydroxy-1-propoxy, (2R)-2-hydroxy-1-propoxy, (2S)-2-hydroxy-1-propoxy, (2R)-2,3-dihydroxy-1-propoxy, (2S)-2,3-dihydroxy-1-propoxy, 2-hydroxy-2-methyl-1-propoxy, 3-hydroxy-2-(hydroxymethyl)-1-propoxy, 3-hydroxy-3-methyl-1-butoxy or 3-hydroxy-2-(hydroxymethyl)-2-methyl-1-propoxy.

The "($C_1$-$C_6$ alkoxy)-($C_1$-$C_6$ alkoxy)" represents the above-described $C_1$-$C_6$ alkoxy which is substituted with one $C_1$-$C_6$ alkoxy described above and may be, for example, methoxymethoxy, ethoxymethoxy, propoxymethoxy, butoxymethoxy, pentyloxymethoxy, hexyloxymethoxy, methoxyethoxy, methoxypropoxy, methoxybutoxy, methoxypentyloxy or methoxyhexyloxy, and preferably ($C_1$-$C_4$ alkoxy)-($C_1$-$C_4$ alkoxy).

The "($C_1$-$C_6$ alkyl)sulfonyl-($C_1$-$C_6$ alkoxy)" represents the above-described $C_1$-$C_6$ alkoxy which is substituted with one $C_1$-$C_6$ alkylsulfonyl described below and may be, for example, methanesulfonylmethoxy, ethanesulfonylmethoxy, propanesulfonylmethoxy, butanesulfonylmethoxy, pentanesulfonylmethoxy, hexanesulfonylmethoxy, methanesulfonylethoxy, methanesulfonylpropoxy, methanesulfonylbutoxy, methanesulfonylpentyloxy or methanesulfonylhexyloxy, preferably ($C_1$-$C_4$ alkyl)sulfonyl-($C_1$-$C_4$ alkoxy), more preferably ($C_1$-$C_2$ alkyl)sulfonyl-($C_1$-$C_3$ alkoxy), and most preferably 3-methanesulfonyl-1-propoxy.

The "carboxy($C_1$-$C_6$ alkoxy)" represents the above-described $C_1$-$C_6$ alkoxy which is substituted with 1 or 2 carboxy groups and may be, for example, carboxymethoxy, carboxyethoxy, carboxypropoxy, carboxybutoxy, carboxypentyloxy, carboxyhexyloxy, dicarboxypropoxy, dicarboxybutoxy, dicarboxypentyloxy or dicarboxyhexyloxy, preferably carboxy($C_2$-$C_5$ alkoxy), more preferably carboxy($C_3$-$C_4$ alkoxy), and most preferably 4-carboxy-1-butoxy.

The "halogeno($C_1$-$C_6$ alkoxy)" represents the above-described $C_1$-$C_6$ alkoxy which is substituted with 1 to 7 halogeno groups described below that are independently selected and may be, for example, fluoromethoxy, difluoromethoxy, dichloromethoxy, dibromomethoxy, trifluoromethoxy, trichloromethoxy, fluoroethoxy, chloroethoxy, bromoethoxy, iodoethoxy, difluoroethoxy, trifluoroethoxy, trichloroethoxy, pentafluoroethoxy, fluoropropoxy, chloropropoxy, fluorobutoxy, fluoropentyloxy or fluorohexyloxy. The halogeno($C_1$-$C_6$ alkoxy) in $R^1$ is preferably halogeno($C_1$-$C_4$ alkoxy) in which the halogeno is 1 to 5 groups selected from the group consisting of fluoro and chloro, more preferably halogeno ($C_1$-$C_3$ alkoxy) in which the halogeno is 1 to 5 fluoro groups, and most preferably difluoromethoxy or 3,3,3-trifluoro-1-propoxy. The halogeno($C_1$-$C_6$ alkoxy) in the substituent group α is preferably halogeno($C_1$-$C_4$ alkoxy) in which the halogeno is 1 to 5 groups selected from the group consisting of fluoro and chloro, and more preferably halogeno($C_1$-$C_2$ alkoxy) in which the halogeno is 1 to 5 fluoro groups.

The "$C_1$-$C_6$ alkylthio" represents mercapto (—SH) which is substituted with one $C_1$-$C_6$ alkyl described above and may be, for example, methylthio, ethylthio, propylthio, butylthio, pentylthio or hexylthio, preferably $C_1$-$C_4$ alkylthio, more preferably $C_1$-$C_2$ alkylthio, and most preferably methylthio.

The "$C_1$-$C_6$ alkylsulfinyl" represents sulfinyl (—SO—) which is substituted with one $C_1$-$C_6$ alkyl described above and may be, for example, methylsulfinyl, ethylsulfinyl, propylsulfinyl, butylsulfinyl, pentylsulfinyl or hexylsulfinyl, preferably $C_1$-$C_4$ alkylsulfinyl, and more preferably $C_1$-$C_2$ alkylsulfinyl.

The "$C_1$-$C_6$ alkylsulfonyl" represents sulfonyl (—$SO_2$—) which is substituted with one $C_1$-$C_6$ alkyl described above and may be, for example, methanesulfonyl, ethanesulfonyl, propanesulfonyl, butanesulfonyl, pentanesulfonyl or hexanesulfonyl, preferably $C_1$-$C_4$ alkylsulfonyl, more preferably $C_1$-$C_2$ alkylsulfonyl, and most preferably methanesulfonyl.

The "$C_1$-$C_6$ alkylamino" represents amino which is substituted with one $C_1$-$C_6$ alkyl described above and may be, for example, methylamino, ethylamino, propylamino, butylamino, pentylamino or hexylamino, preferably $C_1$-$C_4$ alkylamino, and more preferably $C_1$-$C_2$ alkylamino.

The "di($C_1$-$C_6$ alkyl)amino" represents amino which is substituted with two $C_1$-$C_6$ alkyl groups described above that are independently selected and may be, for example, dimethylamino, ethylmethylamino, methylpropylamino, butylmethylamino, methylpentylamino, hexylmethylamino, diethylamino, ethylpropylamino, butylethylamino, dipropylamino, butylpropylamino, dibutylamino, dipentylamino or dihexylamino, preferably di($C_1$-$C_4$ alkyl)amino, and more preferably di($C_1$-$C_2$ alkyl)amino.

The "hydroxy($C_1$-$C_6$ alkyl)amino" represents amino which is substituted with one hydroxy($C_1$-$C_6$ alkyl) described above and may be, for example, hydroxymethylamino, hydroxyethylamino, hydroxypropylamino, hydroxybutylamino, hydroxypentylamino, hydroxyhexylamino, dihydroxypropylamino, dihydroxybutylamino, dihydroxypentylamino, dihydroxyhexylamino, trihydroxybutylamino, trihydroxypentylamino, trihydroxyhexylamino, tetrahydroxypentylamino or tetrahydroxyhexylamino, and preferably hydroxy($C_1$-$C_4$ alkyl)amino.

The "N—($C_1$-$C_6$ alkyl)-N-hydroxy($C_1$-$C_6$ alkyl)amino" represents amino which is substituted with one hydroxy($C_1$-$C_6$ alkyl) described above and one $C_1$-$C_6$ alkyl described above and may be, for example, N-methyl-N-hydroxymethylamino, N-methyl-N-hydroxyethylamino, N-methyl-N-hydroxypropylamino, N-methyl-N-hydroxybutylamino, N-methyl-N-hydroxypentylamino, N-methyl-N-hydroxyhexylamino, N-ethyl-N-hydroxyethylamino, N-propyl-N-hydroxyethylamino, N-butyl-N-hydroxyethylamino, N-pentyl-N-hydroxyethylamino or N-hexyl-N-hydroxyethylamino, preferably N—($C_1$-$C_4$ alkyl)-N-hydroxy ($C_1$-$C_4$ alkyl)amino, more preferably N—($C_1$-$C_2$ alkyl)-N-hydroxy($C_1$-$C_2$ alkyl)amino, and most preferably N-methyl-N-hydroxyethylamino.

The "($C_1$-$C_6$ alkyl)carbonylamino" represents a group in which the carbon atom of carbonylamino (—CONH—) is substituted with one $C_1$-$C_6$ alkyl described above and may be, for example, methylcarbonylamino (acetylamino), ethylcarbonylamino, propylcarbonylamino, butylcarbonylamino, pentylcarbonylamino or hexylcarbonylamino, preferably ($C_1$-$C_4$ alkyl)carbonylamino, and more preferably ($C_1$-$C_2$ alkyl)carbonylamino.

The "($C_1$-$C_6$ alkoxy)carbonyl" represents carbonyl (—CO—) which is substituted with one $C_1$-$C_6$ alkoxy described above and may be, for example, methoxycarbonyl, ethoxycarbonyl, propoxycarbonyl, butoxycarbonyl, pentyloxycarbonyl or hexyloxycarbonyl, preferably ($C_1$-$C_4$ alkoxy)carbonyl, and more preferably ($C_1$-$C_2$ alkoxy)carbonyl. The ($C_1$-$C_6$ alkoxy)carbonyl in the substituent group α is preferably ($C_1$-$C_4$ alkoxy)carbonyl, more preferably ($C_1$-$C_2$ alkoxy)carbonyl, and most preferably ethoxycarbonyl.

The "($C_1$-$C_6$ alkylamino)carbonyl" represents carbonyl (—CO—) which is substituted with one $C_1$-$C_6$ alkylamino described above and may be, for example, methylaminocarbonyl, ethylaminocarbonyl, propylaminocarbonyl, butylaminocarbonyl, pentylaminocarbonyl or hexylaminocarbonyl, preferably ($C_1$-$C_4$ alkylamino)carbonyl, more preferably ($C_1$-$C_2$ alkylamino)carbonyl, and most preferably methylaminocarbonyl.

The "di($C_1$-$C_6$ alkyl)aminocarbonyl" represents carbonyl (—CO—) which is substituted with one di($C_1$-$C_6$ alkyl) amino described above and may be, for example, dimethylaminocarbonyl, (N-ethyl-N-methylamino)carbonyl, (N-methyl-N-propylamino)carbonyl, (N-butyl-N-methylamino) carbonyl, (N-methyl-N-pentylamino)carbonyl, (N-hexyl-N-methylamino)carbonyl, diethylaminocarbonyl, dipropylaminocarbonyl, dibutylaminocarbonyl, dipentylaminocarbonyl or dihexylaminocarbonyl, preferably di($C_1$-$C_4$ alkyl)aminocarbonyl, more preferably di($C_1$-$C_2$ alkyl) aminocarbonyl, and most preferably dimethylaminocarbonyl.

The "halogeno" may be fluoro, chloro, bromo or iodo, and preferably fluoro, chloro or bromo.

The "5- or 6-membered aromatic heterocyclyl" represents a 5- or 6-membered aromatic heterocyclic group which contains 1 to 4 atoms selected from the group consisting of a nitrogen atom, an oxygen atom and a sulfur atom and may be, for example, pyrrolyl, furyl, thienyl, pyrazolyl, imidazolyl, oxazolyl, isoxazolyl, thiazolyl, isothiazolyl, triazolyl, oxadiazolyl, thiadiazolyl, tetrazolyl, pyranyl, pyridyl, pyridazinyl, pyrimidinyl or pyrazinyl, preferably 5- or 6-membered nitrogen-containing aromatic heterocyclyl, more preferably 5-membered nitrogen-containing aromatic heterocyclyl, and most preferably oxadiazolyl.

The "5- or 6-membered saturated heterocyclyl" represents a 5- or 6-membered saturated heterocyclic group which contains 1 to 3 atoms selected from the group consisting of a nitrogen atom, an oxygen atom and a sulfur atom and may be, for example, pyrrolidinyl, imidazolidinyl, pyrazolidinyl, oxazolidinyl, thiazolidinyl, dioxolanyl, dithiolanyl, piperidinyl, tetrahydropyranyl, tetrahydrothiopyranyl, piperazinyl, morpholinyl, thiomorpholinyl, dioxanyl, thioxanyl, dithianyl, trioxanyl or trithianyl, preferably 5- or 6-membered nitrogen-containing saturated heterocyclyl, and more preferably pyrrolidinyl, piperidinyl, piperazinyl, morpholinyl or thiomorpholinyl. In the 5- or 6-membered nitrogen-containing saturated heterocyclyl, preferably, the nitrogen atom thereof binds to the pyrimidinyl group in general formula (I).

The "5- or 6-membered saturated heterocyclyl-($C_1$-$C_6$ alkyl)" represents the above-described $C_1$-$C_6$ alkyl which is substituted with one 5- or 6-membered saturated heterocyclyl described above and may be, for example, pyrrolidinylmethyl, piperidinylmethyl, piperazinylmethyl, morpholinylmethyl or thiomorpholinylmethyl, preferably 5- or 6-membered nitrogen-containing saturated heterocyclyl-($C_1$-$C_4$ alkyl), and more preferably 5- or 6-membered nitrogen-containing saturated heterocyclyl-($C_1$-$C_2$ alkyl).

The "5- or 6-membered saturated heterocyclyloxy" represents hydroxy which is substituted with one 5- or 6-membered saturated heterocyclyl described above and may be, for example, pyrrolidinyloxy, piperidinyloxy, piperazinyloxy, morpholinyloxy or thiomorpholinyloxy, preferably 5- or 6-membered nitrogen-containing saturated heterocyclyloxy, and more preferably pyrrolidinyloxy or piperidinyloxy. In the 5- or 6-membered saturated heterocyclyloxy, the heteroatom of the heterocyclyl portion is not directly bonded to the oxygen atom of the oxy portion.

The "5- or 6-membered saturated heterocyclylcarbonyl" represents carbonyl (—CO—) which is substituted with one 5- or 6-membered saturated heterocyclyl described above and may be, for example, pyrrolidinylcarbonyl, piperidinylcarbonyl, piperazinylcarbonyl, morpholinylcarbonyl or thiomorpholinylcarbonyl, preferably 5- or 6-membered nitrogen-containing saturated heterocyclylcarbonyl, and most preferably morpholinylcarbonyl. In the 5- or 6-membered nitrogen-containing saturated heterocyclylcarbonyl, preferably, the nitrogen atom of the nitrogen-containing saturated heterocyclyl portion binds to the carbonyl portion.

In the case where the compound represented by general formula (I) or a pharmacologically acceptable salt thereof of the present invention has one or more of an asymmetric center, carbon-carbon double bond, axial chirality and the like, optical isomers (including enantiomers and diastereomers), geometric isomers, tautomers and rotational isomers may exist, and these isomers and mixtures thereof are described by a single formula such as general formula (I). The present invention encompasses each of these isomers and mixtures thereof at any ratio (including racemates).

The compound represented by general formula (I) in the present invention encompasses a compound represented by general formula (I-1), (I-2), (I-3) or (I-4) or mixtures thereof (including racemates and diastereomer mixtures) and is preferably a compound represented by general formula (I-1) or (I-2) or mixtures thereof (including racemates), and more preferably a compound represented by general formula (I-1).

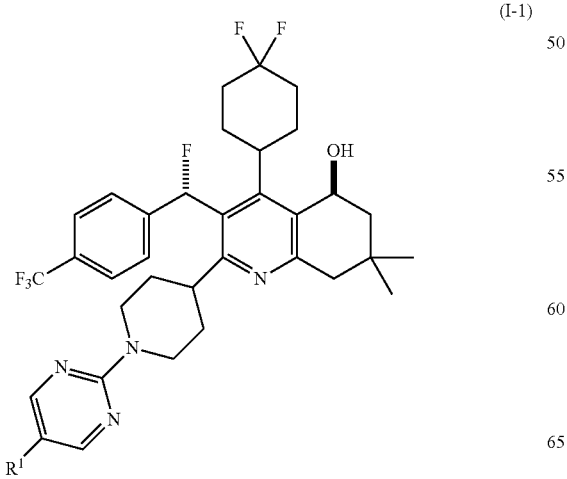

(I-1)

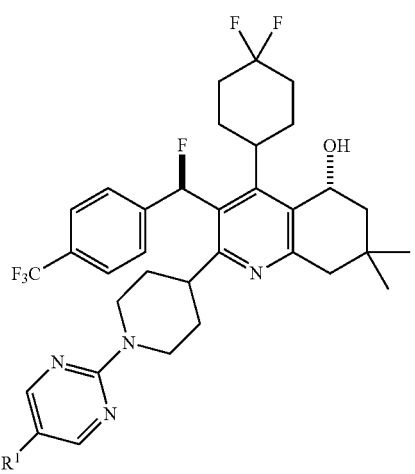

(I-2)

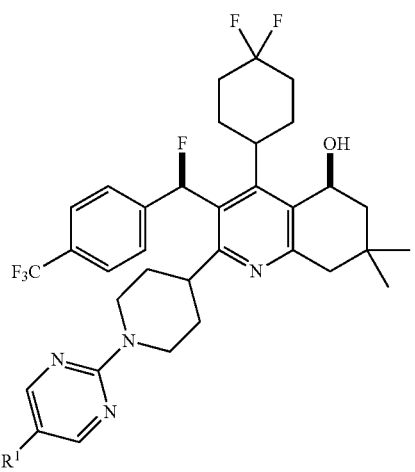

(I-3)

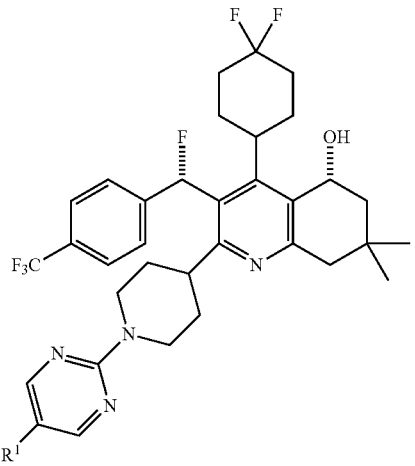

(I-4)

The compound represented by general formula (I-1) may contain a certain amount of a compound represented by general formula (I-2), (I-3) or (I-4). The "compound represented by general formula (I-1)" in the present invention encompasses "a compound represented by general formula (I-1) which contains a certain amount of a compound represented by general formula (I-2), (I-3) or (I-4)" and preferably encompasses "a compound represented by general formula (I-1) which contains a certain amount of a compound represented by general formula (I-2)", "a compound represented by general formula (I-1) which contains a certain amount of a compound represented by general formula (I-3)" and "a compound represented by general formula (I-1) which contains a certain amount of a compound represented by general formula (I-4)". In each case, the percentage content of the compound represented by general formula (I-2), (I-3) or (I-4) in the compound represented by the general formula (I-1) may be for example, 5% or less, preferably 3% or less, more preferably 1% or less, further preferably 0.5% or less, further more preferably 0.3% or less, particularly preferably 0.1% or less, and most preferably 0.05% or less. The above-described percentage content of the compound represented by the general formulae (I-2), (I-3) or (I-4) may be calculated, for example, using the peak area ratio in high performance liquid chromatography (HPLC) or the weight ratio, and preferably the peak area ratio in HPLC.

The compound represented by general formula (I) of the present invention may form an acid addition salt and the acid addition salt thereof may be, for example, a hydrochloric acid salt, a hydrobromic acid salt, a sulfuric acid salt, a nitric acid salt, a phosphoric acid salt, an acetic acid salt, an oxalic acid salt, a malonic acid salt, a fumaric acid salt, a maleic acid salt, a phthalic acid salt, a trifluoroacetic acid salt, a methanesulfonic acid salt, a benzenesulfonic acid salt, a p-toluenesulfonic acid salt, a 2,4-dimethyl benzenesulfonic acid salt, a 2,4,6-trimethyl benzenesulfonic acid salt, a 4-ethyl benzenesulfonic acid salt or a naphthalenesulfonic acid salt. The acid addition salt thereof is encompassed in the pharmacologically acceptable salt of the present invention. The compound represented by general formula (I) of the present invention may form an acid addition salt with an acid at any ratio and each of them (for example, a monohydrochloride, a dihydrochloride or the like) or a mixture thereof is encompassed in the present invention.

In the case where the compound represented by general formula (I) of the present invention has an acidic group, it may form a base addition salt and the base addition salt thereof may be, for example, a metal salt, an inorganic amine salt, an organic amine salt or an amino acid salt. The metal salt may be, for example, an alkali metal salt such as a sodium salt, a potassium salt and a lithium salt; an alkaline earth metal salt such as a calcium salt and a magnesium salt; an aluminum salt; an iron salt; a zinc salt; a copper salt; a nickel salt; or a cobalt salt. The inorganic amine salt may be, for example, an ammonium salt. The organic amine salt may be, for example, a morpholine salt, a glucosamine salt, an ethylenediamine salt, a guanidine salt, a diethylamine salt, a triethylamine salt, a dicyclohexylamine salt, a diethanolamine salt, a piperazine salt or a tetramethylammonium salt. The amino acid salt may be, for example, a glycine salt, a lysine salt, an arginine salt, an ornithine salt, a glutamic acid salt or an aspartic acid salt. The base addition salt thereof is encompassed in the pharmacologically acceptable salt of the present invention.

The acid addition salt or base addition salt of the compound represented by general formula (I) of the present invention may be prepared in the method described below, for example:

(i) dissolving the compound represented by general formula (I) of the invention in a solvent (for example, dichloromethane, acetone, ethyl acetate or the like);

(ii) adding an acid or base to the reaction solution and stirring the reaction mixture;

(iii) performing heating and cooling of the reaction mixture, distillation of the solvent, addition of a poor solvent or addition of a seed crystal of a desired salt compound as necessary; and (iv) obtaining precipitated solid by filtration.

In the case where the compound represented by general formula (I) of the present invention has a group which may form an ester group such as a hydroxy group or a carboxy group, the compound may be converted to a pharmacologically acceptable ester and this pharmacologically acceptable ester is encompassed in the present invention. The pharmacologically acceptable ester of the compound represented by general formula (I) may be a prodrug of the compound represented by general formula (I) and be decomposed in a metabolic process (for example, hydrolysis) when administered to a living body of a warm-blooded animal to produce the compound represented by general formula (I).

The group which may form an ester group with a hydroxy group may be, for example, aliphatic acyl [for example, ($C_1$-$C_{20}$ alkyl)carbonyl], aromatic acyl or alkoxycarbonyl [for example, ($C_1$-$C_6$ alkoxy)carbonyl]. The group which may form an ester group with a carboxy group may be, for example, aliphatic alkyl [for example, a $C_1$-$C_6$ alkyl], alkylcarbonyloxyalkyl [for example, ($C_1$-$C_6$ alkyl)carbonyloxy-($C_1$-$C_6$ alkyl)], cycloalkylcarbonyloxyalkyl [for example, ($C_3$-$C_8$ cycloalkyl)carbonyloxy-($C_1$-$C_6$ alkyl)], alkoxycarbonyloxyalkyl [for example, ($C_1$-$C_6$ alkoxy)carbonyloxy-($C_1$-$C_6$ alkyl)] or cycloalkyloxycarbonyloxyalkyl [for example, ($C_3$-$C_8$ cycloalkyl)oxycarbonyloxy-($C_1$-$C_6$ alkyl)].

The compound represented by general formula (I) or a pharmacologically acceptable salt thereof of the present invention may form a hydrate or a solvate. Each of these or a mixture thereof is encompassed in the present invention.

The compound represented by general formula (I) or a pharmacologically acceptable salt thereof of the present invention may form an isotopic compound in which one or more atom constituting the compound is substituted with an isotopic atom at non-natural ratio. The isotopic atom may be radioactive or non-radioactive, for example, deuterium ($^2$H; D), tritium ($^3$H; T), carbon-14 ($^{14}$C), iodine-125 ($^{125}$I) and the like. The radioactive or non-radioactive isotopic compound may be used as a medicament for treatment or prophylaxis of a disease, a reagent for research (for example, a reagent for assay), a diagnostic medicament (for example, an image diagnostic medicament) and the like. The present invention encompasses a radioactive or non-radioactive isotopic compound.

The "dyslipidemia" in the present invention encompasses hyperlipidemia. The "arteriosclerosis" encompasses (i) arteriosclerosis due to various factors such as smoking and genetics (including multiple factors); and (ii) arteriosclerosis due to a disease which may cause arteriosclerosis such as dyslipidemia, low HDL cholesterolemia, high LDL cholesterolemia, a lipid-related disease, an inflammatory disease, diabetes, obesity or hypertension, and encompasses, for example, atherosclerosis, arteriolosclerosis, arteriosclerosis obliterans and atheromatous atherosclerosis. The "arteriosclerotic heart disease" represents a heart vascular disease which develops due to arteriosclerosis as one of the causes. The "a coronary heart disease" represents a heart vascular disease which develops due to arteriosclerosis or other diseases as one of the causes and encompasses, for example, heart failure, myocardial infarction, angina pectoris, cardiac ischemia, cardiovascular disorder or angioplasty-related restenosis. The "cerebrovascular disease" encompasses, for example, stroke or cerebral infarction. The "peripheral vascular disease" encompasses, for example, diabetic vascular complications.

The compound represented by formula (I) or a pharmacologically acceptable salt thereof of the present invention may be applied, without limitation, to treatment or prophylaxis of (i) a disease caused by a decrease in the blood concentration of HDL cholesterol, (ii) a disease caused by an increase in the blood concentration of LDL, cholesterol, and (iii) a disease which can be treated or prevented by inhibition of CETP activity, besides the specific diseases as described above or described below.

In the case where the compound represented by general formula (I) or a pharmacologically acceptable salt thereof of the present invention is used as a medicament, the compound may form a pharmaceutical composition in combination with other medicaments depending on the purpose. The pharmaceutical composition may be (i) a combination of a formulation which contains the compound represented by general formula (I) or a pharmacologically acceptable salt thereof of the present invention as an active ingredient and a formulation which contains other medicaments as an active ingredient; or (ii) a single formulation (combination drug) which contains both of the compound represented by general formula (I) or a pharmacologically acceptable salt thereof of the present invention and the other medicaments as an active ingredient, and preferably the combination drug.

The pharmaceutical composition may be administered simultaneously or separately at an interval. In the case where the pharmaceutical composition is administered separately at an interval, the dosage form is not particularly limited as long as it is a dosage form in which the pharmaceutical composition may be administered separately at a different time. The time from administration of one active ingredient to administration of another active ingredient is not particularly limited and the other active ingredient is preferably administered within a time when the action of the previously administered active ingredient persists.

The other medicament which may be used in combination with the compound represented by general formula (I) or a pharmacologically acceptable salt thereof of the present invention is not particularly limited as long as it has effects depending on the purpose thereof.

The nomenclature of the compound represented by general formula (I), (I-1), (I-2), (I-3) or (I-4) (including the compounds of the Examples) in the present invention and the intermediates for synthesizing them (including the intermediates in the Examples or the compounds of the Reference Examples) may be performed according to the nomenclature which is unified with the tetrahydroquinoline structure as a central scaffold or the nomenclature of IUPAC. Although compound names according to the two nomenclatures above may be different, each compound name correctly represents a compound specified by a described chemical structural formula.

The compound represented by general formula (I) of the present invention [hereinafter, also referred to as the compound (I); the same for other formulae] can be prepared according to Method A (Methods A-1, A-2, A-3 and A-4), Method B (Methods B-1 and B-2), Method C, Method D, Method E or Method F described below.

Method A-1

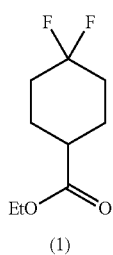
(1)

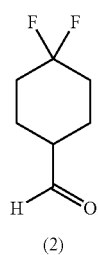
(2)

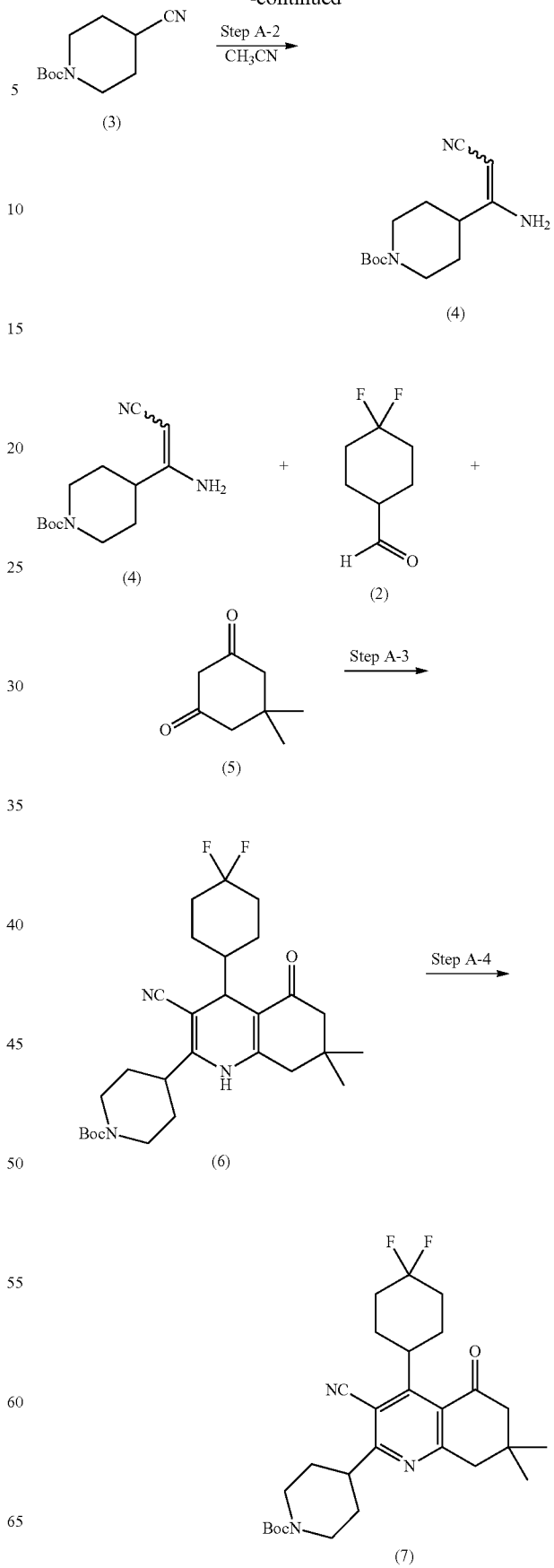

Method A-2
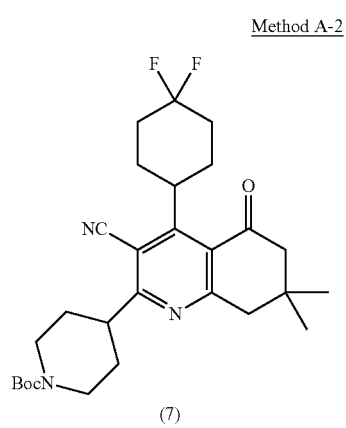
(7)
Step A-5 →
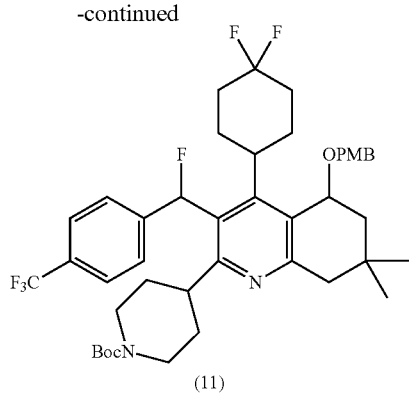
(11)
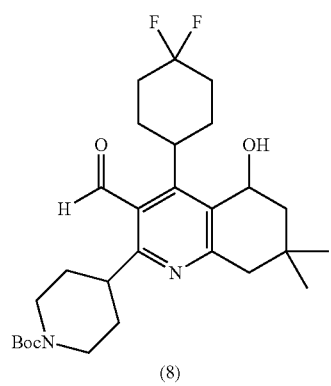 [SMILES: CC1(C)CC(=O)c2c(nc(C3CCN(C(=O)OC(C)(C)C)CC3)c(C#N)c2C2CCC(F)(F)CC2)C1]
(8)
Step A-6 →
Method A-3
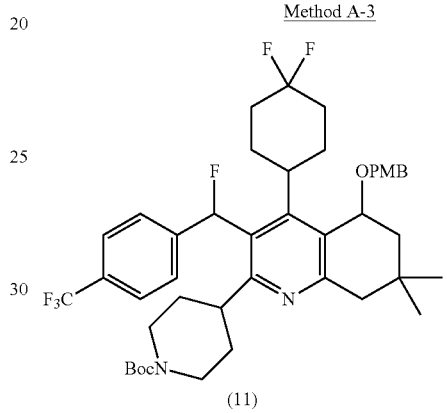
(11)
Step A-9 →
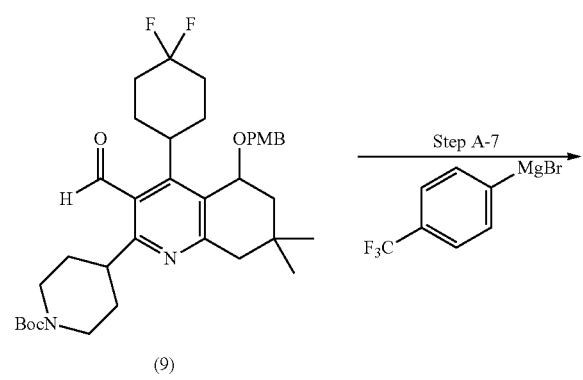
(9)
Step A-7 →
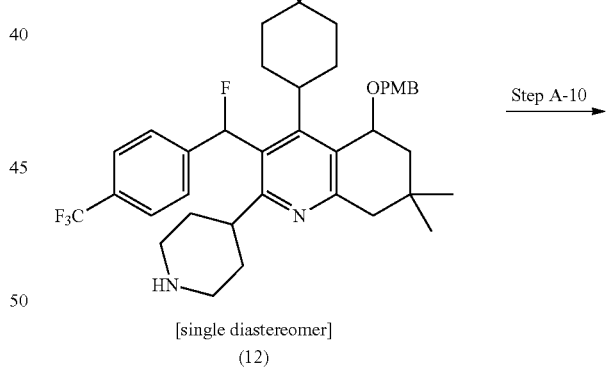
[single diastereomer]
(12)
Step A-10 →
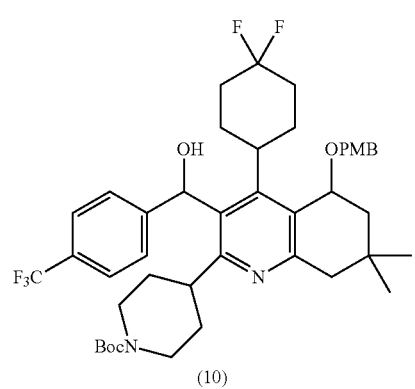
(10)
Step A-8 →
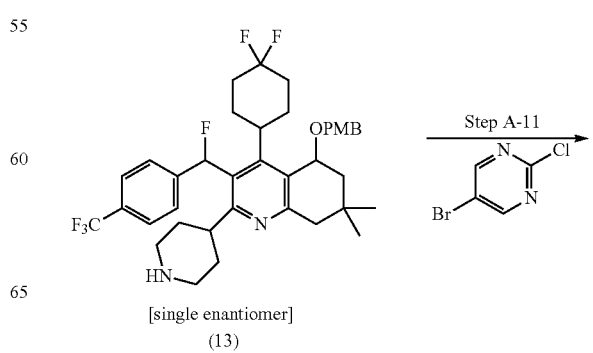
[single enantiomer]
(13)
Step A-11 →

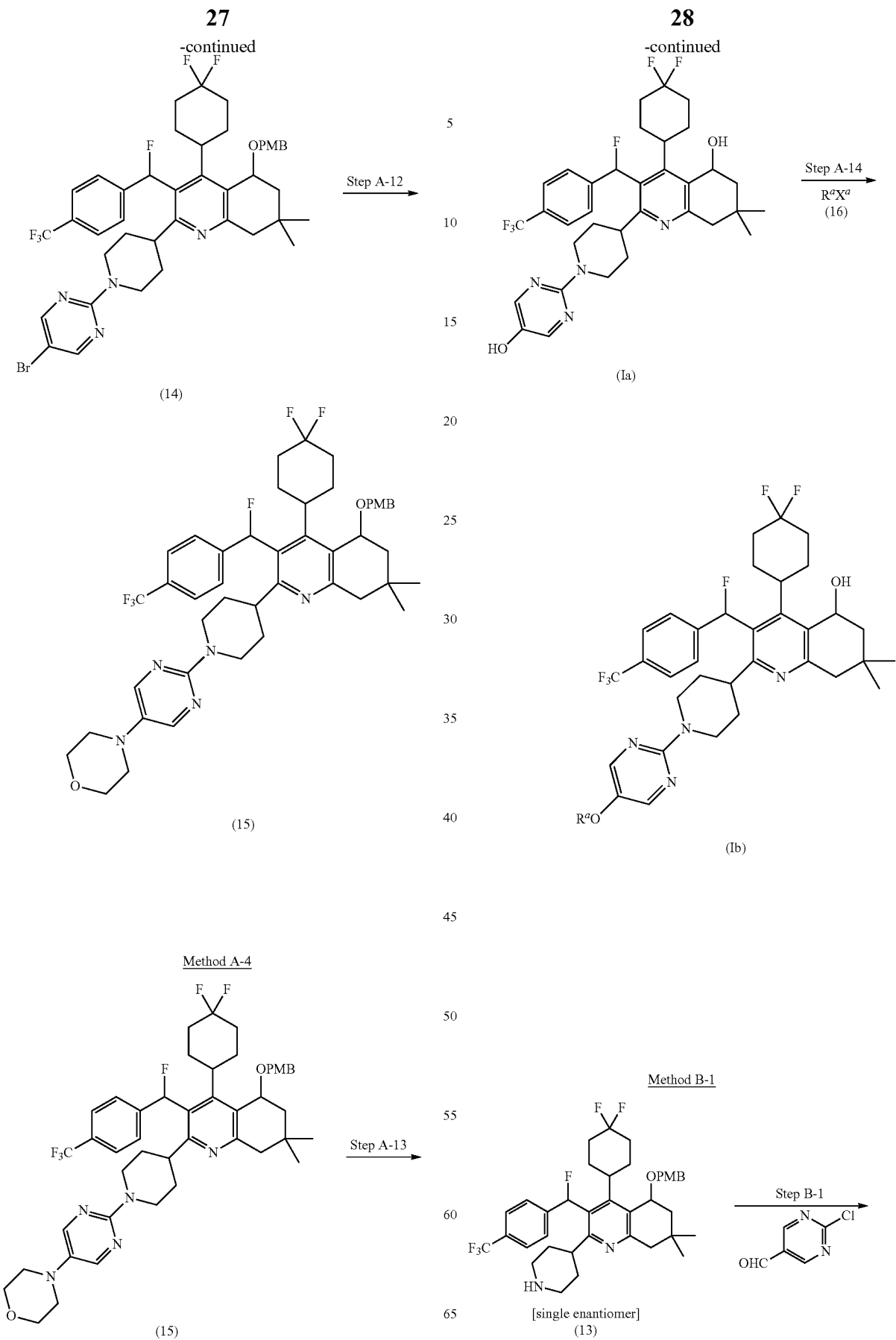

29
-continued
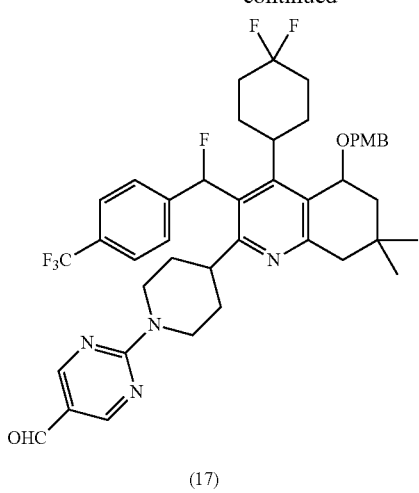
(17)
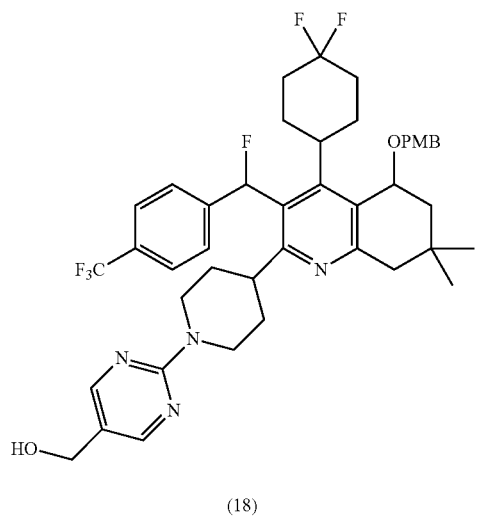
(18)
Method B-2
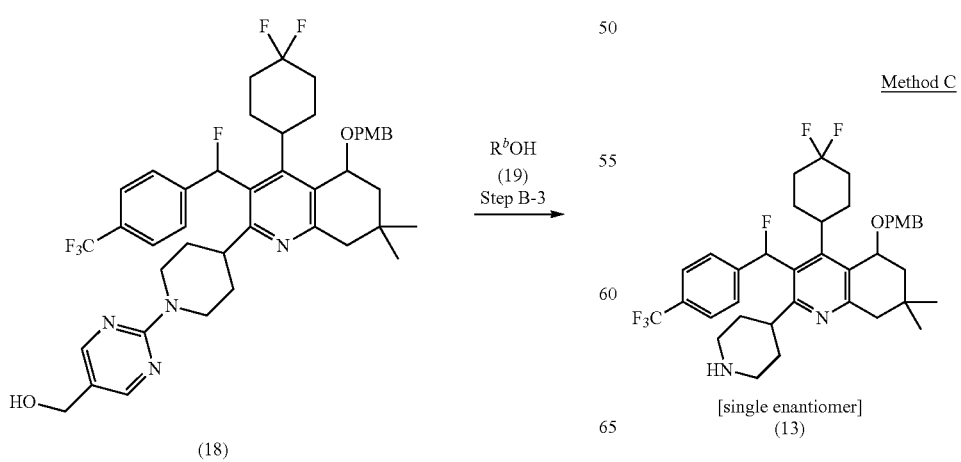
(18)
30
-continued
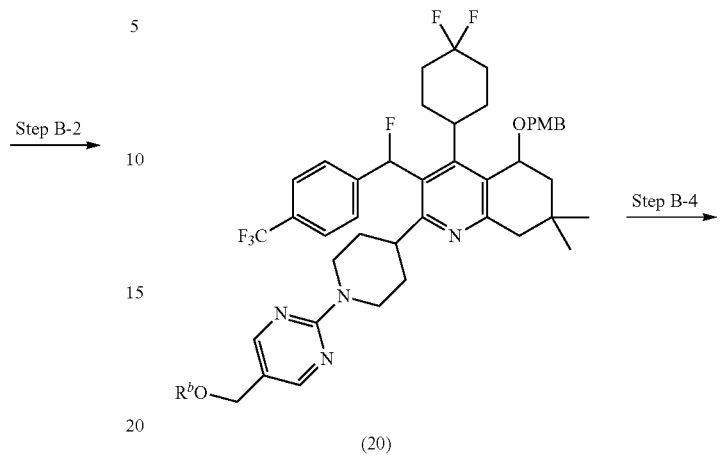
(20)
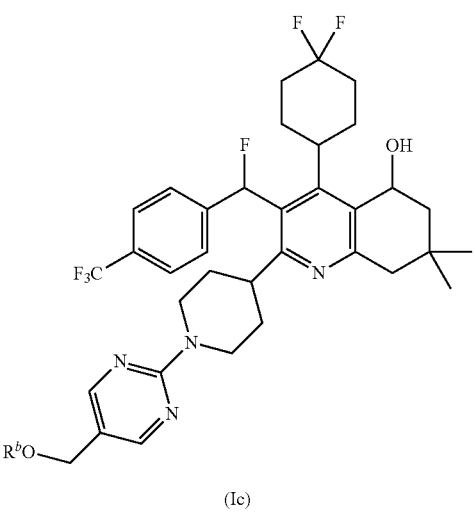
(Ic)
Method C
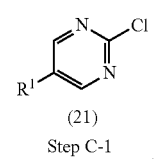

31
-continued
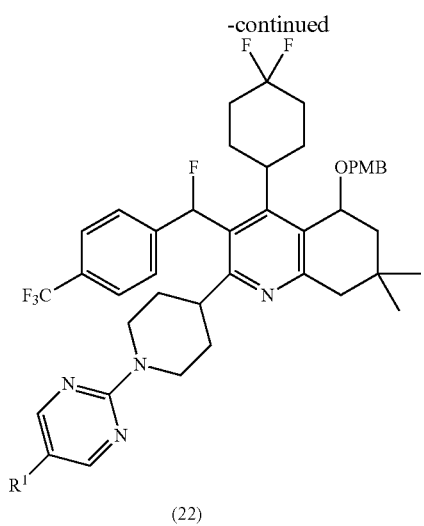
(22)
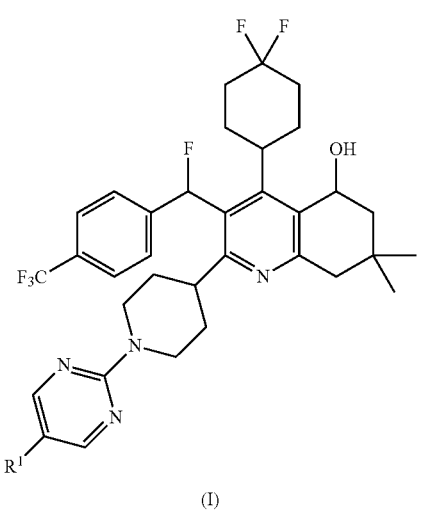
(I)
Method D
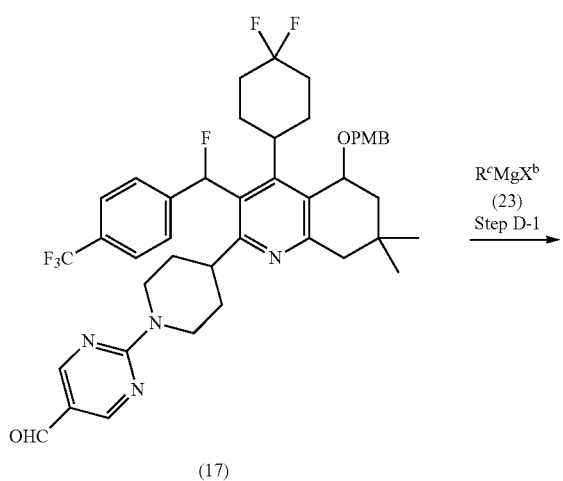
(17)
32
-continued
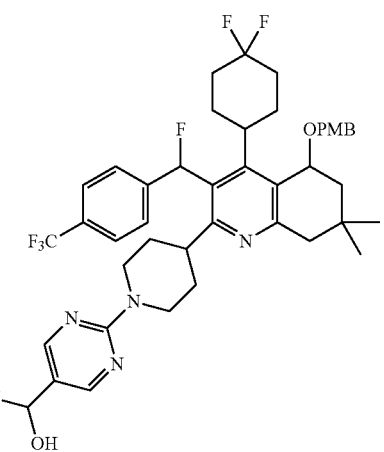
(24)
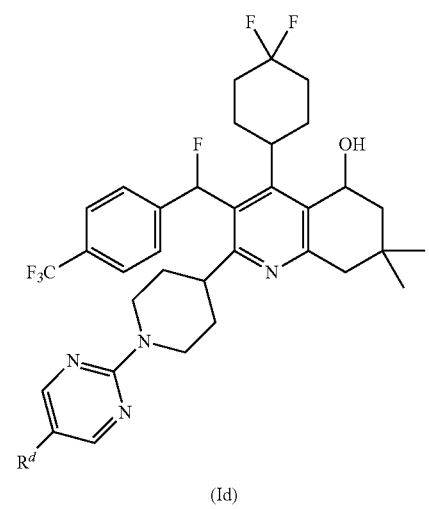
(Id)
Method E
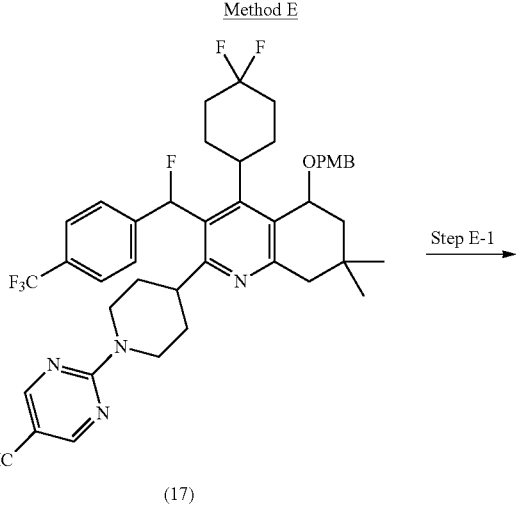
(17)

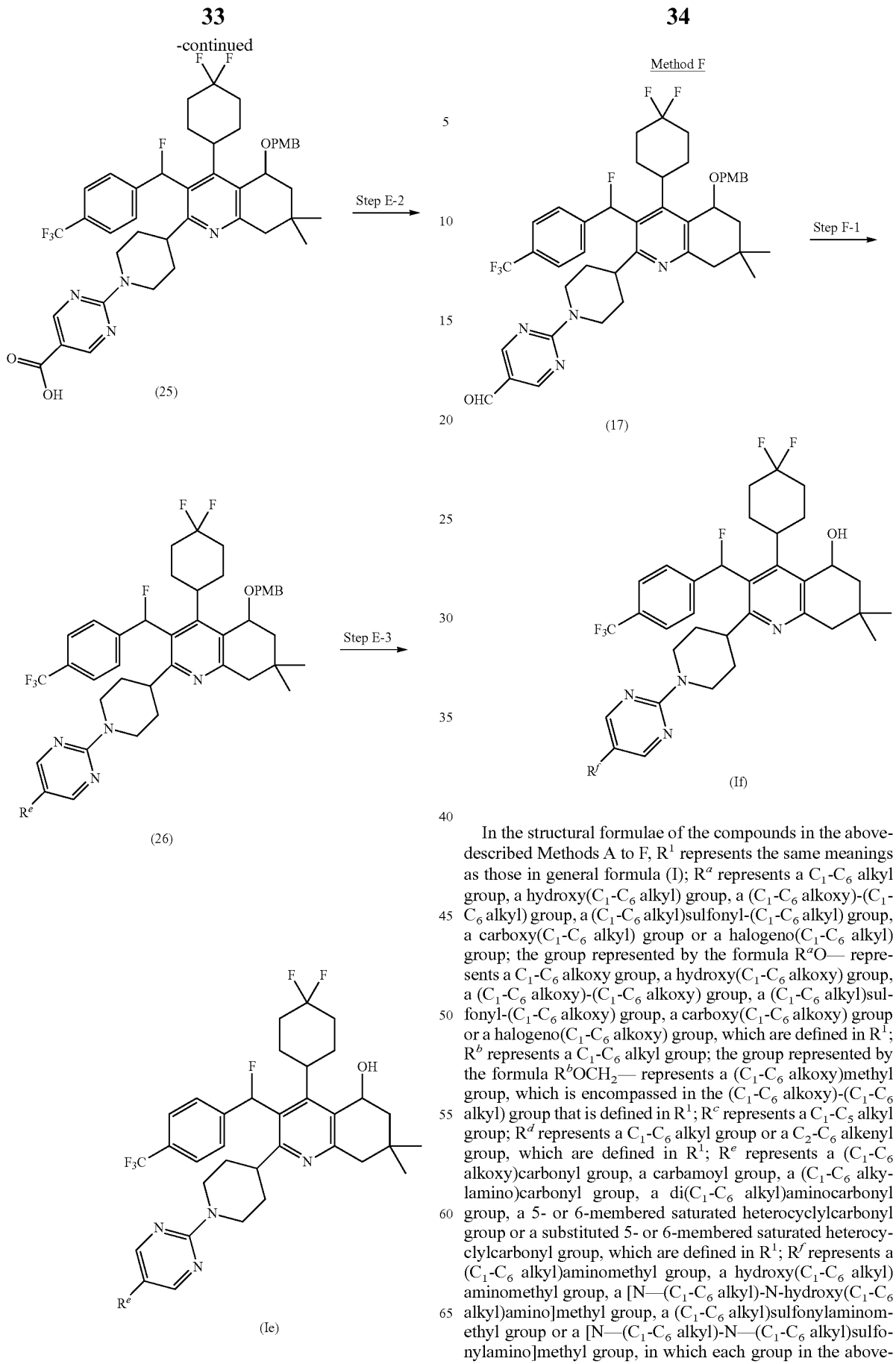

In the structural formulae of the compounds in the above-described Methods A to F, $R^1$ represents the same meanings as those in general formula (I); $R^a$ represents a $C_1$-$C_6$ alkyl group, a hydroxy($C_1$-$C_6$ alkyl) group, a ($C_1$-$C_6$ alkoxy)-($C_1$-$C_6$ alkyl) group, a ($C_1$-$C_6$ alkyl)sulfonyl-($C_1$-$C_6$ alkyl) group, a carboxy($C_1$-$C_6$ alkyl) group or a halogeno($C_1$-$C_6$ alkyl) group; the group represented by the formula $R^aO$— represents a $C_1$-$C_6$ alkoxy group, a hydroxy($C_1$-$C_6$ alkoxy) group, a ($C_1$-$C_6$ alkoxy)-($C_1$-$C_6$ alkoxy) group, a ($C_1$-$C_6$ alkyl)sulfonyl-($C_1$-$C_6$ alkoxy) group, a carboxy($C_1$-$C_6$ alkoxy) group or a halogeno($C_1$-$C_6$ alkoxy) group, which are defined in $R^1$; $R^b$ represents a $C_1$-$C_6$ alkyl group; the group represented by the formula $R^bOCH_2$— represents a ($C_1$-$C_6$ alkoxy)methyl group, which is encompassed in the ($C_1$-$C_6$ alkoxy)-($C_1$-$C_6$ alkyl) group that is defined in $R^1$; $R^c$ represents a $C_1$-$C_5$ alkyl group; $R^d$ represents a $C_1$-$C_6$ alkyl group or a $C_2$-$C_6$ alkenyl group, which are defined in $R^1$; $R^e$ represents a ($C_1$-$C_6$ alkoxy)carbonyl group, a carbamoyl group, a ($C_1$-$C_6$ alkylamino)carbonyl group, a di($C_1$-$C_6$ alkyl)aminocarbonyl group, a 5- or 6-membered saturated heterocyclylcarbonyl group or a substituted 5- or 6-membered saturated heterocyclylcarbonyl group, which are defined in $R^1$; $R^f$ represents a ($C_1$-$C_6$ alkyl)aminomethyl group, a hydroxy($C_1$-$C_6$ alkyl)aminomethyl group, a [N—($C_1$-$C_6$ alkyl)-N-hydroxy($C_1$-$C_6$ alkyl)amino]methyl group, a ($C_1$-$C_6$ alkyl)sulfonylaminomethyl group or a [N—($C_1$-$C_6$ alkyl)-N—($C_1$-$C_6$ alkyl)sulfonylamino]methyl group, in which each group in the above-described $R^f$ is encompassed in a ($C_1$-$C_6$ alkyl)amino-($C_1$-$C_6$ alkyl) group, a hydroxy($C_1$-$C_6$ alkyl)amino-($C_1$-$C_6$ alkyl) group, a [N—($C_1$-$C_6$ alkyl)-N-hydroxy($C_1$-$C_6$ alkyl)amino]-($C_1$-$C_6$ alkyl) group, a ($C_1$-$C_6$ alkyl)sulfonylamino-($C_1$-$C_6$ alkyl) group or a [N—($C_1$-$C_6$ alkyl)-N—($C_1$-$C_6$ alkyl)sulfonylamino]-($C_1$-$C_6$ alkyl) group, respectively, which are defined in $R^1$; $X^a$ represents a chloro group, a bromo group, an iodo group, a methanesulfonyloxy group, a trifluoromethanesulfonyloxy group or a p-toluenesulfonyloxy group; $X^b$ represents a chloro group, a bromo group or an iodo group; Boc represents a tert-butoxycarbonyl group; and PMB represents a p-methoxybenzyl group.

The acid used in the reaction of each step of Methods A to F described below is not particularly limited as long as it does not inhibit the reaction and is selected from the group of acids described below. The group of acids consists of organic acids such as acetic acid, propionic acid, trifluoroacetic acid or pentafluoropropionic acid; organic sulfonic acids such as p-toluenesulfonic acid, camphorsulfonic acid or trifluoromethanesulfonic acid; and inorganic acids such as hydrochloric acid, hydrobromic acid, hydroiodic acid, phosphoric acid, sulfuric acid or nitric acid.

The base used in the reaction of each step of Methods A to F described below is not particularly limited as long as it does not inhibit the reaction and is selected from the group of bases described below. The group of bases consists of alkali metal carbonates such as lithium carbonate, sodium carbonate, potassium carbonate or cesium carbonate; alkali metal hydrogencarbonate such as lithium hydrogencarbonate, sodium hydrogencarbonate or potassium hydrogencarbonate; alkali metal hydroxides such as lithium hydroxide, sodium hydroxide or potassium hydroxide; alkaline earth metal hydroxides such as calcium hydroxide or barium hydroxide; alkali metal hydrides such as lithium hydride, sodium hydride or potassium hydride; alkali metal amides such as lithium amide, sodium amide or potassium amide; alkali metal alkoxides such as lithium methoxide, sodium methoxide, sodium ethoxide, sodium tert-butoxide or potassium tert-butoxide; lithium alkyl amides such as lithium diisopropylamide; alkali metal silyl amides such as lithium bistrimethylsilyl amide or sodium bistrimethylsilyl amide; alkyl lithiums such as n-butyl lithium, sec-butyl lithium or tert-butyl lithium; and organic amines such as triethylamine, tributylamine, diisopropylethylamine, N-methylmorpholine, pyridine, picoline, lutidine, 4-(N,N-dimethylamino)pyridine, 4-pyrrolidinopyridine, quinoline, N,N-dimethylaniline, 1,5-diazabicyclo[4,3,0]non-5-ene (DBN), 1,4-diazabicyclo[2,2,2]octane (DABCO) or 1,8-diazabicyclo[5,4,0]undec-7-ene (DBU).

The solvent used in the reaction of each step of Methods A to F described below is not particularly limited as long as it does not inhibit the reaction and partially dissolves starting raw materials and for example, is selected from the group of solvents described below. The group of solvents consists of aliphatic hydrocarbons such as hexane (for example, n-hexane), pentane (for example, n-pentane), heptane (for example, n-heptane), petroleum ether or cyclohexane; aromatic hydrocarbons such as benzene, toluene, xylene or ethyl benzene; halogenated hydrocarbons such as dichloromethane, chloroform, carbon tetrachloride, dichloroethane, chlorobenzene or dichlorobenzene; ethers such as diethyl ether, diisopropyl ether, tetrahydrofuran, 2-methyltetrahydrofuran, 1,4-dioxane, dimethoxyethane or diethylene glycol dimethyl ether; ketones such as acetone, methylethyl ketone, methylisobutyl ketone or cyclohexanone; esters such as methyl acetate, ethyl acetate, propyl acetate, isopropyl acetate or butyl acetate; nitriles such as acetonitrile, propionitrile, butyronitrile or isobutyronitrile; carboxylic acids such as acetic acid or propionic acid; alcohols such as methanol, ethanol, 1-propanol, 2-propanol, 1-butanol, 2-butanol, 2-methyl-1-propanol, 2-methyl-2-propanol (tort-butanol) or 1,2-propanediol; amides such as formamide, N,N-dimethylformamide, N,N-dimethylacetamide, 1-methyl-2-pyrrolidone, dimethylimidazolone or hexamethylphosphorotriamide; sulfoxides such as dimethyl sulfoxide; sulfones such as sulfolane; water; and a mixture thereof.

In the reaction of each step of Methods A to F described below, the reaction temperature varies depending on the solvent, starting raw materials, reagents or the like, and the reaction time varies depending on the solvent, starting raw materials, reagents, reaction temperature or the like.

In the reaction of each step of Methods A to F described below, the desired compound of each step may be isolated from the reaction mixture after the reaction completion according to a method which is well known in the field of organic chemistry. The desired compound is obtained, for example, by (i) filtering off insoluble materials such as a catalyst as necessary, (ii) adding water and a solvent which is immiscible with water (for example, dichloromethane, diethyl ether, ethyl acetate or the like) to the reaction mixture and extracting the desired compound, (iii) washing the organic layer with water and drying it with a drying agent such as anhydrous magnesium sulfate, and (iv) distilling off the solvent. The obtained desired compound may be further purified by a method which is well known in the field of organic chemistry (for example, recrystallization, reprecipitation, silica gel column chromatography or the like) as necessary. In addition, the desired compound of each process may be also used in the next reaction as it is without purification.

In the case where the compound as a starting raw material in the reaction of each step of Methods A to F described below has a group which inhibits the desired reactions such as an amino group, a hydroxyl group and a carboxyl group, introduction of a protective group for such groups and removal of the introduced protective group may be performed suitably as necessary. Such a protective group is not particularly limited as long as it is a protective group usually used and may be, for example, a protective group described in T. W. Greene, P. G. Wuts, Greene's Protective Groups in Organic Synthesis, Fourth Edition, 2007, John Wiley & Sons, Inc. and the like. The introduction reaction of such a protective group and the removal reaction of the protective group may be performed according to a method which is well known in the field of organic chemistry (for example, a method as described in the above-described literature).

In the reaction of each step of Methods A to F described below (Steps A-5 to A-14 in Method A), isolation of a single diastereomer (a racemate) from a mixture of two kinds of diastereomers (a mixture of four kinds of enantiomers) may be performed by column chromatography, a crystallization method or the like and isolation of a single enantiomer from a single diastereomer (a racemate) may be performed by optically active column chromatography, a fractional crystallization method using an optically active compound (for example, an optically active carboxylic acid compound or an optically active amine compound) or the like. Isolation of a single enantiomer from a mixture of two kinds of diastereomers (a mixture of four kinds of enantiomers) may be performed by optically active column chromatography in any step.

In the examples shown in Methods A to F described below, isolation of a single diastereomer (a racemate) from a mixture of two kinds of diastereomers is performed in Step A-7 and isolation of a single enantiomer from a single diastereomer (a racemate) is performed in Step A-10. The compounds (10), (11) and (12) are the single diastereomers (racemates) described in Reference Examples 7, 8 and 9, respectively and the compound (13) is the single enantiomer described in Reference Example 10. The compounds (14), (15), (17), (18), (20), (22), (24), (25), (26), (Ia), (Ib), (Ic), (Id), (Ie), (If) and (I) which are prepared from the compound (13) are single enantiomers.

Isolation of a single diastereomer (a racemate) and isolation of a single enantiomer are not limited to the above-described examples and may be performed in any process (the same or different process) of Methods A to F, respectively. For example, in the case where isolation of a single diastereomer (a racemate) is not performed in Step A-7, Steps A-8 to A-9, Steps A-11 to A-14, Steps B-1 to B-4, Steps C-1 to C-2, Steps D-1 to D-2, Steps E-1 to E-3 or Steps F-1 may be performed respectively using a mixture of two kinds of diastereomers as a raw material. In the case where isolation of a single diastereomer (a racemate) is performed in any one of the above-described steps, the steps following those may be performed respectively using the single diastereomer (a racemate) as a raw material. In the case where isolation of a single enantiomer is further performed in any one of the above-described steps, the process following those may be performed respectively using the single enantiomer as a raw material and the compound (I) [preferably the compound (I-1)] as a single enantiomer is obtained. In the case where only isolation of a single diastereomer (a racemate) in any one of the above-described steps is performed, the compound (I) as a single diastereomer (a racemate) is obtained and the compound (I) [preferably, the compound (I-1)] as a single enantiomer is obtained by further performing isolation of a single enantiomer. In the case where isolation of a single diastereomer (a racemate) and isolation of a single enantiomer are not performed in any one of the above-described steps, the compound (I) as a mixture of two kinds of diastereomers is obtained and the compound (I) [preferably, the compound (I-1)] as a single enantiomer is obtained by performing isolation of a single diastereomer (a racemate) and isolation of a single enantiomer.

Hereinafter, the reaction of each step of Methods A to F is described.

(Method A)

Method A is a method of preparing the compounds (Ia) and (Ib) which are encompassed in the compound (I).

(Step A-1)

Step A-1 is a step of preparing the compound (2) by reducing the compound (1). The compound (1) is known.

The reduction reagent to be used is not limited as long as it may be used in the reduction reaction of an alkoxycarbonyl group to a formyl group and is preferably diisobutyl aluminum hydride.

The solvent to be used is preferably an aromatic hydrocarbon, and more preferably toluene.

The reaction temperature is preferably −100° C. to 0° C.

The reaction time is preferably 30 minutes to 12 hours.

(Step A-2)

Step A-2 is a step of preparing the compound (4) by reacting the compound (3) with acetonitrile in the presence of a base. The compound (3) is known.

A protective group which is well known in the field of organic chemistry may be used as the protective group of the amino group in the compound (3) instead of the tert-butoxycarbonyl group (for example, T. W. Greene, P. G. Wuts, Greene's Protective Groups in Organic Synthesis, Fourth Edition, 2007, John Wiley & Sons, Inc.).

The base to be used is preferably a lithium alkyl amide, and more preferably lithium diisopropylamide.

The solvent to be used is preferably an aliphatic hydrocarbon, aromatic hydrocarbon, ether or a mixture thereof, and more preferably n-heptane, ethylbenzene, tetrahydrofuran or a mixture thereof.

The reaction temperature is preferably −78° C. to 50° C.

The reaction time is preferably 30 minutes to 48 hours.

(Step A-3)

Step A-3 is a step of preparing the compound (6) by reacting the compounds (2) and (4) and then reacting the compound (5). The compound (5) is known. An excess amount of the compound (5) may be used in Step A-3.

The solvent to be used is preferably an aromatic hydrocarbon, and more preferably toluene.

The reaction temperature is preferably 50° C. to 150° C.

The reaction time is preferably 30 minutes to 48 hours.

(Step A-4)

Step A-4 is a step of preparing the compound (7) by oxidizing the compound (6).

The oxidation reagent to be used is not limited as long as it may be used in the oxidation reaction of a dihydropyridyl group to a pyridyl group, and is preferably 2,3-dichloro-5,6-dicyano-p-benzoquinone (DDQ).

The solvent to be used is preferably a halogenated hydrocarbon, and more preferably dichloromethane.

The reaction temperature is preferably 0° C. to 50° C.

The reaction time is preferably 30 minutes to 12 hours.

(Step A-5)

Step A-5 is a step of preparing the compound (8) by reducing the compound (7).

The reduction reagent to be used is not limited as long as it may be used in the reduction reaction of a cyano group to a formyl group and is preferably diisobutyl aluminum hydride.

The solvent to be used is preferably an aromatic hydrocarbon, and more preferably toluene.

The reaction temperature is preferably −100° C. to 0° C.

The reaction time is preferably 30 minutes to 12 hours.

(Step A-6)

Step A-6 is a step of preparing the compound (9) by reacting the compound (8) with p-methoxybenzyl bromide in the presence of a base.

The base to be used is not limited as long as it may be used in the alkylation reaction of a hydroxy group and is preferably an alkali metal hydride, and more preferably sodium hydride.

The solvent to be used is preferably an amide, and more preferably N,N-dimethylformamide.

The reaction temperature is preferably −50° C. to 50° C.

The reaction time is preferably 30 minutes to 12 hours.

In Step A-6, a protective group which is well known in the field of organic chemistry may be used as the protective group of the hydroxy group instead of the p-methoxybenzyl group (for example, T. W. Greene, P. G. Wuts, Greene's Protective Groups in Organic Synthesis, Fourth Edition, 2007, John Wiley & Sons, Inc.).

(Step A-7)

Step A-7 is a step of preparing the compound (10) by reacting the compound (9) with 4-trifluoromethylphenyl magnesium bromide. 4-Trifluoromethylphenyl magnesium bromide can be prepared by a method which is well known in the field of organic chemistry from 4-trifluoromethylphenyl bromide and magnesium.

The solvent to be used is preferably an ether, and more preferably tetrahydrofuran.

The reaction temperature is preferably −20° C. to 50° C.

The reaction time is preferably 30 minutes to 12 hours.

In Step A-7, the compound (10) has two asymmetric carbon atoms (the carbon atoms to which a hydroxy group or a p-methoxybenzyloxy group is bonded) and may be obtained as a mixture of stereoisomers (a mixture of four kinds of optical isomers, namely, a mixture of diastereomers). The diastereomer mixture obtained in Step A-7 may be isolated into single diastereomer compounds depending on the properties of the mixture. This isolation may be performed by a method which is well known in the field of organic chemistry (for example, resolution by column chromatography or fractional crystallization of a diastereomer mixture). Each of the isolated diastereomer compounds (a mixture of enantiomers) may be isolated into single enantiomer compounds depending on the properties of the compound. This isolation may be performed by a method which is well known in the field of organic chemistry (for example, optical resolution by column chromatography or fractional crystallization with formation of diastereomer salt). In Step A-7, this is the same in the case of the compound which is obtained using a protective group other than the p-methoxybenzyloxy group and the tert-butoxycarbonyl group as the two protective groups in the compound (9). This is the same in the case of the compound (11) which is obtained in Step A-8.

(Step A-8)

Step A-8 is a step of preparing the compound (11) by reacting the compound (10) with a fluorination reagent.

The fluorination reagent to be used is not limited as long as it may be used in the fluorination reaction of a hydroxy group and is preferably bis(methoxyethyl)aminosulfur trifluoride [Deoxo-Fluor (trade name)].

The solvent to be used is preferably a halogenated hydrocarbon, and more preferably dichloromethane.

The reaction temperature is preferably −100° C. to 0° C.

The reaction time is preferably 30 minutes to 24 hours.

(Step A-9)

Step A-9 is a step of preparing the compound (12) by reacting the compound (11) with zinc bromide.

The solvent to be used is preferably a halogenated hydrocarbon, and more preferably dichloromethane.

The reaction temperature is preferably 0° C. to 50° C.

The reaction time is preferably 1 hour to 5 days.

The diastereomer mixture obtained in Step A-9 may be isolated into single diastereomer compounds and the compound (12) may be obtained as a single diastereomer compound.

The removal reaction of the tert-butoxycarbonyl group in Step A-9 may be also performed by a method which is well known in the field of organic chemistry (for example, T. W. Greene, P. G. Wuts, Greene's Protective Groups in Organic Synthesis, Fourth Edition, 2007, John Wiley & Sons, Inc.).

(Step A-10)

Step A-10 is a step of obtaining the compound (13) as a single enantiomer by subjecting the compound (12) to optical resolution by optically active column chromatography.

The optically active column and the resolution conditions to be used are not limited as long as they can achieve optical resolution of the compound (12) and are preferably those described in Reference Example 10.

(Step A-11)

Step A-11 is a step of preparing the compound (14) by reacting the compound (13) with 5-bromo-2-chloropyrimidine in the presence of a base.

The base to be used is preferably an organic amine, and more preferably diisopropylethylamine or 1,8-diazabicyclo [5,4,0]undeca-7-ene (DBU).

The solvent to be used is preferably an ether or amide, and more preferably 1,4-dioxane.

The reaction temperature is preferably 20° C. to 150° C.

The reaction time is preferably 30 minutes to 12 hours.

(Step A-12)

Step A-12 is a step of preparing the compound (15) by reacting the compound (14) with morpholine in the presence of a palladium catalyst, a phosphorus reagent and a base.

The palladium catalyst to be used is not limited as long as it may be used in the amination reaction on the aromatic ring and may be, for example, a palladium catalyst described in J. Tsuji, Palladium Reagents and Catalysis: New Perspectives for the 21st Century, 2004, John Wiley & Sons, Inc., and the like. The palladium catalyst to be used is preferably tetrakis (triphenyl phosphine) palladium (0), tris(dibenzylidene acetone)dipalladium (0), palladium chloride (II), palladium acetate (II) or palladium dichlorobis(triphenyl phosphine) (II), and more preferably palladium acetate (11).

The phosphorus reagent to be used is not limited as long as it may be used in the amination reaction on the aromatic ring and is preferably 2-(di-tert-butylphosphino)biphenyl, 2-(dicyclohexylphosphino)biphenyl, 2-dicyclohexylphosphino-2',4',6'-triisopropylbiphenyl, 5-(di-tert-butylphosphino)-1', 3',5'-triphenyl-1'H-[1,4']bipyrazole, cyclohexyl phosphine, 1,2,3,4,5-pentaphenyl-1'-(di-tert-butylphosphino)ferrocene or 2-(diphenylphosphino)-2'-(N,N-dimethylamino)biphenyl, and more preferably 2-dicyclohexylphosphino-2',4',6'-triisopropylbiphenyl.

The base to be used is preferably an alkali metal alkoxide, and more preferably sodium tert-butoxide.

The solvent to be used is preferably an aromatic hydrocarbon, alcohol or a mixture thereof, and more preferably toluene, 2-methyl-2-propanol or a mixture thereof.

The reaction temperature is preferably 20° C. to 150° C.

The reaction time is preferably 30 minutes to 12 hours.

In Step A-12, the amination reaction may be performed using an optionally substituted 5- or 6-membered nitrogen-containing saturated cyclic amine other than morpholine instead of morpholine. The palladium catalyst used in this amination reaction is preferably tris(dibenzylidene acetone) dipalladium (0) and stirring under microwave irradiation is preferable. A compound in which $R^1$ in the compound (I) is an optionally substituted 5- or 6-membered nitrogen-containing saturated heterocyclyl group and the nitrogen atom binds to the 5-position of the pyrimidine may be prepared by removing the p-methoxybenzyl group in the compound obtained in the above-described reaction according to a method similar to that of Step B-4.

In Step A-12, the carbon-carbon coupling reaction may be performed using a compound represented by a formula $R^gB$ $(OH)_2$ wherein $R^g$ represents a $C_3$-$C_8$ cycloalkyl group, a $C_3$-$C_8$ cycloalkenyl group, a phenyl group, a substituted phenyl group, a 5- or 6-membered aromatic heterocyclyl group or a substituted 5- or 6-membered aromatic heterocyclyl group, which are defined in $R^1$, or boronic acid ester thereof instead of morpholine. The palladium catalyst used in this carbon-carbon coupling reaction is preferably palladium acetate (II). A compound in which $R^1$ is $R^g$ in the compound (I) can be prepared by removing the p-methoxybenzyl group in the compound obtained in the above-described reaction according to a method similar to that of Step B-4.

(Step A-13)

Step A-13 is a step of preparing the compound (Ia) by treating the compound (15) with an acid.

The acid to be used is preferably an inorganic acid, and more preferably hydrochloric acid.

The solvent to be used is preferably an ether, alcohol or a mixture thereof, and more preferably 1,4-dioxane, methanol or a mixture thereof.

The reaction temperature is preferably 20° C. to 150° C.

The reaction time is preferably 30 minutes to 6 hours.

(Step A-14)

Step A-14 is a step of preparing the compound (Ib) by reacting the compound (Ia) with the compound (16) in the presence of a base.

The base to be used is preferably an alkali metal carbonate, and more preferably cesium carbonate.

The solvent to be used is preferably an ether or amide, and more preferably tetrahydrofuran, N,N-dimethylformamide or 1-methyl-2-pyrrolidone.

The reaction temperature is preferably 0° C. to 100° C.

The reaction time is preferably 30 minutes to 50 hours.

(Method B)

Method B is a method of preparing the compound (Ic) which is encompassed in the compound (I).

(Step B-1)

Step B-1 is a step of preparing the compound (17) by reacting the compound (13) with 2-chloro-5-formyl pyrimidine in the presence of a base.

The base to be used is preferably an organic amine, and more preferably 1,8-diazabicyclo[5,4,0]undec-7-ene (DBU).

The solvent to be used is preferably an amide, and more preferably 1-methyl-2-pyrrolidone.

The reaction temperature is preferably 0° C. to 100° C.

The reaction time is preferably 30 minutes to 12 hours.

(Step B-2)

Step B-2 is a step of preparing the compound (18) by reducing the compound (17).

The reduction reagent to be used is not limited as long as it may be used in the reduction reaction of a formyl group to a hydroxy group and is preferably an alkali metal borohydride such as sodium borohydride, sodium triacetoxyborohydride, sodium cyanoborohydride and lithium borohydride, and more preferably sodium borohydride.

The solvent to be used is preferably an ether, alcohol or a mixture thereof, and more preferably tetrahydrofuran, ethanol or a mixture thereof.

The reaction temperature is preferably −20° C. to 50° C.

The reaction time is preferably 10 minutes to 6 hours.

(Step B-3)

Step B-3 is a step of preparing the compound (20) by reacting the compound (18) with methanesulfonyl chloride in the presence of a base followed by the compound (19). The compound (19) is known.

The base to be used is preferably an organic amine, and more preferably diisopropylethylamine.

The solvent to be used is preferably a halogenated hydrocarbon, and more preferably dichloromethane.

The reaction temperature is preferably 0° C. to 100° C.

The reaction time is preferably 10 minutes to 6 hours.

(Step B-4)

Step B-4 is a step of preparing the compound (Ic) by removing the p-methoxybenzyl group in the compound (20) in the presence of anisole and an acid.

The acid to be used is preferably an organic acid, and more preferably trifluoroacetic acid.

The solvent to be used is preferably a halogenated hydrocarbon, and more preferably dichloromethane.

The reaction temperature is preferably 0° C. to 100° C.

The reaction time is preferably 30 minutes to 48 hours.

The removal reaction of the p-methoxybenzyl group in Step B-4 may be also performed by a method which is well known in the field of organic chemistry (for example, T. W. Greene, P. G. Wuts, Greene's Protective Groups in Organic Synthesis, Fourth Edition, 2007, John Wiley & Sons, Inc.).

(Method C)

Method C is a method of preparing the compound (1).

(Step C-1)

Step C-1 is a step of preparing the compound (22) by reacting the compound (13) with the compound (21) in the presence of a base. The compound (21) is known, may be easily prepared from a known compound or may be prepared according to the Reference Examples. Step C-1 may be also performed using a palladium catalyst, a phosphorus reagent and a base, similar to those of Step A-12.

The base to be used is preferably an organic amine, and more preferably diisopropylethylamine, 1,8-diazabicyclo[5,4,0]undec-7-ene (DBU) or a mixture thereof.

The solvent to be used is preferably an ether, alcohol or amide, and more preferably 1,4-dioxane, 2-propanol, 2-methyl-2-propanol, N,N-dimethylformamide or 1-methyl-2-pyrrolidone.

The reaction temperature is preferably 20 to 160° C.

The reaction time is preferably 30 minutes to 12 hours.

Step C-1 may be performed under microwave irradiation.

(Step C-2)

Step C-2 is a step of preparing the compound (1) by removing the p-methoxybenzyl group in the compound (22) in the presence of anisole and an acid.

Step C-2 may be performed according to a method similar to that of Step B-4.

(Method D)

Method D is a method of preparing the compound (Id) which is encompassed in the compound (I).

(Step D-1)

Step D-1 is a step of preparing the compound (24) by reacting the compound (17) with the compound (23). The compound (23) is known or may be easily prepared from a known compound.

The solvent to be used is preferably an ether, and more preferably tetrahydrofuran.

The reaction temperature is preferably 0° C. to 60° C.

The reaction time is preferably 10 minutes to 6 hours.

(Step D-2)

Step D-2 consists of (Step D-2A) Step of removing the p-methoxybenzyl group in the compound (24) in the presence of an acid; and (Step D-2B) Step of preparing the compound (Id) by subjecting the compound obtained in Step D-2A to a dehydration reaction or reduction reaction.

The removal reaction of the p-methoxybenzyl group and the dehydration reaction may proceed simultaneously. The acid used in the reaction is preferably an inorganic acid or organic acid, and more preferably hydrochloric acid or trifluoroacetic acid.

The solvent to be used is preferably a halogenated hydrocarbon or ether, and more preferably dichloromethane or 1,4-dioxane.

The reaction temperature is preferably 0° C. to 110° C.

The reaction time is preferably 30 minutes to 48 hours.

The reduction reagent used in the reduction reaction is not limited as long as it may be used in the reduction reaction of a hydroxyl group and is preferably triethylsilane.

The removal reaction of the p-methoxybenzyl group in Step D-2 may also be performed by a method which is well known in the field of organic chemistry (for example, T. W. Greene, P. G. Wuts, Greene's Protective Groups in Organic Synthesis, Fourth Edition, 2007, John Wiley & Sons, Inc.).

(Method E)

Method E is a method of preparing the compound (Ie) which is encompassed in the compound (I).

(Step E-1)

Step E-1 is a step of preparing the compound (25) by oxidizing the compound (17).

The oxidation reagent to be used is not limited as long as it may be used in the oxidation reaction of a formyl group to a carboxyl group and is preferably potassium permanganate, sodium chlorite, sodium hypochlorite, hydrogen peroxide, chromic acid, meta-chloroperbenzoic acid, silver nitrate or pyridinium dichromate, and more preferably sodium chlorite. In the case where sodium chlorite is used as the oxidation reagent, 2-methyl-2-butene and sodium dihydrogen phosphate are preferably used in combination.

The solvent to be used is preferably an ether, alcohol, water or a mixture thereof, and more preferably tetrahydrofuran, tert-butanol, water or a mixture thereof.

The reaction temperature is preferably 0° C. to 70° C.

The reaction time is preferably 30 minutes to 6 hours.

(Step E-2)

Step E-2 is a step of preparing the compound (26) by reacting the compound (25) with an alcohol compound or an amine compound in the presence of a condensing reagent.

The condensing reagent to be used is not limited as long as it may be used in the condensing reaction of a carboxy group and a hydroxy group or an amino group and is preferably 1,1'-carbonyldiimidazole, 1-ethyl-3-(3-dimethylaminopropyl)carbodiimide or a combination thereof with 1-hydroxybenzotriazole.

A base may be used in combination with the above-described condensing reagent. The base to be used is preferably an organic amine, and more preferably triethylamine.

The solvent to be used is preferably an ether, nitrile, amide or a mixture thereof, and more preferably tetrahydrofuran, acetonitrile, N,N-dimethyl acetamide or a mixture thereof.

The reaction temperature is preferably 0° C. to 120° C.

The reaction time is preferably 30 minutes to 6 hours.

(Step E-3)

Step E-3 is a step of preparing the compound (Ie) by removing the p-methoxybenzyl group in the compound (26) in the presence of anisole and an acid.

Step E-3 may be performed according to a method similar to that of Step B-4.

(Method F)

Method F is a method of preparing the compound (11) which is encompassed in the compound (I).

(Step F-1)

Step F-1 consists of (Step F-1A) Step of removing the p-methoxybenzyl group in the compound (17) in the presence of anisole and an acid; and (Step F-1B) Step of preparing the compound (If) by reacting the compound obtained in Step F-1A with an amine compound in the presence of a reduction reagent.

(Step F-1A)

Step F-1A may be performed according to a method similar to that of Step B-4.

(Step F-1B)

The reduction reagent to be used is not limited as long as it may be used in a reductive amination reaction of a formyl group and is preferably sodium triacetoxyborohydride or sodium borohydride.

The solvent to be used is preferably an ether, alcohol or a mixture thereof, and more preferably tetrahydrofuran, methanol or a mixture thereof.

The reaction temperature is preferably 0° C. to 60° C.

The reaction time is preferably 30 minutes to 14 hours.

A compound in which $R^1$ is a [N—($C_1$-$C_6$ alkyl)-N—($C_1$-$C_6$ alkyl)sulfonylamino]methyl group in the compound (I) may be prepared by reacting the compound obtained in Step F-1B with ($C_1$-$C_6$ alkyl)sulfonyl chloride in the presence of a base.

When the compound represented by general formula (I) or a pharmacologically acceptable salt thereof of the present invention is used as a medicament, it may be administered (i) as a bulk powder per se; (ii) orally as a formulation such as a tablet, a capsule, granules, a powder or a syrup, which is prepared by mixing with a suitable pharmacologically acceptable excipient, diluent or the like; or (iii) parenterally as a formulation such as an injection or a suppository, which is prepared as described above. It is preferably orally administered.

These formulations are prepared by well-known methods using additives such as an excipient, a binder, a disintegrator, a lubricant, an emulsifier, a stabilizer, a flavoring agent, a diluent or a solvent for injection.

The excipient may be, for example, an organic excipient or an inorganic excipient. The organic excipient may be, for example, a sugar derivative such as lactose, sucrose, glucose, mannitol or sorbitol; a starch derivative such as corn starch; a cellulose derivative such as crystalline cellulose; gum arabic; dextran; pullulan; or the like. The inorganic excipient may be, for example, a silicic acid salt derivative such as light anhydrous silicic acid, synthesized aluminum silicate; a sulfuric acid salt such as calcium sulfate; or the like.

The binder may be, for example, the compounds shown in the above-described excipient; gelatin; polyvinyl pyrrolidone; polyethylene glycol; or the like.

The disintegrator may be, for example, the compounds shown in the above-described excipient; a chemically modified starch or cellulose derivative such as sodium croscarmellose or sodium carboxymethyl starch; cross-linking polyvinyl pyrrolidone; or the like.

The lubricant may be, for example, talc; colloidal silica; waxes such as beeswax or sperm whale; glycol; D, L-leucine; a sulfuric acid salt such as sodium sulfate; the starch derivatives in the above-described excipient; or the like.

The emulsifier may be, for example, a colloidal clay such as bentonite or begum; an anionic surfactant such as lauryl sodium sulfate; a cationic surfactant such as benzalkonium chloride; a non-ionic surfactant such as polyoxyethylene alkyl ether; or the like.

The stabilizer may be, for example, a parahydroxybenzoic acid ester such as methyl paraben; an alcohol such as chlorobutanol; benzalkonium chloride; phenol; thimerosal; or the like.

The flavoring agent may be, for example, a sweetener, an acidulant, a perfume or the like, which are usually used.

The diluent may be, for example, water, ethanol, propylene glycol or the like.

The solvent for injection may be, for example, water, ethanol, glycerin or the like.

The dosage amount of the compound represented by general formula (I) or a pharmacologically acceptable salt thereof which is an active ingredient of the invention varies depending on symptoms, age and the like of a patient. The compound represented by general formula (I) or a pharmacologically acceptable salt thereof may be administered depending on symptoms, 1 to 6 times per one day for an adult human, at 0.01 mg/kg (preferably 0.05 mg/kg) as lower limit and at 500 mg/kg (preferably 50 mg/kg) as upper limit per once when orally administered, or at 0.001 mg/kg (preferably 0.005 mg/kg) as lower limit and at 50 mg/kg (preferably 5 mg/kg) as upper limit per once when parenterally administered.

Effect of the Invention

The compound represented by general formula (I) or a pharmacologically acceptable salt thereof of the present invention has excellent properties in terms of CETP inhibition activity, increasing action on the concentration of HDL cholesterol, decreasing action on the concentration of LDL cholesterol, rapid onset of pharmacological effect, prolonged pharmacological effect, physical stability, solubility, oral absorbability, blood concentration, cell membrane permeability, metabolic stability, tissue migration, bioavailability (BA), drug-drug interaction, toxicity or the like, and is useful as a medicament for a warm-blooded animal (particularly, for a human). The above-described medicament is a medicament for treatment or prophylaxis of, preferably dyslipidemia, hypercholesterolemia, low HDL cholesterolemia, high LDL cholesterolemia, hypertriglyceridemia, arteriosclerosis, arteriosclerotic heart disease, coronary heart disease (including heart failure, myocardial infarction, angina pectoris, cardiac ischemia, cardiovascular disorder and angioplasty-related restenosis), cerebrovascular disease (including stroke and cerebral infarction), peripheral vascular disease (including diabetic vascular complications) or obesity, more preferably dyslipidemia, low HDL cholesterolemia, high LDL cholesterolemia, arteriosclerosis, arteriosclerotic heart disease or coronary heart disease, further preferably dyslipidemia, low HDL cholesterolemia, arteriosclerosis or coronary heart disease, and even more preferably low HDL cholesterolemia or arteriosclerosis.

MODE FOR CARRYING OUT THE INVENTION

Hereinafter, the present invention is further explained in detail with Examples, Reference Examples, Test Examples and Formulation Examples. However, the scope of the present invention is not limited thereto. Although the bonds between a fluoro group or a hydroxy group and a carbon atom described below may be represented by planar structural formulae, respectively in the chemical structural formulae in the Examples and Reference Examples described below, each compound represented by a compound name including (+) or (−) is a single enantiomer which is prepared using the intermediate compound of Reference Example 10 that is a single enantiomer.

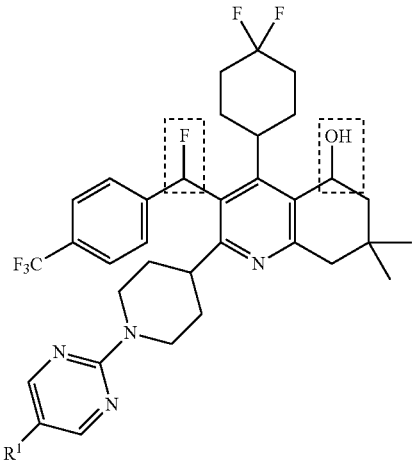

Although the compounds of Examples 2, 7, 12, 13, 30, 32, 33, 35, 38, 41, 44, 52, 56 and 58 are not represented by a compound name including (+) or (−), each of the compounds is a single enantiomer which is prepared using the intermediate compound of Reference Example 10 which is a single enantiomer. The chemical structural formula in the parentheses represents the chemical structural formula of a reaction intermediate in each of the Examples or Reference Examples.

The abbreviations described below are used in the Examples and Reference Examples.

Boc: tert-butoxycarbonyl
PMB: p-methoxybenzyl
TBS: tert-butyldimethylsilyl

EXAMPLES

Example 1

(−)-4-(4,4-Difluorocyclohexyl)-3-{fluoro[4-(trifluoromethyl)phenyl]methyl}-7,7-dimethyl-2-[1-(pyrimidin-2-yl)-piperidin-4-yl]-5,6,7,8-tetrahydroquinolin-5-ol

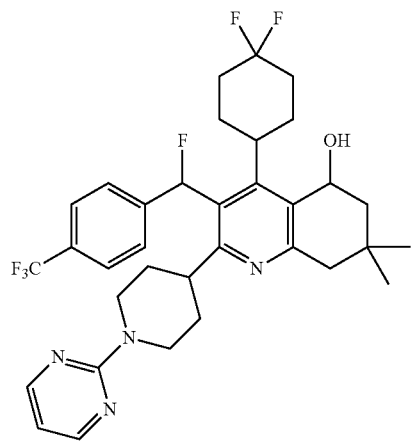 [SMILES: CC1(C)Cc2nc(C3CCN(c4ncccn4)CC3)c(C(F)c3ccc(C(F)(F)F)cc3)c(C3CCC(F)(F)CC3)c2C(O)C1]

To a solution of 1.28 g (1.70 mmol) of (−)-4-(4,4-Difluorocyclohexyl)-3-{fluoro[4-(trifluoromethyl)phenyl]methyl}-5-[(4-methoxybenzyl)oxy]-7,7-dimethyl-2-[1-(pyrimidin-2-yl)piperidin-4-yl]-5,6,7,8-tetrahydroquinoline, which was prepared by a method similar to that of Reference Example 15, in 8 ml of 1,4-dioxane, 4 ml of 6 N hydrochloric acid was added, and the reaction solution was stirred at 70° C. for 3 hours. After completion of the reaction, the reaction solution was poured into saturated sodium hydrogencarbonate aqueous solution and extracted with ethyl acetate. The organic layer was washed with saturated sodium chloride aqueous solution and dried with anhydrous magnesium sulfate, and then the solvent was distilled off under reduced pressure. n-Heptane was added to the obtained residue and the precipitate was obtained by filtration to provide 0.93 g of the title compound as a white solid (yield: 86%).

Specific optical rotation: $[\alpha]_D^{23} = -120°$ (C=0.13, methanol).

$^1$H-NMR spectrum (300 MHz, $CD_2Cl_2$) δ ppm: 8.22 (2H, d, J=5 Hz), 7.66 (2H, d, J=8 Hz), 7.39 (2H, d, J=8 Hz), 7.23 (1H, d, J=47 Hz), 6.39 (1H, t, J=5 Hz), 5.13 (1H, dt, J=6, 6 Hz), 4.87-4.72 (1H, m), 4.57-4.43 (1H, m), 3.72-3.56 (1H, m), 2.91-2.55 (4H, m), 2.37-1.45 (15H, m), 1.13 (3H, s), 0.99 (3H, s), 0.71-0.55 (1H, m).

Mass spectrum (EI, m/z): 632 [M$^+$].

Example 2

2-[1-(5-Bromopyrimidin-2-yl)piperidin-4-yl]-4-(4,4-difluorocyclohexyl)-3-{fluoro[4-(trifluoromethyl)phenyl]methyl}-7,7-dimethyl-5,6,7,8-tetrahydroquinolin-5-ol

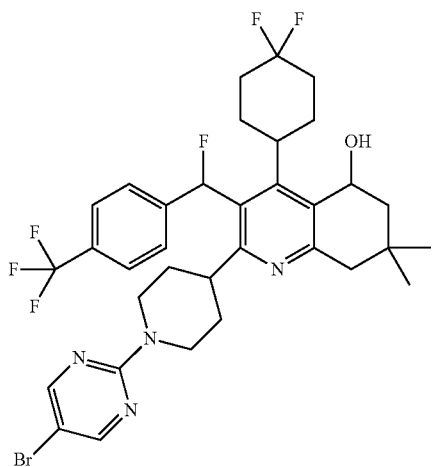 [SMILES: CC1(C)Cc2nc(C3CCN(c4ncc(Br)cn4)CC3)c(C(F)c3ccc(C(F)(F)F)cc3)c(C3CCC(F)(F)CC3)c2C(O)C1]

To a solution of 1.0 g (1.5 mmol) of (−)-4-(4,4-Difluorocyclohexyl)-3-{fluoro[4-(trifluoromethyl)phenyl]methyl}-5-[(4-methoxybenzyl)oxy]-7,7-dimethyl-2-(piperidin-4-yl)-5,6,7,8-tetrahydroquinoline, which was prepared by a method similar to that of Reference Example 10, in 5 ml of N,N-dimethylformamide, 0.58 g (3.0 mmol) of 5-bromo-2-chloropyrimidine and 0.27 ml (1.8 mmol) of 1,8-diazabicyclo[5.4.0]-7-undecene were added, and the reaction solution was stirred at 100° C. for 3 hours. After completion of the reaction, the reaction solution was poured into water and extracted with ethyl acetate. The organic layer was washed with saturated sodium chloride aqueous solution and dried with anhydrous magnesium sulfate, and then the solvent was distilled off under reduced pressure. 5% Ethyl acetate/n-hexane solution was added to the obtained residue and the precipitate was obtained by filtration to provide 0.78 g of 2-[1-(5-Bromopyrimidin-2-yl)piperidin-4-yl]-4-(4,4-difluorocyclohexyl)-3-{fluoro[4-(trifluoromethyl)phenyl]methyl}-5-[(4-methoxybenzyl)oxy]-7,7-dimethyl-5,6,7,8-tetrahydroquinoline as a white solid (yield: 64%).

To a solution of 63 mg (0.076 mmol) of 2-[1-(5-Bromopyrimidin-2-yl)piperidin-4-yl]-4-(4,4-difluorocyclohexyl)-3-{fluoro[4-(trifluoromethyl)phenyl]methyl}-5-[(4-methoxybenzyl)oxy]-7,7-dimethyl-5,6,7,8-tetrahydroquinoline obtained above in 0.5 ml of 1,4-dioxane, 1 ml of methanol and 0.2 ml of conc. hydrochloric acid were added, and the reaction solution was stirred at 50° C. for 7 hours. After completion of the reaction, the reaction solution was poured into water and extracted with ethyl acetate. The organic layer was washed with saturated sodium chloride aqueous solution and dried with anhydrous magnesium sulfate, and then the solvent was distilled off under reduced pressure. The obtained residue was purified by preparative thin layer chromatography [n-hexane/ethyl acetate=70/30 (V/V)] to provide 46 mg of the title compound as a white solid (yield: 85%).

$^1$H-NMR spectrum (400 MHz, CDCl$_3$) δ ppm: 8.21 (2H, s), 7.64 (2H, d, J=8 Hz), 7.37 (2H, d, J=8 Hz), 7.21 (1H, d, J=45 Hz), 5.12 (1H, q, J=6 Hz), 4.66-4.77 (1H, m), 4.38-4.49 (1H, m), 3.68-3.55 (1H, m), 2.85-2.60 (4H, m), 2.38-2.21 (2H, m), 2.19-2.04 (4H, m), 1.98-1.48 (9H, m), 1.15 (3H, s), 1.01 (3H, s), 0.68-0.58 (1H, m).

Example 3

(−)-4-(4,4-Difluorocyclohexyl)-3-{fluoro[4-(trifluoromethyl)phenyl]methyl}-2-[1-(5-methoxypyrimidin-2-yl)piperidin-4-yl]-7,7-dimethyl-5,6,7,8-tetrahydroquinolin-5-ol

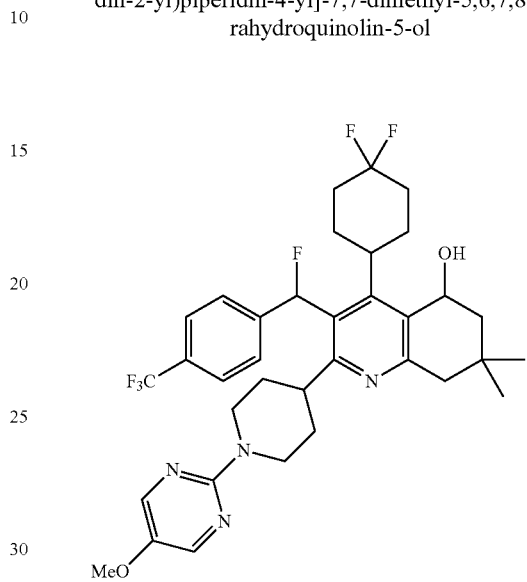

To 100 mg (0.15 mmol) of (−)-4-(4,4-Difluorocyclohexyl)-3-{fluoro[4-(trifluoromethyl)phenyl]methyl}-5-[(4-methoxybenzyl)oxy]-7,7-dimethyl-2-(piperidin-4-yl)-5,6,7,8-tetrahydroquinoline, which was prepared by a method similar to that of Reference Example 10, 64 mg (0.44 mmol) of 2-chloro-5-methoxypyrimidine and 1 ml of 1,4-dioxane were added, and the reaction solution was stirred at 80° C. for 26.6 hours. After completion of the reaction, 0.5 ml of 6 N hydrochloric acid was added to the reaction solution and the mixture was stirred at 50° C. for 8 hours. After completion of the reaction, saturated sodium hydrogencarbonate aqueous solution was added to the reaction mixture and the reaction mixture was extracted with ethyl acetate. The organic layer was washed with saturated sodium chloride aqueous solution and dried with anhydrous magnesium sulfate, and then the solvent was distilled off under reduced pressure. The obtained residue was subjected to silica gel column chromatography [n-hexane/ethyl acetate=4/1 (V/V)] and the fraction including the desired compound was concentrated under reduced pressure. n-Hexane was added to the obtained residue and the precipitate was obtained by filtration to provide 44 mg of the title compound as a white powder (yield: 45%).

Specific optical rotation: $[\alpha]_D^{27}$=−85° (C=0.13, methanol).

$^1$H-NMR spectrum (300 MHz, CDCl$_3$) δ ppm: 8.04 (2H, s), 7.63 (2H, d, J=8 Hz), 7.36 (2H, d, J=8 Hz), 7.20 (1H, d, J=48 Hz), 5.12 (1H, dt, J=6, 6 Hz), 4.72-4.61 (1H, m), 4.44-4.32 (1H, m), 3.77 (3H, s), 3.71-3.54 (1H, m), 2.91-2.57 (4H, m), 2.39-1.61 (15H, m), 1.15 (3H, s), 1.00 (3H, s), 0.70-0.56 (1H, m).

Mass spectrum (EI, m/z): 662 [M$^+$].

Example 4

(−)-4-(4,4-Difluorocyclohexyl)-3-{fluoro[4-(trifluoromethyl)phenyl]methyl}-2-[1-(5-hydroxypyrimidin-2-yl)piperidin-4-yl]-7,7-dimethyl-5,6,7,8-tetrahydroquinolin-5-ol

Example 5

(−)-4-(4,4-Difluorocyclohexyl)-3-{fluoro[4-(trifluoromethyl)phenyl]methyl}-7,7-dimethyl-2-{1-[5-(morpholin-4-yl)pyrimidin-2-yl]piperidin-4-yl}-5,6,7,8-tetrahydroquinolin-5-ol

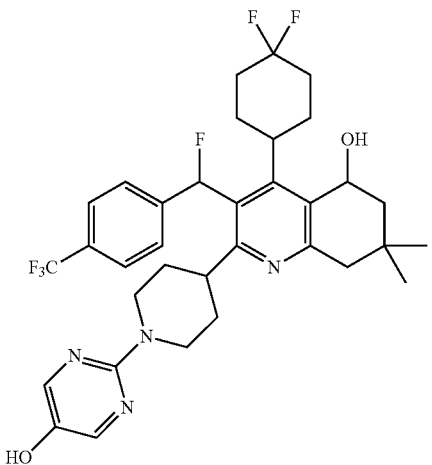 [SMILES: CC1(C)Cc2nc(C3CCN(c4ncc(O)cn4)CC3)c(C(F)c3ccc(C(F)(F)F)cc3)c(C3CCC(F)(F)CC3)c2C(O)C1]

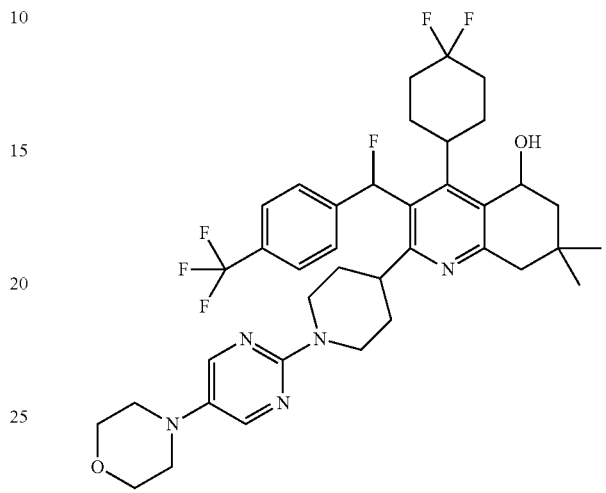

To 4.30 g (5.13 mmol) of (−)-4-(4,4-Difluorocyclohexyl)-3-{fluoro[4-(trifluoromethyl)phenyl]methyl}-5-[(4-methoxybenzyl)oxy]-7,7-dimethyl-2-{1-[5-(morpholin-4-yl)pyrimidin-2-yl]piperidin-4-yl}-5,6,7,8-tetrahydroquinoline, which was prepared by a method similar to that of Reference Example 12, 14 ml of conc. hydrochloric acid, 36 ml of methanol and 40 ml of 1,4-dioxane were added, and the reaction solution was stirred at 70° C. for 1.5 hours. After completion of the reaction, the reaction solution was poured into 200 ml of saturated sodium hydrogencarbonate aqueous solution to which 14 ml of 6 N sodium hydroxide aqueous solution had been added and extracted with ethyl acetate. The organic layer was washed with saturated sodium chloride aqueous solution and dried with anhydrous magnesium sulfate, and then the solvent was distilled off under reduced pressure. The obtained residue was subjected to silica gel column chromatography [n-hexane/ethyl acetate=3/1-2/1 (V/V)] and the fraction including the desired compound was concentrated under reduced pressure. Toluene was added to the obtained residue and the precipitate was obtained by filtration to provide 2.60 g of the title compound as a white solid (yield: 78%).

Specific optical rotation: $[\alpha]_D^{28}=-49°$ (C=0.30, chloroform).

$^1$H-NMR spectrum (300 MHz, $CD_2Cl_2$) δ ppm: 7.92 (2H, s), 7.66 (2H, d, J=8 Hz), 7.39 (2H, d, J=8 Hz), 7.23 (1H, d, J=47 Hz), 5.80 (1H, br s), 5.12 (1H, dt, J=6, 6 Hz), 4.68-4.53 (1H, m), 4.39-4.23 (1H, m), 3.74-3.55 (1H, m), 2.93-2.50 (4H, m), 2.37-1.42 (15H, m), 1.10 (3H, s), 0.97 (3H, s), 0.65-0.52 (1H, m).

Mass spectrum (EI, m/z): 648 [M$^+$].

To a solution of 100 mg (0.120 mmol) of (−)-2-[1-(5-Bromopyrimidin-2-yl)piperidin-4-yl]-4-(4,4-difluorocyclohexyl)-3-{fluoro[4-(trifluoromethyl)phenyl]methyl}-5-[(4-methoxybenzyl)oxy]-7,7-dimethyl-5,6,7,8-tetrahydroquinoline, which was prepared by a method similar to that of Reference Example 11, in 0.6 ml of toluene, 21 mg (0.24 mmol) of morpholine, 14 mg (0.048 mmol) of (2-biphenyl)di-tert-butyl phosphine, 23 mg (0.24 mmol) of sodium tert-butoxide and 11 mg (0.012 mmol) of tris(dibenzylidene acetone)dipalladium (0) were added, and the reaction solution was stirred at 60° C. for 50 minutes while microwave irradiating using a microwave reactor (product name: Initiator, manufactured by Biotage). After completion of the reaction, the reaction solution was poured into saturated sodium hydrogencarbonate aqueous solution and extracted with ethyl acetate. The organic layer was washed with saturated sodium chloride aqueous solution and dried with anhydrous magnesium sulfate, and then the solvent was distilled off under reduced pressure. The obtained residue was subjected to silica gel column chromatography [n-hexane/ethyl acetate=80/20-50/50 (V/V)] to provide 89 mg of 4-(4,4-Difluorocyclohexyl)-3-{fluoro[4-(trifluoromethyl)phenyl]methyl}-5-[(4-methoxybenzyl)oxy]-7,7-dimethyl-2-{1-[5-(morpholin-4-yl)pyrimidin-2-yl]piperidin-4-yl}-5,6,7,8-tetrahydroquinoline as an orange solid (yield: 88%).

To a solution of 89 mg (0.11 mmol) of 4-(4,4-Difluorocyclohexyl)-3-{fluoro[4-(trifluoromethyl)phenyl]methyl}-5-[(4-methoxybenzyl)oxy]-7,7-dimethyl-2-{1-[5-(morpholin-4-yl)pyrimidin-2-yl]piperidin-4-yl}-5,6,7,8-tetrahydroquinoline obtained above in 1.8 ml of 1,4-dioxane, 0.9 ml of 4 N hydrogen chloride-1,4-dioxane solution was added, and the reaction solution was stirred at 50° C. for 5 hours. After completion of the reaction, saturated sodium hydrogencarbonate aqueous solution was poured into the reaction solution under ice cooling and the reaction solution was extracted with ethyl acetate. The organic layer was washed with saturated sodium chloride aqueous solution and dried with anhydrous magnesium sulfate, and then the solvent was distilled off under reduced pressure. The obtained residue was subjected to silica gel column chromatography [n-hexane/ethyl acetate=70/30-50/50 (V/V)] and the fraction including the desired compound was concentrated under reduced pressure. n-Hexane was added to the obtained solid and the insoluble matter was obtained by filtration to provide 63 mg of the title compound as a white solid (yield: 83%).

Specific optical rotation: $[\alpha]_D^{23}$=−74° (C=0.12, chloroform).

$^1$H-NMR spectrum (400 MHz, CDCl$_3$) δ ppm: 8.04 (2H, s), 7.63 (2H, d, J=8 Hz), 7.36 (2H, d, J=8 Hz), 7.21 (1H, d, J=46 Hz), 5.15-5.08 (1H, m), 4.73-4.63 (1H, m), 4.44-4.35 (1H, m), 3.84 (4H, t, J=5 Hz), 3.67-3.56 (1H, m), 2.96 (4H, t, J=5 Hz), 2.84-2.59 (4H, m), 2.36-1.50 (15H, m), 1.15 (3H, s), 1.00 (3H, s), 0.67-0.59 (1H, m).

Mass spectrum (FAB, m/z): 717 [M$^+$].

Example 6

(−)-4-(4,4-Difluorocyclohexyl)-3-{fluoro[4-(trifluoromethyl)phenyl]methyl}-7,7-dimethyl-2-{1-[5-(piperidin-1-yl)pyrimidin-2-yl]piperidin-4-yl}-5,6,7,8-tetrahydroquinolin-5-ol

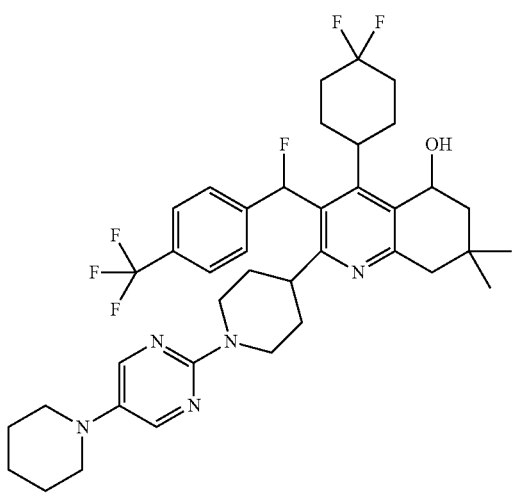 [SMILES: CC1(C)Cc2nc(C3CCN(c4ncc(N5CCCCC5)cn4)CC3)c(C(F)c3ccc(C(F)(F)F)cc3)c(C3CCC(F)(F)CC3)c2C(O)C1]

Reactions similar to those of the first step of Example 5 and Example 7 were performed except for using piperidine instead of morpholine, and from 100 mg (0.120 mmol) of (−)-2-[1-(5-Bromopyrimidin-2-yl)piperidin-4-yl]-4-(4,4-difluorocyclohexyl)-3-{fluoro[4-(trifluoromethyl)phenyl]methyl}-5-[(4-methoxybenzyl)oxy]-7,7-dimethyl-5,6,7,8-tetrahydroquinoline, which was prepared by a method similar to that of Reference Example 11, 41 mg of the title compound was obtained as a light brown solid (yield: 48%).

$^1$H-NMR spectrum (400 MHz, CDCl$_3$) δ ppm: 8.06 (2H, s), 7.63 (2H, d, J=8 Hz), 7.36 (2H, d, J=8 Hz), 7.20 (1H, d, J=48 Hz), 5.16-5.08 (1H, m), 4.71-4.60 (1H, m), 4.43-4.33 (1H, m), 3.68-3.56 (1H, m), 2.92 (4H, t, J=5 Hz), 2.84-2.60 (4H, m), 2.36-1.48 (21H, m), 1.15 (3H, s), 1.01 (3H, s), 0.67-0.59 (1H, m).

Specific optical rotation: $[\alpha]_D^{23}$=−70° (C=0.12, chloroform).

Mass spectrum (FAB, m/z): 715 [M$^+$].

Example 7

4-(4,4-Difluorocyclohexyl)-2-(1-{5-[4-(ethoxycarbonyl)piperidin-1-yl]pyrimidin-2-yl}piperidin-4-yl)-3-{fluoro[4-(trifluoromethyl)phenyl]methyl}-7,7-dimethyl-5,6,7,8-tetrahydroquinolin-5-ol

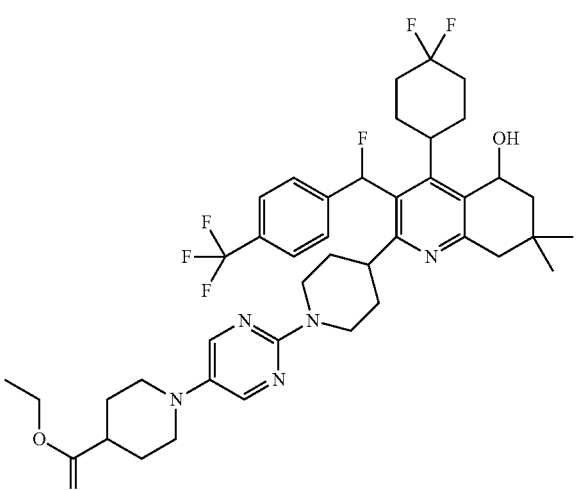

To a solution of 98 mg (0.11 mmol) of 4-(4,4-Difluorocyclohexyl)-2-(1-{5-[4-(ethoxycarbonyl)piperidin-1-yl]pyrimidin-2-yl}piperidin-4-yl)-3-{fluoro[4-(trifluoromethyl)phenyl]methyl}-5-[(4-methoxybenzyl)oxy]-7,7-dimethyl-5,6,7,8-tetrahydroquinoline, which was prepared by a method similar to that of Reference Example 13, in 2 ml of ethanol, 1 ml of 4 N hydrogen chloride/1,4-dioxane solution was added, and the reaction solution was stirred at 50° C. for 3 hours. After completion of the reaction, saturated sodium hydrogencarbonate aqueous solution was poured into the reaction solution under ice cooling and the reaction solution was extracted with ethyl acetate. The organic layer was washed with saturated sodium chloride aqueous solution and dried with anhydrous magnesium sulfate, and then the solvent was distilled off under reduced pressure. The obtained residue was subjected to silica gel column chromatography [n-hexane/ethyl acetate=90/10-60/40 (V/V)] and the fraction including the desired compound was concentrated under reduced pressure to provide 69 mg of the title compound as a light brown solid (yield: 81%).

$^1$H-NMR spectrum (500 MHz, CDCl$_3$) δ ppm: 8.05 (2H, s), 7.63 (2H, d, J=8 Hz), 7.36 (2H, d, J=8 Hz), 7.21 (1H, d, J=53 Hz), 5.15-5.08 (1H, m), 4.72-4.62 (1H, m), 4.44-4.34 (1H, m), 4.16 (2H, q, J=7 Hz), 3.67-3.56 (1H, m), 3.34-3.25 (2H, m), 2.83-2.59 (6H, m), 2.41-1.52 (20H, m), 1.26 (3H, t, J=7 Hz), 1.14 (3H, s), 1.00 (3H, s), 0.66-0.60 (1H, m).

Mass spectrum (FAB, m/z): 787 [M$^+$].

Example 8

(−)-4-(4,4-Difluorocyclohexyl)-3-{fluoro[4-(trifluoromethyl)phenyl]methyl}-7,7-dimethyl-2-{1-[5-(4-methylpiperazin-1-yl)pyrimidin-2-yl]piperidin-4-yl}-5,6,7,8-tetrahydroquinolin-5-ol

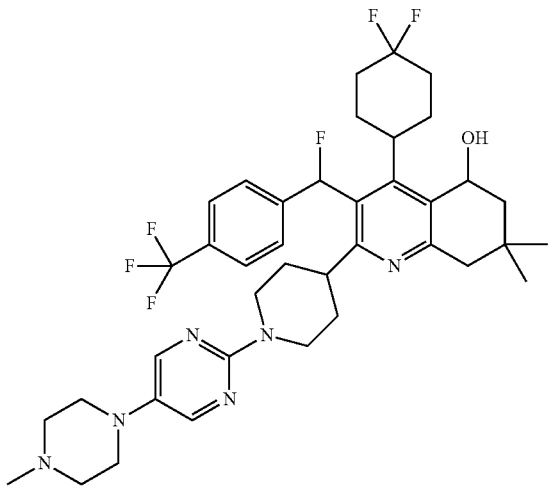

Reactions similar to those of the first step of Example 5 and Example 7 were performed except for using 1-methyl piperazine instead of morpholine, and from 120 mg (0.144 mmol) of (−)-2-[1-(5-Bromopyrimidin-2-yl)piperidin-4-yl]-4-(4,4-difluorocyclohexyl)-3-{fluoro[4-(trifluoromethyl)phenyl]methyl}-5-[(4-methoxybenzyl)oxy]-7,7-dimethyl-5,6,7,8-tetrahydroquinoline, which was prepared by a method similar to that of Reference Example 11, 36 mg of the title compound was obtained as a light yellow solid (yield: 34%).

Specific optical rotation: $[\alpha]_D^{23}=-61°$ (C=0.13, chloroform).

$^1$H-NMR spectrum (500 MHz, CDCl$_3$) δ ppm: 8.06 (2H, s), 7.63 (2H, d, J=8 Hz), 7.36 (2H, d, J=8 Hz), 7.21 (1H, d, J=47 Hz), 5.18-5.06 (1H, m), 4.73-4.60 (1H, m), 4.46-4.33 (1H, m), 3.67-3.55 (1H, m), 3.01 (4H, t, J=4 Hz), 2.91-2.49 (4H, m), 2.57 (4H, t, J=4 Hz), 2.41-1.51 (15H, m), 2.34 (3H, s), 1.14 (3H, s), 1.00 (3H, s), 0.69-0.58 (1H, m).

Mass spectrum (FAB, m/z): 730 [M$^+$].

Example 9

(−)-4-(4,4-Difluorocyclohexyl)-3-{fluoro[4-(trifluoromethyl)phenyl]methyl}-7,7-dimethyl-2-{1-[5-(thiomorpholin-4-yl)pyrimidin-2-yl]piperidin-4-yl}-5,6,7,8-tetrahydroquinolin-5-ol

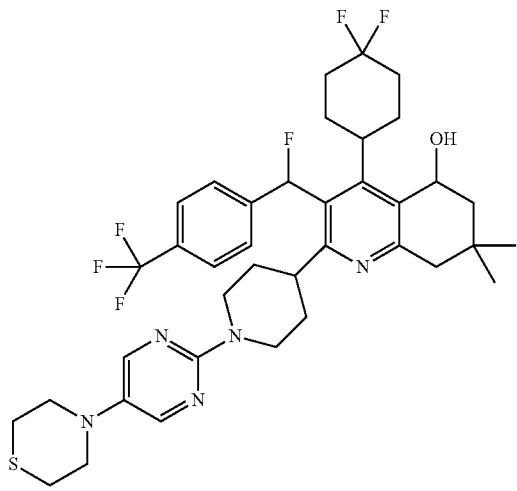 [SMILES: CC1(C)Cc2nc(C3CCN(c4ncc(N5CCSCC5)cn4)CC3)c(C(F)c3ccc(C(F)(F)F)cc3)c(C3CCC(F)(F)CC3)c2C(O)C1]

Reactions similar to those of Reference Example 13 and Example 7 were performed except for using thiomorpholine instead of isonipecotic acid ethyl ester, and from 120 mg (0.144 mmol) of (−)-2-[1-(5-Bromopyrimidin-2-yl)piperidin-4-yl]-4-(4,4-difluorocyclohexyl)-3-{fluoro[4-(trifluoromethyl)phenyl]methyl}-5-[(4-methoxybenzyl)oxy]-7,7-dimethyl-5,6,7,8-tetrahydroquinoline, which was prepared by a method similar to that of Reference Example 11, 61 mg of the title compound was obtained as a white solid (yield: 58%).

Specific optical rotation: $[\alpha]_D^{23}=-64°$ (C=0.22, chloroform).

$^1$H-NMR spectrum (500 MHz, CDCl$_3$) δ ppm: 8.03 (2H, s), 7.63 (2H, d, J=8 Hz), 7.36 (2H, d, J=8 Hz), 7.21 (1H, d, J=52 Hz), 5.15-5.07 (1H, m), 4.74-4.64 (1H, m), 4.46-4.36 (1H, m), 3.67-3.57 (1H, m), 3.22 (4H, t, J=5 Hz), 2.84-2.58 (8H, m), 2.36-1.52 (15H, m), 1.14 (3H, s), 1.00 (3H, s), 0.67-0.60 (1H, m).

Mass spectrum (FAB, m/z): 733 [M$^+$].

Example 10

(−)-4-(4,4-Difluorocyclohexyl)-2-{1-[5-(1,1-dioxidethiomorpholin-4-yl)pyrimidin-2-yl]piperidin-4-yl}-3-{fluoro[4-(trifluoromethyl)phenyl]methyl}-7,7-dimethyl-5,6,7,8-tetrahydroquinolin-5-ol

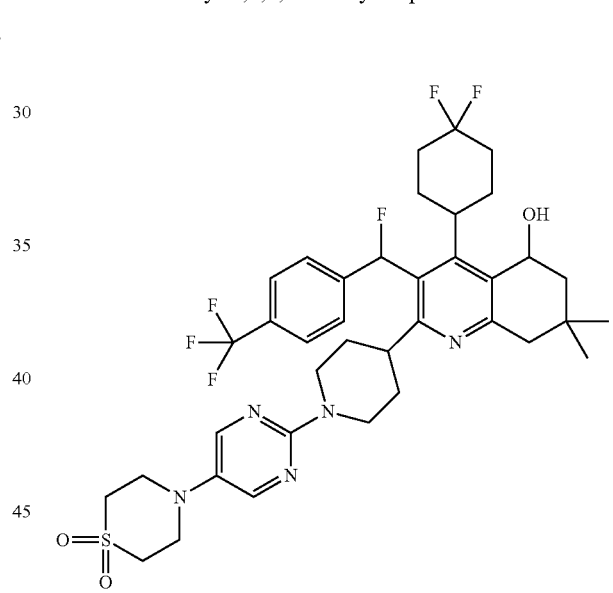

Reactions similar to those of Reference Example 13 and Example 7 were performed except for using thiomorpholine 1,1-dioxide instead of isonipecotic acid ethyl ester, and from 100 mg (0.120 mmol) of (−)-2-[1-(5-Bromopyrimidin-2-yl)piperidin-4-yl]-4-(4,4-difluorocyclohexyl)-3-{fluoro[4-(trifluoromethyl)phenyl]methyl}-5-[(4-methoxybenzyl)oxy]-7,7-dimethyl-5,6,7,8-tetrahydroquinoline, which was prepared by a method similar to that of Reference Example 11, 54 mg of the title compound was obtained as a light yellow solid (yield: 59%).

Specific optical rotation: $[\alpha]_D^{24}=-67°$ (C=0.22, chloroform).

$^1$H-NMR spectrum (400 MHz, CDCl$_3$) δ ppm: 8.08 (2H, s), 7.64 (2H, d, J=8 Hz), 7.37 (2H, d, J=8 Hz), 7.21 (1H, d, J=44 Hz), 5.16-5.08 (1H, m), 4.76-4.66 (1H, m), 4.48-4.38 (1H, m), 3.68-3.57 (1H, m), 3.51 (4H, t, J=5 Hz), 3.16 (4H, t, J=5 Hz), 2.84-2.58 (4H, m), 2.36-1.52 (15H, m), 1.15 (3H, s), 1.01 (3H, s), 0.67-0.59 (1H, m).

Example 11

(−)-4-(4,4-Difluorocyclohexyl)-3-{fluoro[4-(trifluoromethyl)phenyl]methyl}-2-{1-[5-(4-hydroxypiperidin-1-yl)pyrimidin-2-yl]piperidin-4-yl}-7,7-dimethyl-5,6,7,8-tetrahydroquinolin-5-ol

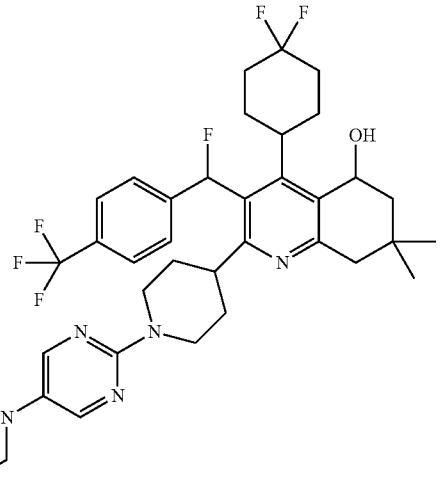

Reactions similar to those of Reference Example 13 and Example 7 were performed except for using 4-hydroxy piperidine and 1,2-dimethoxyethane instead of isonipecotic acid ethyl ester and toluene, and from 150 mg (0.180 mmol) of (−)-2-[1-(5-Bromopyrimidin-2-yl)piperidin-4-yl]-4-(4,4-difluorocyclohexyl)-3-{fluoro[4-(trifluoromethyl)phenyl]methyl}-5-[(4-methoxybenzyl)oxy]-7,7-dimethyl-5,6,7,8-tetrahydroquinoline, which was prepared by a method similar to that of Reference Example 11, 55 mg of the title compound was obtained as a light yellow solid (yield: 42%).

Specific optical rotation: $[\alpha]_D^{25}=-58°$ (C=0.14, chloroform).

$^1$H-NMR spectrum (400 MHz, CDCl$_3$) δ ppm: 8.06 (2H, s), 7.63 (2H, d, J=8 Hz), 7.36 (2H, d, J=8 Hz), 7.21 (1H, d, J=47 Hz), 5.16-5.07 (1H, m), 4.72-4.61 (1H, m), 4.44-4.34 (1H, m), 3.86-3.74 (1H, m), 3.69-3.56 (1H, m), 3.29-3.20 (2H, m), 2.86-2.58 (6H, m), 2.36-1.48 (20H, m), 1.15 (3H, s), 1.00 (3H, s), 0.68-0.58 (1H, m).

Mass spectrum (FAB, m/z): 731 [M$^+$].

Example 12

4-(4,4-Difluorocyclohexyl)-3-{fluoro[4-(trifluoromethyl)phenyl]methyl}-7,7-dimethyl-2-{1-[5-(propan-2-yl)pyrimidin-2-yl]piperidin-4-yl}-5,6,7,8-tetrahydroquinolin-5-ol

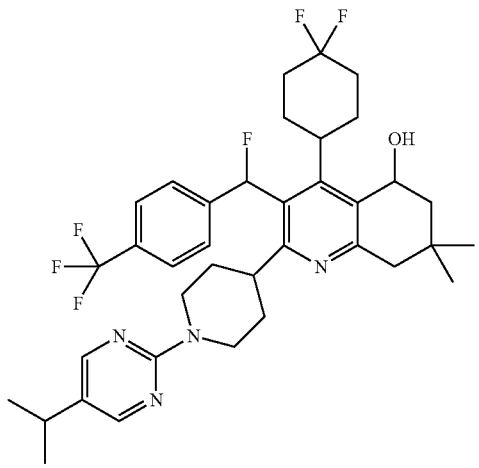 [SMILES: CC(C)c1cnc(N2CCC(c3nc4c(c(C5CCC(F)(F)CC5)c3C(F)c3ccc(C(F)(F)F)cc3)C(O)CC(C)(C)C4)CC2)nc1]

Reactions similar to those of the first step of Example 2 and Example 38 were performed except for using 2-chloro-5-(propan-2-yl) pyrimidine instead of 5-bromo-2-chloropyrimidine, and from 96 mg (0.14 mmol) of (−)-4-(4,4-Difluorocyclohexyl)-3-{fluoro[4-(trifluoromethyl)phenyl]methyl}-5-[(4-methoxybenzyl)oxy]-7,7-dimethyl-2-(piperidin-4-yl)-5,6,7,8-tetrahydroquinoline, which was prepared by a method similar to that of Reference Example 10, 47 mg of the title compound was obtained as a white solid (yield: 50%).

$^1$H-NMR spectrum (400 MHz, CDCl$_3$) δ ppm: 8.14 (2H, s), 7.64 (2H, d, J=8 Hz), 7.37 (2H, d, J=8 Hz), 7.21 (1H, d, J=45 Hz), 5.12 (1H, q, J=6 Hz), 4.80-4.69 (1H, m), 4.52-4.41 (1H, m), 3.68-3.56 (1H, m), 2.84-2.58 (4H, m), 2.34-2.05 (6H, m), 1.97-1.48 (10H, m), 1.20 (6H, d, J=7 Hz), 1.15 (3H, s), 1.00 (3H, s), 0.67-0.58 (1H, m).

Example 13

4-(4,4-Difluorocyclohexyl)-2-[1-(5-ethoxypyrimidine-2-yl)piperidin-4-yl]-3-{fluoro[4-(trifluoromethyl)phenyl]methyl}-7,7-dimethyl-5,6,7,8-tetrahydroquinolin-5-ol

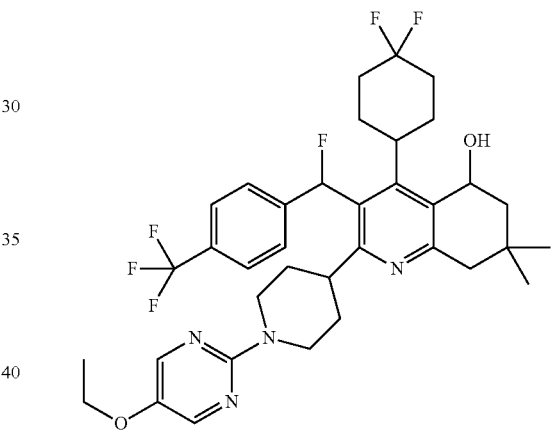

To a solution of 50 mg (0.077 mmol) of (−)-4-(4,4-Difluorocyclohexyl)-3-{fluoro[4-(trifluoromethyl)phenyl]methyl}-2-[1-(5-hydroxypyrimidin-2-yl)piperidin-4-yl]-7,7-dimethyl-5,6,7,8-tetrahydroquinolin-5-ol, which was prepared by a method similar to that of Example 4, in 1.0 ml of N,N-dimethylformamide, 75 mg (0.23 mmol) of cesium carbonate and 12 μl (0.15 mmol) of ethyl iodide were added, and the reaction solution was stirred at room temperature for 1 hour. After completion of the reaction, the reaction solution was poured into water and extracted with ethyl acetate. The organic layer was washed with saturated sodium chloride aqueous solution and dried with anhydrous magnesium sulfate, and then the solvent was distilled off under reduced pressure. The obtained residue was purified by preparative thin layer chromatography [n-hexane/ethyl acetate=70/30 (V/V)] to provide 45 mg of the title compound as a white solid (yield: 85%).

$^1$H-NMR spectrum (400 MHz, CDCl$_3$) δ ppm: 8.03 (2H, s), 7.63 (2H, d, J=8 Hz), 7.36 (2H, d, J=8 Hz), 7.21 (1H, d, J=47 Hz), 5.12 (1H, q, J=6 Hz), 4.71-4.59 (1H, m), 4.43-4.32 (1H, m), 3.97 (2H, q, J=7 Hz), 3.68-3.55 (1H, m), 2.85-2.58 (4H, m), 2.36-2.02 (6H, m), 2.00-1.56 (9H, m), 1.37 (3H, t, J=7 Hz), 1.15 (3H, s), 1.01 (3H, s), 0.67-0.58 (1H, m).

Example 14

(−)-4-(4,4-Difluorocyclohexyl)-3-{fluoro[4-(trifluoromethyl)phenyl]methyl}-7,7-dimethyl-2-{1-[5-(propan-2-yloxy)pyrimidin-2-yl]piperidin-4-yl}-5,6,7,8-tetrahydroquinolin-5-ol

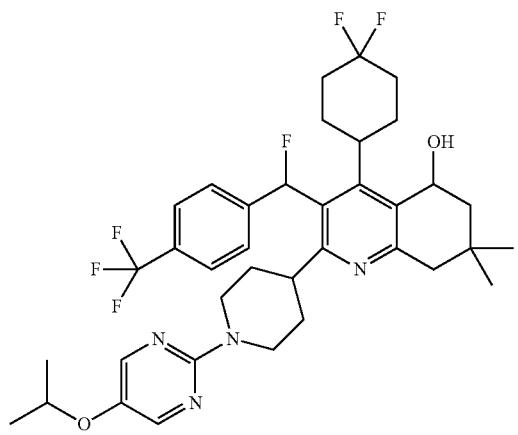 [SMILES: CC(C)Oc1cnc(N2CCC(c3nc4c(c(C5CCC(F)(F)CC5)c3C(F)c3ccc(C(F)(F)F)cc3)C(O)CC(C)(C)C4)CC2)nc1]

Reactions similar to those of Example 13 were performed except for using isopropyl iodide instead of ethyl iodide and setting the reaction temperature to 50° C., and from 60 mg (90 µmol) of (−)-4-(4,4-Difluorocyclohexyl)-3-{fluoro[4-(trifluoromethyl)phenyl]methyl}-2-[1-(5-hydroxypyrimidin-2-yl)piperidin-4-yl]-7,7-dimethyl-5,6,7,8-tetrahydroquinolin-5-ol, which was prepared by a method similar to that of Example 4, 54 mg of the title compound was obtained as a white solid (yield: 90%).

Specific optical rotation: $[\alpha]_D^{24}=-68°$ (C=0.26, chloroform).

$^1$H-NMR spectrum (400 MHz, CDCl$_3$) δ ppm: 8.01 (2H, s), 7.63 (2H, d, J=8 Hz), 7.37 (2H, d, J=8 Hz), 7.21 (1H, d, J=46 Hz), 5.12 (1H, q, J=6 Hz), 4.73-4.61 (1H, m), 4.46-4.33 (1H, m), 4.25 (1H, septet, J=6 Hz), 3.70-3.56 (1H, m), 2.91-2.58 (4H, m), 2.36-2.04 (6H, m), 2.00-1.59 (9H, m), 1.29 (6H, d, J=6 Hz), 1.15 (3H, s), 1.01 (3H, s), 0.70-0.57 (1H, m).

Example 15

(−)-4-(4,4-Difluorocyclohexyl)-3-{fluoro[4-(trifluoromethyl)phenyl]methyl}-2-{1-[5-(2-hydroxyethoxy)pyrimidin-2-yl]piperidin-4-yl}-7,7-dimethyl-5,6,7,8-tetrahydroquinolin-5-ol

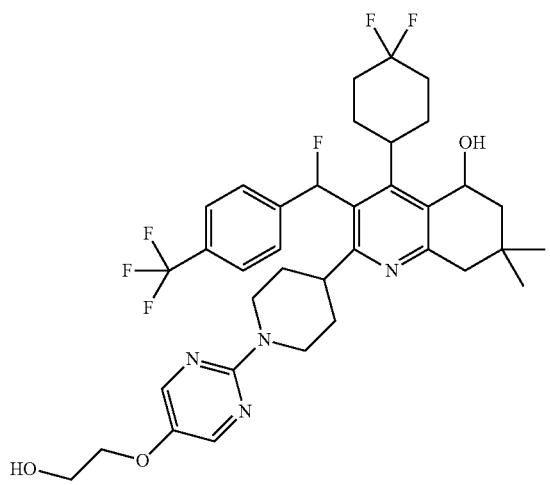

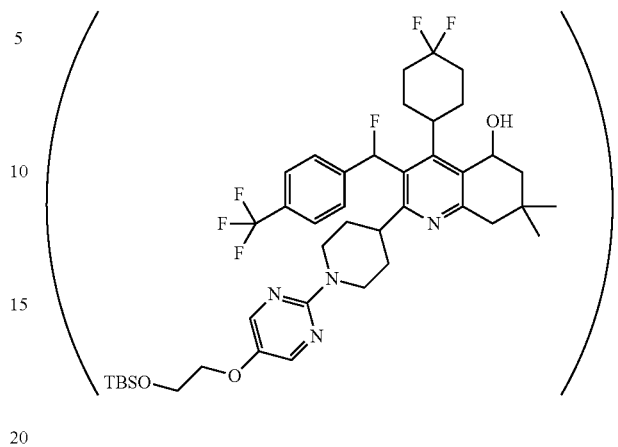

Reactions similar to those of Example 13 were performed except for using (2-bromomethoxy)(tert-butyl)dimethylsilane instead of ethyl iodide and setting the reaction temperature to 50° C., and from 61 mg (94 µmol) of (−)-4-(4,4-Difluorocyclohexyl)-3-{fluoro[4-(trifluoromethyl)phenyl]methyl}-2-[1-(5-hydroxypyrimidin-2-yl)piperidin-4-yl]-7,7-dimethyl-5,6,7,8-tetrahydroquinolin-5-ol, which was prepared by a method similar to that of Example 4, 68 mg of 2-{1-[5-(2-{[tert-Butyl(dimethyl)silyl]oxy}ethoxy)pyrimidin-2-yl]piperidin-4-yl}-4-(4,4-difluorocyclohexyl)-3-{fluoro[4-(trifluoromethyl)phenyl]methyl}-7,7-dimethyl-5,6,7,8-tetrahydroquinolin-5-ol was obtained.

To a solution of 68 mg (84 µmol) of 2-{1-[5-(2-{[tert-Butyl(dimethyl)silyl]oxy}ethoxy)pyrimidin-2-yl]piperidin-4-yl}-4-(4,4-difluorocyclohexyl)-3-{fluoro[4-(trifluoromethyl)phenyl]methyl}-7,7-dimethyl-5,6,7,8-tetrahydroquinolin-5-ol obtained above in 0.5 ml of tetrahydrofuran, 0.13 ml (0.13 mmol) of 1 N tetrabutyl ammonium fluoride/tetrahydrofuran solution was added, and the reaction solution was stirred at room temperature for 1 hour. After completion of the reaction, the reaction solution was poured into water and extracted with ethyl acetate. The organic layer was washed with saturated sodium chloride aqueous solution and dried with anhydrous magnesium sulfate, and then the solvent was distilled off under reduced pressure. The obtained residue was purified by preparative thin layer chromatography [n-hexane/ethyl acetate=50/50 (V/V)] to provide 52 mg of the title compound as a white solid (yield: 89%).

Specific optical rotation: $[\alpha]_D^{24}=-70°$ (C=0.17, chloroform).

$^1$H-NMR spectrum (400 MHz, CDCl$_3$) δ ppm: 8.06 (2H, s), 7.63 (2H, d, J=8 Hz), 7.37 (2H, d, J=8 Hz), 7.21 (1H, d, J=47 Hz), 5.12 (1H, q, J=7 Hz), 4.72-4.63 (1H, m), 4.44-4.33 (1H, m), 4.02 (2H, t, J=5 Hz), 3.92 (2H, brs), 3.68-3.56 (1H, m), 2.84-2.58 (4H, m), 2.39-1.54 (16H, m), 1.15 (3H, s), 1.01 (3H, s), 0.70-0.58 (1H, m).

Example 16

(−)-4-(4,4-Difluorocyclohexyl)-3-{fluoro[4-(trifluoromethyl)phenyl]methyl}-7,7-dimethyl-2-[1-(5-pentylpyrimidin-2-yl)piperidin-4-yl]-5,6,7,8-tetrahydroquinolin-5-ol

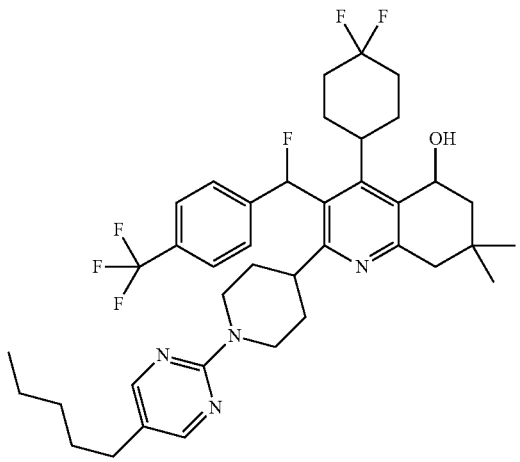 [SMILES: CCCCCc1cnc(N2CCC(c3nc4c(c(C5CCC(F)(F)CC5)c3C(F)c3ccc(C(F)(F)F)cc3)C(O)CC(C)(C)C4)CC2)nc1]

Reactions similar to those of the first step of Example 2 and Example 38 were performed except for using 2-chloro-5-pentyl pyrimidine instead of 5-bromo-2-chloropyrimidine, and from 100 mg (0.148 mmol) of (−)-4-(4,4-Difluorocyclohexyl)-3-{fluoro[4-(trifluoromethyl)phenyl]methyl}-5-[(4-methoxybenzyl)oxy]-7,7-dimethyl-2-(piperidin-4-yl)-5,6,7,8-tetrahydroquinoline, which was prepared by a method similar to that of Reference Example 10, 95 mg of the title compound was obtained as a white solid (yield: 91%).

Specific optical rotation: $[\alpha]_D^{24}=-71°$ (C=0.17, chloroform).

$^1$H-NMR spectrum (500 MHz, CDCl$_3$) δ ppm: 8.08 (2H, s), 7.63 (2H, d, J=8 Hz), 7.36 (2H, d, J=8 Hz), 7.21 (1H, d, J=46 Hz), 5.12 (1H, q, =6 Hz), 4.82-4.68 (1H, m), 4.53-4.41 (1H, m), 3.68-3.55 (1H, m), 2.94-2.58 (4H, m), 2.45-1.48 (19H, m), 1.36-1.21 (4H, m), 1.14 (3H, s), 1.00 (3H, s), 0.88 (3H, t, J=7 Hz), 0.70-0.57 (1H, m).

Mass spectrum (ES, m/z): 703 [M$^+$].

Example 17

(−)-2-[1-(5-cyanopyrimidine-2-yl)piperidin-4-yl]-4-(4,4-difluorocyclohexyl)-3-{fluoro[4-(trifluoromethyl)phenyl]methyl}-7,7-dimethyl-5,6,7,8-tetrahydroquinoline-5-ol

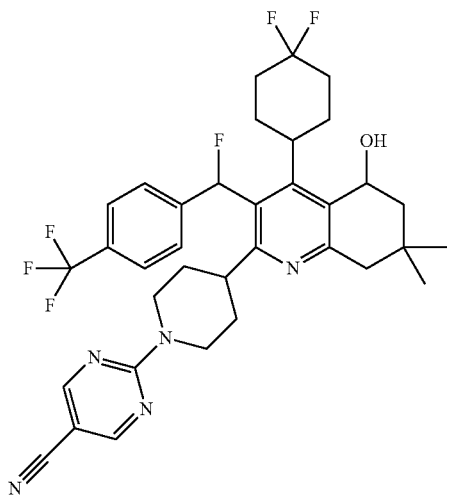 [SMILES: CC1(C)Cc2nc(C3CCN(c4ncc(C#N)cn4)CC3)c(C(F)c3ccc(C(F)(F)F)cc3)c(C3CCC(F)(F)CC3)c2C(O)C1]

Reactions similar to those of the first step of Example 2 and Example 38 were performed except for using 2-chloropyrimidine-5-carbonitrile, which was synthesized by the method described in A. Takamizawa et al., Journal of Organic Chemistry, 1964, Vol. 29, pp. 1740-1742, instead of 5-bromo-2-chloropyrimidine, and from 78 mg (0.12 mmol) of (−)-4-(4,4-Difluorocyclohexyl)-3-{fluoro[4-(trifluoromethyl)phenyl]methyl}-5-[(4-methoxybenzyl)oxy]-7,7-dimethyl-2-(piperidin-4-yl)-5,6,7,8-tetrahydroquinoline, which was prepared by a method similar to that of Reference Example 10, 60 mg of the title compound was obtained as a white solid (yield: 79%).

Specific optical rotation: $[\alpha]_D^{24}=-81°$ (C=0.21, chloroform).

$^1$H-NMR spectrum (400 MHz, CDCl$_3$) δ ppm: 8.42 (2H, s), 7.65 (2H, d, J=8 Hz), 7.38 (2H, d, J=8 Hz), 7.23 (1H, d, J=47 Hz), 5.21-5.07 (1H, m), 4.95-4.82 (1H, m), 4.68-4.54 (1H, m), 3.71-3.55 (1H, m), 2.93-2.74 (3H, m), 2.63 (1H, d, J=17 Hz), 2.38-1.59 (15H, m), 1.15 (3H, s), 1.01 (3H, s), 0.77-0.62 (1H, m).

Mass spectrum (FAB, m/z): 658 [(M+1)$^+$].

Example 18

(−)-2-{1-[5-(Cyclohex-1-ene-1-yl)pyrimidin-2-yl]piperidin-4-yl}-4-(4,4-difluorocyclohexyl)-3-{fluoro[4-(trifluoromethyl)phenyl]methyl}-7,7-dimethyl-5,6,7,8-tetrahydroquinolin-5-ol

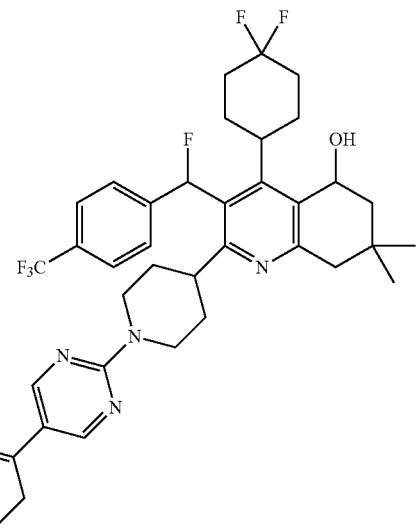

To 78 mg (0.094 mmol) of 2-{1-[5-(Cyclohex-1-en-1-yl)pyrimidin-2-yl]piperidin-4-yl}-4-(4,4-difluorocyclohexyl)-3-{fluoro[4-(trifluoromethyl)phenyl]methyl}-5-[(4-methoxybenzyl)oxy]-7,7-dimethyl-5,6,7,8-tetrahydroquinoline, which was prepared by a method similar to that of Reference Example 18, 0.4 ml of 6 N hydrochloric acid and 2 ml of 1,4-dioxane were added, and the reaction solution was stirred at 80° C. for 3 hours. After completion of the reaction, the reaction solution was poured into saturated sodium hydrogencarbonate aqueous solution and extracted with ethyl acetate. The organic layer was washed with saturated sodium chloride aqueous solution and dried with anhydrous magnesium sulfate, and then the solvent was distilled off under reduced pressure. The obtained residue was subjected to silica gel column chromatography [n-hexane/ethyl acetate=95/5-80/20 (V/V)] and the fraction including the desired compound was concentrated under reduced pressure. Diethyl ether was added to the obtained residue and the precipitate was obtained by filtration to provide 45 mg of the title compound as a white solid (yield: 67%).

Specific optical rotation: $[\alpha]_D^{25}$=−110° (C=0.050, methanol).

$^1$H-NMR spectrum (300 MHz, CD$_2$Cl$_2$) δ: 8.27 (2H, s), 7.66 (2H, d, J=8 Hz), 7.39 (2H, d, J=8 Hz), 7.22 (1H, d, J=47 Hz), 5.99-5.93 (1H, m), 5.13 (1H, dt, J=6, 6 Hz), 4.84-4.70 (1H, m), 4.55-4.42 (1H, m), 3.72-3.56 (1H, m), 2.93-2.54 (4H, m), 2.38-1.55 (23H, m), 1.13 (3H, s), 0.99 (3H, s), 0.69-0.57 (1H, m).

Mass spectrum (EI, m/z): 712 [M$^+$].

Example 19

(−)-2-[1-(5-Cyclopropylpyrimidin-2-yl)piperidin-4-yl]-4-(4,4-difluorocyclohexyl)-3-{fluoro[4-(trifluoromethyl)phenyl]methyl}-7,7-dimethyl-5,6,7,8-tetrahydroquinolin-5-ol

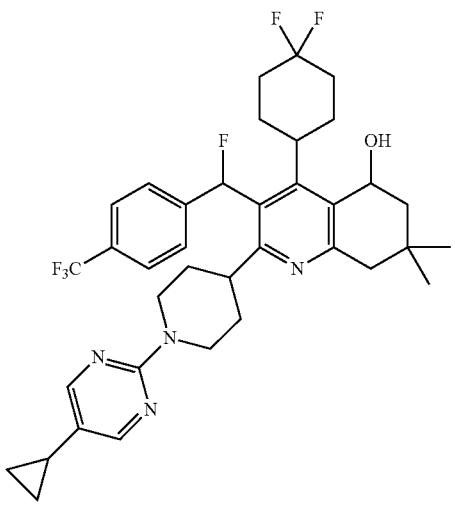 [SMILES: CC1(C)Cc2nc(C3CCN(c4ncc(C5CC5)cn4)CC3)c(C(F)c3ccc(C(F)(F)F)cc3)c(C3CCC(F)(F)CC3)c2C(O)C1]

To a solution of 100 mg (0.12 mmol) of (−)-2-[1-(5-Bromopyrimidin-2-yl)piperidin-4-yl]-4-(4,4-difluorocyclohexyl)-3-{fluoro[4-(trifluoromethyl)phenyl]methyl}-5-[(4-methoxybenzyl)oxy]-7,7-dimethyl-5,6,7,8-tetrahydroquinoline, which was prepared by a method similar to that of Reference Example 11, in 1.2 ml of toluene, 31 mg (0.36 mmol) of cyclopropylboronic acid, 0.1 ml of water and 127 mg (0.60 mmol) of tripotassium phosphate were added and then 38 μl (0.024 mmol) of 20% cyclohexylphosphine-toluene solution and 3.0 mg (0.012 mmol) of palladium acetate were added under an argon gas atmosphere, and the reaction solution was stirred at 100° C. for 6.8 hours. After stirring with heating, 38 μl (0.024 mmol) of 20% cyclohexylphosphine-toluene solution, 3.0 mg (0.012 mmol) of palladium acetate and 10 mg (0.12 mmol) of cyclopropylboronic acid were added and the reaction solution was stirred at 100° C. for 3.5 hours. After stirring with heating, 11 mg (0.024 mmol) of 2-dicyclohexylphosphino-2',4',6'-triisopropylbiphenyl and 7.0 mg (0.012 mmol) of bis(dibenzylideneacetone) palladium (0) were added and the reaction solution was further stirred at 100° C. for 5.5 hours. After completion of the reaction, the reaction solution was poured into water and extracted with ethyl acetate. The organic layer was washed with saturated sodium chloride aqueous solution and dried with anhydrous magnesium sulfate, and then the solvent was distilled off under reduced pressure. The obtained residue was subjected to silica gel column chromatography [n-hexane/ethyl acetate=95/5-70/30 (V/V)] twice and the fraction including the desired compound was concentrated under reduced pressure.

To 25 mg of the obtained residue, 1 ml of 1,4-dioxane and 50 μl of 6 N hydrochloric acid were added, and the reaction solution was stirred at 60° C. for 1.5 hours, at room temperature for 13 hours and further at 60° C. for 5 hours. After stirring with heating, 50 μl of 6 N hydrochloric acid was added thereto and the reaction solution was further stirred at 60° C. for 3.5 hours. After completion of the reaction, the reaction solution was poured into saturated sodium hydrogencarbonate aqueous solution and extracted with ethyl acetate. The organic layer was washed with saturated sodium chloride aqueous solution and dried with anhydrous magnesium sulfate, and then the solvent was distilled off under reduced pressure. The obtained residue was subjected to silica gel column chromatography [n-hexane/ethyl acetate=95/5-70/30 (V/V)] and the fraction including the desired compound was concentrated under reduced pressure. Diisopropyl ether and n-hexane were added to the obtained residue and the precipitate was obtained by filtration to provide 22 mg of the title compound as a white solid (yield: 27%).

Specific optical rotation: $[\alpha]_D^{25}$=−76° (C=0.045, methanol).

$^1$H-NMR spectrum (300 MHz, CD$_2$Cl$_2$) δ: 8.04 (2H, s), 7.65 (2H, d, J=8 Hz), 7.38 (2H, d, J=8 Hz), 7.22 (1H, d, J=48 Hz), 5.13 (1H, dt, J=6, 6 Hz), 4.78-4.66 (1H, m), 4.48-4.38 (1H, m), 3.72-3.56 (1H, m), 2.89-2.55 (4H, m), 2.36-1.55 (16H, m), 1.13 (3H, s), 0.99 (3H, s), 0.89-0.83 (2H, m), 0.67-0.50 (3H, m).

Mass spectrum (EI, m/z): 672 [M$^+$].

Example 20

(−)-4-(4,4-Difluorocyclohexyl)-3-{fluoro[4-(trifluoromethyl)phenyl]methyl}-2-[1-[5-(hydroxymethyl)pyrimidin-2-yl]piperidin-4-yl]-7,7-dimethyl-5,6,7,8-tetrahydroquinolin-5-ol

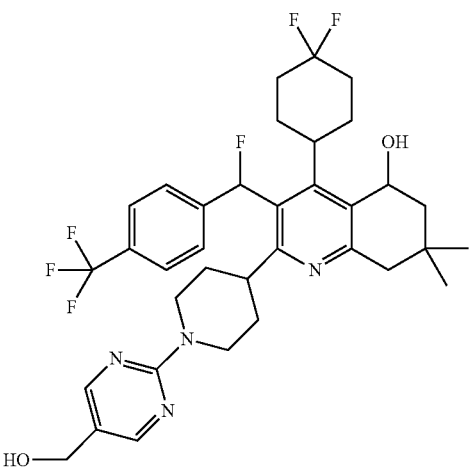

-continued

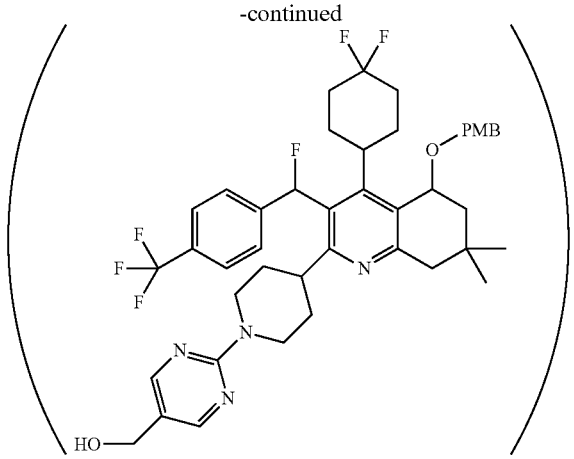

To a solution of 94 mg (0.12 mmol) of 4-(4,4-Difluorocyclohexyl)-3-{fluoro[4-(trifluoromethyl)phenyl]methyl}-2-[1-(5-formylpyrimidin-2-yl)piperidin-4-yl]-5-[(4-methoxybenzyl)oxy]-7,7-dimethyl-5,6,7,8-tetrahydroquinoline, which was prepared by a method similar to that of Reference Example 16, in 0.6 ml of ethanol, 5.0 mg (0.13 mmol) of sodium borohydride was added, and the reaction solution was stirred at 0° C. for 2 hours. After completion of the reaction, saturated ammonium chloride aqueous solution was poured into the reaction solution and the reaction solution was extracted with ethyl acetate. The organic layer was washed with saturated sodium chloride aqueous solution and dried with anhydrous magnesium sulfate, and then the solvent was distilled off under reduced pressure. The obtained residue was subjected to silica gel column chromatography [n-hexane/ethyl acetate=100/0-60/40 (V/V)] and the fraction including the desired compound was concentrated under reduced pressure to provide 89 mg of 4-(4,4-difluorocyclohexyl)-3-{fluoro[4-(trifluoromethyl)phenyl]methyl}-2-[1-[5-(hydroxymethyl)pyrimidin-2-yl]piperidin-4-yl]-5-[(4-methoxybenzyl)oxy]-7,7-dimethyl-5,6,7,8-tetrahydroquinoline.

To 89 mg (0.11 mmol) of 4-(4,4-Difluorocyclohexyl)-3-{fluoro[4-(trifluoromethyl)phenyl]methyl}-2-[1-[5-(hydroxymethyl)pyrimidin-2-yl]piperidin-4-yl]-5-[(4-methoxybenzyl)oxy]-7,7-dimethyl-5,6,7,8-tetrahydroquinoline obtained above, 0.5 ml of 1,4-dioxane, 0.5 ml of water and 0.5 ml of 4 N hydrogen chloride-1,4-dioxane solution were added, and the reaction solution was stirred at 50° C. for 6 hours. After completion of the reaction, the reaction solution was poured into saturated sodium hydrogencarbonate aqueous solution and extracted with ethyl acetate. The organic layer was washed with saturated sodium chloride aqueous solution and dried with anhydrous magnesium sulfate, and then the solvent was distilled off under reduced pressure. The obtained residue was subjected to silica gel column chromatography [n-hexane/ethyl acetate=100/0-50/50 (V/V)] and the fraction including the desired compound was concentrated under reduced pressure to provide 41 mg of the title compound as a white solid (yield: 54%).

Specific optical rotation: $[\alpha]_D^{24}=-81°$ (C=0.15, chloroform).

$^1$H-NMR spectrum (400 MHz, CDCl$_3$) δ ppm: 8.23 (2H, s), 7.64 (2H, d, J=8 Hz), 7.37 (2H, d, J=8 Hz), 7.21 (1H, d, J=46 Hz), 5.16-5.06 (1H, m), 4.84-4.74 (1H, m), 4.56-4.44 (1H, m), 4.46 (2H, s), 3.71-3.54 (1H, m), 2.88-2.69 (3H, m), 2.63 (1H, d, J=17 Hz), 2.37-1.50 (16H, m), 1.14 (3H, s), 1.00 (3H, s), 0.70-0.57 (1H, m).

Mass spectrum (FAB, m/z): 663 [(M+1)$^+$].

Example 21

(−)-4-(4,4-difluorocyclohexyl)-3-{fluoro[4-(trifluoromethyl)phenyl]methyl}-7,7-dimethyl-2-{1-[5-(2-methylpropoxy)pyrimidin-2-yl]piperidin-4-yl}-5,6,7,8-tetrahydroquinoline-5-ol

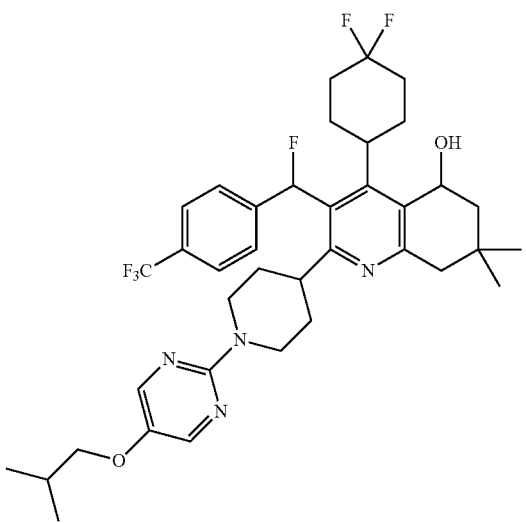 [SMILES: CC(C)COc1cnc(N2CCC(c3nc4c(c(C5CCC(F)(F)CC5)c3C(F)c3ccc(C(F)(F)F)cc3)C(O)CC(C)(C)C4)CC2)nc1]

To a solution of 55 mg (0.085 mmol) of (−)-4-(4,4-Difluorocyclohexyl)-3-{fluoro[4-(trifluoromethyl)phenyl]methyl}-2-[1-(5-hydroxypyrimidin-2-yl)piperidin-4-yl]-7,7-dimethyl-5,6,7,8-tetrahydroquinolin-5-ol, which was prepared by a method similar to that of Example 4, in 1 ml of tetrahydrofuran, 33 mg (0.10 mmol) of cesium carbonate and 11 μl (0.094 mmol) of 1-iodo-2-methyl propane were added, and the reaction solution was stirred at room temperature for 2 hours, at 50° C. for 3 hours and further at room temperature for 14 hours. After stirring at room temperature, 50 (0.43 mmol) of 1-iodo-2-methyl propane and 50 mg (0.15 mmol) of cesium carbonate were added and the reaction solution was stirred at 70° C. for 9 hours. After stirring with heating, 50 μl (0.43 mmol) of 1-iodo-2-methyl propane and 100 mg (0.31 mmol) of cesium carbonate were further added and the reaction solution was stirred at room temperature for 14.5 hours. After completion of the reaction, the reaction solution was poured into water and extracted with ethyl acetate. The organic layer was washed with saturated sodium chloride aqueous solution and dried with anhydrous magnesium sulfate, and then the solvent was distilled off under reduced pressure. The obtained residue was subjected to silica gel column chromatography [n-hexane/ethyl acetate=95/5-70/30 (V/V)] and the fraction including the desired compound was concentrated under reduced pressure. n-Hexane was added to the obtained residue and the precipitate was obtained by filtration to provide 41 mg of the title compound as a white solid (yield: 68%).

Specific optical rotation: $[\alpha]_D^{27}=-65°$ (C=0.15, methanol).

$^1$H-NMR spectrum (300 MHz, CD$_2$Cl$_2$) δ: 8.01 (2H, s), 7.65 (2H, d, J=8 Hz), 7.38 (2H, d, J=8 Hz), 7.22 (1H, d, =47 Hz), 5.13 (1H, dt, J=6, 6 Hz), 4.71-4.59 (1H, m), 4.41-4.30 (1H, m), 3.70-3.57 (1H, m), 3.67 (2H, d, J=7 Hz), 2.88-2.55 (4H, m), 2.37-1.57 (16H, m), 1.13 (3H, s), 1.00 (3H, s), 0.99 (6H, d, J=7 Hz), 0.66-0.55 (1H, m).

Mass spectrum (EI, m/z): 704 [M$^+$].

Example 22

(−)-4-(4,4-difluorocyclohexyl)-3-{fluoro[4-(trifluoromethyl)phenyl]methyl}-7,7-dimethyl-2-{1-[5-(3-methylbutoxyl)pyrimidine-2-yl]piperidin-4-yl}-5,6,7,8-tetrahydroquinoline-5-ol

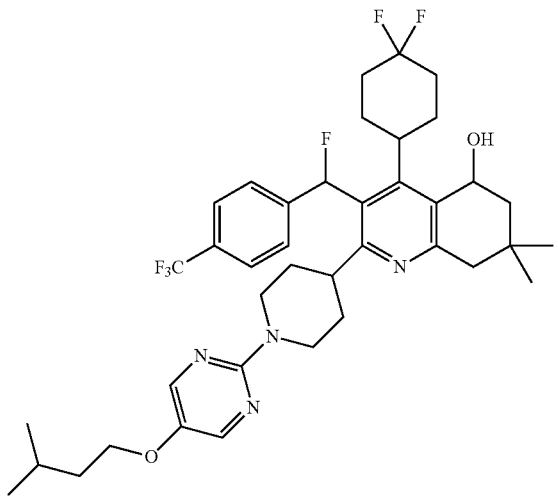 [SMILES: CC(C)CCOc1cnc(N2CCC(c3nc4c(c(C5CCC(F)(F)CC5)c3C(F)c3ccc(C(F)(F)F)cc3)C(O)CC(C)(C)C4)CC2)nc1]

Reactions similar to those of Example 21 were performed except for using 62 (0.47 mmol) of 1-iodo-3-methylbutane instead of 1-iodo-2-methylpropane, and from 55 mg (0.085 mmol) of (−)-4-(4,4-Difluorocyclohexyl)-3-{fluoro[4-(trifluoromethyl)phenyl]methyl}-2-[1-(5-hydroxypyrimidin-2-yl)piperidin-4-yl]-7,7-dimethyl-5,6,7,8-tetrahydroquinolin-5-ol, which was prepared by a method similar to that of Example 4, 40 mg of the title compound was obtained as a white solid (yield: 65%).

Specific optical rotation: $[\alpha]_D^{27} = -69°$ (C=0.18, methanol).

$^1$H-NMR spectrum (300 MHz, CD$_2$Cl$_2$) δ: 8.01 (2H, s), 7.65 (2H, d, J=8 Hz), 7.38 (2H, d, J=8 Hz), 7.22 (1H, d, J=48 Hz), 5.13 (1H, dt, J=6, 6 Hz), 4.70-4.59 (1H, m), 4.42-4.30 (1H, m), 3.93 (2H, t, J=7 Hz), 3.72-3.56 (1H, m), 2.86-2.55 (4H, m), 2.37-1.56 (18H, m), 1.13 (3H, s), 1.00 (3H, s), 0.94 (6H, d, J=7 Hz), 0.67-0.57 (1H, m).

Mass spectrum (EI, m/z): 718 [M$^+$].

Example 23

(−)-2-{1-[5-(4-Carboxybutoxyl)pyrimidin-2-yl]piperidin-4-yl}-4-(4,4-difluorocyclohexyl)-3-{fluoro[4-(trifluoromethyl)phenyl]methyl}-7,7-dimethyl-5,6,7,8-tetrahydroquinolin-5-ol

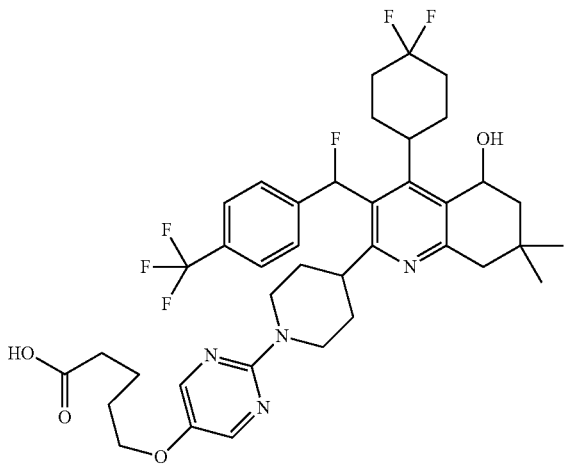 [SMILES: CC1(C)Cc2nc(C3CCN(c4ncc(OCCCCC(=O)O)cn4)CC3)c(C(F)c3ccc(C(F)(F)F)cc3)c(C3CCC(F)(F)CC3)c2C(O)C1]

(23-1) 2-{1-[5-(4-Ethoxycarbonylbutoxyl)pyrimidin-2-yl]piperidin-4-yl}-4-(4,4-difluorocyclohexyl)-3-{fluoro[4-(trifluoromethyl)phenyl]methyl}-7,7-dimethyl-5,6,7,8-tetrahydroquinolin-5-ol

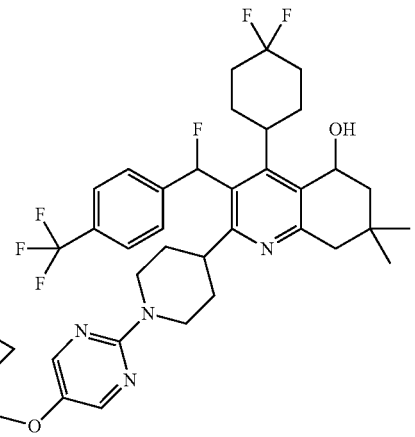

Reactions similar to those of Example 13 were performed except for using ethyl 5-bromovalerate instead of ethyl iodide, and from 85 mg (0.13 mmol) of (−)-4-(4,4-Difluorocyclohexyl)-3-{fluoro[4-(trifluoromethyl)phenyl]methyl}-2-[1-(5-hydroxypyrimidin-2-yl)piperidin-4-yl]-7,7-dimethyl-5,6,7,8-tetrahydroquinolin-5-ol, which was prepared by a method similar to that of Example 10, the crude title compound was obtained. The total amount of the obtained compound was used in Example (23-2).

(23-2) (−)-2-{1-[5-(4-Carboxybutoxyl)pyrimidin-2-yl]piperidin-4-yl}-4-(4,4-difluorocyclohexyl)-3-{fluoro[4-(trifluoromethyl)phenyl]methyl}-7,7-dimethyl-5,6,7,8-tetrahydroquinolin-5-ol

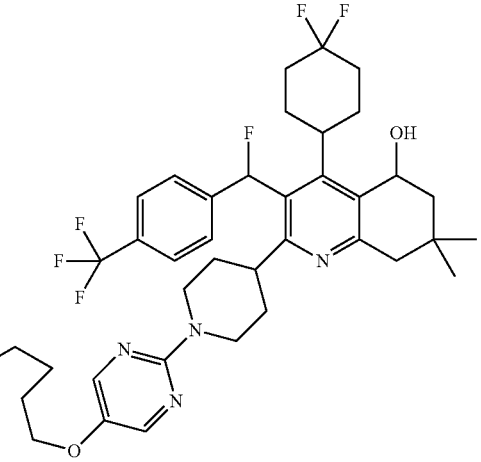

To the crude (−)-2-{1-[5-(4-Ethoxycarbonylbutoxyl)pyrimidin-2-yl]piperidin-4-yl}-4-(4,4-difluorocyclohexyl)-3-{fluoro[4-(trifluoromethyl)phenyl]methyl}-7,7-dimethyl-5,6,7,8-tetrahydroquinolin-5-ol obtained in Example (23-1), 2 ml of tetrahydrofuran, 2 ml of ethanol and 1 ml (1.00 mmol) of 1 N sodium hydroxide aqueous solution were added, and the reaction solution was stirred at room temperature for 1 hour. After completion of the reaction, 1 N hydrochloric acid was poured into the reaction solution under ice cooling and the reaction solution was extracted with methylene chloride. The organic layer was washed with saturated sodium chloride aqueous solution and dried with anhydrous magnesium sulfate, and then the solvent was distilled off under reduced pressure. The obtained residue was purified by high performance liquid chromatography [YMC-pack ODS-A; acetonitrile/aqueous solution of 0.1% acetic acid and 0.1% triethylamine=85/15 (V/V)] to provide 63 mg of the title compound as a white solid (yield in two steps: 64%).

Specific optical rotation: $[\alpha]_D^{24}=-92°$ (C=0.13, chloroform).

$^1$H-NMR spectrum (400 MHz, CDCl$_3$) δ ppm: 8.01 (2H, s), 7.63 (2H, d, J=8 Hz), 7.35 (2H, d, J=8 Hz), 7.20 (1H, d, J=48 Hz), 5.12 (1H, t, J=5 Hz), 4.68-4.59 (1H, m), 4.40-4.30 (1H, m), 3.95-3.85 (2H, m), 3.67-3.55 (1H, m), 2.86-2.58 (4H, m), 2.46-1.58 (21H, m), 1.14 (3H, s), 1.00 (3H, s), 0.67-0.56 (1H, m).

Mass spectrum (FAB, m/z): 749 [(M+1)$^+$].

Example 24

(−)-4-(4,4-Difluorocyclohexyl)-3-{fluoro[4-(trifluoromethyl)phenyl]methyl}-7,7-dimethyl-2-{1-[5-(2-methylpropyl)pyrimidin-2-yl]piperidin-4-yl}-5,6,7,8-tetrahydroquinolin-5-ol

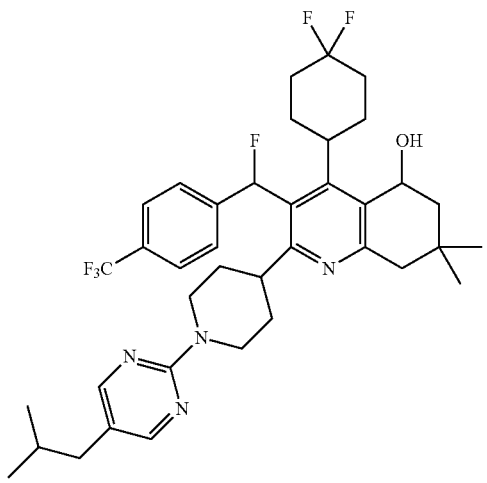 [SMILES: CC(C)Cc1cnc(N2CCC(c3nc4c(c(C5CCC(F)(F)CC5)c3C(F)c3ccc(C(F)(F)F)cc3)C(O)CC(C)(C)C4)CC2)nc1]

To a solution of 70 mg (0.085 mmol) of 4-(4,4-Difluorocyclohexyl)-3-{fluoro[4-(trifluoromethyl)phenyl]methyl}-2-{1-[5-(1-hydroxy-2-methylpropyl)pyrimidin-2-yl]piperidin-4-yl}-5-[(4-methoxybenzyl)oxy]-7,7-dimethyl-5,6,7,8-tetrahydroquinoline, which was prepared by a method similar to that of Reference Example 19, in 5 ml of dichloromethane, 2 ml of triethyl silane and 1 ml of trifluoroacetic acid were added, and the reaction solution was stirred at room temperature for 41 hours. After completion of the reaction, the reaction solution was poured into saturated sodium hydrogencarbonate aqueous solution and extracted with ethyl acetate. The organic layer was washed with saturated sodium chloride aqueous solution and dried with anhydrous magnesium sulfate, and then the solvent was distilled off under reduced pressure. The obtained residue was subjected to silica gel column chromatography [n-hexane/ethyl acetate=95/5-85/15 (V/V)] and the fraction including the desired compound was concentrated under reduced pressure. n-Hexane was added to the obtained residue and the precipitate was obtained by filtration to provide 16 mg of the title compound as a white solid (yield: 27%).

Specific optical rotation: $[\alpha]_D^{24}=-88°$ (C=0.050, methanol).

$^1$H-NMR spectrum (300 MHz, CD$_2$Cl$_2$) δ: 8.05 (2H, s), 7.65 (2H, d, J=8 Hz), 7.39 (2H, d, J=8 Hz), 7.22 (1H, d, J=47 Hz), 5.13 (1H, dt, J=6, 6 Hz), 4.80-4.68 (1H, m), 4.51-4.39 (1H, m), 3.72-3.55 (1H, m), 2.88-2.55 (4H, m), 2.37-1.49 (18H, m), 1.13 (3H, s), 0.99 (3H, s), 0.88 (6H, d, J=7 Hz), 0.68-0.57 (1H, m).

Mass spectrum (EI, m/z): 688 [M$^+$].

Example 25

(−)-2-{1-[5-(4-carboxybutyl)pyrimidine-2-yl]piperidin-4-yl}-4-(4,4-difluorocyclohexyl)-3-{fluoro[4-(trifluoromethyl)phenyl]methyl}-7,7-dimethyl-5,6,7,8-tetrahydroquinoline-5-ol

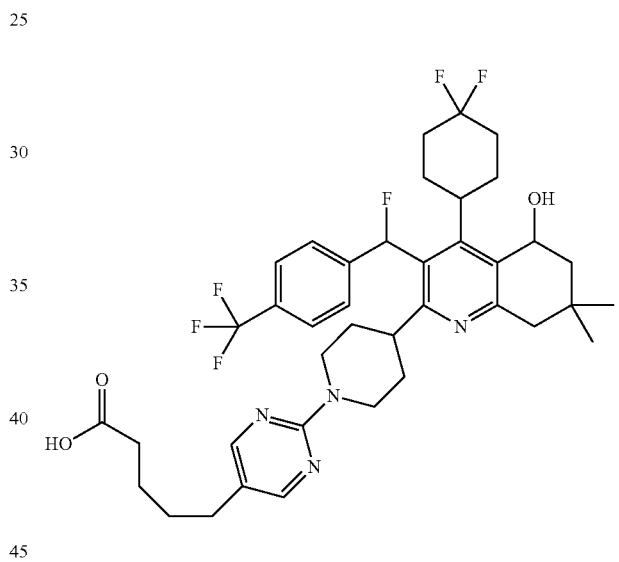

Reactions similar to those of the first step of Example 2, Example 38 and Example (23-2) were performed, and from 100 mg (0.148 mmol) of (−)-4-(4,4-Difluorocyclohexyl)-3-{fluoro[4-(trifluoromethyl)phenyl]methyl}-5-[(4-methoxybenzyl)oxy]-7,7-dimethyl-2-(piperidin-4-yl)-5,6,7,8-tetrahydroquinoline, which was prepared by a method similar to that of Reference Example 10, 79 mg of the title compound was obtained as a white solid (yield: 73%). Methyl 5-(2-chloropyrimidin-5-yl)pentanoate, which was prepared by a method similar to that of Reference Example 20, was used instead of 5-bromo-2-chloropyrimidine in the step corresponding to the first step of Example 2.

Specific optical rotation: $[\alpha]_D^{25}=-68°$ (C=0.14, chloroform).

$^1$H-NMR spectrum (500 MHz, CDCl$_3$) δ ppm: 8.09 (2H, s), 7.63 (2H, d, J=8 Hz), 7.36 (2H, d, J=8 Hz), 7.21 (1H, d, J=47 Hz), 5.15-5.08 (1H, m), 4.78-4.68 (1H, m), 4.50-4.40 (1H, m), 3.67-3.57 (1H, m), 2.84-2.59 (4H, m), 2.47-1.49 (23H, m), 1.14 (3H, s), 1.00 (3H, s), 0.67-0.59 (1H, m).

Mass spectrum (FAB, m/z): 733[(M+1)$^+$].

Example 26

(−)-4-(4,4-Difluorocyclohexyl)-2-{1-[5-(ethoxymethyl)pyrimidin-2-yl]piperidin-4-yl}-3-{fluoro[4-(trifluoromethyl)phenyl]methyl}-7,7-dimethyl-5,6,7,8-tetrahydroquinolin-5-ol

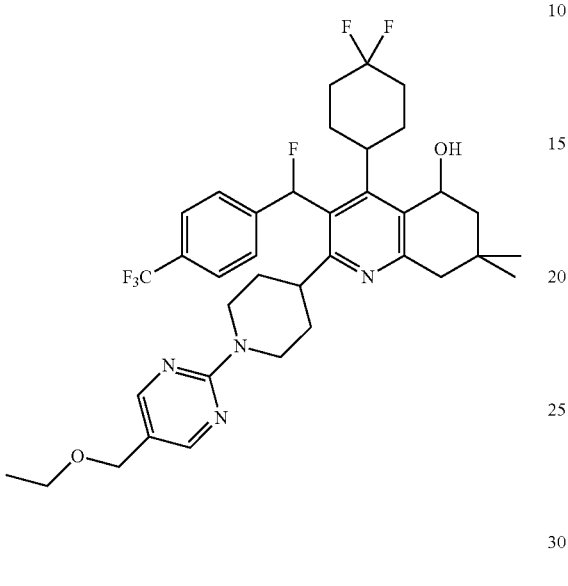

To a solution of 68 mg (0.085 mmol) of 4-(4,4-Difluorocyclohexyl)-2-{1-[5-(ethoxymethyl)pyrimidin-2-yl]piperidin-4-yl}-3-{fluoro[4-(trifluoromethyl)phenyl]methyl}-5-[(4-methoxybenzyl)oxy]-7,7-dimethyl-5,6,7,8-tetrahydroquinoline, which was prepared by a method similar to that of Reference Example 21, in 1 ml of dichloromethane, 46 μl of anisole and 130 μl of trifluoroacetic acid were added, and the reaction solution was stirred at room temperature for 19 hours. Then, 100 μl of trifluoroacetic acid was further added and the reaction solution was stirred at room temperature for 1 hour. After completion of the reaction, the reaction solution was poured into saturated sodium hydrogencarbonate aqueous solution and extracted with ethyl acetate. The organic layer was washed with saturated sodium chloride aqueous solution and dried with anhydrous magnesium sulfate, and then the solvent was distilled off under reduced pressure. The obtained residue was subjected to silica gel column chromatography [n-hexane/ethyl acetate=98/2-70/30 (V/V)] and the fraction including the desired compound was concentrated under reduced pressure. n-Hexane was added to the obtained residue and the precipitate was obtained by filtration to provide 34 mg of the title compound as a white solid (yield: 58%).

Specific optical rotation: $[\alpha]_D^{24}=-65°$ (C=0.055, methanol).

$^1$H-NMR spectrum (300 MHz, CD$_2$Cl$_2$) δ: 8.20 (2H, s), 7.66 (2H, d, J=8 Hz), 7.39 (2H, d, J=8 Hz), 7.22 (1H, d, J=47 Hz), 5.12 (1H, dt, J=6, 6 Hz), 4.84-4.74 (1H, m), 4.55-4.44 (1H, m), 4.25 (2H, s), 3.71-3.56 (1H, m), 3.47 (2H, q, J=7 Hz), 2.91-2.55 (4H, m), 2.36-1.55 (15H, m), 1.17 (3H, t, J=7 Hz), 1.13 (3H, s), 0.99 (3H, s), 0.68-0.58 (1H, m).

Mass spectrum (EI, m/z): 690 [M$^+$].

Example 27

(−)-4-(4,4-Difluorocyclohexyl)-3-{fluoro[4-(trifluoromethyl)phenyl]methyl}-2-{1-[5-(methoxymethyl)pyrimidin-2-yl]piperidin-4-yl}-7,7-dimethyl-5,6,7,8-tetrahydroquinolin-5-ol

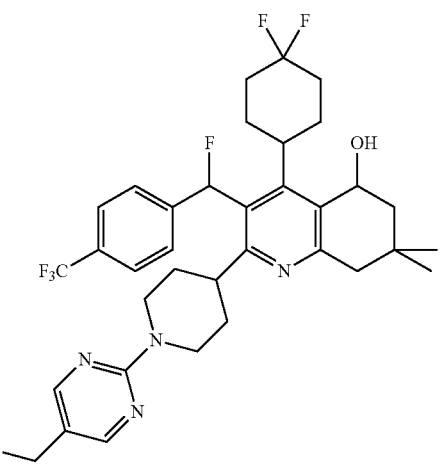

Reactions similar to those of Example 24 were performed except for using 42 mg (0.053 mmol) of 4-(4,4-Difluorocyclohexyl)-3-{fluoro[4-(trifluoromethyl)phenyl]methyl}-5-[(4-methoxybenzyl)oxy]-2-{1-[5-(methoxymethyl)pyrimidin-2-yl]piperidin-4-yl}-7,7-dimethyl-5,6,7,8-tetrahydroquinoline, which was prepared by a method similar to that of Reference Example 22 instead of 4-(4,4-difluorocyclohexyl)-3-{fluoro[4-(trifluoromethyl)phenyl]methyl}-2-{1-[5-(1-hydroxy-2-methylpropyl)pyrimidin-2-yl]piperidin-4-yl}-5-[(4-methoxybenzyl)oxy]-7,7-dimethyl-5,6,7,8-tetrahydroquinoline to provide 34 mg of the title compound as a foam (yield: 96%).

Specific optical rotation: $[\alpha]_D^{24}=-82°$ (C=0.090, methanol).

$^1$H-NMR spectrum (300 MHz, CD$_2$Cl$_2$) δ: 8.19 (2H, s), 7.66 (2H, d, J=8 Hz), 7.39 (2H, d, J=8 Hz), 7.23 (1H, d, J=47 Hz), 5.13 (1H, dt, J=6, 6 Hz), 4.86-4.74 (1H, m), 4.56-4.45 (1H, m), 4.20 (2H, s), 3.72-3.56 (1H, m), 3.30 (3H, s), 2.90-2.55 (4H, m), 2.37-1.48 (15H, m), 1.13 (3H, s), 0.99 (3H, s), 0.68-0.58 (1H, m).

Mass spectrum (EI, m/z): 676 [M$^+$].

Example 28

(−)-4-(4,4-difluorocyclohexyl)-3-{fluoro[4-(trifluoromethyl)phenyl]methyl}-7,7-dimethyl-2-(1-{5-[(propan-2-yloxy)methyl]pyrimidine-2-yl}piperidin-4-yl)-5,6,7,8-tetrahydroquinolin-5-ol

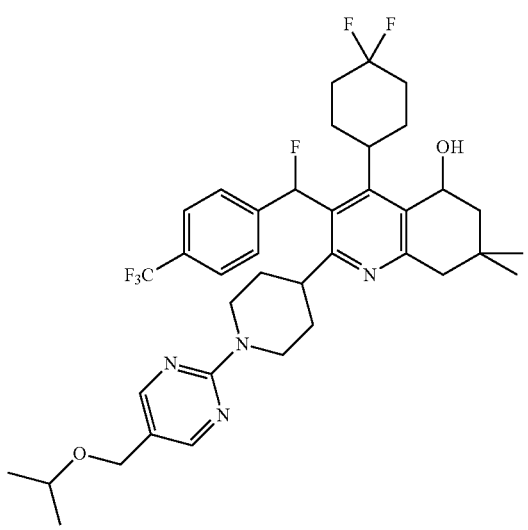 [SMILES: CC(C)OCc1cnc(N2CCC(c3nc4c(c(C5CCC(F)(F)CC5)c3C(F)c3ccc(C(F)(F)F)cc3)C(O)CC(C)(C)C4)CC2)nc1]

Reactions similar to those of Example 26 were performed except for using 54 mg (0.065 mmol) of 4-(4,4-Difluorocyclohexyl)-3-{fluoro[4-(trifluoromethyl)phenyl]methyl}-5-[(4-methoxybenzyl)oxy]-7,7-dimethyl-2-(1-{5-[(propan-2-yloxy)methyl]pyrimidin-2-yl}piperidin-4-yl)-5,6,7,8-tetrahydroquinoline, which was prepared by a method similar to that of Reference Example 23 instead of 4-(4,4-Difluorocyclohexyl)-2-{1-[5-(ethoxymethyl)pyrimidin-2-yl]piperidin-4-yl}-3-{fluoro[4-(trifluoromethyl)phenyl]methyl}-5-[(4-methoxybenzyl)oxy]-7,7-dimethyl-5,6,7,8-tetrahydroquinoline to provide 31 mg of the title compound as a white solid (yield: 67%).

Specific optical rotation: $[\alpha]_D^{24} = -92°$ (C=0.050, methanol).

$^1$H-NMR spectrum (300 MHz, CD$_2$Cl$_2$) δ: 8.19 (2H, s), 7.66 (2H, d, J=8 Hz), 7.39 (2H, d, J=8 Hz), 7.22 (1H, d, J=47 Hz), 5.13 (1H, dt, J=6, 6 Hz), 4.83-4.72 (1H, m), 4.56-4.43 (1H, m), 4.25 (2H, s), 3.72-3.56 (1H, m), 3.63 (1H, dq, J=6, 6 Hz), 2.92-2.54 (4H, m), 2.38-1.44 (15H, m), 1.15 (6H, d, J=6 Hz), 1.13 (3H, s), 0.99 (3H, s), 0.67-0.57 (1H, m).

Mass spectrum (EI, m/z): 704 [M$^+$].

Example 29

(−)-4-(4,4-Difluorocyclohexyl)-3-{fluoro[4-(trifluoromethyl)phenyl]methyl}-7,7-dimethyl-2-(1-{5-[(2-methylpropoxy)methyl]pyrimidin-2-yl}piperidin-4-yl)-5,6,7,8-tetrahydroquinolin-5-ol

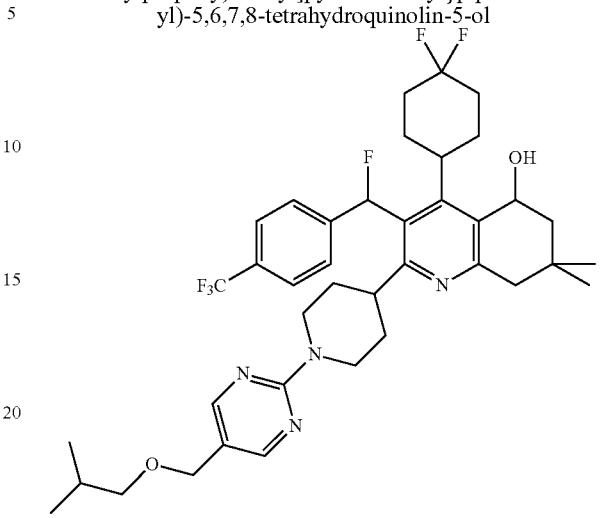

Reactions similar to those of Example 26 were performed except for using 59 mg (0.070 mmol) of 4-(4,4-Difluorocyclohexyl)-3-{fluoro[4-(trifluoromethyl)phenyl]methyl}-5-[(4-methoxybenzyl)oxy]-7,7-dimethyl-2-(1-{5-[(2-methylpropoxy)methyl]pyrimidin-2-yl}piperidin-4-yl)-5,6,7,8-tetrahydroquinoline, which was prepared by a method similar to that of Reference Example 24 instead of 4-(4,4-difluorocyclohexyl)-2-{1-[5-(ethoxymethyl)pyrimidin-2-yl]piperidin-4-yl}-3-{fluoro[4-(trifluoromethyl)phenyl]methyl}-5-[(4-methoxybenzyl)oxy]-7,7-dimethyl-5,6,7,8-tetrahydroquinoline to provide 35 mg of the title compound as a white solid (yield: 69%).

Specific optical rotation: $[\alpha]_D^{24} = -110°$ (C=0.050, methanol).

$^1$H-NMR spectrum (300 MHz, CD$_2$Cl$_2$) δ: 8.20 (2H, s), 7.66 (2H, d, J=8 Hz), 7.39 (2H, d, J=8 Hz), 7.23 (1H, d, J=47 Hz), 5.13 (1H, dt, J=6, 6 Hz), 4.84-4.74 (1H, m), 4.56-4.45 (1H, m), 4.25 (2H, s), 3.71-3.57 (1H, m), 3.17 (2H, d, J=7 Hz), 2.89-2.55 (4H, m), 2.36-1.56 (16H, m), 1.13 (3H, s), 0.99 (3H, s), 0.88 (6H, d, J=7 Hz), 0.67-0.57 (1H, m).

Mass spectrum (EI, m/z): 718 [M$^+$].

Example 30

4-(4,4-Difluorocyclohexyl)-3-{fluoro[4-(trifluoromethyl)phenyl]methyl}-7,7-dimethyl-2-{1-[5-(methylcarbamoyl)pyrimidin-2-yl]piperidin-4-yl}-5,6,7,8-tetrahydroquinolin-5-ol

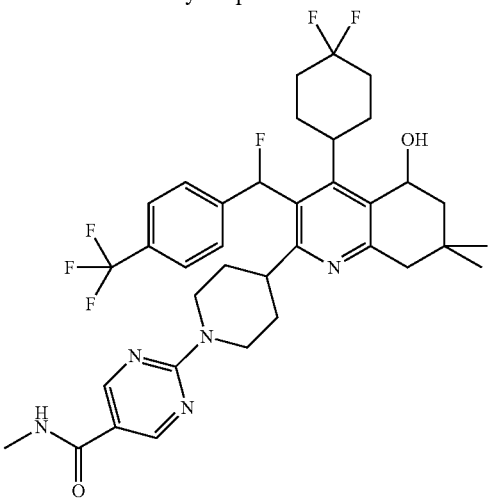

Reactions similar to those of Example 38 were performed, and from the total amount of the crude product of 4-(4,4-Difluorocyclohexyl)-3-{fluoro[4-(trifluoromethyl)phenyl]methyl}-5-[(4-methoxybenzyl)oxy]-7,7-dimethyl-2-{1-[5-(methylcarbamoyl)pyrimidin-2-yl]piperidin-4-yl}-5,6,7,8-tetrahydroquinoline, which was prepared in Reference Example 25, 28 mg of the title compound was obtained as a white solid (yield: 54%).

¹H-NMR spectrum (500 MHz, CDCl₃) δ ppm: 8.60 (2H, s), 7.64 (2H, d, J=8 Hz), 7.37 (2H, d, J=8 Hz), 7.22 (1H, d, J=46 Hz), 5.89 (1H, br s), 5.15-5.08 (1H, m), 4.92-4.84 (1H, m), 4.65-4.56 (1H, m), 3.69-3.59 (1H, m), 2.97 (3H, d, J=5 Hz), 2.89-2.47 (4H, m), 2.35-1.55 (15H, m), 1.14 (3H, s), 1.00 (3H, s), 0.70-0.62 (1H, m).

Mass spectrum (ES, m/z): 690 [M⁺].

Example 31

(−)-4-(4,4-Difluorocyclohexyl)-2-{1-[5-(dimethylcarbamoyl)pyrimidin-2-yl]piperidin-4-yl}-3-{fluoro[4-(trifluoromethyl)phenyl]methyl}-7,7-dimethyl-5,6,7,8-tetrahydroquinolin-5-ol

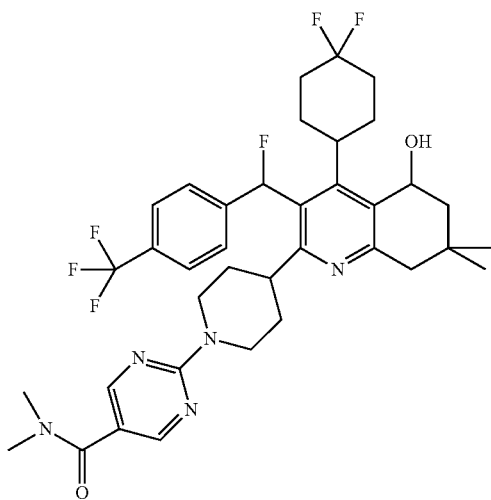

Reactions similar to those of the second step of Reference Example 25 and Example 38 were performed except for using dimethylamine aqueous solution instead of methylamine aqueous solution, and from 70 mg of the crude product of 2-[1-(5-Carboxypyrimidin-2-yl)piperidin-4-yl]-4-(4,4-difluorocyclohexyl)-3-{fluoro[4-(trifluoromethyl)phenyl]methyl}-5-[(4-methoxybenzyl)oxy]-7,7-dimethyl-5,6,7,8-tetrahydroquinoline, which was prepared in the first step of Reference Example 25, 30 mg of the title compound was obtained as a white solid (yield: 56%).

Specific optical rotation: [α]_D^25=−87° (C=0.12, chloroform).

¹H-NMR spectrum (500 MHz, CDCl₃) δ ppm: 8.40 (2H, s), 7.64 (2H, d, J=8 Hz), 7.37 (2H, d, J=8 Hz), 7.22 (1H, d, J=47 Hz), 5.15-5.09 (1H, m), 4.91-4.82 (1H, m), 4.62-4.55 (1H, m), 3.67-3.59 (1H, m), 3.08 (6H, s), 2.93-2.60 (4H, m), 2.35-1.54 (15H, m), 1.14 (3H, s), 1.00 (3H, s), 0.69-0.62 (1H, m).

Mass spectrum (ES, m/z): 704 [M⁺].

Example 32

4-(4,4-Difluorocyclohexyl)-3-{fluoro[4-(trifluoromethyl)phenyl]methyl}-7,7-dimethyl-2-{1-[5-(morpholin-4-yl-carbonyl)pyrimidin-2-yl]piperidin-4-yl}-5,6,7,8-tetrahydroquinolin-5-ol

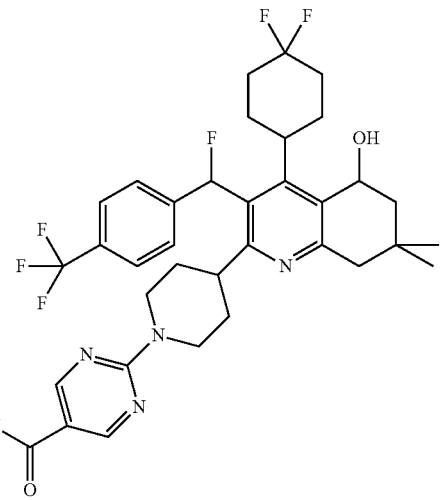

Reactions similar to those of the second step of Reference Example 25 and Example 38 were performed except for using morpholine instead of methylamine aqueous solution, and from 70 mg of the crude product of 2-[1-(5-Carboxypyrimidin-2-yl)piperidin-4-yl]-4-(4,4-difluorocyclohexyl)-3-{fluoro[4-(trifluoromethyl)phenyl]methyl}-5-[(4-methoxybenzyl)oxy]-7,7-dimethyl-5,6,7,8-tetrahydroquinoline, which was prepared in the first step of Reference Example 25, 27 mg of the title compound was obtained as a white solid (yield: 49%).

¹H-NMR spectrum (500 MHz, CDCl₃) δ ppm: 8.37 (2H, s), 7.64 (2H, d, J=8 Hz), 7.37 (2H, d, J=8 Hz), 7.22 (1H, d, J=47 Hz), 5.12 (1H, q, J=6 Hz), 4.90-4.82 (1H, m), 4.63-4.54 (1H, m), 3.78-3.54 (9H, m), 2.90-2.59 (4H, m), 2.36-1.56 (15H, m), 1.14 (3H, s), 1.00 (3H, s), 0.70-0.61 (1H, m).

Mass spectrum (ES, m/z): 746 [M⁺].

Example 33

4-(4,4-Difluorocyclohexyl)-3-{fluoro[4-(trifluoromethyl)phenyl]methyl}-7,7-dimethyl-2-{1-[5-(4,4,4-trifluorobutyl)pyrimidin-2-yl]piperidin-4-yl}-5,6,7,8-tetrahydroquinolin-5-ol

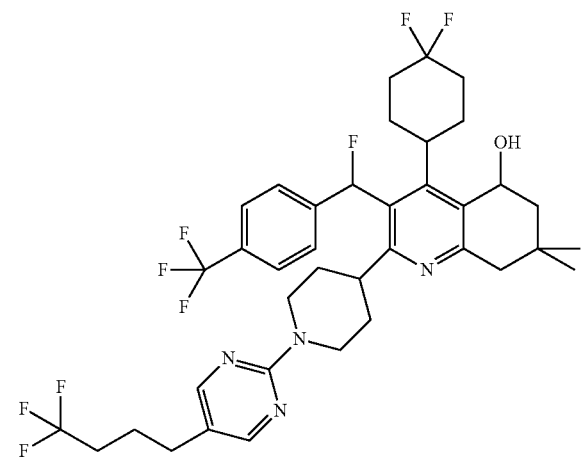

Reactions similar to those of the first step of Example 2 and Example 38 were performed except for using 2-chloro-5-(4,4,4-trifluorobutyl) pyrimidine, which was prepared by a method similar to that of Reference Example 26, instead of 5-bromo-2-chloropyrimidine, and from 70 mg (0.10 mmol) of (−)-4-(4,4-Difluorocyclohexyl)-3-{fluoro[4-(trifluoromethyl)phenyl]methyl}-5-[(4-methoxybenzyl)oxy]-7,7-dimethyl-2-(piperidin-4-yl)-5,6,7,8-tetrahydroquinoline, which was prepared by a method similar to that of Reference Example 10, 45 mg of the title compound was obtained as a white solid (yield: 61%).

$^1$H-NMR spectrum (400 MHz, CDCl$_3$) δ ppm: 8.09 (2H, s), 7.64 (2H, d, J=8 Hz), 7.37 (2H, d, J=8 Hz), 7.21 (1H, d, J=45 Hz), 5.17-5.07 (1H, m), 4.81-4.71 (1H, m), 4.53-4.43 (1H, m), 3.68-3.57 (1H, m), 2.85-2.58 (4H, m), 2.47 (2H, t, J=7 Hz), 2.37-1.59 (19H, m), 1.15 (3H, s), 1.01 (3H, s), 0.68-0.59 (1H, m).

Mass spectrum (FAB, m/z): 743 [(M+1)$^+$].

Example 34

(−)-4-(4,4-Difluorocyclohexyl)-3-{fluoro[4-(trifluoromethyl)phenyl]methyl}-7,7-dimethyl-2-(1-{5-[(1E)-3-methylbut-1-ene-1-yl]pyrimidin-2-yl}piperidin-4-yl)-5,6,7,8-tetrahydroquinolin-5-ol

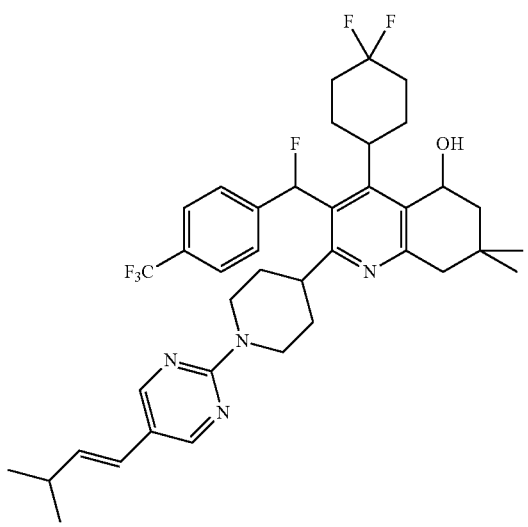 [SMILES: CC(C)/C=C/c1cnc(N2CCC(c3nc4c(c(C5CCC(F)(F)CC5)c3C(F)c3ccc(C(F)(F)F)cc3)C(O)CC(C)(C)C4)CC2)nc1]

To a solution of 118 mg (0.141 mmol) of 4-(4,4-Difluorocyclohexyl)-3-{fluoro[4-(trifluoromethyl)phenyl]methyl}-2-{1-[5-(1-hydroxy-3-methylbutyl)pyrimidin-2-yl]piperidin-4-yl}-5-[(4-methoxybenzyl)oxy]-7,7-dimethyl-5,6,7,8-tetrahydroquinoline, which was prepared by a method similar to that of Reference Example 27, in 2 ml of 1,4-dioxane, 2 ml of 2 N hydrochloric acid was added, and the reaction solution was stirred at 100° C. for 3.5 hours. After completion of the reaction, the reaction solution was poured into saturated sodium hydrogencarbonate aqueous solution and extracted with ethyl acetate. The organic layer was washed with saturated sodium chloride aqueous solution and dried with anhydrous magnesium sulfate, and then the solvent was distilled off under reduced pressure. The obtained residue was subjected to silica gel column chromatography [n-hexane/ethyl acetate=92/8-88/12 (V/V)] and the fraction including the desired compound was concentrated under reduced pressure to provide 72 mg of the title compound as a white solid (yield: 73%).

Specific optical rotation: [α]$_D^{24}$=−89° (C=0.15, methanol).

$^1$H-NMR spectrum (300 MHz, CD$_2$Cl$_2$) δ: 8.24 (2H, s), 7.66 (2H, d, J=8 Hz), 7.39 (2H, d, J=8 Hz), 7.23 (1H, d, J=47 Hz), 6.11 (1H, d, J=16 Hz), 6.02 (1H, dd, J=16, 6 Hz), 5.13 (1H, dt, J=6, 6 Hz), 4.85-4.71 (1H, m), 4.56-4.41 (1H, m), 3.73-3.56 (1H, m), 2.89-2.54 (4H, m), 2.49-1.55 (16H, m), 1.13 (3H, s), 1.06 (6H, d, J=7 Hz), 0.99 (3H, s), 0.69-0.57 (1H, m).

Mass spectrum (EI, m/z): 700 [M$^+$].

Example 35

4-(4,4-Difluorocyclohexyl)-3-{fluoro[4-(trifluoromethyl)phenyl]methyl}-7,7-dimethyl-2-{1-[5-(3-methyl-1,2,4-oxadiazol-5-yl)pyrimidin-2-yl]piperidin-4-yl}-5,6,7,8-tetrahydroquinolin-5-ol

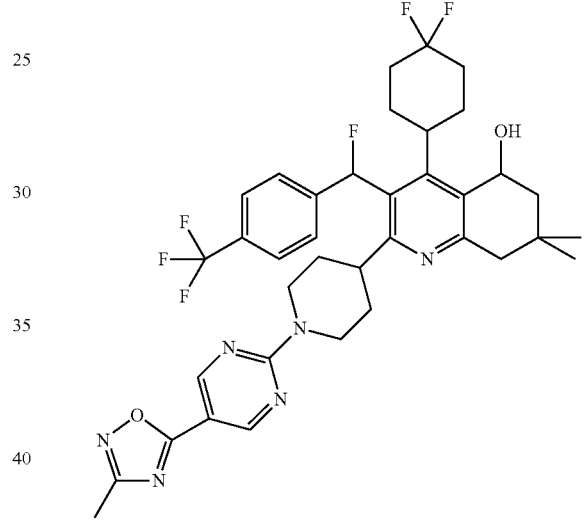

To 96 mg (0.12 mmol) of 2-[1-(5-Carboxypyrimidin-2-yl)piperidin-4-yl]-4-(4,4-difluorocyclohexyl)-3-{fluoro[4-(trifluoromethyl)phenyl]methyl}-5-[(4-methoxybenzyl)oxy]-7,7-dimethyl-5,6,7,8-tetrahydroquinoline, which was prepared by a method similar to that of the first step of Reference Example 25, 3 ml of acetonitrile, 2 ml of tetrahydrofuran, 27 mg (0.36 mmol) of N-hydroxyacetamidine, 58 mg (0.30 mmol) of 1-ethyl-3-(3-dimethylaminopropyl)carbodiimide hydrochloride, 50 µl (0.36 mmol) of triethylamine and 41 mg (0.30 mmol) of 1-hydroxybenzotriazole were added, and the reaction solution was stirred at room temperature for 3 hours. After completion of the reaction, the reaction solution was poured into water and extracted with ethyl acetate. The organic layer was washed with 0.1 N hydrochloric acid, saturated sodium hydrogencarbonate aqueous solution and saturated sodium chloride aqueous solution in order and dried with anhydrous sodium sulfate, and then the solvent was distilled off under reduced pressure.

The obtained crude product was dissolved in 2 ml of N,N-dimethylacetamide and the reaction solution was stirred at 120° C. for 2 hours. After completion of the reaction, the reaction solution was poured into water and extracted with ethyl acetate. The organic layer was washed with saturated sodium hydrogencarbonate aqueous solution and saturated sodium chloride aqueous solution and dried with anhydrous sodium sulfate, and then the solvent was distilled off under reduced pressure. The obtained residue was subjected to silica gel column chromatography [n-hexane/ethyl acetate=97/3-4/1 (V/V)] and the fraction including the desired compound was concentrated under reduced pressure to provide 57 mg (0.068 mmol) of 4-(4,4-Difluorocyclohexyl)-3-{fluoro[4-(trifluoromethyl)phenyl]methyl}-5-[(4-methoxybenzyl)oxy]-7,7-dimethyl-2-{1-[5-(3-methyl-1,2,4-oxadiazol-5-yl)pyrimidin-2-yl]piperidin-4-yl}-5,6,7,8-tetrahydroquinoline.

Reactions similar to those of Example 38 were performed, from 57 mg (0.068 mmol) of 4-(4,4-Difluorocyclohexyl)-3-{fluoro[4-(trifluoromethyl)phenyl]methyl}-5-[(4-methoxybenzyl)oxy]-7,7-dimethyl-2-{1-[5-(3-methyl-1,2,4-oxadiazol-5-yl)pyrimidin-2-yl]piperidin-4-yl}-5,6,7,8-tetrahydroquinoline obtained above to provide the title compound 35 mg of as a white solid (yield: 72%).

$^1$H-NMR spectrum (400 MHz, CDCl$_3$) δ ppm: 8.87 (2H, s), 7.65 (2H, d, J=8 Hz), 7.38 (2H, d, J=8 Hz), 7.22 (1H, d, J=47 Hz), 5.16-5.08 (1H, m), 4.99-4.90 (1H, m), 4.73-4.63 (1H, m), 3.69-3.57 (1H, m), 2.90-2.58 (4H, m), 2.43 (3H, s), 2.36-2.06 (6H, m), 1.98-1.58 (9H, m), 1.14 (3H, s), 1.00 (3H, s), 0.73-0.64 (1H, m).

Mass spectrum (FAB, m/z): 715 [(M+1)$^+$].

Example 36

(−)-4-(4,4-difluorocyclohexyl)-3-{fluoro[4-(trifluoromethyl)phenyl]methyl}-2-{1-(5-{[(2-hydroxyethyl)(methyl)amino]methyl}pyrimidine-2-yl)piperidin-4-yl}-7,7-dimethyl-5,6,7,8-tetrahydroquinoline-5-ol (36-1) 4-(4,4-Difluorocyclohexyl)-3-{fluoro[4-(trifluoromethyl)phenyl]methyl}-2-[1-(5-formylpyrimidin-2-yl)piperidin-4-yl]-7,7-dimethyl-5,6,7,8-tetrahydroquinolin-5-ol

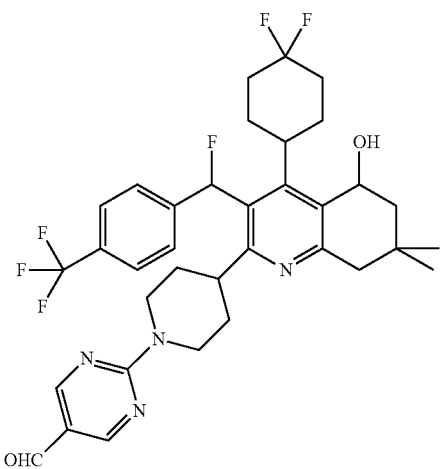 [SMILES: CC1(C)Cc2nc(C3CCN(c4ncc(C=O)cn4)CC3)c(C(F)c3ccc(C(F)(F)F)cc3)c(C3CCC(F)(F)CC3)c2C(O)C1]

Reactions similar to those of Example 38 were performed, from 410 mg (0.525 mmol) of 4-(4,4-Difluorocyclohexyl)-3-{fluoro[4-(trifluoromethyl)phenyl]methyl}-2-[1-(5-formylpyrimidin-2-yl)piperidin-4-yl]-5-[(4-methoxybenzyl)oxy]-7,7-dimethyl-5,6,7,8-tetrahydroquinoline, which was prepared by a method similar to that of Reference Example 16 to provide 309 mg (0.468 mmol) of 4-(4,4-Difluorocyclohexyl)-3-{fluoro[4-(trifluoromethyl)phenyl]methyl}-2-[1-(5-formylpyrimidin-2-yl)piperidin-4-yl]-7,7-dimethyl-5,6,7,8-tetrahydroquinolin-5-ol.

(36-2) (−)-4-(4,4-Difluorocyclohexyl)-3-{fluoro[4-(trifluoromethyl)phenyl]methyl}-2-{1-(5-{[(2-hydroxyethyl)(methyl)amino]methyl}pyrimidin-2-yl)piperidin-4-yl}-7,7-dimethyl-5,6,7,8-tetrahydroquinolin-5-ol

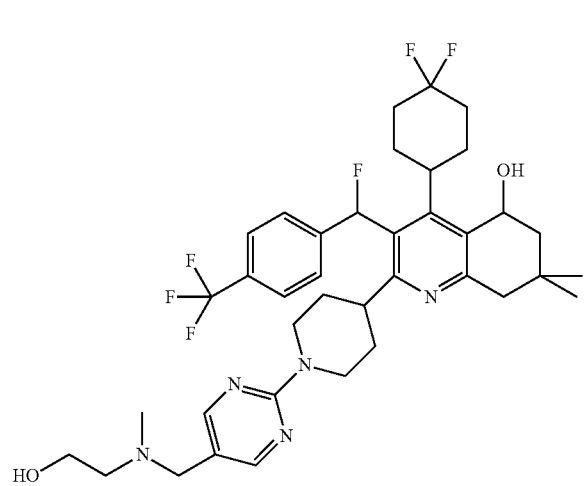 [SMILES: CN(CCO)Cc1cnc(N2CCC(c3nc4c(c(C5CCC(F)(F)CC5)c3C(F)c3ccc(C(F)(F)F)cc3)C(O)CC(C)(C)C4)CC2)nc1]

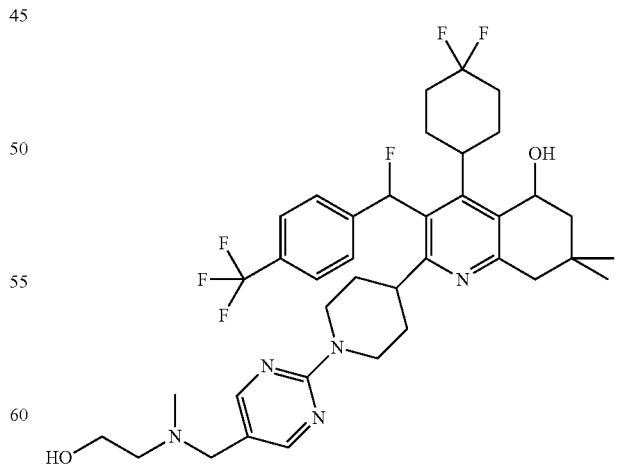

To a solution of 70 mg (0.11 mmol) of 4-(4,4-Difluorocyclohexyl)-3-{fluoro[4-(trifluoromethyl)phenyl]methyl}-2-[1-(5-formyl pyrimidin-2-yl)piperidin-4-yl]-7,7-dimethyl-5,6,7,8-tetrahydroquinolin-5-ol obtained in Example (36-1) in 1.0 ml of tetrahydrofuran, 6.1 μl (0.11 mmol) of acetic acid, 26 μl (0.32 mmol) of 2-(methylamino)ethanol and 68 mg (0.32 mmol) of sodium triacetoxyborohydride were added, and the reaction solution was stirred at room temperature for 3 hours. After completion of the reaction, saturated sodium hydrogencarbonate aqueous solution was added to the reaction solution and the reaction solution was extracted with dichloromethane. The organic layer was dried with anhydrous sodium sulfate, and then the solvent was distilled off under reduced pressure. The obtained residue was subjected to silica gel column chromatography [dichloromethane/methanol/28% ammonia aqueous solution=95/4.75/0.25-80/19/1 (V/V/V)] to provide 68 mg of the title compound as a white solid (yield: 89%).

Specific optical rotation: $[α]_D^{25}$=−80° (C=0.11, chloroform).

$^1$H-NMR spectrum (500 MHz, CDCl$_3$) δ ppm: 8.15 (2H, s), 7.64 (2H, d, J=8 Hz), 7.37 (2H, d, J=8 Hz), 7.21 (1H, d, J=49 Hz), 5.16-5.09 (1H, m), 4.83-4.74 (1H, m), 4.55-4.47 (1H, m), 3.68-3.57 (3H, m), 3.38 (2H, s), 2.94-2.60 (5H, m), 2.57 (2H, t, J=5 Hz), 2.37-1.56 (15H, m), 2.20 (3H, s), 1.14 (3H, s), 1.00 (3H, s), 0.68-0.61 (1H, m).

Mass spectrum (ES, m/z): 720 [M$^+$].

Example 37

(−)-4-(4,4-Difluorocyclohexyl)-3-{fluoro[4-(trifluoromethyl)phenyl]methyl}-2-[1-(5-{[(2S)-2-hydroxypropyl]oxy}pyrimidin-2-yl)piperidin-4-yl]-7,7-dimethyl-5,6,7,8-tetrahydroquinolin-5-ol

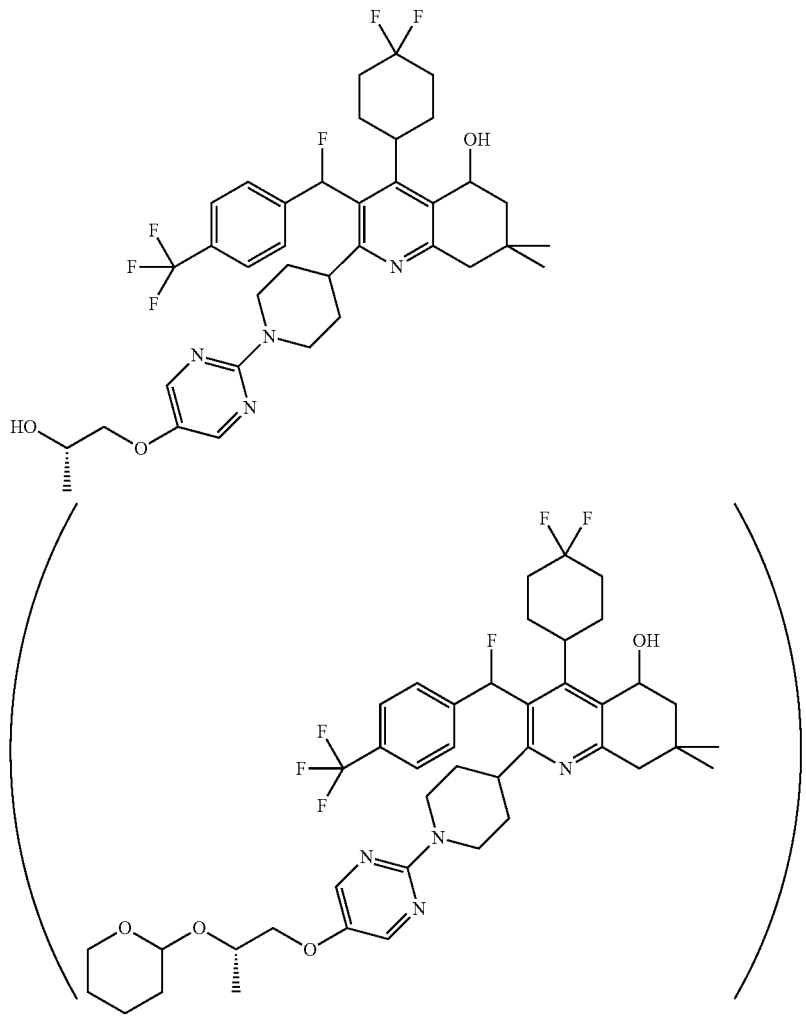

Reactions similar to those of Example 13 were performed except for using (2S)-2-(tetrahydro-2H-pyran-2-yloxy)propyl 4-methyl benzene sulfonate which was synthesized by the method described in P. Huszthy et al., Journal of Organic Chemistry, 1992, Vol. 57, pp. 5383-5394, instead of ethyl iodide, and from 50 mg (77 μmol) of (−)-4-(4,4-Difluorocyclohexyl)-3-{fluoro[4-(trifluoromethyl)phenyl]methyl}-2-[1-(5-hydroxypyrimidin-2-yl)piperidin-4-yl]-7,7-dimethyl-5,6,7,8-tetrahydroquinolin-5-ol, which was prepared by a method similar to that of Example 4, 49 mg (62 μmol) of 4-(4,4-Difluorocyclohexyl)-3-{fluoro[4-(trifluoromethyl)phenyl]methyl}-7,7-dimethyl-2-[1-(5-{[(2S)-2-(tetrahydro-2H-pyran-2-yloxy)propyl]oxy}pyrimidin-2-yl)piperidin-4-yl]-5,6,7,8-tetrahydroquinolin-5-ol was obtained.

To a solution of 49 mg (62 μmol) of 4-(4,4-Difluorocyclohexyl)-3-{fluoro[4-(trifluoromethyl)phenyl]methyl}-7,7-dimethyl-2-{1-(5-{[(2S)-2-(tetrahydro-2H-pyran-2-yloxy)propyl]oxy}pyrimidin-2-yl)piperidin-4-yl}-5,6,7,8-tetrahydroquinolin-5-ol obtained above in 1.0 ml of methanol, 0.1 mg (0.6 μmol) of p-toluenesulfonic acid monohydrate was added, and the reaction solution was stirred at 60° C. for 2 hours. After completion of the reaction, saturated sodium hydrogencarbonate aqueous solution was added to the reaction solution and the reaction solution was extracted with ethyl acetate. The organic layer was washed with saturated sodium chloride aqueous solution and dried with anhydrous sodium sulfate, and then the solvent was distilled off under reduced pressure. The obtained residue was subjected to silica gel column chromatography [n-hexane/ethyl acetate=9/1-3/2 (V/V)] and the fraction including the desired compound was concentrated under reduced pressure to provide 41 mg of the title compound as a white solid (yield: 93%).

Specific optical rotation: $[\alpha]_D^{24}=-64°$ (C=0.24, chloroform).

$^1$H-NMR spectrum (500 MHz, CDCl$_3$) δ ppm: 8.04 (2H, s), 7.63 (2H, d, J=8 Hz), 7.36 (2H, d, J=8 Hz), 7.21 (1H, d, J=47 Hz), 5.12 (1H, q, J=6 Hz), 4.71-4.63 (1H, m), 4.42-4.35 (1H, m), 4.18-4.10 (1H, m), 3.86 (1H, dd, J=3, 9 Hz), 3.73 (1H, dd, J=8, 9 Hz), 3.67-3.58 (1H, m), 2.91-2.62 (4H, m), 2.37-1.59 (16H, m), 1.25 (3H, d, J=6 Hz), 1.14 (3H, s), 1.00 (3H, s), 0.67-0.59 (1H, m).

Mass spectrum (ES, m/z): 707 [M$^+$].

Example 38

4-(4,4-Difluorocyclohexyl)-3-{fluoro[4-(trifluoromethyl)phenyl]methyl}-7,7-dimethyl-2-(1-{5-[(1-methylpiperidin-4-yl)oxy]pyrimidin-2-yl}piperidin-4-yl)-5,6,7,8-tetrahydroquinolin-5-ol

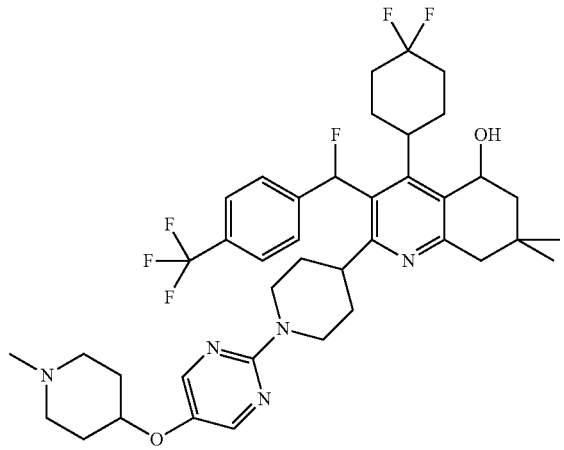

To a solution of 86 mg (99 μmol) of 4-(4,4-Difluorocyclohexyl)-3-{fluoro[4-(trifluoromethyl)phenyl]methyl}-5-[(4-methoxybenzyl)oxy]-7,7-dimethyl-2-(1-{5-[(1-methylpiperidin-4-yl)oxy]pyrimidin-2-yl}piperidin-4-yl)-5,6,7,8-tetrahydroquinoline, which was prepared by a method similar to that of Reference Example 29, in 1.0 ml of dichloromethane, 0.2 ml of anisole and 0.2 ml of trifluoroacetic acid were added, and the reaction solution was stirred at room temperature for 12 hours. After completion of the reaction, the solvent in the reaction solution and trifluoroacetic acid were distilled off under reduced pressure. The obtained residue was purified by silica gel column chromatography [dichloromethane/methanol/28% ammonia water=100/0/0-90/9.5/0.5 (V/V/V)] and thin layer chromatography [dichloromethane/methanol/28% ammonia water=90/9.5/0.5 (V/V/V)] to provide 12 mg of the title compound as a white solid (yield: 17%).

$^1$H-NMR spectrum (400 MHz, CDCl$_3$) δ ppm: 8.03 (2H, s), 7.63 (2H, d, J=8 Hz), 7.36 (2H, d, J=8 Hz), 7.21 (1H, d, J=46 Hz), 5.17-5.06 (1H, m), 4.73-4.62 (1H, m), 4.45-4.34 (1H, m), 4.06-3.92 (1H, m), 3.70-3.56 (1H, m), 2.88-2.57 (6H, m), 2.38-1.53 (21H, m), 2.28 (3H, s), 1.15 (3H, s), 1.01 (3H, s), 0.69-0.59 (1H, m).

Mass spectrum (FAB, m/z): 746 [(M+1)$^+$].

Example 39

(−)-4-(4,4-Difluorocyclohexyl)-2-[1-(5-{[(2S)-2,3-dihydroxypropyl]oxy}pyrimidin-2-yl)piperidin-4-yl]-3-{fluoro[4-(trifluoromethyl)phenyl]methyl}-7,7-dimethyl-5,6,7,8-tetrahydroquinolin-5-ol

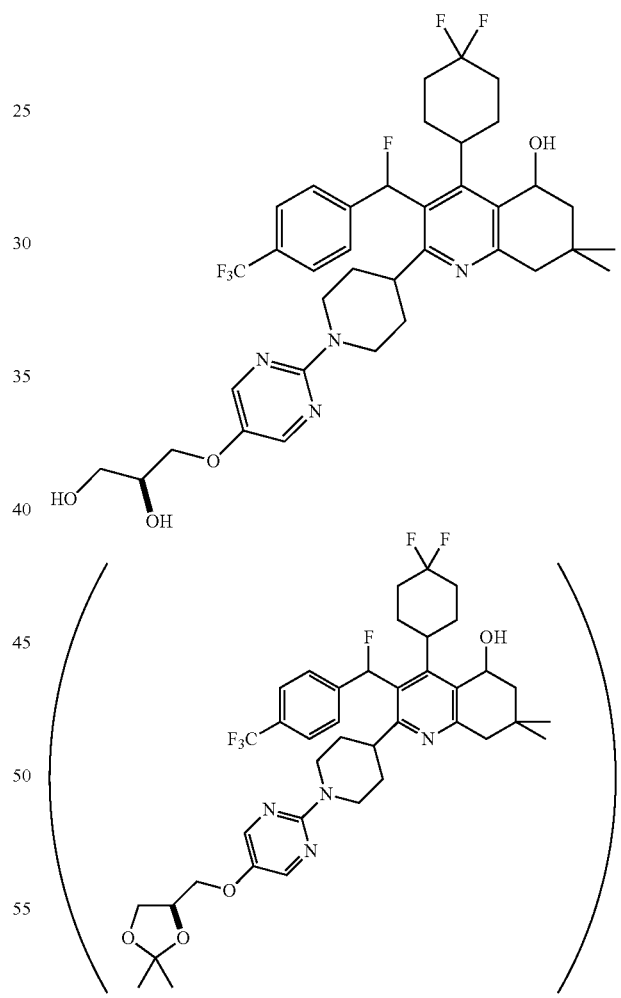

To a solution of 389 mg (0.600 mmol) of (−)-4-(4,4-Difluorocyclohexyl)-3-{fluoro[4-(trifluoromethyl)phenyl]methyl}-2-[1-(5-hydroxypyrimidin-2-yl)piperidin-4-yl]-7,7-dimethyl-5,6,7,8-tetrahydroquinolin-5-ol, which was prepared by a method similar to that of Example 4, in 3 ml of 1-methyl-2-pyrrolidone, 489 mg (1.50 mmol) of cesium carbonate and 344 mg (1.20 mmol) of (S)-(+)-2,2-dimethyl-1,3-dioxolan-4-ylmethyl p-toluene sulfonate were added, and the reaction solution was stirred at 70° C. for 2 hours. After completion of the reaction, water and ethyl acetate were poured into the reaction solution and the reaction solution was extracted with ethyl acetate. The organic layer was washed with saturated sodium chloride aqueous solution and dried with anhydrous magnesium sulfate, and then the solvent was distilled off under reduced pressure. The obtained residue was subjected to silica gel column chromatography [n-hexane/ethyl acetate=95/5-50/50 (V/V)] and the fraction including the desired compound was concentrated under reduced pressure to provide 400 mg (0.524 mmol) of 4-(4,4-difluorocyclohexyl)-2-[1-(5-{[(4R)-2,2-dimethyl-1,3-dioxolan-4-yl]methoxy}pyrimidin-2-yl)piperidin-4-yl]-3-{fluoro[4-(trifluoromethyl)phenyl]methyl}-7,7-dimethyl-5,6,7,8-tetrahydroquinolin-5-ol as a white solid.

To 400 mg (0.524 mmol) of 4-(4,4-Difluorocyclohexyl)-2-[1-(5-{[(4R)-2,2-dimethyl-1,3-dioxolan-4-yl]methoxy}pyrimidin-2-yl)piperidin-4-yl]-3-{fluoro[4-(trifluoromethyl)phenyl]methyl}-7,7-dimethyl-5,6,7,8-tetrahydroquinolin-5-ol obtained above, 5.2 ml of methanol and 1.3 ml of 2 N hydrochloric acid were added, and the reaction solution was stirred at 60° C. for 2 hours. After completion of the reaction, 1.3 ml of 2 N sodium hydroxide aqueous solution, saturated sodium chloride aqueous solution and ethyl acetate were poured into the reaction solution and the reaction solution was extracted with ethyl acetate. The organic layer was washed with saturated sodium chloride aqueous solution and dried with anhydrous sodium sulfate, and then the solvent was distilled off under reduced pressure. n-Hexane was added to the obtained residue and the precipitate was obtained by filtration to provide 307 mg of the title compound as a white solid (yield: 71%).

Specific optical rotation: $[\alpha]_D^{27}=-72°$ (C=0.12, methanol).

$^1$H-NMR spectrum (300 MHz, CD$_2$Cl$_2$) δ: 8.05 (2H, s), 7.65 (2H, d, J=8 Hz), 7.38 (2H, d, J=8 Hz), 7.22 (1H, d, J=47 Hz), 5.13 (1H, dt, J=6, 6 Hz), 4.72-4.60 (1H, m), 4.43-4.31 (1H, m), 4.07-3.90 (3H, m), 3.76 (1H, ddd, J=11, 6, 4 Hz), 3.67 (1H, dt, J=11, 5 Hz), 3.64-3.57 (1H, m), 2.85-2.56 (4H, m), 2.51 (1H, d, J=5 Hz), 2.36-1.58 (16H, m), 1.13 (3H, s), 1.00 (3H, s), 0.67-0.57 (1H, m).

Mass spectrum (EI, m/z): 722 [M$^+$].

Example 40

(−)-4-(4,4-Difluorocyclohexyl)-2-[1-(5-{[(2R)-2,3-dihydroxypropyl]oxy}pyrimidin-2-yl)piperidin-4-yl]-3-{fluoro[4-(trifluoromethyl)phenyl]methyl}-7,7-dimethyl-5,6,7,8-tetrahydroquinolin-5-ol

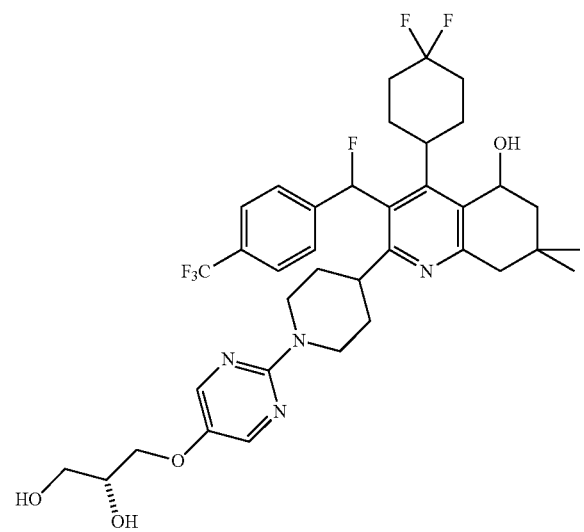 [SMILES: CC1(C)Cc2nc(C3CCN(c4ncc(OC[C@H](O)CO)cn4)CC3)c(C(F)c3ccc(C(F)(F)F)cc3)c(C3CCC(F)(F)CC3)c2C(O)C1]

Reactions similar to those of Example 39 were performed except for using (R)-(−)-2,2-dimethyl-1,3-dioxolan-4-ylmethyl p-toluene sulfonate instead of (S)-(+)-2,2-dimethyl-1,3-dioxolan-4-ylmethyl p-toluene sulfonate to provide 252 mg of the title compound as a white solid (yield: 58%).

Specific optical rotation: $[\alpha]_D^{27}=-102°$ (C=0.14, methanol).

$^1$H-NMR spectrum (300 MHz, CD$_2$Cl$_2$) δ: 8.05 (2H, s), 7.65 (2H, d, J=8 Hz), 7.39 (2H, d, J=8 Hz), 7.22 (1H, d, J=47 Hz), 5.13 (1H, dt, J=6, 6 Hz), 4.72-4.60 (1H, m), 4.43-4.31 (1H, m), 4.07-3.90 (3H, m), 3.76 (1H, ddd, J=11, 6, 4 Hz), 3.67 (1H, dt, J=11, 6 Hz), 3.64-3.57 (1H, m), 2.86-2.56 (4H, m), 2.52 (1H, d, J=4 Hz), 2.35-1.57 (16H, m), 1.13 (3H, s), 1.00 (3H, s), 0.68-0.56 (1H, m).

Mass spectrum (EI, m/z): 722 [M$^+$].

Example 41

4-(4,4-Difluorocyclohexyl)-3-{fluoro[4-(trifluoromethyl)phenyl]methyl}-7,7-dimethyl-2-[1-(5-{[(3R)-1-methylpyrrolidin-3-yl]oxy}pyrimidin-2-yl)piperidin-4-yl]-5,6,7,8-tetrahydroquinolin-5-ol

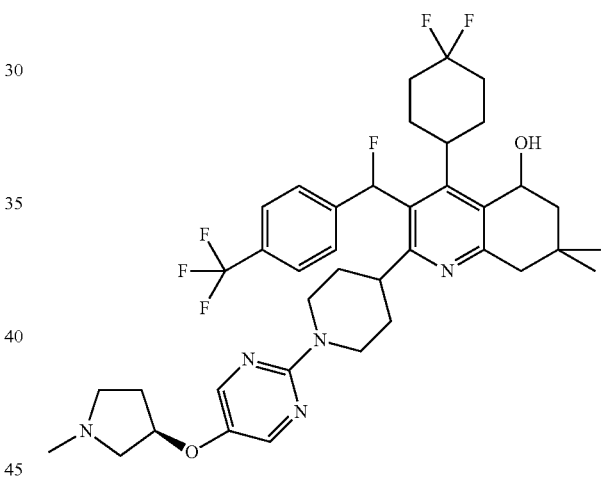

Reactions similar to those of Reference Example 29 and Example 38 were performed except for using 2-chloro-5-[(3R)-1-methylpyrrolidin-3-yl]oxy}pyrimidine, which was prepared by a method similar to that of Reference Example 30, instead of 2-chloro-5-[(1-methylpiperidin-4-yl)oxy]pyrimidine, and from 100 mg (0.155 mmol) of (−)-4-(4,4-Difluorocyclohexyl)-3-{fluoro[4-(trifluoromethyl)phenyl]methyl}-5-[(4-methoxybenzyl)oxy]-7,7-dimethyl-2-(piperidin-4-yl)-5,6,7,8-tetrahydroquinoline, which was prepared by a method similar to that of Reference Example 10, 58 mg of the title compound was obtained as a white solid (yield: 44%).

$^1$H-NMR spectrum (400 MHz, CDCl$_3$) δ ppm: 7.99 (2H, s), 7.63 (2H, d, J=8 Hz), 7.36 (2H, d, J=8 Hz), 7.21 (1H, d, J=48 Hz), 5.16-5.06 (1H, m), 4.72-4.57 (2H, m), 4.43-4.31 (1H, m), 3.70-3.55 (1H, m), 2.90-2.57 (6H, m), 2.47-1.57 (19H, m), 2.38 (3H, s), 1.15 (3H, s), 1.00 (3H, s), 0.70-0.58 (1H, m).

Mass spectrum (FAB, m/z): 732 [(M+1)$^+$].

Example 42

(−)-4-(4,4-Difluorocyclohexyl)-3-{fluoro[4-(trifluoromethyl)phenyl]methyl}-2-[1-(5-{[(2R)-2-hydroxypropyl]oxy}pyrimidin-2-yl)piperidin-4-yl]-7,7-dimethyl-5,6,7,8-tetrahydroquinolin-5-ol

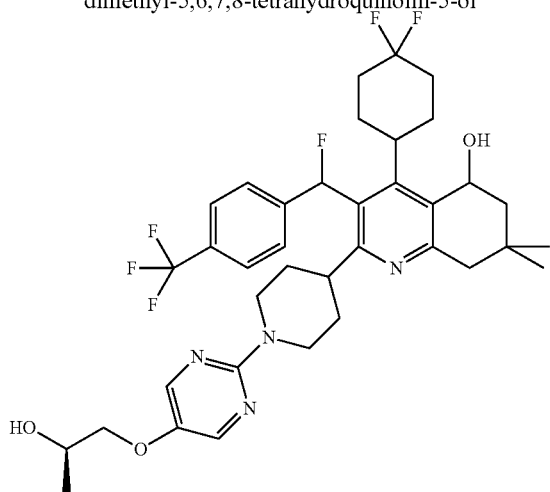

Reactions similar to those of Example 37 were performed except for using (2R)-2-(tetrahydro-2H-pyran-2-yloxy)propyl 4-methylbenzenesulfonate, which was synthesized by the method described in B. A. Jones et al., Journal of Heterocyclic Chemistry, 1982, Vol. 19, pp. 551-556, instead of (2S)-2-(tetrahydro-2H-pyran-2-yloxy)propyl 4-methylbenzenesulfonate, and from 50 mg (77 μmol) of 4-(4,4-Difluorocyclohexyl)-3-{fluoro[4-(trifluoromethyl)phenyl]methyl}-2-[1-(5-hydroxy pyrimidin-2-yl)piperidin-4-yl]-7,7-dimethyl-5,6,7,8-tetrahydroquinolin-5-ol, which was prepared by a method similar to that of Example 4, 39 mg of the title compound was obtained as a white solid (yield: 71%).

Specific optical rotation: $[\alpha]_D^{24}=-80°$ (C=0.14, chloroform).

$^1$H-NMR spectrum (500 MHz, CDCl$_3$) δ ppm: 8.04 (2H, s), 7.63 (2H, d, J=8 Hz), 7.36 (2H, d, J=8 Hz), 7.21 (1H, d, J=47 Hz), 5.12 (1H, q J=6 Hz), 4.71-4.62 (1H, m), 4.43-4.34 (1H, m), 4.19-4.11 (1H, m), 3.87 (1H, dd, J=3, 9 Hz), 3.73 (1H, dd, J=8, 9 Hz), 3.67-3.57 (1H, m), 2.93-2.60 (4H, m), 2.40-1.56 (16H, m), 1.25 (3H, d, J=6 Hz), 1.14 (3H, s), 1.00 (3H, s), 0.67-0.59 (1H, m).

Mass spectrum (ES, m/z): 707 [M+].

Example 43

(−)-4-(4,4-Difluorocyclohexyl)-3-{fluoro[4-(trifluoromethyl)phenyl]methyl}-2-{1-[5-(3-hydroxy-3-methylbutoxy)pyrimidin-2-yl]piperidin-4-yl}-7,7-dimethyl-5,6,7,8-tetrahydroquinolin-5-ol

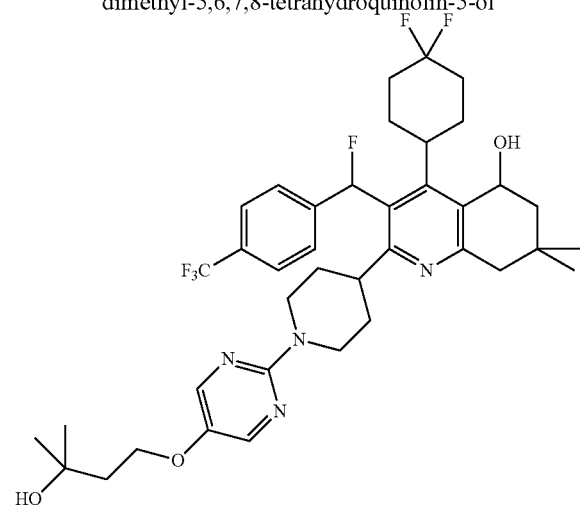

To a solution of 300 mg (0.462 mmol) of (−)-4-(4,4-difluorocyclohexyl)-3-{fluoro[4-(trifluoromethyl)phenyl]methyl}-2-[1-(5-hydroxypyrimidin-2-yl)piperidin-4-yl]-7,7-dimethyl-5,6,7,8-tetrahydroquinolin-5-ol, which was prepared by a method similar to that of Example 4, in 2.3 ml of N,N-dimethylformamide, 301 mg (0.924 mmol) of cesium carbonate and 93 mg (0.55 mmol) of 4-bromo-2-methylbutan-2-ol, which was synthesized by the method described in Yagamare Fall et al., Tetrahedron Letters, 2000, Vol. 41, pp. 7337-7340, were added, and the reaction solution was stirred at 50° C. for 1 hour. After completion of the reaction, water was poured into the reaction solution and the reaction solution was extracted with ethyl acetate. The organic layer was washed with saturated sodium chloride aqueous solution and dried with anhydrous magnesium sulfate, and then the solvent was distilled off under reduced pressure. The obtained residue was subjected to silica gel column chromatography [n-hexane/ethyl acetate=70/30-50/50 (V/V)] and the fraction including the desired compound was concentrated under reduced pressure. n-Hexane was added to the obtained residue and the precipitate was obtained by filtration to provide 161 mg of the title compound as a white powder (yield: 47%).

Specific optical rotation: $[\alpha]_D^{20}=-72.2°$ (C=1.03, chloroform).

$^1$H-NMR spectrum (300 MHz, CDCl$_3$) δ: 8.04 (2H, s), 7.63 (2H, d, J=8 Hz), 7.36 (2H, d, J=8 Hz), 7.20 (1H, d, J=46 Hz), 5.12 (1H, dt, J=6, 6 Hz), 4.74-4.61 (1H, m), 4.46-4.33 (1H, m), 4.11 (2H, t, J=6 Hz), 3.70-3.54 (1H, m), 2.91-2.58 (4H, m), 2.40-1.62 (18H, m), 1.30 (6H, s), 1.15 (3H, s), 1.00 (3H, s), 0.68-0.58 (1H, m).

Mass spectrum (EI, m/z): 734 [M+].

Example 44

4-(4,4-Difluorocyclohexyl)-3-{fluoro[4-(trifluoromethyl)phenyl]methyl}-2-{1-[5-(2-hydroxy-2-methylpropoxy)pyrimidin-2-yl]piperidin-4-yl}-7,7-dimethyl-5,6,7,8-tetrahydroquinolin-5-ol

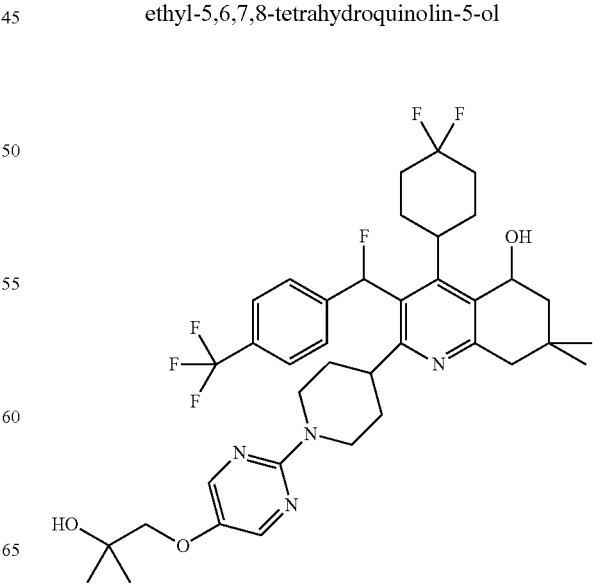

-continued

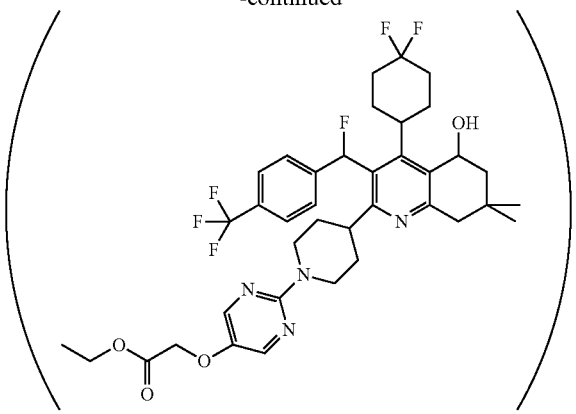

Reactions similar to those of Example 13 were performed except for using ethyl bromoacetate instead of ethyl iodide, and from 82 mg (0.13 mmol) of (−)-4-(4,4-Difluorocyclohexyl)-3-{fluoro[4-(trifluoromethyl)phenyl]methyl}-2-[1-(5-hydroxypyrimidin-2-yl)piperidin-4-yl]-7,7-dimethyl-5,6,7,8-tetrahydroquinolin-5-ol, which was prepared by a method similar to that of Example 4, 61 mg of 4-(4,4-Difluorocyclohexyl)-2-{1-[5-(2-ethoxy-2-oxoethoxy)pyrimidin-2-yl]piperidin-4-yl}-3-{fluoro[4-(trifluoromethyl)phenyl]methyl}-7,7-dimethyl-5,6,7,8-tetrahydroquinolin-5-ol was obtained. To a solution of 61 mg (0.083 mmol) of 4-(4,4-Difluorocyclohexyl)-2-{1-[5-(2-ethoxy-2-oxoethoxy)pyrimidin-2-yl]piperidin-4-yl}-3-{fluoro[4-(trifluoromethyl)phenyl]methyl}-7,7-dimethyl-5,6,7,8-tetrahydroquinolin-5-ol obtained above in 5 ml of diethyl ether, 0.30 ml (0.33 mmol) of 1.1 N methyl magnesium bromide-diethyl ether solution was added at 0° C. The temperature of the reaction solution was raised to room temperature and the reaction solution was stirred for 1 hour. After completion of the reaction, an ammonium chloride aqueous solution was poured into the reaction solution and the reaction solution was extracted with ethyl acetate. The organic layer was washed with saturated sodium chloride aqueous solution and dried with anhydrous sodium sulfate, and then the solvent was distilled off under reduced pressure. The obtained residue was purified by thin layer silica gel chromatography [n-hexane/ethyl acetate=5/6 (V/V)] to provide 18 mg of the title compound as a white solid (yield: 30%).

$^1$H-NMR spectrum (400 MHz, CDCl$_3$) δ ppm: 8.05 (2H, s), 7.63 (2H, d, J=8 Hz), 7.37 (2H, d, J=8 Hz), 7.21 (1H, d, J=47 Hz), 5.16-5.08 (1H, m), 4.71-4.63 (1H, m), 4.43-4.34 (1H, m), 3.73 (2H, s), 3.68-3.56 (1H, m), 2.84-2.59 (4H, m), 2.37-1.47 (16H, m), 1.32 (6H, s), 1.15 (3H, s), 1.01 (3H, s), 0.67-0.58 (1H, m)

Mass spectrum (FAB, m/z): 721 [(M+1)$^+$]. .

Example 45

(−)-4-(4,4-Difluorocyclohexyl)-3-{fluoro[4-(trifluoromethyl)phenyl]methyl}-7,7-dimethyl-2-(1-{5-[3-(methylsulphonyl)propoxy]pyrimidin-2-yl}piperidin-4-yl)-5,6,7,8-tetrahydroquinolin-5-ol

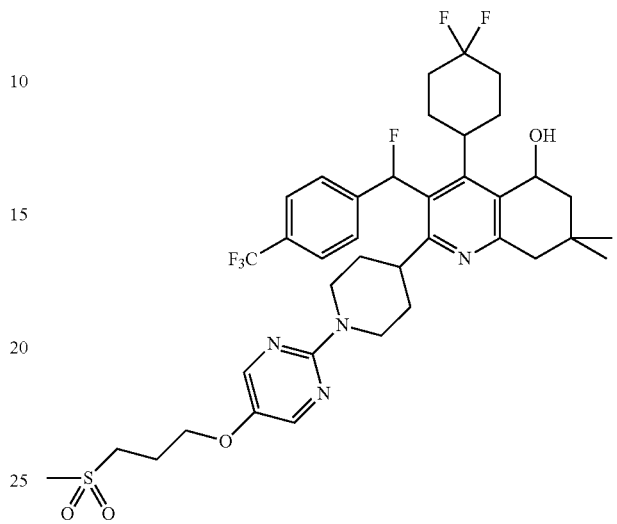

Reactions similar to those of Example 43 were performed except for using 3-(methylsulfonyl)propyl p-toluenesulfonate, which was synthesized with the method described in the specification of U.S. Pat. No. 6,593,333, instead of 4-bromo-2-methylbutan-2-ol and 1-methyl-2-pyrrolidone instead of N,N-dimethylformamide to provide 266 mg of the title compound as a white solid (yield: 44%).

Specific optical rotation: $[α]_D^{27}$=−74° (C=0.16, chloroform).

$^1$H-NMR spectrum (300 MHz, CD$_2$Cl$_2$) δ: 8.03 (2H, s), 7.65 (2H, d, J=8 Hz), 7.39 (2H, d, J=8 Hz), 7.22 (1H, d, J=47 Hz), 5.13 (1H, dt, J=6, 6 Hz), 4.71-4.60 (1H, m), 4.43-4.31 (1H, m), 4.04 (2H, t, J=6 Hz), 3.72-3.56 (1H, m), 3.20 (2H, dd, J=9, 7 Hz), 2.91 (3H, s), 2.85-2.55 (4H, m), 2.35-1.57 (17H, m), 1.13 (3H, s), 1.00 (3H, s), 0.68-0.56 (1H, m).

Mass spectrum (EI, m/z): 768 [M$^+$].

Example 46

(−)-4-(4,4-Difluorocyclohexyl)-3-{fluoro[4-(trifluoromethyl)phenyl]methyl}-2-{1-[5-(3-hydroxypropoxy)pyrimidin-2-yl]piperidin-4-yl}-7,7-dimethyl-5,6,7,8-tetrahydroquinolin-5-ol

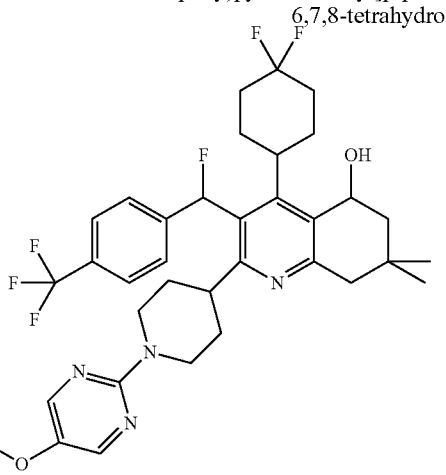

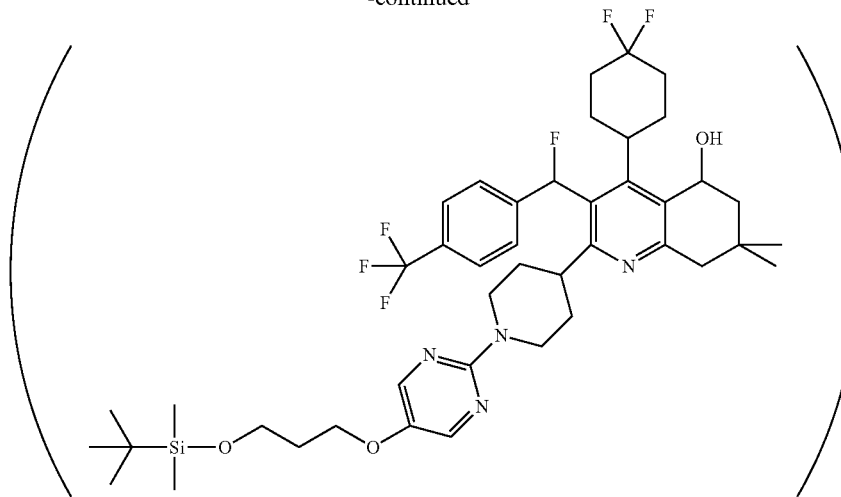

Reactions similar to those of Example 13 were performed except for using (3-bromopropoxy)(tert-butyl)dimethylsilane instead of ethyl iodide, and from 61 mg (94 μmol) of (−)-4-(4,4-Difluorocyclohexyl)-3-{fluoro[4-(trifluoromethyl)phenyl]methyl}-2-[1-(5-hydroxypyrimidin-2-yl)piperidin-4-yl]-7,7-dimethyl-5,6,7,8-tetrahydroquinolin-5-ol, which was prepared by a method similar to that of Example 4, 71 mg (87 μmol) of 2-{1-[5-(3-{[tert-Butyl(dimethyl)silyl]oxy}propoxy)pyrimidin-2-yl]piperidin-4-yl}-4-(4,4-difluorocyclohexyl)-3-{fluoro[4-(trifluoromethyl)phenyl]methyl}-7,7-dimethyl-5,6,7,8-tetrahydroquinolin-5-ol was obtained.

To a solution of 71 mg (87 μmol) of 2-{1-[5-(3-{[tert-Butyl(dimethyl)silyl]oxy}propoxy)pyrimidin-2-yl]piperidin-4-yl}-4-(4,4-difluorocyclohexyl)-3-{fluoro[4-(trifluoromethyl)phenyl]methyl}-7,7-dimethyl-5,6,7,8-tetrahydroquinolin-5-ol obtained above in 1 ml of tetrahydrofuran, 0.5 ml (0.5 mmol) of 1 N tetrabutyl ammonium fluoride-tetrahydrofuran solution was added, and the reaction solution was stirred at room temperature for 1 hour. After completion of the reaction, the reaction solution was poured into water and extracted with ethyl acetate. The organic layer was washed with saturated sodium chloride aqueous solution and dried with anhydrous magnesium sulfate, and then the solvent was distilled off under reduced pressure. The obtained residue was subjected to silica gel column chromatography [n-hexane/ethyl acetate=3/1 (V/V)] and the fraction including the desired compound was concentrated under reduced pressure to provide 59 mg of the title compound as a white solid (yield: 88%).

Specific optical rotation: $[\alpha]_D^{24}=-74°$ (C=0.15, chloroform).

$^1$H-NMR spectrum 400 MHz, CDCl$_3$) δ ppm: 8.03 (2H, s), 7.63 (2H, d, J=8 Hz), 7.36 (2H, d, J=8 Hz), 7.21 (1H, d, J=48 Hz), 5.16-5.07 (1H, m), 4.72-4.62 (1H, m), 4.43-4.33 (1H, m), 4.05 (2H, t, J=6 Hz), 3.84 (2H, t, J=6 Hz), 3.68-3.55 (1H, m), 2.93-2.57 (4H, m), 2.38-1.57 (18H, m), 1.14 (3H, s), 1.00 (3H, s), 0.67-0.58 (1H, m).

Mass spectrum (FAB, m/z): 707 [(M+1)$^+$].

Example 47

(−)-4-(4,4-Difluorocyclohexyl)-3-{fluoro[4-(trifluoromethyl)phenyl]methyl}-7,7-dimethyl-2-{1-[5-(3,3,3-trifluoropropoxyl)pyrimidin-2-yl]piperidin-4-yl}-5,6,7,8-tetrahydroquinolin-5-ol

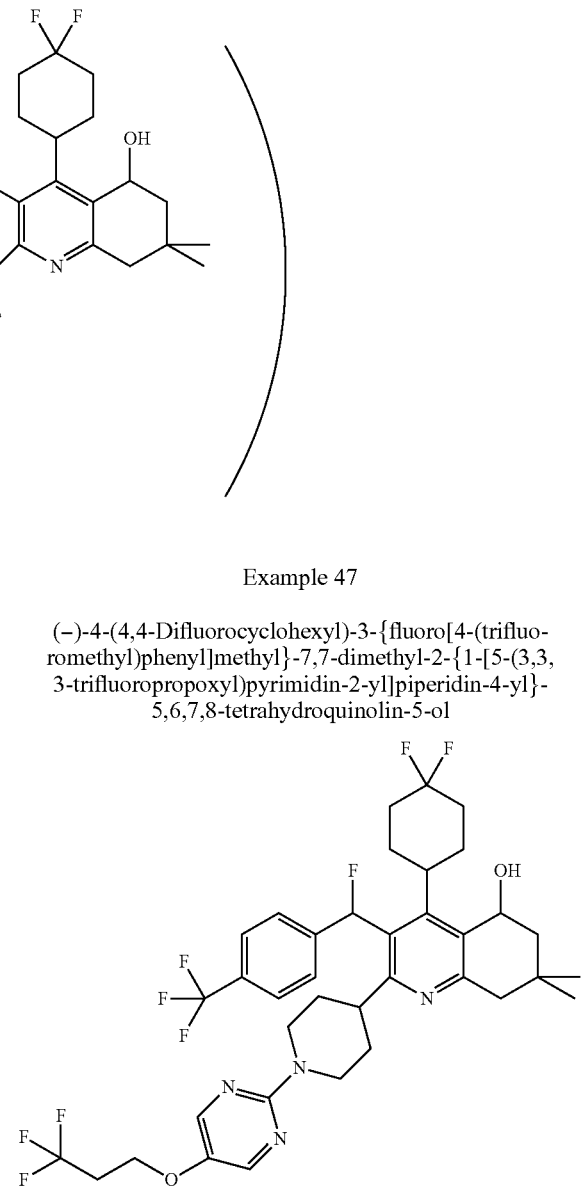

Reactions similar to those of Reference Example 29 and Example 38 were performed except for using 2-chloro-5-(3,3,3-trifluoropropoxy) pyrimidine, which was prepared by a method similar to that of Reference Example 31, instead of 2-chloro-5-[(1-methylpiperidin-4-yl)oxy]pyrimidine, and from 150 mg (222 μmol) of (−)-4-(4,4-Difluorocyclohexyl)-3-{fluoro[4-(trifluoromethyl)phenyl]methyl}-5-[(4-methoxybenzyl)oxy]-7,7-dimethyl-2-(piperidin-4-yl)-5,6,7,8-tetrahydroquinoline, which was prepared by a method similar to that of Reference Example 10, 85 mg of the title compound was obtained as a white solid (yield: 51%).

Specific optical rotation: $[\alpha]_D^{25}=-69°$ (C=0.20, chloroform).

$^1$H-NMR spectrum (400 MHz, CDCl$_3$) δ ppm: 8.03 (2H, s), 7.63 (2H, d, J=8 Hz), 7.37 (2H, d, J=8 Hz), 7.21 (1H, d, J=46 Hz), 5.17-5.07 (1H, m), 4.73-4.66 (1H, m), 4.45-4.34 (1H, m), 4.18-4.06 (2H, m), 3.69-3.56 (1H, m), 2.86-2.48 (6H, m), 2.30-1.54 (15H, m), 1.15 (3H, s), 1.01 (3H, s), 0.69-0.58 (1H, m).

Mass spectrum (FAB, m/z): 745 [(M+1)$^+$].

Example 48

(−)-4-(4,4-Difluorocyclohexyl)-2-{1-[5-(difluoromethoxy)pyrimidin-2-yl]piperidin-4-yl}-3-{fluoro[4-(trifluoromethyl)phenyl]methyl}-7,7-dimethyl-5,6,7,8-tetrahydroquinolin-5-ol

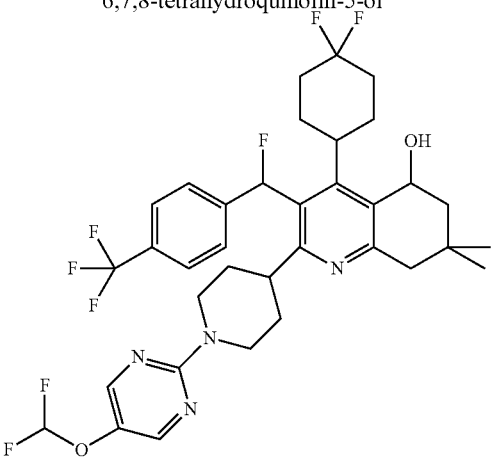

Reactions similar to those of Reference Example 29 and Example 38 were performed except for using 2-chloro-5-(difluoromethoxy)pyrimidine, which was prepared by a method similar to that of Reference Example 32, instead of 2-chloro-5-[(1-methylpiperidin-4-yl)oxy]pyrimidine, and from 102 mg (151 μmol) of (−)-4-(4,4-Difluorocyclohexyl)-3-{fluoro[4-(trifluoromethyl)phenyl]methyl}-5-[(4-methoxybenzyl)oxy]-7,7-dimethyl-2-(piperidin-4-yl)-5,6,7,8-tetrahydroquinoline, which was prepared by a method similar to that of Reference Example 10, 52 mg of the title compound was obtained as a white solid (yield: 49%).

Specific optical rotation: $[\alpha]_D^{25}=-77°$ (C=0.15, chloroform).

$^1$H-NMR spectrum (400 MHz, CDCl$_3$) δ ppm: 8.12 (2H, s), 7.64 (2H, d, J=8 Hz), 7.37 (2H, d, J=8 Hz), 7.21 (1H, d, =47 Hz), 6.36 (1H, t, J=73 Hz), 5.16-5.08 (1H, m), 4.80-4.70 (1H, m), 4.52-4.43 (1H, m), 3.68-3.57 (1H, m), 2.86-2.59 (4H, m), 2.35-1.54 (15H, m), 1.15 (3H, s), 1.01 (3H, s), 0.69-0.60 (1H, m).

Mass spectrum (FAB, m/z): 699 [(M+1)$^+$].

Example 49

(−)-4-(4,4-Difluorocyclohexyl)-3-{fluoro[4-(trifluoromethyl)phenyl]methyl}-2-(1-{5-[3-hydroxy-2-(hydroxymethyl)propoxy]pyrimidin-2-yl}piperidin-4-yl)-7,7-dimethyl-5,6,7,8-tetrahydroquinolin-5-ol

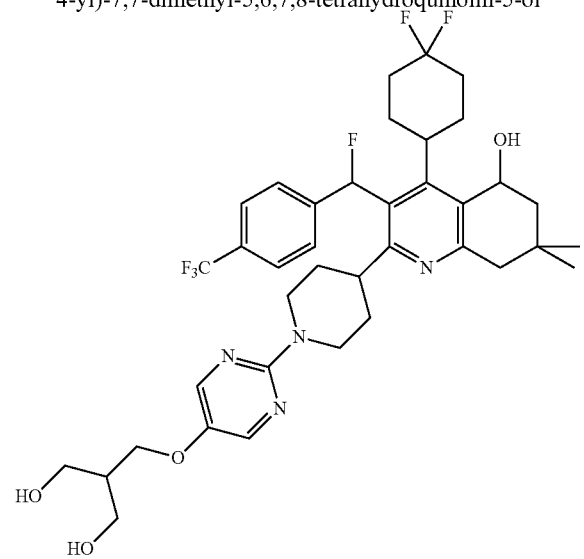

Reactions similar to those of Example 39 were performed except for using (2,2-dimethyl-1,3-dioxan-5-yl)methyl p-toluenesulfonate, which was synthesized with the method described in J. Dubois et al., Tetrahedron, 1991, Vol. 47, pp. 1001-1012, instead of (S)-(+)-2,2-dimethyl-1,3-dioxolan-4-ylmethyl p-toluenesulfonate, and from 4.04 g (6.23 mmol) of (−)-4-(4,4-Difluorocyclohexyl)-3-{fluoro[4-(trifluoromethyl)phenyl]methyl}-2-[1-(5-hydroxypyrimidin-2-yl)piperidin-4-yl]-7,7-dimethyl-5,6,7,8-tetrahydroquinolin-5-ol, which was prepared by a method similar to that of Example 4, 2.73 g of the title compound was obtained as a white solid (yield: 59%).

Specific optical rotation: $[\alpha]_D^{28}=-91°$ (C=0.21, methanol).

$^1$H-NMR spectrum (300 MHz, CD$_2$Cl$_2$) δ: 8.04 (2H, s), 7.65 (2H, d, J=8 Hz), 7.38 (2H, d, J=8 Hz), 7.22 (1H, d, J=47 Hz), 5.13 (1H, dt, J=6, 6 Hz), 4.71-4.59 (1H, m), 4.42-4.32 (1H, m), 4.03 (2H, d, J=6 Hz), 3.91-3.78 (4H, m), 3.71-3.57 (1H, m), 2.86-2.55 (4H, m), 2.36-1.58 (18H, m), 1.13 (3H, s), 1.00 (3H, s), 0.68-0.57 (1H, m).

Mass spectrum (EI, m/z): 736 [M$^+$].

Example 50

(−)-4-(4,4-Difluorocyclohexyl)-3-{fluoro[4-(trifluoromethyl)phenyl]methyl}-2-(1-{5-[3-hydroxy-2-(hydroxymethyl)-2-methylpropoxy]pyrimidin-2-yl}piperidin-4-yl)-7,7-dimethyl-5,6,7,8-tetrahydroquinolin-5-ol

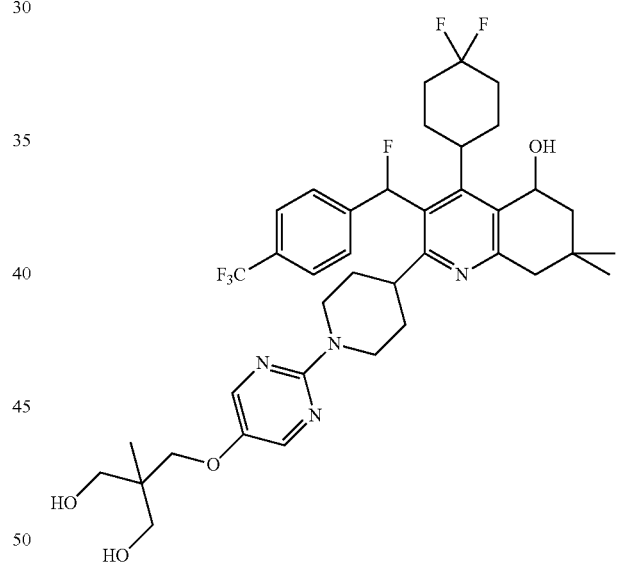

To a solution of 182 mg (0.200 mmol) of 4-(4,4-Difluorocyclohexyl)-3-{fluoro[4-(trifluoromethyl)phenyl]methyl}-5-[(4-methoxybenzyl)oxy]-7,7-dimethyl-2-(1-{5-[(2,2,5-trimethyl-1,3-dioxan-5-yl)methoxy]pyrimidin-2-yl}piperidin-4-yl)-5,6,7,8-tetrahydroquinoline, which was prepared by a method similar to that of Reference Example 34, in 9.1 ml of 1,4-dioxane, 0.91 ml of 6 N hydrochloric acid was added, and the reaction solution was stirred at 70° C. for 1 hour. After completion of the reaction, the reaction solution was poured into saturated sodium hydrogencarbonate aqueous solution and extracted with ethyl acetate. The organic layer was washed with saturated sodium chloride aqueous solution and dried with anhydrous magnesium sulfate, and then the solvent was distilled off under reduced pressure. The obtained residue was subjected to silica gel column chromatography [n-hexane/ethyl acetate=20/30 (V/V)] and to the fraction including the desired compound, 30 mg of the white solid which was obtained by performing reactions similar to the above from 50 mg (0.055 mmol) of 4-(4,4-Difluorocyclohexyl)-3-{fluoro [4-(trifluoromethyl)phenyl]methyl}-5-[(4-methoxybenzyl) oxy]-7,7-dimethyl-2-(1-{5-[(2,2,5-trimethyl-1,3-dioxan-5-yl)methoxy]pyrimidin-2-yl}piperidin-4-yl)-5,6,7,8-tetrahydroquinoline, which was prepared by a method similar to that of Reference Example 34 was added, and the mixture was concentrated under reduced pressure. n-Hexane was added to the obtained residue and the precipitate was obtained by filtration to provide 133 mg of the title compound as a white powder (yield: 69%).

Specific optical rotation: $[\alpha]_D^{27}$=−60.8° (C=0.530, chloroform).

$^1$H-NMR spectrum (300 MHz, CDCl$_3$) δ: 8.04 (2H, s), 7.63 (2H, d, J=8 Hz), 7.36 (2H, d, J=8 Hz), 7.20 (1H, d, J=46 Hz), 5.12 (1H, dt, J=6, 6 Hz), 4.72-4.60 (1H, m), 4.45-4.32 (1H, m), 3.92 (2H, s), 3.77 (2H, dd, J=11, 5 Hz), 3.70 (2H, dd, J=11, 5 Hz), 3.66-3.54 (1H, m), 2.89-2.58 (4H, m), 2.38-1.57 (17H, m), 1.15 (3H, s), 1.00 (3H, s), 0.94 (3H, s), 0.68-0.57 (1H, m).

Mass spectrum (EI, m/z): 750 [M$^+$].

Example 51

(−)-4-(4,4-Difluorocyclohexyl)-3-{fluoro[4-(trifluoromethyl)phenyl]methyl}-7,7-dimethyl-2-[1-(5-{[methyl(methylsulphonyl)amino]methyl}pyrimidin-2-yl)piperidin-4-yl]-5,6,7,8-tetrahydroquinolin-5-ol

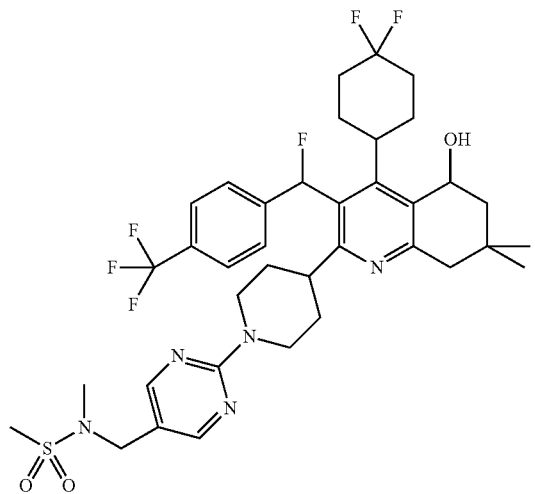

To a solution of 65 mg (95 μmol) of 4-(4,4-Difluorocyclohexyl)-3-{fluoro[4-(trifluoromethyl)phenyl]methyl}-7,7-dimethyl-2-(1-{5-[(methylamino)methyl]pyrimidin-2-yl}piperidin-4-yl)-5,6,7,8-tetrahydroquinolin-5-ol, which was prepared by a method similar to that of Example 58, in 0.2 ml of dichloromethane, 30 μl (0.19 mmol) of triethylamine and 8 μl (0.1 mmol) of methanesulfonyl chloride were added, and the reaction solution was stirred at room temperature for 1 hour. After completion of the reaction, saturated sodium hydrogencarbonate aqueous solution was poured into the reaction solution and the reaction solution was extracted with ethyl acetate. The organic layer was washed with saturated sodium chloride aqueous solution and dried with anhydrous magnesium sulfate, and then the solvent was distilled off under reduced pressure. The obtained residue was subjected to silica gel column chromatography [n-hexane/ethyl acetate=100/0-40/60 (V/V)] and the fraction including the desired compound was concentrated under reduced pressure to provide 37 mg of the title compound as a white solid (yield: 52%).

Specific optical rotation: $[\alpha]_D^{25}$=−76° (C=0.16, chloroform).

$^1$H-NMR spectrum (500 MHz, CDCl$_3$) δ ppm: 8.22 (2H, s), 7.64 (2H, d, J=8 Hz), 7.37 (2H, d, J=8 Hz), 7.22 (1H, d, J=48 Hz), 5.16-5.07 (1H, m), 4.85-4.76 (1H, m), 4.59-4.47 (1H, m), 4.11 (2H, s), 3.70-3.54 (1H, m), 2.88-2.71 (3H, m), 2.82 (3H, s), 2.75 (3H, s), 2.63 (1H, d, J=17 Hz), 2.37-2.21 (2H, m), 2.21-2.07 (4H, m), 1.98-1.52 (9H, m), 1.14 (3H, s), 1.00 (3H, s), 0.72-0.61 (1H, m).

Mass spectrum (FAB, m/z): 754 [(M+1)$^+$].

Example 52

4-(4,4-Difluorocyclohexyl)-3-{fluoro[4-(trifluoromethyl)phenyl]methyl}-7,7-dimethyl-2-[1-(5-{[methyl(propan-2-ylsulfonyl)amino]methyl}pyrimidin-2-yl)piperidin-4-yl]-5,6,7,8-tetrahydroquinolin-5-ol

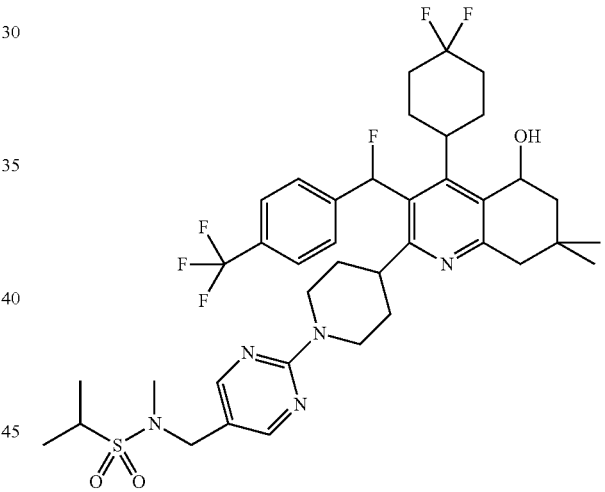

Reactions similar to those of Example 51 were performed except for using isopropylsulfonyl chloride instead of methanesulfonyl chloride, and from 64 mg (94 μmol) of 4-(4,4-Difluorocyclohexyl)-3-{fluoro[4-(trifluoromethyl)phenyl]methyl}-7,7-dimethyl-2-(1-{5-[(methylamino)methyl]pyrimidin-2-yl}piperidin-4-yl)-5,6,7,8-tetrahydroquinolin-5-ol, which was prepared by a method similar to that of Example 58, 14 mg of the title compound was obtained as a white solid (yield: 19%).

$^1$H-NMR spectrum (400 MHz, CDCl$_3$) δ ppm: 8.23 (2H, s), 7.64 (2H, d, J=8 Hz), 7.37 (2H, d, J=8 Hz), 7.21 (1H, d, J=45 Hz), 5.21-5.06 (1H, m), 4.85-4.76 (1H, m), 4.59-4.47 (1H, m), 4.18 (2H, s), 3.71-3.55 (1H, m), 3.24 (1H, septet, J=7 Hz), 2.87-2.70 (3H, m), 2.77 (3H, s), 2.63 (1H, d, J=17 Hz), 2.42-1.56 (15H, m), 1.37 (6H, d, J=7 Hz), 1.14 (3H, s), 1.00 (3H, s), 0.71-0.59 (1H, m).

Mass spectrum (FAB, m/z): 782 [(M+1)$^+$].

Example 53

(−)-4-(4,4-Difluorocyclohexyl)-3-{fluoro[4-(trifluoromethyl)phenyl]methyl}-7,7-dimethyl-2-[1-(5-methylthiopyrimidin-2-yl)-piperidin-4-yl]-5,6,7,8-tetrahydroquinolin-5-ol

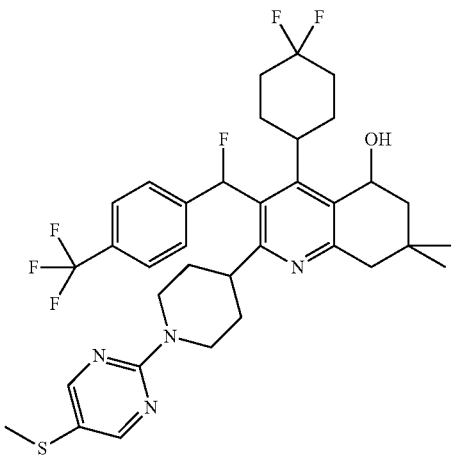

Reactions similar to those of the first step of Example 2 and Example 38 were performed except for using 2-chloro-5-methylthiopyrimidine, which was prepared by a method similar to that of Reference Example 36, instead of 5-bromo-2-chloropyrimidine, and from 60 mg (89 μmol) of (−)-4-(4,4-Difluorocyclohexyl)-3-{fluoro[4-(trifluoromethyl)phenyl]methyl}-5-[(4-methoxybenzyl)oxy]-7,7-dimethyl-2-(piperidin-4-yl)-5,6,7,8-tetrahydroquinoline, which was prepared by a method similar to that of Reference Example 10, 50 mg of the title compound was obtained as a white solid (yield: 84%).

Specific optical rotation: $[\alpha]_D^{26} = -89°$ (C=0.17, chloroform).

$^1$H-NMR spectrum (500 MHz, CDCl$_3$) δ ppm: 8.31 (2H, s), 7.64 (2H, d, J=8 Hz), 7.37 (2H, d, J=8 Hz), 7.21 (1H, d, J=47 Hz), 5.15-5.09 (1H, m), 4.83-4.74 (1H, m), 4.57-4.47 (1H, m), 3.68-3.57 (1H, m), 2.94-2.59 (4H, m), 2.42-1.47 (15H, m), 2.32 (3H, s), 1.14 (3H, s), 1.00 (3H, s), 0.69-0.60 (1H, m).

Example 54

(−)-4-(4,4-Difluorocyclohexyl)-3-{fluoro[4-(trifluoromethyl)phenyl]methyl}-7,7-dimethyl-2-{1-[5-(methylsulphonyl)pyrimidin-2-yl]piperidin-4-yl}-5,6,7,8-tetrahydroquinolin-5-ol

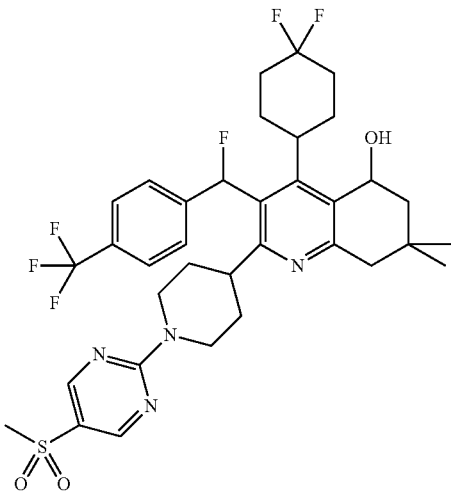

Reactions similar to those of the first step of Example 2 and Example 38 were performed except for using 2-chloro-5-(methylsulfonyl)pyrimidine, which was prepared by a method similar to that of Reference Example 14, instead of 5-bromo-2-chloropyrimidine, and from 49 mg (72 μmol) of (−)-4-(4,4-Difluorocyclohexyl)-3-{fluoro[4-(trifluoromethyl)phenyl]methyl}-5-[(4-methoxybenzyl)oxy]-7,7-dimethyl-2-(piperidin-4-yl)-5,6,7,8-tetrahydroquinoline, which was prepared by a method similar to that of Reference Example 10, 45 mg of the title compound was obtained as a white solid (yield: 88%).

Specific optical rotation: $[\alpha]_D^{26} = -88°$ (C=0.16, chloroform).

$^1$H-NMR spectrum (500 MHz, CDCl$_3$) δ ppm: 8.62 (2H, s), 7.65 (2H, d, J=8 Hz), 7.38 (2H, d, J=8 Hz), 7.22 (1H, d, J=47 Hz), 5.13 (1H, q, J=6 Hz), 4.98-4.89 (1H, m), 4.72-4.63 (1H, m), 3.69-3.58 (1H, m), 3.04 (3H, s), 2.93-2.59 (4H, m), 2.36-1.55 (15H, m), 1.14 (3H, s), 1.00 (3H, s), 0.75-0.65 (1H, m).

Mass spectrum (ES, m/z): 711 [M$^+$].

Example 55

(−)-2-{1-[5-(3-Carboxyphenyl)pyrimidin-2-yl]piperidin-4-yl}-4-(4,4-difluorocyclohexyl)-3-{fluoro[4-(trifluoromethyl)phenyl]methyl}-7,7-dimethyl-5,6,7,8-tetrahydroquinolin-5-ol

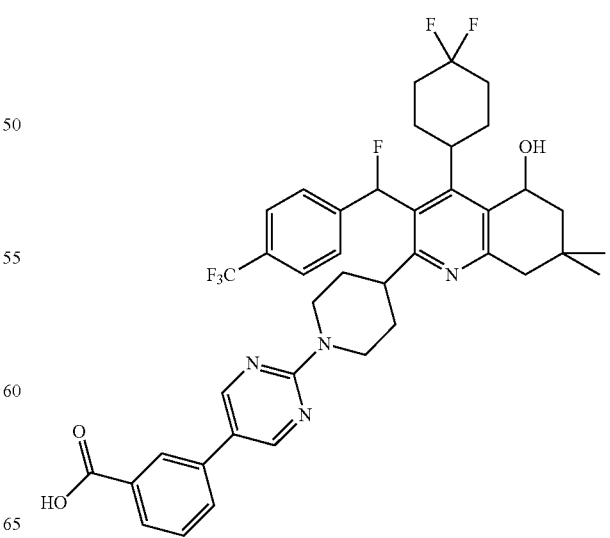

-continued

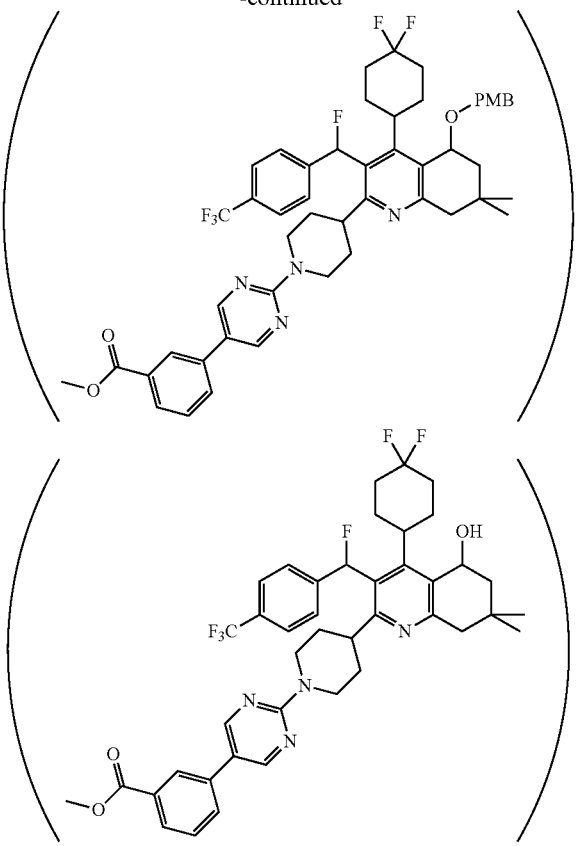

To a solution of 303 mg (0.450 mmol) of (−)-4-(4,4-Difluorocyclohexyl)-3-{fluoro[4-(trifluoromethyl)phenyl]methyl}-5-[(4-methoxybenzyl)oxy]-7,7-dimethyl-2-(piperidin-4-yl)-5,6,7,8-tetrahydroquinoline, which was prepared by a method similar to that of Reference Example 10, in 3 ml of 1,4-dioxane, 127 mg (0.495 mmol) of 2-chloro-5-[3-(methoxycarbonyl)phenyl]pyrimidine, which was prepared by a method similar to that of Reference Example 35, and 115 μl (0.675 mmol) of diisopropylethylamine were added, and the reaction solution was stirred at 60° C. for 1.5 hours, at 70° C. 4 hours and then at 80° C. for 1.5 hours. After stirring with heating, 35 μl (0.23 mmol) of 1,8-diazabicyclo[5,4,0]-7-undecene was added and the reaction solution was stirred at 80° C. for 1 hour, at 90° C. for 1.5 hours and then at 100° C. for 1 hour. After completion of the reaction, the reaction solution was poured into water and extracted with ethyl acetate. The organic layer was washed with saturated sodium chloride aqueous solution and dried with anhydrous magnesium sulfate, and then the solvent was distilled off under reduced pressure. The obtained residue was subjected to silica gel column chromatography [n-hexane/ethyl acetate=90/10-50/50 (V/V)] and the fraction including the desired compound was concentrated under reduced pressure to provide 351 mg of 4-(4,4-Difluorocyclohexyl)-3-{fluoro[4-(trifluoromethyl)phenyl]methyl}-5-[(4-methoxybenzyl)oxy]-2-(1-{5-[3-(methoxycarbonyl)phenyl]pyrimidin-2-yl}piperidin-4-yl)-7,7-dimethyl-5,6,7,8-tetrahydroquinoline as a white solid.

To 351 mg of 4-(4,4-Difluorocyclohexyl)-3-{fluoro[4-(trifluoromethyl)phenyl]methyl}-5-[(4-methoxybenzyl)oxy]-2-(1-{5-[3-(methoxycarbonyl)phenyl]pyrimidin-2-yl}piperidin-4-yl)-7,7-dimethyl-5,6,7,8-tetrahydroquinoline obtained above, 2 ml of dichloromethane, 0.24 ml of anisole and 1 ml of trifluoroacetic acid were added, and the reaction solution was stirred at room temperature for 12.5 hours. After completion of the reaction, the reaction solution was poured into saturated sodium hydrogencarbonate aqueous solution and extracted with ethyl acetate. The organic layer was washed with saturated sodium chloride aqueous solution and dried with anhydrous magnesium sulfate, and then the solvent was distilled off under reduced pressure. The obtained residue was subjected to silica gel column chromatography [n-hexane/ethyl acetate=95/5-50/50 (V/V)] and the fraction including the desired compound was concentrated under reduced pressure to provide 257 mg of 4-(4,4-Difluorocyclohexyl)-3-{fluoro[4-(trifluoromethyl)phenyl]methyl}-2-(1-{5-[3-(meth oxycarbonyl)phenyl]pyrimidin-2-yl}piperidin-4-yl)-7,7-dimethyl-5,6,7,8-tetrahydroquinolin-5-ol as a white solid.

To 257 mg of 4-(4,4-Difluorocyclohexyl)-3-{fluoro[4-(trifluoromethyl)phenyl]methyl}-2-(1-{5-[3-(methoxycarbonyl)phenyl]pyrimidin-2-yl}piperidin-4-yl)-7,7-dimethyl-5,6,7,8-tetrahydroquinolin-5-ol obtained above, 2 ml of tetrahydrofuran, 3 ml of ethanol and 1 ml of 2 N sodium hydroxide aqueous solution were added, and the reaction solution was stirred at room temperature for 3.5 hours. After completion of the reaction, 1 ml of 2 N hydrochloric acid was added to the reaction solution. After stirring at room temperature, saturated sodium chloride aqueous solution and ethyl acetate were poured into the reaction solution and the reaction solution was extracted with ethyl acetate. The organic layer was washed with saturated sodium chloride aqueous solution and dried with anhydrous magnesium sulfate, and then the solvent was distilled off under reduced pressure. n-Heptane was added to the obtained residue and the precipitate was obtained by filtration to provide 240 mg of the title compound as a white solid (yield: 71%).

Specific optical rotation: $[\alpha]_D^{28}=-67.8°$ (C=0.520, chloroform).

$^1$H-NMR spectrum (300 MHz, CDCl$_3$) δ: 8.44 (2H, s), 8.07 (1H, s), 7.98 (1H, d, J=7 Hz), 7.66 (2H, d, J=8 Hz), 7.47 (1H, d, J=7 Hz), 7.46 (1H, t, J=7 Hz), 7.39 (2H, d, J=8 Hz), 7.24 (1H, d, J=47 Hz), 5.13 (1H, t, J=6 Hz), 4.93-4.81 (1H, m), 4.65-4.52 (1H, m), 3.72-3.56 (1H, m), 3.01-2.61 (4H, m), 2.41-1.61 (15H, m), 1.13 (3H, s), 0.99 (3H, s), 0.72-0.58 (1H, m).

Mass spectrum (EI, m/z): 752 [M$^+$].

Example 56

4-(4,4-Difluorocyclohexyl)-3-{fluoro[4-(trifluoromethyl)phenyl]methyl}-2-(1-{5-[(2-hydr oxyethyl)(methyl)amino]pyrimidin-2-yl}piperidin-4-yl)-7,7-dimethyl-5,6,7,8-tetrahydroquinolin-5-ol

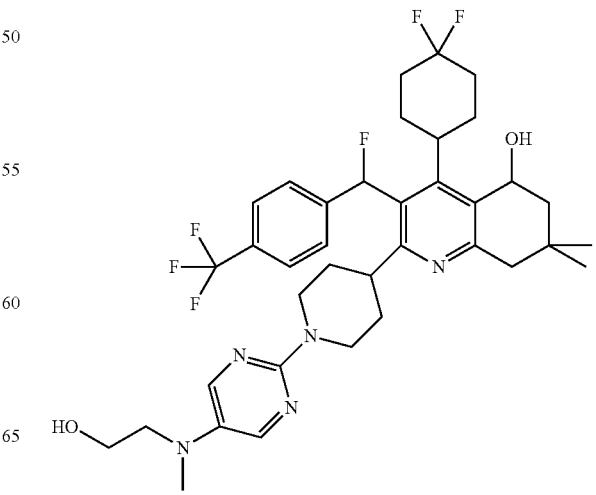

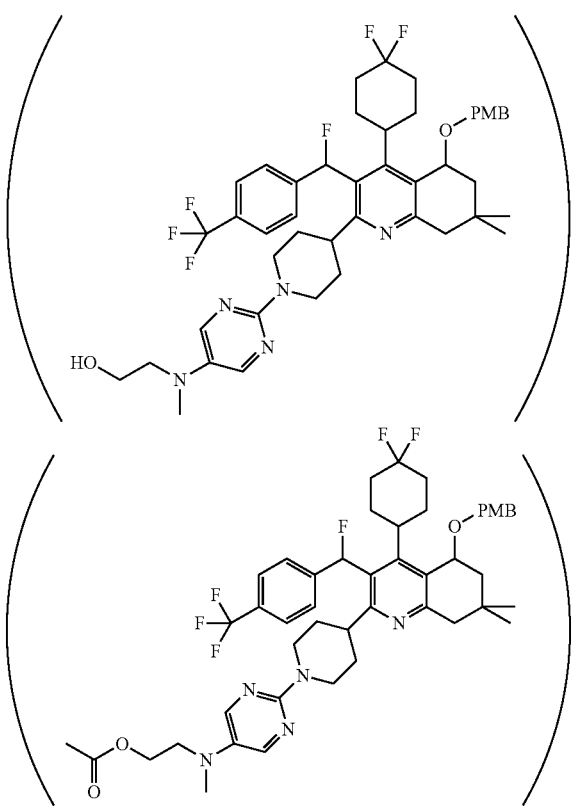

Reactions similar to those of Reference Example 13 were performed except for using 2-(methylamino)ethanol instead of isonipecotic acid ethyl ester, and from 100 mg (0.120 mmol) of 2-[1-(5-Bromopyrimidin-2-yl)piperidin-4-yl]-4-(4,4-difluorocyclohexyl)-3-{fluoro[4-(trifluoromethyl)phenyl]methyl}-5-[(4-methoxybenzyl)oxy]-7,7-dimethyl-5,6,7,8-tetrahydroquinoline, which was prepared by a method similar to that of Reference Example 11, 25 mg of 4-(4,4-Difluorocyclohexyl)-3-{fluoro[4-(trifluoromethyl)phenyl]methyl}-2-(1-{5-[(2-hydroxyethyl)(methyl)amino]pyrimidin-2-yl}piperidin-4-yl)-5-[(4-methoxybenzyl)oxy]-7,7-dimethyl-5,6,7,8-tetrahydroquinoline was obtained (yield: 26%).

To a solution of 25 mg (30 μmol) of 4-(4,4-Difluorocyclohexyl)-3-{fluoro[4-(trifluoromethyl)phenyl]methyl}-2-(1-{5-[(2-hydroxyethyl)(methyl)amino]pyrimidin-2-yl}piperidin-4-yl)-5-[(4-methoxybenzyl)oxy]-7,7-dimethyl-5,6,7,8-tetrahydroquinoline obtained above in 1.0 ml of dichloromethane, 0.1 ml of pyridine, 15 μl (0.16 mmol) of acetic anhydride and 0.4 mg (3 μmol) of 4-dimethylaminopyridine were added, and the reaction solution was stirred at room temperature for 10 minutes. After completion of the reaction, water was added to the reaction solution and the reaction solution was extracted with ethyl acetate. The organic layer was washed with saturated sodium chloride aqueous solution and dried with anhydrous sodium sulfate, and then the solvent was distilled off under reduced pressure. The obtained residue was subjected to silica gel column chromatography [n-hexane/ethyl acetate=3/1-1/1 (V/V)] and the fraction including the desired compound was concentrated under reduced pressure to provide 25 mg of 2-(1-{5-[(2-Acetoxyethyl)(methyl)amino]pyrimidin-2-yl}piperidin-4-yl)-4-(4,4-difluorocyclohexyl)-3-{fluoro[4-(trifluoromethyl)phenyl]methyl}-5-[(4-methoxybenzyl)oxy]-7,7-dimethyl-5,6,7,8-tetrahydroquinoline as a white solid (yield: 93%).

Reactions similar to those of Example 38 and Example (23-2) were performed, and from 25 mg (29 μmol) of 2-(1-{5-[(2-Acetoxyethyl)(methyl)amino]pyrimidin-2-yl}piperidin-4-yl)-4-(4,4-difluorocyclohexyl)-3-{fluoro[4-(trifluoromethyl)phenyl]methyl}-5-[(4-methoxybenzyl)oxy]-7,7-dimethyl-5,6,7,8-tetrahydroquinoline obtained above, 13 mg of the title compound was obtained as a white solid (yield: 65%). Potassium carbonate aqueous solution was used instead of 1 N sodium hydroxide aqueous solution in the step corresponding to Example (23-2).

$^1$H-NMR spectrum (500 MHz, CD$_3$OD) δ ppm: 8.02 (2H, s), 7.73 (2H, d, J=8 Hz), 7.46 (2H, d, J=8 Hz), 7.28 (1H, d, J=47 Hz), 5.20-5.12 (1H, m), 4.60-5.50 (1H, m), 4.28-4.18 (1H, m), 3.77-3.63 (3H, m), 3.36-3.23 (2H, m), 2.95-2.56 (4H, m), 2.87 (3H, s), 2.36-1.53 (14H, m), 1.13 (3H, s), 0.97 (3H, s), 0.64-0.55 (1H, m).

Mass spectrum (ES, m/z): 706 [M$^+$].

Example 57

(−)-4-(4,4-Difluorocyclohexyl)-3-{fluoro[4-(trifluoromethyl)phenyl]methyl}-2-(1-{5-[(3S)-3-hydroxypyrrolidin-1-yl]pyrimidin-2-yl}piperidin-4-yl)-7,7-dimethyl-5,6,7,8-tetrahydroquinolin-5-ol

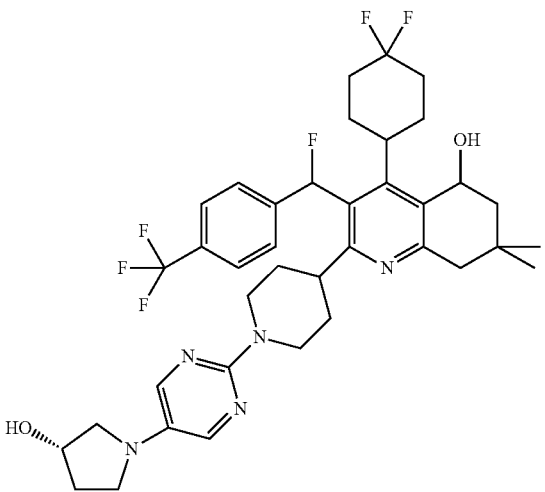 [SMILES: CC1(C)Cc2nc(C3CCN(c4ncc(N5CC[C@H](O)C5)cn4)CC3)c(C(F)c3ccc(C(F)(F)F)cc3)c(C3CCC(F)(F)CC3)c2C(O)C1]

Reactions similar to those of Reference Example 13 were performed except for using (3S)-3-pyrrolidinol instead of isonipecotic acid ethyl ester, and from 100 mg (0.120 mmol) of (−)-2-[1-(5-Bromopyrimidin-2-yl)piperidin-4-yl]-4-(4,4-difluorocyclohexyl)-3-{fluoro[4-(trifluoromethyl)phenyl]methyl}-5-[(4-methoxybenzyl)oxy]-7,7-dimethyl-5,6,7,8-tetrahydroquinoline, which was prepared by a method similar to that of Reference Example 11, 56 mg of the title compound was obtained as a white solid (yield: 65%).

Specific optical rotation: $[\alpha]_D^{26}=-63°$ (C=0.13, chloroform).

$^1$H-NMR spectrum (500 MHz, DMSO-D$_6$) δ ppm: 7.84 (2H, d, J=8 Hz), 7.83 (2H, s), 7.42 (2H, d, J=8 Hz), 7.19 (1H, d, J=46 Hz), 5.19-5.11 (1H, m), 5.09-5.00 (1H, m), 4.93-4.90 (1H, m), 4.56-4.48 (1H, m), 4.39-4.34 (1H, m), 4.23-4.16 (1H, m), 3.75-3.67 (1H, m), 3.39-3.14 (4H, m), 3.00-2.95

(1H, m), 2.77-2.46 (4H, m), 2.24-1.39 (15H, m), 1.06 (3H, s), 0.90 (3H, s), 0.44-0.38 (1H, m).

Example 58

4-(4,4-Difluorocyclohexyl)-3-{fluoro[4-(trifluoromethyl)phenyl]methyl}-7,7-dimethyl-2-(1-{5-[(methylamino)methyl]pyrimidin-2-yl}piperidin-4-yl)-5,6,7,8-tetrahydroquinolin-5-ol

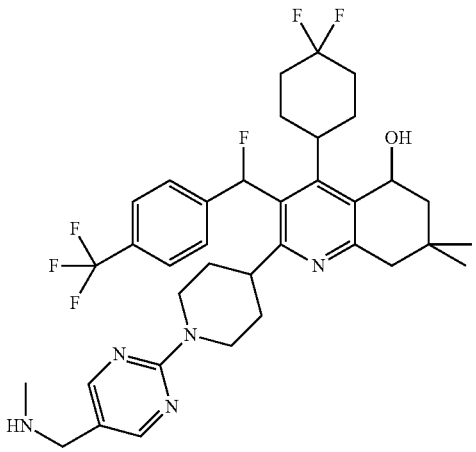 [SMILES: CNCc1cnc(N2CCC(c3nc4c(c(C5CCC(F)(F)CC5)c3C(F)c3ccc(C(F)(F)F)cc3)C(O)CC(C)(C)C4)CC2)nc1]

To 165 mg (0.250 mmol) of 4-(4,4-Difluorocyclohexyl)-3-{fluoro[4-(trifluoromethyl)phenyl]methyl}-2-[1-(5-formyl pyrimidin-2-yl)piperidin-4-yl]-7,7-dimethyl-5,6,7,8-tetrahydroquinolin-5-ol, which was prepared by a method similar to that of Example (36-1), 1.0 ml of methanol, 0.1 ml of tetrahydrofuran and 0.20 ml (about 2.5 mmol) of about 40% methylamine-methanol solution were added, and the reaction solution was stirred at room temperature for 12 hours. Then, 95 mg (2.5 mmol) of sodium borohydride was added thereto and the reaction solution was stirred at room temperature for 1 hour. After completion of the reaction, saturated ammonium chloride aqueous solution was poured into the reaction solution until the bubbling disappeared. Saturated sodium hydrogencarbonate aqueous solution was poured into the reaction solution to make the reaction solution basic and the reaction solution was extracted with ethyl acetate. The organic layer was washed with saturated sodium chloride aqueous solution and dried with anhydrous magnesium sulfate, and then the solvent was distilled off under reduced pressure. The obtained residue was subjected to silica gel column chromatography [dichloromethane/methanol/28% ammonia water=100/0/0-90/9.5/0.5 (V/V/V)] and the fraction including the desired compound was concentrated under reduced pressure to provide 128 mg of the title compound as a colorless oil (yield: 76%).

$^1$H-NMR spectrum (400 MHz, CDCl$_3$) δ ppm: 8.23 (2H, s), 7.64 (2H, d, J=8 Hz), 7.37 (2H, d, J=8 Hz), 7.21 (1H, d, J=49 Hz), 5.16-5.06 (1H, m), 4.83-4.72 (1H, m), 4.56-4.42 (1H, m), 3.71-3.50 (1H, m), 3.58 (2H, s), 2.87-2.49 (4H, m), 2.43 (3H, s), 2.34-1.54 (16H, m), 1.14 (3H, s), 0.99 (3H, s), 0.68-0.57 (1H, m).

Reference Example 1

4,4-Difluorocyclohexanecarboaldehyde

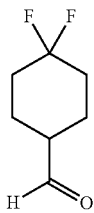

To a solution of 173 g (0.900 mol) of 4,4-difluorocyclohexanecarboxylic acid ethyl ester in 1.0 L toluene, 945 ml (0.945 mol) of 1.0 M diisobutyl aluminum hydride-toluene solution was added dropwise at −55° C. or lower temperatures and then the reaction solution was stirred at −65° C. for 30 minutes. After completion of the reaction, saturated ammonium chloride aqueous solution was added at −40° C. or lower temperatures to the reaction solution and then 1.0 L of 4 N hydrochloric acid was added at 0° C. or lower temperatures. The organic layer was separated and then the aqueous layer was extracted with toluene, and the combined organic layers were washed with 1 N hydrochloric acid, saturated sodium hydrogencarbonate aqueous solution and saturated sodium chloride aqueous solution in order and dried with anhydrous magnesium sulfate. The solvent was distilled off under reduced pressure and the obtained oily residue was subjected to distillation under reduced pressure (55-57° C./6 mmHg) to provide 75.3 g of the title compound as a colorless oil (yield: 57%).

$^1$H-NMR spectrum (300 MHz, CDCl$_3$) δ ppm: 9.68 (1H, d, J=1 Hz), 2.42-2.28 (1H, m), 2.16-1.70 (8H, m).

Reference Example 2

4-(1-Amino-2-cyanoethenyl)piperidin-1-carboxylic acid tert-butyl ester

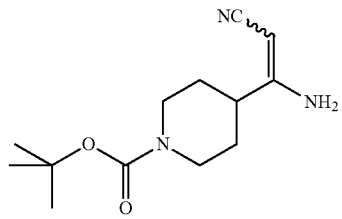 [SMILES: CC(C)(C)OC(=O)N1CCC(C(N)=CC#N)CC1]

47.7 ml (85.9 mmol) of 1.8 M lithium diisopropylamide-n-heptane/tetrahydrofuran/ethylbenzene solution was added to 50 ml of tetrahydrofuran and 4.14 ml (79.3 mmol) of acetonitrile was added dropwise under cooling with a dry ice-acetone bath, and the reaction solution was stirred for 3.0 hours. Under the same conditions, a solution of 13.9 g (66.1 mmol) of 4-cyanopiperidine-1-carboxylic acid tert-butyl ester in 30 ml of tetrahydrofuran was further added dropwise and then the reaction solution was stirred for 24 hours while the temperature of the reaction solution was slowly raised to room temperature. After completion of the reaction, ice water was added to the reaction solution and the reaction solution was extracted with ethyl acetate. The organic layer was washed with saturated sodium chloride aqueous solution and then dried with anhydrous magnesium sulfate. The solvent was distilled off under reduced pressure and the obtained residue was subjected to silica gel column chromatography [n-hexane/ethyl acetate=90/10-50/50 (V/V)], and the fraction including the desired compound was concentrated under reduced pressure to provide 10.7 g of the title compound as a yellow oil (yield: 64%).

$^1$H-NMR spectrum (300 MHz, CDCl$_3$) δ ppm: 4.65 (2H, br s), 4.34-4.15 (2H, m), 3.87 (1H, s), 2.77-2.59 (2H, m), 2.16 (1H, tt, J=12, 4 Hz), 1.84-1.73 (2H, m), 1.53-1.40 (2H, m), 1.46 (9H, s).

Mass spectrum (EI, m/z): 251 [M$^+$].

Reference Example 3

2-[(1-tert-Butyloxycarbonyl)piperidin-4-yl]-3-cyano-4-(4,4-difluorocyclohexyl)-7,7-dimethyl-5-oxo-1,4,5,6,7,8-hexahydroquinoline

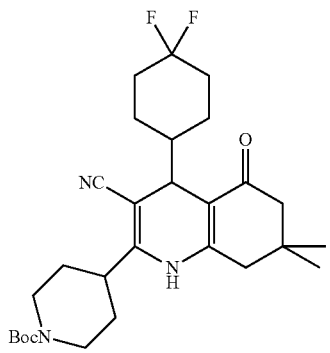 [SMILES: CC1(C)CC(=O)C2=C(C1)NC(C1CCN(C(=O)OC(C)(C)C)CC1)=C(C#N)C2C1CCC(F)(F)CC1]

To a solution of 14.6 g (57.9 mmol) of 4,4-difluorocyclohexanecarboaldehyde, which was prepared by a method similar to that of Reference Example 1, in 174 ml of toluene, 12.8 g (69.7 mmol) of 4-(1-amino-2-cyanovinyl)-piperidin-1-carboxylic acid tert-butyl ester, which was prepared by a method similar to that of Reference Example 2, was added. After stirring with heating at 100° C. for 10 minutes, 9.74 g (69.5 mmol) of dimedone was added thereto and the reaction solution was stirred under heating-to-reflux conditions for 5 hours. Furthermore, 2.43 g (17.3 mmol) of dimedone was added thereto and the reaction solution was stirred under heating-to-reflux conditions for 10 hours. After completion of the reaction, the precipitate was obtained by filtration to provide 17.9 g of the title compound as a white solid (yield: 60%).

$^1$H-NMR spectrum (300 MHz, CDCl$_3$) δ ppm: 6.27 (1H, s), 4.36-4.13 (2H, m), 3.70 (1H, d, J=2 Hz), 3.03 (1H, tt, J=12, 3 Hz), 2.91-2.73 (2H, m), 2.40-2.19 (5H, m), 2.17-1.98 (2H, m), 1.84-1.40 (9H, m), 1.48 (9H, s), 1.35-1.20 (1H, m), 1.10 (3H, s), 1.09 (3H, s).

Mass spectrum (CI, m/z): 504 [(M+1)$^+$].

Reference Example 4

2-[(1-tert-Butyloxycarbonyl)piperidin-4-yl]-3-cyano-4-(4,4-difluorocyclohexyl)-7,7-dimethyl-5-oxo-5,6,7,8-tetrahydroquinoline

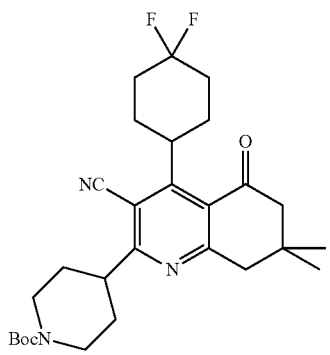 [SMILES: CC1(C)CC(=O)c2c(nc(C3CCN(C(=O)OC(C)(C)C)CC3)c(C#N)c2C2CCC(F)(F)CC2)C1]

To a solution of 26.9 g (53.4 mmol) of 2-[(1-tert-butyloxycarbonyl)piperidin-4-yl]-3-cyano-4-(4,4-difluorocyclohexyl)-7,7-dimethyl-5-oxo-1,4,5,6,7,8-hexahydroquinoline, which was prepared by a method similar to that of Reference Example 3 in 150 ml of dichloromethane, 18.2 g (80.0 mmol) of 2,3-dichloro-5,6-dicyano-p-benzoquinone was added, and the reaction solution was stirred at room temperature for 4 hours. After completion of the reaction, the reaction solution was filtered through Celite (trade name) and the filtrate was washed with saturated sodium hydrogencarbonate aqueous solution. The obtained organic layer was washed with saturated sodium hydrogencarbonate aqueous solution and saturated sodium chloride aqueous solution in order and dried with anhydrous magnesium sulfate, and then the solvent was distilled off under reduced pressure. Methanol was added to the obtained residue and the precipitate was obtained by filtration to provide 20.7 g of the title compound as a white solid (yield: 87%).

$^1$H-NMR spectrum (300 MHz, CDCl$_3$) δ ppm: 4.38-4.15 (2H, m), 4.13-3.97 (1H, m), 3.38 (1H, tt, J=11, 4 Hz), 3.06 (2H, s), 2.97-2.80 (2H, m), 2.69-2.52 (2H, m), 2.61 (2H, s), 2.33-2.17 (2H, m), 2.01-1.72 (8H, m), 1.48 (9H, s), 1.11 (6H, s).

Mass spectrum (EI, m/z): 501 [M$^+$].

Reference Example 5

2-[(1-tert-Butyloxycarbonyl)piperidin-4-yl]-4-(4,4-difluorocyclohexyl)-3-formyl-7,7-dimethyl-5,6,7,8-tetrahydroquinolin-5-ol

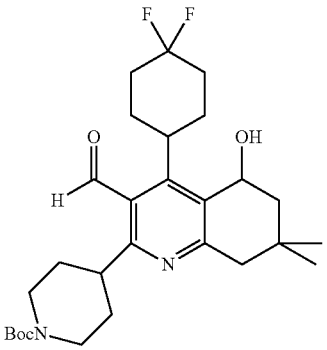 [SMILES: CC1(C)Cc2nc(C3CCN(C(=O)OC(C)(C)C)CC3)c(C=O)c(C3CCC(F)(F)CC3)c2C(O)C1]

To a solution of 20.1 g (40.0 mmol) of 2-[(1-tert-Butyloxycarbonyl)piperidin-4-yl]-3-cyano-4-(4,4-difluorocyclohexyl)-7,7-dimethyl-5-oxo-5,6,7,8-tetrahydroquinoline, which was prepared by a method similar to that of Reference Example 4, in 300 ml of toluene, 100 ml (100 mmol) of 1.0 M diisobutyl aluminum hydride-toluene solution was added dropwise at −50° C., and the reaction solution was stirred at the same temperature for 2 hours. Furthermore, 100 ml (100 mmol) of 1.0 M diisobutyl aluminum hydride-toluene solution was added dropwise at the same temperature, and the temperature of the reaction solution was raised to −21° C. and the reaction solution was stirred for 2 hours. After completion of the reaction, the reaction solution was poured into a mixed solution of 6 N hydrochloric acid, ice and ethyl acetate and the mixture was stirred vigorously. After separation, the obtained organic layer was filtered to remove the gelled substance therefrom and washed with saturated sodium hydrogencarbonate aqueous solution and saturated sodium chloride aqueous solution in order and dried with anhydrous magnesium sulfate, and then the solvent was distilled off under reduced pressure. Methanol was added to the obtained residue and the precipitate was obtained by filtration to provide 10.6 g of the title compound as a white solid (yield: 52%).

$^1$H-NMR spectrum (300 MHz, CDCl$_3$) δ ppm: 10.81 (1H, s), 5.09 (1H, q, J=6 Hz), 4.32-4.09 (2H, m), 3.53-3.37 (1H, m), 3.11 (1H, tt, J=11, 4 Hz), 2.97-2.56 (2H, m), 2.88 (1H, d, J=17 Hz), 2.65 (1H, d, J=17 Hz), 2.31-1.50 (15H, m), 1.47 (9H, s), 1.15 (3H, s), 1.00 (3H, s).

Mass spectrum (CI, m/z): 507 [(M+1)$^+$].

Reference Example 6

2-[(1-tert-Butyloxycarbonyl)piperidin-4-yl]-4-(4,4-difluorocyclohexyl)-3-formyl-5-[(4-methoxybenzyl)oxy]-7,7-dimethyl-5,6,7,8-tetrahydroquinoline

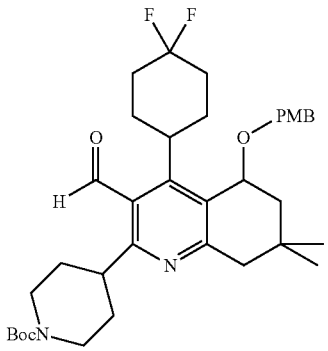

To a solution of 0.846 g (19.4 mmol) of sodium hydride (55% dispersion in mineral oil) in 19 ml of N,N-dimethylformamide, a solution of 9.63 g (19.0 mmol) of 2-[(1-tert-butyloxycarbonyl)piperidin-4-yl]-4-(4,4-difluorocyclohexyl)-3-formyl-7,7-dimethyl-5,6,7,8-tetrahydroquinolin-5-ol, which was prepared by a method similar to that of Reference Example 5, in 50 ml N,N-dimethylformamide was added under ice cooling, and the reaction solution was stirred for 0.5 hour. Then, 2.7 ml (19 mmol) of p-methoxybenzyl bromide was added thereto and the reaction solution was stirred under ice cooling for 2 hours and then at room temperature for 1.5 hours. After completion of the reaction, the reaction solution was poured into saturated sodium hydrogencarbonate aqueous solution and extracted with ethyl acetate. The obtained organic layer was washed with saturated sodium chloride aqueous solution and dried with anhydrous magnesium sulfate, and then the solvent was distilled off under reduced pressure. The obtained residue was subjected to silica gel column chromatography [n-hexane/ethyl acetate=90/10-70/30 (V/V)] and the fraction including the desired compound was concentrated under reduced pressure to provide 6.97 g of the title compound as a white solid (yield: 49%).

$^1$H-NMR spectrum (300 MHz, CDCl$_3$) δ ppm: 10.76 (1H, s), 7.23 (2H, d, J=9 Hz), 6.86 (2H, d, J=9 Hz), 4.80 (1H, dd, J=9, 5 Hz), 4.77 (1H, d, J=11 Hz), 4.36 (1H, d, J=11 Hz), 4.29-4.08 (2H, m), 3.79 (3H, s), 3.14-2.67 (3H, m), 3.08 (1H, tt, J=11, 3 Hz), 2.92 (1H, d, J=17 Hz), 2.67 (1H, d, J=17 Hz), 2.26-1.50 (14H, m), 1.47 (9H, s), 1.19 (3H, s), 1.04 (3H, s).

Mass spectrum (CI, m/z): 627 [(M+1)$^+$].

Reference Example 7

2-[(1-tert-Butyloxycarbonyl)piperidin-4-yl]-4-(4,4-difluorocyclohexyl)-3-{hydroxy[4-(trifluoromethyl)phenyl]methyl}-5-[(4-methoxybenzyl)oxy]-7,7-dimethyl-5,6,7,8-tetrahydroquinoline

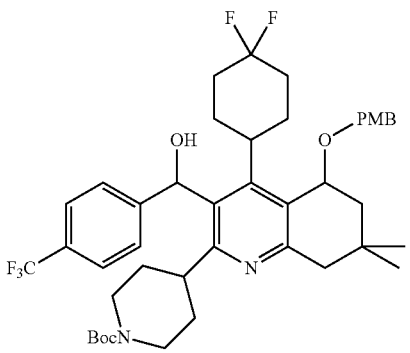

To a solution of 7.52 g (12.0 mmol) of 2-[(1-tert-Butyloxycarbonyl)piperidin-4-yl]-4-(4,4-difluorocyclohexyl)-3-formyl-5-[(4-methoxybenzyl)oxy]-7,7-dimethyl-5,6,7,8-tetrahydroquinoline, which was prepared by a method similar to that of Reference Example 6, in 60 ml of tetrahydrofuran, 48 ml (corresponding to 24.0 mmol) of tetrahydrofuran solution of 4-trifluoromethylphenyl magnesium bromide, which was prepared from 16.5 g (73.5 mmol) of 4-trifluoromethylphenyl bromide, 1.70 g (70.0 mmol) of magnesium and 140 ml of tetrahydrofuran, was added dropwise under ice cooling. After completion of the dropwise addition above, the reaction solution was stirred at room temperature for 2.3 hours. After completion of the reaction, the reaction solution was added to saturated ammonium chloride aqueous solution and extracted with ethyl acetate. The obtained organic layer was washed with saturated sodium hydrogencarbonate aqueous solution and saturated sodium chloride aqueous solution in order and dried with anhydrous magnesium sulfate, and then the solvent was distilled off under reduced pressure. The obtained residue was subjected to silica gel column chromatography [n-hexane/ethyl acetate=90/10-70/30 (V/V)] three times to provide Diastereomer 1 eluting earlier as a foam and 3.18 g (yield: 34%) of Diastereomer 2 eluting later as a foam for the title compound.

[Diastereomer 1]

Rf value: 0.29 [n-hexane/ethyl acetate=7/3 (V/V)].

$^1$H-NMR spectrum (300 MHz, CDCl$_3$) δ ppm: 7.57 (2H, d, J=8 Hz), 7.37 (2H, d, J=8 Hz), 7.25 (2H, d, J=9 Hz), 6.87 (2H, d, J=9 Hz), 6.43 (1H, s), 4.83 (1H, d, J=11 Hz), 4.81 (1H, t, J=5 Hz), 4.38 (1H, d, J=11 Hz), 4.25-4.02 (1H, m), 3.83-3.75 (1H, m), 3.80 (3H, s), 3.24-2.42 (3H, m), 2.86 (1H, d, J=17 Hz), 2.65 (1H, d, J=17 Hz), 2.29-1.52 (15H, m), 1.41 (9H, s), 1.20 (3H, s), 1.09 (3H, s), 0.50-0.40 (1H, m).

Mass spectrum (CI, m/z): 773 [(M+1)+].

[Diastereomer 2]

Rf value: 0.21 [n-hexane/ethyl acetate=7/3 (V/V)].

1H-NMR spectrum (300 MHz, CDCl3) δ ppm: 7.56 (2H, d, J=8 Hz), 7.39 (2H, d, J=8 Hz), 7.26 (2H, d, J=9 Hz), 6.88 (2H, d, J=9 Hz), 6.43 (1H, s), 4.83 (1H, t, J=5 Hz), 4.81 (1H, d, J=11 Hz), 4.39 (1H, d, J=11 Hz), 4.27-4.02 (1H, m), 3.84-3.70 (1H, m), 3.80 (3H, s), 3.23-2.47 (3H, m), 2.86 (1H, d, J=17 Hz), 2.65 (1H, d, J=17 Hz), 2.32-2.06 (4H, m), 2.03-1.50 (11H, m), 1.41 (9H, s), 1.21 (3H, s), 1.04 (3H, s), 0.47-0.37 (1H, m).

Mass spectrum (CI, m/z): 773 [(M+1)+].

Reference Example 8

2-[(1-tert-Butyloxycarbonyl)piperidin-4-yl]-4-(4,4-difluorocyclohexyl)-3-{fluoro[4-(trifluoromethyl)phenyl]methyl}-5-[(4-methoxybenzyl)oxy]-7,7-dimethyl-5,6,7,8-tetrahydroquinoline (diastereomer 2)

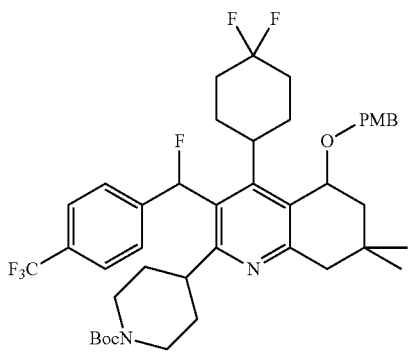

To a solution of 3.09 g (4.00 mmol) of 2-[(1-tert-Butyloxycarbonyl)piperidin-4-yl]-4-(4,4-difluorocyclohexyl)-3-{hydroxy[4-(trifluoromethyl)phenyl]methyl}-5-[(4-methoxybenzyl)oxy]-7,7-dimethyl-5,6,7,8-tetrahydroquinoline (Diastereomer 2), which was prepared by a method similar to that of Reference Example 7, in 12 ml of dichloromethane, 1.47 ml (8.00 mmol) of bis(methoxyethyl)aminosulfur trifluoride was added under cooling with a dry ice-acetone bath, and the reaction solution was stirred under the same conditions for 5.3 hours. Furthermore, 0.15 ml (0.800 mmol) of bis(methoxyethyl)aminosulfur trifluoride was added thereto and the reaction solution was stirred under the same conditions for 1 hour. After completion of the reaction, the reaction solution was added to a mixed solution of ice and saturated sodium hydrogencarbonate aqueous solution and extracted with chloroform. The obtained organic layer was washed with saturated sodium chloride aqueous solution and dried with anhydrous magnesium sulfate, and then the solvent was distilled off under reduced pressure. Cyclohexane was added to the obtained residue and the precipitate was obtained by filtration to provide 2.55 g of the title compound as a white solid (yield: 82%).

$^1$H-NMR spectrum (300 MHz, CDCl$_3$) δ ppm: 7.60 (2H, d, J=8 Hz), 7.33 (2H, d, J=8 Hz), 7.25 (2H, d, J=9 Hz), 7.12 (1H, d, J=49 Hz), 6.87 (2H, d, J=9 Hz), 4.83 (1H, t, J=5 Hz), 4.81 (1H, d, J=11 Hz), 4.39 (1H, d, J=11 Hz), 4.20-4.01 (1H, m), 3.90-3.74 (1H, m), 3.79 (3H, s), 3.24-3.08 (1H, m), 2.88 (1H, d, J=17 Hz), 2.68 (1H, d, J=17 Hz), 2.68-2.46 (2H, m), 2.32-2.08 (3H, m), 2.00-1.37 (11H, m), 1.41 (9H, s), 1.21 (3H, s), 1.05 (3H, s), 0.63-0.51 (1H, m).

Mass spectrum (CI, m/z): 775 [(M+1)$^+$].

Reference Example 9

4-(4,4-Difluorocyclohexyl)-3-{fluoro[4-(trifluoromethyl)phenyl]methyl}-5-[(4-methoxybenzyl)oxy]-7,7-dimethyl-2-(piperidin-4-yl)-5,6,7,8-tetrahydroquinoline (diastereomer 2)

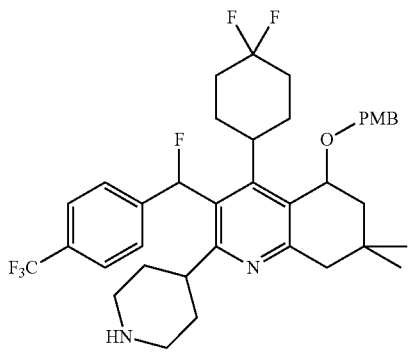

To a solution of 387 mg (0.500 mmol) of 2-[(1-tert-Butyloxycarbonyl)piperidin-4-yl]-4-(4,4-difluorocyclohexyl)-3-{fluoro[4-(trifluoromethyl)phenyl]methyl}-5-[(4-methoxybenzyl)oxy]-7,7-dimethyl-5,6,7,8-tetrahydroquinoline (Diastereomer 2), which was prepared by a method similar to that of Reference Example 8, in 2.5 ml of dichloromethane, 236 mg (1.05 mmol) of zinc bromide was added, and then the reaction solution was stirred at 30° C. for 68.5 hours. After completion of the reaction, the reaction solution was subjected to aminopropyl group-modified silica gel column chromatography [n-hexane/ethyl acetate/methanol=50/50/0-0/100/0-0/90/10 (V/V/V)] and the fraction including the desired compound was concentrated under reduced pressure to provide 320 mg of the title compound as a foam (yield: 95%).

$^1$H-NMR spectrum (300 MHz, CDCl$_3$) δ ppm: 7.60 (2H, d, J=8 Hz), 7.33 (2H, d, J=8 Hz), 7.25 (2H, d, J=9 Hz), 7.11 (1H, d, J=47 Hz), 6.87 (2H, d, J=9 Hz), 4.83 (1H, t, J=5 Hz), 4.81 (1H, d, J=11 Hz), 4.39 (1H, d, J=11 Hz), 3.79 (3H, s), 3.23-2.98 (2H, m), 2.95-2.55 (4H, m), 2.48 (1H, td, J=12, 2 Hz), 2.33-2.08 (3H, m), 2.01-1.47 (11H, m), 1.22 (3H, s), 1.06 (3H, s), 0.62-0.51 (1H, m).

Mass spectrum (CI, m/z): 675 [(M+1)$^+$].

Reference Example 10

(−)-4-(4,4-Difluorocyclohexyl)-3-{fluoro[4-(trifluoromethyl)phenyl]methyl}-5-[(4-methoxybenzyl)oxy]-7,7-dimethyl-2-(piperidin-4-yl)-5,6,7,8-tetrahydroquinoline

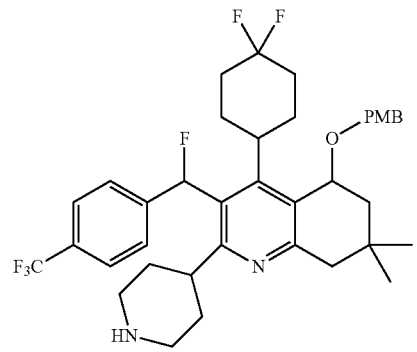

10 g of 4-(4,4-Difluorocyclohexyl)-3-{fluoro[4-(trifluoromethyl)phenyl]methyl}-5-[(4-methoxybenzyl)oxy]-7,7-dimethyl-2-(piperidin-4-yl)-5,6,7,8-tetrahydroquinoline (Diastereomer 2), which was prepared by a method similar to that of Reference Example 9, was optically resolved by high performance liquid chromatography [CHIRALPAK (trade name) AD-H 5 cmID×25 cmL (manufactured by Daicel Chemical Industries, Ltd.), eluent: n-hexane/2-propanol/isopropylamine=80/20/0.1 (V/V/V)] to provide 4.2 g of the title compound eluting later as a white solid and 4.4 g of the enantiomer of the title compound eluting earlier as a white solid, respectively.

[Title Compound]

Specific optical rotation: $[α]_D^{24}$=−101° (C=0.25, methanol).

$^1$H-NMR spectrum (300 MHz, CD$_2$Cl$_2$) δ ppm: 7.61 (2H, d, J=8 Hz), 7.35 (2H, d, J=8 Hz), 7.26 (2H, d, J=9 Hz), 7.14 (1H, d, J=47 Hz), 6.86 (2H, d, J=9 Hz), 4.85 (1H, t, J=5 Hz), 4.80 (1H, d, J=11 Hz), 4.39 (1H, d, J=11 Hz), 3.77 (3H, s), 3.25-3.09 (1H, m), 3.03-2.93 (1H, m), 2.92-2.80 (1H, m), 2.75-2.53 (3H, m), 2.45 (1H, td, J=12, 3 Hz), 2.30-2.11 (3H, m), 2.00-1.39 (11H, m), 1.20 (3H, s), 1.07 (3H, s), 0.61-0.51 (1H, m).

Mass spectrum (CI, m/z): 675 [(M+1)$^+$].

Analysis conditions of the high performance liquid chromatography:

Column: CHIRALPAK (trade name) AD-H (0.46 cm ID×25 cm, manufactured by Daicel Chemical Industries, Ltd.)

Eluent: n-hexane/2-propanol/isopropylamine=80/20/0.1 (V/V/V)

Flow rate: 1.0 ml/min

Column temperature: 40° C.

Detection wavelength: 271 nm

Retention time: 5.5 minutes
[Enantiomer of Title Compound]
Specific optical rotation: $[\alpha]_D^{24}$=100° (C=0.25, methanol).
$^1$H-NMR spectrum (300 MHz, CD$_2$Cl$_2$) δ ppm: 7.61 (2H, d, J=8 Hz), 7.35 (2H, d, J=8 Hz), 7.26 (2H, d, J=9 Hz), 7.14 (1H, d, J=47 Hz), 6.86 (2H, d, J=9 Hz), 4.85 (1H, t, J=5 Hz), 4.80 (1H, d, J=11 Hz), 4.39 (1H, d, J=11 Hz), 3.77 (3H, s), 3.25-3.08 (1H, m), 3.04-2.92 (1H, m), 2.91-2.80 (1H, m), 2.76-2.53 (3H, m), 2.45 (1H, td, J=12, 3 Hz), 2.28-2.10 (3H, m), 2.00-1.39 (11H, m), 1.20 (3H, s), 1.07 (3H, s), 0.61-0.50 (1H, m).
Mass spectrum (CI, m/z): 675 [(M+1)$^+$].
Analysis conditions of the high performance liquid chromatography:
Column: CHIRALPAK (trade name) AD-H (0.46 cm ID×25 cm, manufactured by Daicel Chemical Industries, Ltd.)
Eluent: n-hexane/2-propanol/isopropylamine=80/20/0.1 (V/V/V)
Flow rate: 1.0 ml/min
Column temperature: 40° C.
Detection wavelength: 271 nm
Retention time: 4.0 minutes Reference Example 11

(−)-2-[1-(5-Bromopyrimidine-2-yl)piperidin-4-yl]-4-(4,4-difluorocyclohexyl)-3-{fluoro[4-(trifluoromethyl)phenyl]methyl}-5-[(4-methoxybenzyl)oxy]-7,7-dimethyl-5,6,7,8-tetrahydroquinoline

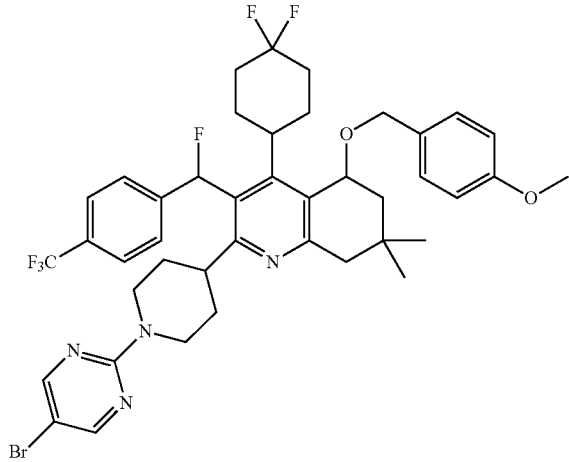 [SMILES: COc1ccc(COC2CC(C)(C)Cc3nc(C4CCN(c5ncc(Br)cn5)CC4)c(C(F)c4ccc(C(F)(F)F)cc4)c(C4CCC(F)(F)CC4)c32)cc1]

To a solution of 4.80 g (7.11 mmol) of (−)-4-(4,4-Difluorocyclohexyl)-3-{fluoro[4-(trifluoromethyl)phenyl]methyl}-5-[(4-methoxybenzyl)oxy]-7,7-dimethyl-2-(piperidin-4-yl)-5,6,7,8-tetrahydroquinoline, which was prepared by a method similar to that of Reference Example 10, in 16 ml of 1,4-dioxane, 1.40 g (7.24 mmol) of 5-bromo-2-chloropyrimidine and 1.6 ml (9.4 mmol) of diisopropylethylamine were added, and the reaction solution was stirred at 80° C. for 3 hours. After completion of the reaction, the reaction solution was poured into 40 ml of 0.5 N hydrochloric acid and extracted with ethyl acetate. The organic layer was washed with saturated sodium chloride aqueous solution, saturated sodium hydrogencarbonate aqueous solution and saturated sodium chloride aqueous solution in order and dried with anhydrous magnesium sulfate, and then the solvent was distilled off under reduced pressure. n-Heptane was added to the obtained residue and the precipitate was obtained by filtration to provide 5.09 g of the title compound as a white solid (yield: 86%).
$^1$H-NMR spectrum (300 MHz, CD$_2$Cl$_2$) δ ppm: δ: 8.22 (2H, s), 7.64 (2H, d, J=8 Hz), 7.38 (2H, d, J=8 Hz), 7.26 (2H, d, J=9 Hz), 7.17 (1H, d, J=46 Hz), 6.86 (2H, d, J=9 Hz), 4.85 (1H, t, J=5 Hz), 4.80 (1H, d, J=11 Hz), 4.75-4.63 (1H, m), 4.48-4.38 (1H, m), 4.39 (1H, d, J=11 Hz), 3.77 (3H, s), 3.26-3.07 (1H, m), 2.90-2.55 (4H, m), 2.32-1.35 (14H, m), 1.17 (3H, s), 1.04 (3H, s), 0.74-0.61 (1H, m).

Reference Example 12

(−)-4-(4,4-Difluorocyclohexyl)-3-{fluoro[4-(trifluoromethyl)phenyl]methyl}-5-[(4-methoxybenzyl)oxy]-7,7-dimethyl-2-{1-[5-(morpholin-4-yl)pyrimidin-2-yl]piperidin-4-yl}-5,6,7,8-tetrahydroquinoline

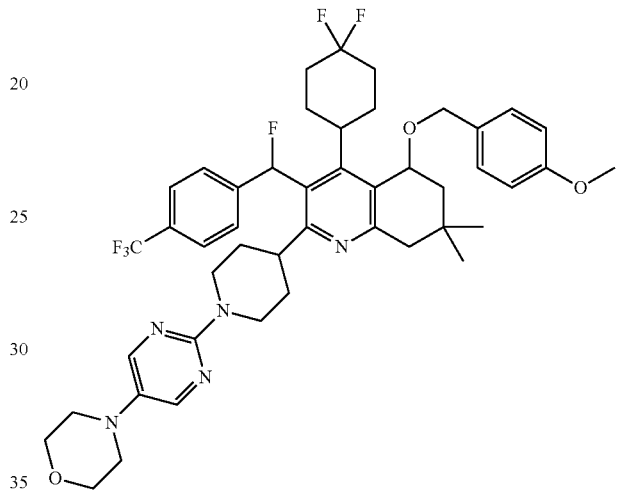

To a solution of 5.09 g (6.12 mmol) of (−)-2-[1-(5-Bromopyrimidin-2-yl)piperidin-4-yl]-4-(4,4-difluorocyclohexyl)-3-{fluoro[4-(trifluoromethyl)phenyl]methyl}-5-[(4-methoxybenzyl)oxy]-7,7-dimethyl-5,6,7,8-tetrahydroquinoline, which was prepared by a method similar to that of Reference Example 11, in 50 ml of toluene, 10 ml of tert-butanol, 1.6 ml (18 mmol) of morpholine, 1.73 g (18.0 mmol) of tert-butoxy sodium, 437 mg (0.917 mmol) of 2-dicyclohexylphosphino-2',4',6'-triisopropylbiphenyl and 107 mg (0.477 mmol) of palladium acetate were added under an argon gas atmosphere, and the reaction solution was stirred at 110° C. for 2.8 hours. After completion of the reaction, the reaction solution was poured into water and extracted with ethyl acetate. The organic layer was washed with saturated sodium chloride aqueous solution and then the solvent was distilled off under reduced pressure. The obtained residue was subjected to silica gel column chromatography [n-hexane/ethyl acetate=8/2-7/3-6/4 (V/V)] and the fraction including the desired compound was concentrated under reduced pressure to provide 4.30 g of the title compound as a white solid (yield: 84%).
Specific optical rotation: $[\alpha]_D^{28}$=−119° (C=0.645, chloroform).
$^1$H-NMR spectrum (300 MHz, CD$_2$Cl$_2$) δ ppm: 8.03 (2H, s), 7.63 (2H, d, J=8 Hz), 7.38 (2H, d, J=8 Hz), 7.26 (2H, d, J=9 Hz), 7.17 (1H, d, J=46 Hz), 6.86 (2H, d, J 9 Hz), 4.85 (1H, t, J=5 Hz), 4.80 (1H, d, J=11 Hz), 4.70-4.60 (1H, m), 4.43-4.32 (1H, m), 4.39 (1H, d, J=11 Hz), 3.86-3.71 (4H, m), 3.77 (3H, s), 3.26-3.09 (1H, m), 3.02-2.89 (4H, m), 2.87-2.57 (4H, m), 2.33-1.45 (14H, m), 1.18 (3H, s), 1.04 (3H, s), 0.72-0.59 (1H, m).

Reference Example 13

4-(4,4-Difluorocyclohexyl)-2-(1-{5-[4-(ethoxycarbonyl)piperidin-1-yl]pyrimidin-2-yl}piperidin-4-yl-3-{fluoro[4-(trifluoromethyl)phenyl]methyl}-5-[(4-methoxybenzyl)oxy]-7,7-dimethyl-5,6,7,8-tetrahydroquinoline

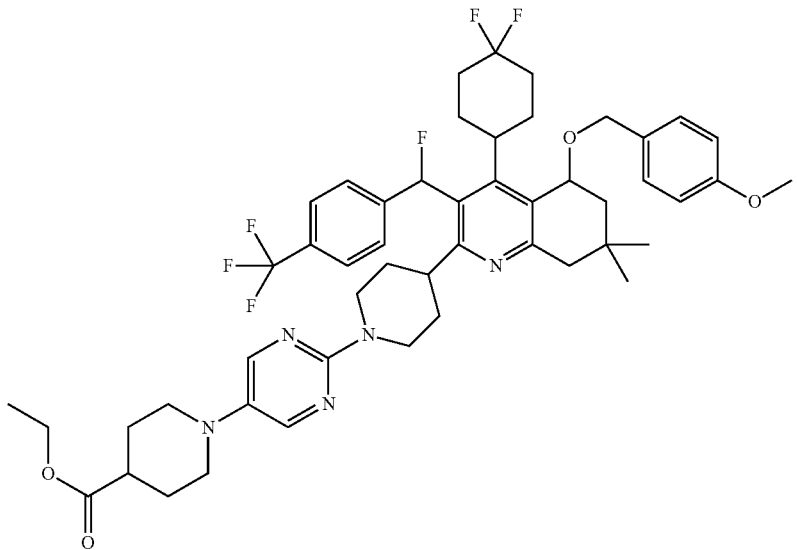 [SMILES: CCOC(=O)C1CCN(c2cnc(N3CCC(c4nc5c(c(C6CCC(F)(F)CC6)c4C(F)c4ccc(C(F)(F)F)cc4)C(OCc4ccc(OC)cc4)CC(C)(C)C5)CC3)nc2)CC1]

To a solution of 250 mg (0.301 mmol) of (–)-2-[1-(5-Bromopyrimidin-2-yl)piperidin-4-yl]-4-(4,4-difluorocyclohexyl)-3-{fluoro[4-(trifluoromethyl)phenyl]methyl}-5-[(4-methoxybenzyl)oxy]-7,7-dimethyl-5,6,7,8-tetrahydroquinoline, which was prepared by a method similar to that of Reference Example 11, in 1.5 ml of toluene, 61 mg (0.39 mmol) of isonipecotic acid ethyl ester, 38 mg (0.075 mmol) of 5-(di-tert-butylphosphino)-1',3',5'-triphenyl-1'H-[1,4']bipyrazole, 38 mg (0.39 mmol) of sodium tert-butoxide and 28 mg (0.030 mmol) of tris(dibenzylideneacetone)dipalladium (0) were added, and the reaction solution was stirred at 100° C. for 40 minutes while microwave irradiating using a microwave reactor (product name: Initiator, manufactured by Biotage). After completion of the reaction, the reaction solution was poured into saturated sodium hydrogencarbonate aqueous solution and extracted with ethyl acetate. The organic layer was washed with saturated sodium chloride aqueous solution and dried with anhydrous magnesium sulfate, and then the solvent was distilled off under reduced pressure. The obtained residue was subjected to silica gel column chromatography [n-hexane/ethyl acetate=85/15-65/35 (V/V)] and the fraction including the desired compound was concentrated under reduced pressure to provide 98 mg of the title compound as a light brown solid (yield: 36%).

$^1$H-NMR spectrum (400 MHz, CDCl$_3$) δ ppm: 8.05 (2H, s), 7.61 (2H, d, J=8 Hz), 7.36 (2H, d, J=8 Hz), 7.26 (2H, d, J=9 Hz), 7.15 (1H, d, J=47 Hz), 6.87 (2H, d, J=9 Hz), 4.86-4.76 (2H, m), 4.71-4.62 (1H, m), 4.43-4.34 (2H, m), 4.16 (2H, q, J=7 Hz), 3.79 (3H, s), 3.34-3.08 (3H, m), 2.88-2.58 (6H, m), 2.42-1.49 (19H, m), 1.27 (3H, t, J=7 Hz), 1.19 (3H, s), 1.04 (3H, s), 0.70-0.60 (1H, m).

Mass spectrum (FAB, m/z): 907 [M$^+$].

Reference Example 14

2-Chloro-5-(methylsulphonyl)pyrimidin

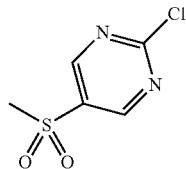

To a solution of 80 mg (0.50 mmol) of 2-chloro-5-methylthiopyrimidine, which was prepared by a method similar to that of Reference Example 36, in 2.5 ml of dichloromethane, 264 mg (1.0 mmol) of 3-chloro-perbenzoic acid (purity: 65%) was added, and the reaction solution was stirred at room temperature for 90 minutes. After completion of the reaction, saturated sodium hydrogencarbonate aqueous solution was added to the reaction solution and the reaction solution was extracted with dichloromethane. The organic layer was washed with 1.5 mol/L sodium sulfite aqueous solution and dried with anhydrous sodium sulfate, and then the solvent was distilled off under reduced pressure. The obtained residue was subjected to silica gel column chromatography [n-hexane/ethyl acetate=70/30-40/60 (V/V)] and the fraction including the desired compound was concentrated under reduced pressure to provide 80 mg of the title compound as a white solid (yield: 82%).

$^1$H-NMR spectrum (500 MHz, CDCl$_3$) δ ppm: 9.11 (2H, s), 3.19 (3H, s).

Reference Example 15

4-(4,4-Difluorocyclohexyl)-3-{fluoro[4-(trifluoromethyl)phenyl]methyl}-5-[(4-methoxybenzyl)oxy]-7,7-dimethyl-2-[1-(pyrimidin-2-yl)piperidin-4-yl]-5,6,7,8-tetrahydroquinoline

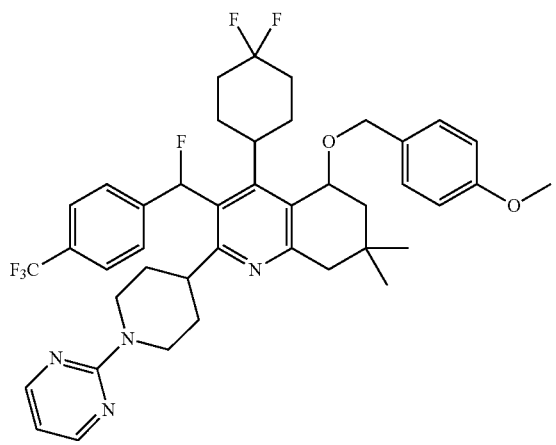 [SMILES: COc1ccc(COC2CC(C)(C)Cc3nc(C4CCN(c5ncccn5)CC4)c(C(F)c4ccc(C(F)(F)F)cc4)c(C4CCC(F)(F)CC4)c32)cc1]

To 1.21 g (1.79 mmol) of (−)-4-(4,4-Difluorocyclohexyl)-3-{fluoro[4-(trifluoromethyl)phenyl]methyl}-5-[(4-methoxybenzyl)oxy]-7,7-dimethyl-2-(piperidin-4-yl)-5,6,7,8-tetrahydroquinoline, which was prepared by a method similar to that of Reference Example 10, 0.90 g (5.7 mmol) of 2-bromopyrimidine, 1.0 ml (5.9 mmol) of diisopropylethylamine and 20 ml of tert-butanol were added, and the reaction solution was stirred at 65° C. for 2.5 hours. After completion of the reaction, the reaction solution was poured into water and extracted with ethyl acetate. The organic layer was washed with saturated sodium chloride aqueous solution and dried with anhydrous magnesium sulfate, and then the solvent was distilled off under reduced pressure. n-Hexane was added to the obtained residue and the precipitate was obtained by filtration to provide 1.17 g of the title compound as a white solid (yield: 87%).

$^1$H-NMR spectrum (300 MHz, $CD_2Cl_2$) δ ppm: 8.22 (2H, d, J=5 Hz), 7.64 (2H, d, J=8 Hz), 7.38 (2H, d, J=8 Hz), 7.26 (2H, d, J=9 Hz), 7.18 (1H, d, J=46 Hz), 6.86 (2H, d, J=9 Hz), 6.39 (1H, t, J=5 Hz), 4.85 (1H, t, J=5 Hz), 4.81-4.72 (1H, m), 4.80 (1H, d, J=11 Hz), 4.56-4.44 (1H, m), 4.39 (1H, d, J=11 Hz), 3.77 (3H, s), 3.26-3.10 (1H, m), 2.90-2.56 (4H, m), 2.32-2.02 (4H, m), 2.00-1.31 (10H, m), 1.17 (3H, s), 1.04 (3H, s), 0.74-0.62 (1H, m).

Mass spectrum (CI, m/z): 753 [(M+1)$^+$].

Reference Example 16

4-(4,4-Difluorocyclohexyl)-3-{fluoro[4-(trifluoromethyl)phenyl]methyl}-2-[1-(5-formylpyrimidin-2-yl)piperidin-4-yl]-5-[(4-methoxybenzyl)oxy]-7,7-dimethyl-5,6,7,8-tetrahydroquinoline

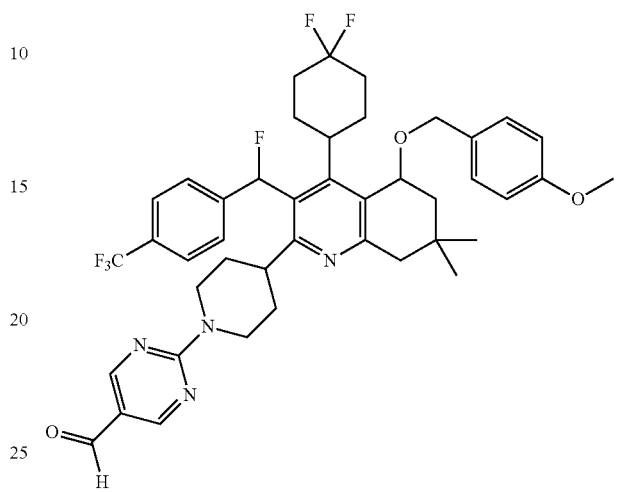

To a solution of 1.00 g (1.48 mmol) of (−)-4-(4,4-Difluorocyclohexyl)-3-{fluoro[4-(trifluoromethyl)phenyl]methyl}-5-[(4-methoxybenzyl)oxy]-7,7-dimethyl-2-(piperidin-4-yl)-5,6,7,8-tetrahydroquinoline, which was prepared by a method similar to that of Reference Example 10, in 5 ml of 1-methyl-2-pyrrolidone, 0.23 g (1.6 mmol) of 2-chloro-5-formyl pyrimidine and 265 µl (1.78 mmol) of diazabicycloundecene were added, and the reaction solution was stirred at room temperature for 1 hour. Then, 0.023 g (0.16 mmol) of 2-chloro-5-formyl pyrimidine was added thereto and the reaction solution was further stirred at room temperature for 0.58 hours. Furthermore, 0.023 g (0.16 mmol) of 2-chloro-5-formyl pyrimidine was added thereto and the reaction solution was stirred at room temperature for 1.5 hours. After completion of the reaction, the reaction solution was poured into saturated sodium hydrogencarbonate aqueous solution and extracted with ethyl acetate. The organic layer was washed with saturated sodium chloride aqueous solution and dried with anhydrous magnesium sulfate, and then the solvent was distilled off under reduced pressure. The obtained residue was subjected to silica gel column chromatography [n-hexane/ethyl acetate=40/10 (V/V)] and the fraction including the desired compound was concentrated under reduced pressure to provide 1.00 g of the title compound as a light yellow solid (yield: 87%).

$^1$H-NMR spectrum (300 MHz, $CDCl_3$) δ ppm: 9.71 (1H, s), 8.65 (2H, s), 7.63 (2H, d, J=8 Hz), 7.37 (2H, d, J=8 Hz), 7.25 (2H, d, J=9 Hz), 7.16 (1H, d, J=48 Hz), 6.87 (2H, d, J=9 Hz), 5.03-4.91 (1H, m), 4.83 (1H, t, J=5 Hz), 4.81 (1H, d, J=11 Hz), 4.77-4.67 (1H, m), 4.39 (1H, d, J=11 Hz), 3.79 (3H, s), 3.25-3.09 (1H, m), 2.92-2.74 (2H, m), 2.84 (1H, d, J=17 Hz), 2.65 (1H, d, J=17 Hz), 2.34-1.46 (14H, m), 1.19 (3H, s), 1.03 (3H, s), 0.79-0.68 (1H, m).

Mass spectrum (EI, m/z): 780 [M$^+$].

Reference Example 17

(−)-4-(4,4-Difluorocyclohexyl)-3-{fluoro[4-(trifluoromethyl)phenyl]methyl}-2-[1-[5-(hydroxymethyl)pyrimidin-2-yl]piperidin-4-yl]-5-[(4-methoxybenzyl)oxy]-7,7-dimethyl-5,6,7,8-tetrahydroquinoline

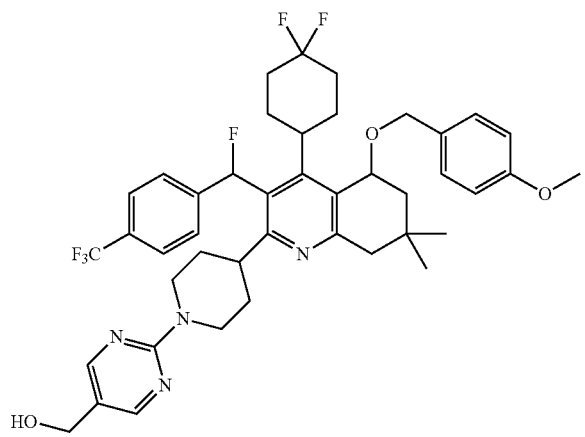 [SMILES: COc1ccc(COC2CC(C)(C)Cc3nc(C4CCN(c5ncc(CO)cn5)CC4)c(C(F)c4ccc(C(F)(F)F)cc4)c(C4CCC(F)(F)CC4)c32)cc1]

To a solution of 500 mg (0.64 mmol) of 4-(4,4-Difluorocyclohexyl)-3-{fluoro[4-(trifluoromethyl)phenyl]methyl}-2-[1-(5-formyl pyrimidin-2-yl)piperidin-4-yl]-5-[(4-methoxybenzyl)oxy]-7,7-dimethyl-5,6,7,8-tetrahydroquinoline, which was prepared by a method similar to that of Reference Example 16, in a mixture of 5 ml ethanol and 5 ml tetrahydrofuran, 12 mg (0.32 mmol) of sodium borohydride was added under ice cooling, and the reaction solution was stirred under ice cooling conditions for 0.83 hour. After completion of the reaction, the solvent was distilled off under reduced pressure and 1 N hydrochloric acid and 1 N sodium hydroxide aqueous solution were added in order, and the reaction solution was extracted with ethyl acetate. The organic layer was washed with saturated sodium chloride aqueous solution and dried with anhydrous magnesium sulfate, and then the solvent was distilled off under reduced pressure to provide 0.52 g of the title compound as a white foam (yield: quantitative).

Specific optical rotation: $[\alpha]_D^{28}=125°$ (C=0.600, chloroform).

$^1$H-NMR spectrum (300 MHz, CDCl$_3$) δ ppm: 8.25 (2H, s), 7.62 (2H, d, J=8 Hz), 7.36 (2H, d, J=8 Hz), 7.25 (2H, d, J=9 Hz), 7.15 (1H, d, J=47 Hz), 6.87 (2H, d, J=9 Hz), 4.85-4.74 (1H, m), 4.83 (1H, t, J=5 Hz), 4.81 (1H, d, J=11 Hz), 4.57-4.44 (3H, m), 4.39 (1H, d, J=11 Hz), 3.79 (3H, s), 3.25-3.08 (1H, m), 2.90-2.59 (4H, m), 2.33-2.06 (4H, m), 2.01-1.42 (11H, m), 1.19 (3H, s), 1.03 (3H, s), 0.72-0.62 (1H, m).

Mass spectrum (EI, m/z): 782 [M$^+$].

Reference Example 18

2-{1-[5-(Cyclohex-1-ene-1-yl)pyrimidin-2-yl]piperidin-4-yl}-4-(4,4-difluorocyclohexyl)-3-{fluoro[4-(trifluoromethyl)phenyl]methyl}-5-[(4-methoxybenzyl)oxy]-7,7-dimethyl-5,6,7,8-tetrahydroquinoline

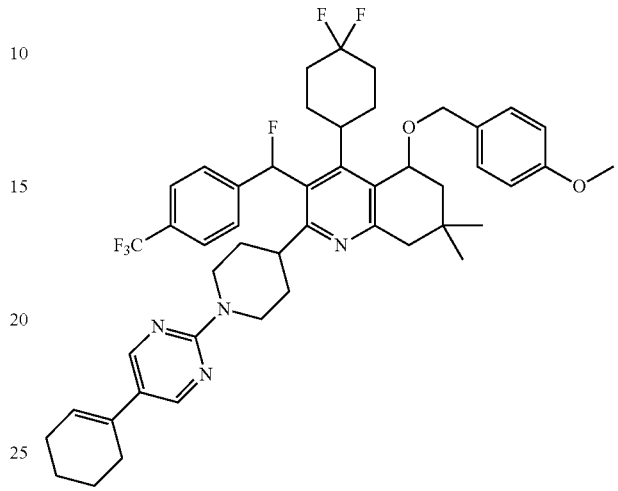

To 97 mg (0.12 mmol) of (−)-2-[1-(5-Bromopyrimidin-2-yl)piperidin-4-yl]-4-(4,4-difluorocyclohexyl)-3-{fluoro[4-(trifluoromethyl)phenyl]methyl}-5-[(4-methoxybenzyl)oxy]-7,7-dimethyl-5,6,7,8-tetrahydroquinoline, which was prepared by a method similar to that of Reference Example 11, 114 mg (1.19 mmol) of tert-butoxy sodium, 26 mg (0.055 mmol) of 2-dicyclohexylphosphino-2',4',6'-triisopropylbiphenyl, 3.4 mg (0.015 mmol) of palladium acetate, 3 ml of toluene, 1.5 ml of tert-butanol and 100 μl (0.471 mmol) of cyclohexenylboronic acid pinacol ester were added under an argon gas atmosphere, and the reaction solution was stirred at 120° C. for 5 hours. After completion of the reaction, the reaction solution was poured into water and extracted with ethyl acetate. The organic layer was washed with saturated sodium chloride aqueous solution and dried with anhydrous magnesium sulfate, and then the solvent was distilled off under reduced pressure. The obtained residue was combined with the residue which was obtained by performing similar reactions using 99 mg (0.12 mmol) of (−)-2-[1-(5-bromopyrimidin-2-yl)piperidin-4-yl]-4-(4,4-difluorocyclohexyl)-3-{fluoro[4-(trifluoromethyl)phenyl]methyl}-5-[(4-methoxybenzyl)oxy]-7,7-dimethyl-5,6,7,8-tetrahydroquinoline, and they were subjected to silica gel column chromatography [n-hexane/ethyl acetate=100/0-95/5-92/8-88/12 (V/V)], and the fraction including the desired compound was concentrated under reduced pressure to provide 80 mg of the title compound as a white solid (yield: 41%).

$^1$H-NMR spectrum (300 MHz, CD$_2$Cl$_2$) δ ppm: 8.27 (2H, s), 7.64 (2H, d, J=8 Hz), 7.38 (2H, d, J=8 Hz), 7.26 (2H, d, J=9 Hz), 7.17 (1H, d, J=45 Hz), 6.86 (2H, d, J=9 Hz), 6.02-5.91 (1H, m), 4.85 (1H, t, J=5 Hz), 4.81-4.70 (1H, m), 4.80 (1H, d, J=11 Hz), 4.54-4.44 (1H, m), 4.39 (1H, d, J=11 Hz), 3.77 (3H, s), 3.26-3.10 (1H, m), 2.91-2.54 (4H, m), 2.39-1.46 (22H, m), 1.17 (3H, s), 1.04 (3H, s), 0.74-0.61 (1H, m).

Reference Example 19

4-(4,4-Difluorocyclohexyl)-3-{fluoro[4-(trifluoromethyl)phenyl]methyl}-2-{1-[5-(1-hydroxy-2-methylpropyl)pyrimidin-2-yl]piperidin-4-yl}-5-[(4-methoxybenzyl)oxy]-7,7-dimethyl-5,6,7,8-tetrahydroquinoline

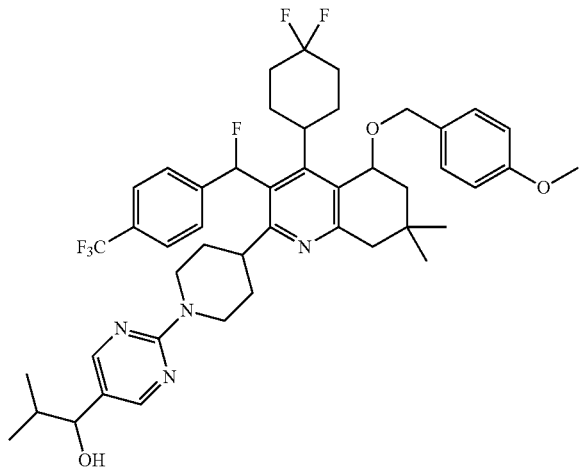 [SMILES: COc1ccc(COC2CC(C)(C)Cc3nc(C4CCN(c5ncc(C(O)C(C)C)cn5)CC4)c(C(F)c4ccc(C(F)(F)F)cc4)c(C4CCC(F)(F)CC4)c32)cc1]

To a solution of 213 mg (0.273 mmol) of 4-(4,4-Difluorocyclohexyl)-3-{fluoro[4-(trifluoromethyl)phenyl]methyl}-2-[1-(5-formyl pyrimidin-2-yl)piperidin-4-yl]-5-[(4-methoxybenzyl)oxy]-7,7-dimethyl-5,6,7,8-tetrahydroquinoline, which was prepared by a method similar to that of Reference Example 16, in 5 ml of tetrahydrofuran, 0.5 ml (0.5 mmol) of 1.0 mol/L isopropyl magnesium bromide-tetrahydrofuran solution was added under an argon gas atmosphere, and the reaction solution was stirred at room temperature for 0.5 hour. Then, 0.5 ml (0.5 mmol) of 1.0 mol/L isopropyl magnesium bromide-tetrahydrofuran solution was further added and the reaction solution was stirred at room temperature for 0.5 hour. After completion of the reaction, the reaction solution was poured into saturated ammonium chloride aqueous solution and the reaction solution was extracted with ethyl acetate. The organic layer was washed with saturated sodium chloride aqueous solution and dried with anhydrous magnesium sulfate, and then the solvent was distilled off under reduced pressure. The obtained residue was subjected to silica gel column chromatography [n-hexane/ethyl acetate=85/15-80/20 (V/V)] and the fraction including the desired compound was concentrated under reduced pressure to provide 174 mg of the title compound as a white solid (yield: 77%).

$^1$H-NMR spectrum (300 MHz, CD$_2$Cl$_2$) δ ppm: 8.18 (2H, s), 7.64 (2H, d, J=8 Hz), 7.38 (2H, d, J=8 Hz), 7.26 (2H, d, J=9 Hz), 7.18 (1H, d, J=45 Hz), 6.86 (2H, d, J 9 Hz), 4.85 (1H, t, J=5 Hz), 4.81-4.71 (1H, m), 4.80 (1H, d, J=11 Hz), 4.54-4.45 (1H, m), 4.39 (1H, d, J=11 Hz), 4.19 (1H, d, J=7 Hz), 3.77 (3H, s), 3.26-3.10 (1H, m), 2.89-2.57 (4H, m), 2.29-1.44 (16H, m), 1.17 (3H, s), 1.04 (3H, s), 0.97 (3H, d, J=7 Hz), 0.79 (3H, d, J=7 Hz), 0.72-0.63 (1H, m).

Reference Example 20

Methyl 5-(2-chloropyrimidin-5-yl)pentanoate

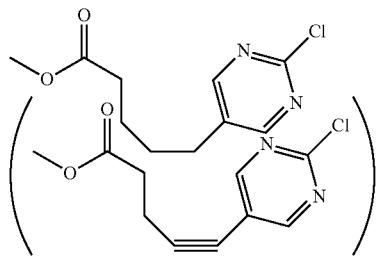

To a solution of 500 mg (2.58 mmol) of 5-bromo-2-chloropyrimidine in 10 ml of N,N-dimethylformamide, 397 mg (3.54 mmol) of methyl 4-pentinoate, which was synthesized by the method described in W. D. Wulff et al., Journal of the American Chemical Society, 1988, Vol. 110, pp. 7419-7434, 49 mg (0.26 mmol) of copper iodide, 149 mg (0.129 mmol) of tetrakis(triphenylphosphine)palladium (0) and 5.0 ml of triethylamine were added, and the reaction solution was stirred at 80° C. for 4 hours. After completion of the reaction, saturated ammonium chloride aqueous solution was added to the reaction solution and the reaction solution was extracted with ethyl acetate. The organic layer was washed with saturated sodium chloride aqueous solution and dried with anhydrous sodium sulfate, and then the solvent was distilled off under reduced pressure. The obtained residue was subjected to silica gel column chromatography [n-hexane/ethyl acetate=93/7-75/25 (V/V)] and the fraction including the desired compound was concentrated under reduced pressure to provide 347 mg (yield: 60%) of methyl 5-(2-chloropyrimidin-5-yl)-4-pentinoate.

To a solution of 337 mg (1.50 mmol) of methyl 5-(2-chloropyrimidin-5-yl)-4-pentinoate obtained above in 7 ml of ethyl acetate, 70 mg of 10% palladium-carbon was added, and the reaction solution was stirred at room temperature for 20 hours under a hydrogen gas atmosphere. The catalyst was removed by filtration and then the solvent was distilled off under reduced pressure to provide 177 mg of the title compound as a colorless oil (yield: 52%).

$^1$H-NMR spectrum (500 MHz, CDCl$_3$) δ ppm: 8.46 (2H, s), 3.68 (3H, s), 2.63 (2H, t, J=7 Hz), 2.36 (2H, t, J=7 Hz), 1.74-1.63 (4H, m).

Mass spectrum (EI, m/z): 228 [M$^+$].

Reference Example 21

4-(4,4-Difluorocyclohexyl)-2-{1-[5-(ethoxymethyl)pyrimidin-2-yl]piperidin-4-yl}-3-{fluoro[4-(trifluoromethyl)phenyl]methyl}-5-[(4-methoxybenzyl)oxy]-7,7-dimethyl-5,6,7,8-tetrahydroquinoline

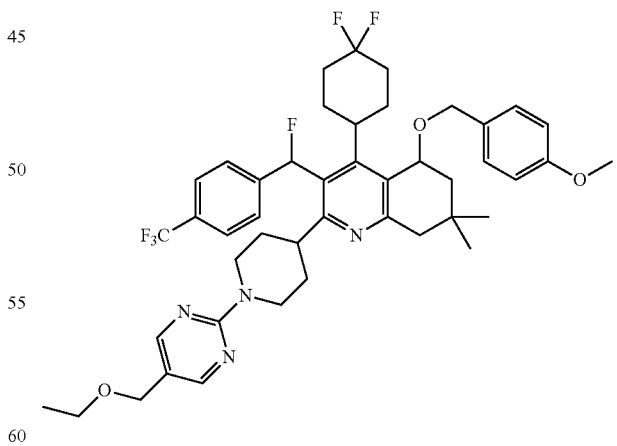

To a solution of 78 mg (0.10 mmol) of (−)-4-(4,4-Difluorocyclohexyl)-3-{fluoro[4-(trifluoromethyl)phenyl]methyl}-2-[1-[5-(hydroxymethyl)pyrimidin-2-yl]piperidin-4-yl]-5-[(4-methoxybenzyl)oxy]-7,7-dimethyl-5,6,7,8-tetrahydroquinoline, which was prepared by a method similar to that of Reference Example 17, in 2 ml of dichloromethane, 340 µl (2.0 mmol) of diisopropylethylamine and 77 µl (1.0 mmol) of methanesulfonyl chloride were added, and 2 ml of ethanol was added thereto immediately after initiation of stirring at room temperature and the reaction solution was further stirred at room temperature for 0.25 hour. After completion of the reaction, the reaction solution was poured into saturated sodium hydrogencarbonate aqueous solution and extracted with ethyl acetate. The organic layer was washed with saturated sodium chloride aqueous solution and dried with anhydrous magnesium sulfate, and then the solvent was distilled off under reduced pressure. The obtained residue was subjected to silica gel column chromatography [n-hexane/ethyl acetate=98/2-70/30 (V/V)] and the fraction including the desired compound was concentrated under reduced pressure to provide 68 mg of the title compound as a foam (yield: 85%).

$^1$H-NMR spectrum (300 MHz, CDCl$_3$) δ ppm: 8.22 (2H, s), 7.62 (2H, d, J=8 Hz), 7.36 (2H, d, J=8 Hz), 7.25 (2H, d, J=9 Hz), 7.15 (1H, d, J=48 Hz), 6.87 (2H, d, J=9 Hz), 4.87-4.73 (2H, m), 4.81 (1H, d, J=11 Hz), 4.56-4.46 (1H, m), 4.38 (1H, d, J=11 Hz), 4.28 (2H, s), 3.79 (3H, s), 3.48 (2H, q, J=7 Hz), 3.24-3.08 (1H, m), 2.91-2.59 (4H, m), 2.31-2.05 (4H, m), 2.02-1.47 (10H, m), 1.21 (3H, t, J=7 Hz), 1.19 (3H, s), 1.03 (3H, s), 0.70-0.60 (1H, m).

Mass spectrum (EI, m/z): 810 [M$^+$].

Reference Example 22

4-(4,4-Difluorocyclohexyl)-3-{fluoro[4-(trifluoromethyl)phenyl]methyl}-5-[(4-methoxybenzyl)oxy]-2-{1-[5-(methoxymethyl)pyrimidin-2-yl]piperidin-4-yl}-7,7-dimethyl-5,6,7,8-tetrahydroquinoline

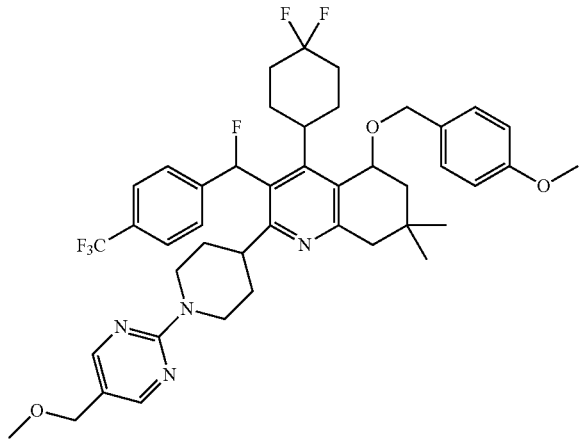

Reactions similar to those of Reference Example 21 were performed except for using methanol instead of ethanol, and from 72 mg (0.092 mmol) of 4-(4,4-Difluorocyclohexyl)-3-{fluoro[4-(trifluoromethyl)phenyl]methyl}-2-[1-[5-(hydroxymethyl)pyrimidin-2-yl]piperidin-4-yl]-5-[(4-methoxybenzyl)oxy]-7,7-dimethyl-5,6,7,8-tetrahydroquinoline, which was prepared by a method similar to that of Reference Example 17, 48 mg of the title compound was obtained as a foam (yield: 66%).

$^1$H-NMR spectrum 300 MHz, CD$_2$Cl$_2$) δ ppm: 8.19 (2H, s), 7.64 (2H, d, J=8 Hz), 7.38 (2H, d, J=8 Hz), 7.26 (2H, d, J=9 Hz), 7.18 (1H, d, J=48 Hz), 6.86 (2H, d, J=9 Hz), 4.89-4.72 (1H, m), 4.85 (1H, t, J=5 Hz), 4.80 (1H, d, J=11 Hz), 4.56-4.46 (1H, m), 4.39 (1H, d, J=11 Hz), 4.20 (2H, s), 3.77 (3H, s), 3.29 (3H, s), 3.24-3.09 (1H, m), 2.89-2.58 (4H, m), 2.29-2.03 (4H, m), 2.00-1.46 (10H, m), 1.17 (3H, s), 1.04 (3H, s), 0.72-0.63 (1H, m).

Mass spectrum (EI, m/z): 796 [M+].

Reference Example 23

4-(4,4-Difluorocyclohexyl)-3-{fluoro[4-(trifluoromethyl)phenyl]methyl}-5-[(4-methoxybenzyl)oxy]-7,7-dimethyl-2-(1-{5-[(propan-2-yloxy)methyl]pyrimidin-2-yl}piperidin-4-yl)-5,6,7,8-tetrahydroquinoline

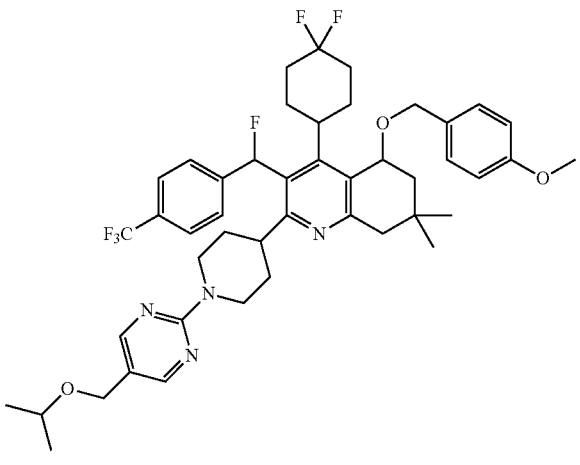 [SMILES: COc1ccc(COC2CC(C)(C)Cc3nc(C4CCN(c5ncc(COC(C)C)cn5)CC4)c(C(F)c4ccc(C(F)(F)F)cc4)c(C4CCC(F)(F)CC4)c32)cc1]

Reactions similar to those of Reference Example 21 were performed except for using isopropanol instead of ethanol, and from 78 mg (0.10 mmol) of 4-(4,4-Difluorocyclohexyl)-3-{fluoro[4-(trifluoromethyl)phenyl]methyl}-2-[1-[5-(hydroxymethyl)pyrimidin-2-yl]piperidin-4-yl]-5-[(4-methoxybenzyl)oxy]-7,7-dimethyl-5,6,7,8-tetrahydroquinoline, which was prepared by a method similar to that of Reference Example 17, 54 mg of the title compound was obtained as a foam (yield: 65%).

$^1$H-NMR spectrum (300 MHz, CDCl$_3$) δ ppm: 8.22 (2H, s), 7.62 (2H, d, J=8 Hz), 7.36 (2H, d, J=8 Hz), 7.25 (2H, d, J=9 Hz), 7.15 (1H, d, J=48 Hz), 6.87 (2H, d, J=9 Hz), 4.86-4.72 (1H, m), 4.82 (1H, t, J=5 Hz), 4.81 (1H, d, J=11 Hz), 4.55-4.46 (1H, m), 4.38 (1H, d, J=11 Hz), 4.28 (2H, s), 3.79 (3H, s), 3.64 (1H, dq, J=6, 6 Hz), 3.22-3.08 (1H, m), 2.91-2.60 (4H, m), 2.31-2.05 (4H, m), 2.01-1.46 (10H, m), 1.19 (3H, s), 1.18 (6H, d, J=6 Hz), 1.03 (3H, s), 0.70-0.59 (1H, m).

Mass spectrum (EI, m/z): 824 [M+].

Reference Example 24

4-(4,4-Difluorocyclohexyl)-3-{fluoro[4-(trifluoromethyl)phenyl]methyl}-5-[(4-methoxybenzyl)oxy]-7,7-dimethyl-2-(1-{5-[(2-methylpropoxy)methyl]pyrimidin-2-yl}piperidin-4-yl)-5,6,7,8-tetrahydroquinoline

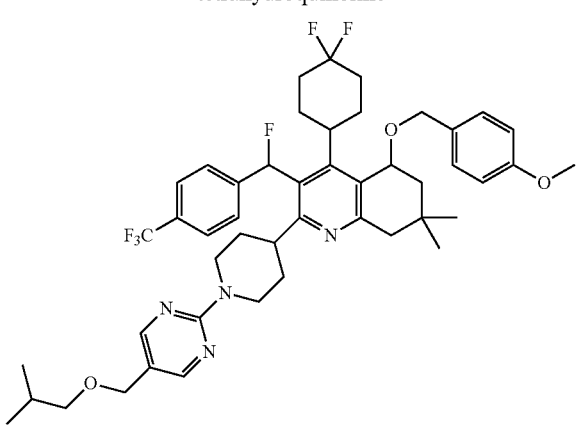

Reactions similar to those of Reference Example 21 were performed except for using isobutanol instead of ethanol, and from 78 mg (0.10 mmol) of 4-(4,4-Difluorocyclohexyl)-3-{fluoro[4-(trifluoromethyl)phenyl]methyl}-2[1-[5-(hydroxymethyl)pyrimidin-2-yl]piperidin-4-yl]-5-[(4-methoxybenzyl)oxy]-7,7-dimethyl-5,6,7,8-tetrahydroquinoline, which was prepared by a method similar to that of Reference Example 17, 59 mg of the title compound was obtained as a foam (yield: 70%).

$^1$H-NMR spectrum (300 MHz, CDCl$_3$) δ ppm: 8.22 (2H, s), 7.62 (2H, d, J=8 Hz), 7.36 (2H, d, J=8 Hz), 7.25 (2H, d, J=9 Hz), 7.15 (1H, d, J=47 Hz), 6.87 (2H, d, J=9 Hz), 4.86-4.73 (2H, m), 4.81 (1H, d, J=11 Hz), 4.57-4.47 (1H, m), 4.39 (1H, d, J=11 Hz), 4.27 (2H, s), 3.79 (3H, s), 3.23-3.08 (1H, m), 3.17 (2H, d, J=7 Hz), 2.91-2.59 (4H, m), 2.32-2.06 (4H, m), 1.99-1.49 (11H, m), 1.19 (3H, s), 1.03 (3H, s), 0.89 (6H, d, J=7 Hz), 0.71-0.61 (1H, m).

Mass spectrum (EI, m/z): 838 [M+].

Reference Example 25

4-(4,4-Difluorocyclohexyl)-3-{fluoro[4-(trifluoromethyl)phenyl]methyl}-5-[(4-methoxybenzyl)oxy]-7,7-dimethyl-2-{1-[5-(methylcarbamoyl)pyrimidin-2-yl]piperidin-4-yl}-5,6,7,8-tetrahydroquinoline To 391 mg (0.501 mmol) of 4-(4,4-Difluorocyclohexyl)-3-{fluoro[4-(trifluoromethyl)phenyl]methyl}-2-[1-(5-formylpyrimidin-2-yl)piperidin-4-yl]-5-[(4-methoxybenzyl)oxy]-7,7-dimethyl-5,6,7,8-tetrahydroquinoline, which was prepared by a method similar to that of Reference Example 16, 3.0 ml of tetrahydrofuran, 1.5 ml of tert-butanol, 0.6 ml of water, 1.2 ml of 2-methyl-2-butene, 391 mg (2.50 mmol) of sodium dihydrogen phosphate and 226 mg (2.50 mmol) of sodium chlorite were added, and the reaction solution was stirred at room temperature for 2 hours. After completion of the reaction, saturated ammonium chloride aqueous solution was added to the reaction solution and the reaction solution was extracted with ethyl acetate. The organic layer was washed with saturated sodium chloride aqueous solution and dried with anhydrous sodium sulfate, and then the solvent was distilled off under reduced pressure to provide 465 mg of the crude product of 2-[1-(5-Carboxypyrimidin-2-yl)piperidin-4-yl]-4-(4,4-difluorocyclohexyl)-3-{fluoro[4-(trifluoromethyl)phenyl]methyl}-5-[(4-methoxybenzyl)oxy]-7,7-dimethyl-5,6,7,8-tetrahydroquinoline.

To a solution of 70 mg of the obtained crude product in 0.5 ml of tetrahydrofuran, 21 mg (0.13 mmol) of 1,1'-carbonyldiimidazole was added, and the reaction solution was stirred at room temperature for 30 minutes. 0.5 ml of about 40% methylamine aqueous solution was added to this reaction

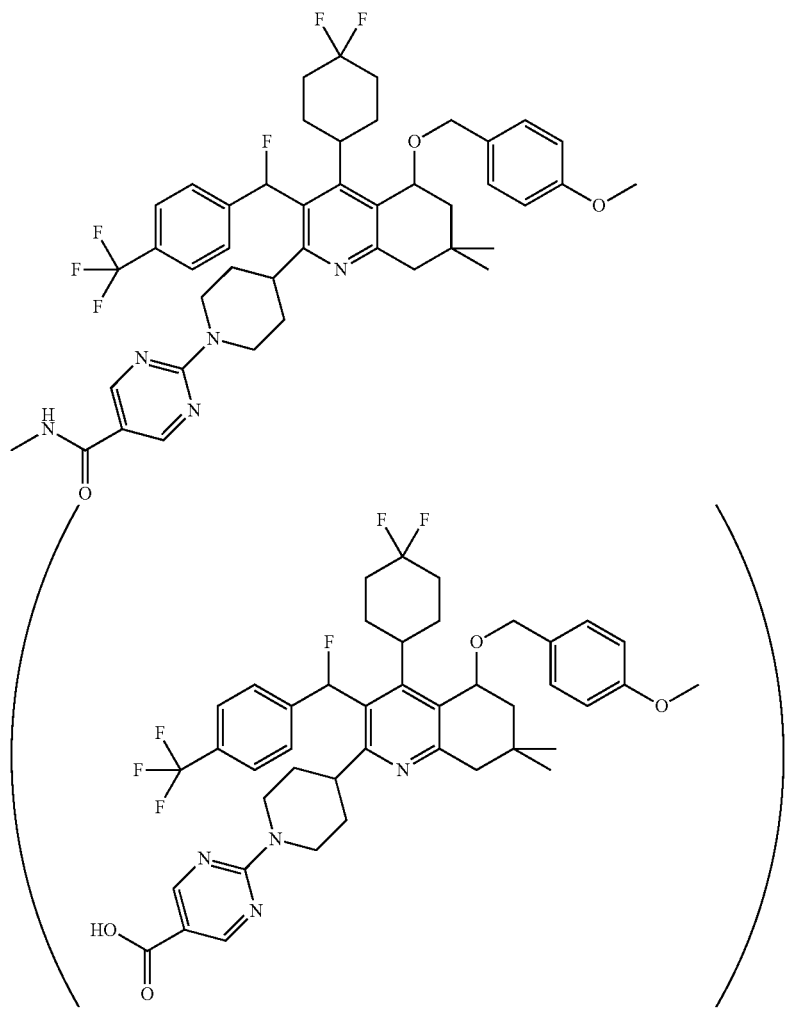

solution and the reaction solution was further stirred at room temperature for 30 minutes. After completion of the reaction, water was added to the reaction solution and the reaction solution was extracted with ethyl acetate. The organic layer was washed with saturated sodium chloride aqueous solution and dried with anhydrous sodium sulfate, and then the solvent was distilled off under reduced pressure to provide the crude product of the title compound.

$^1$H-NMR spectrum (500 MHz, CDCl$_3$) δ ppm: 8.61 (2H, s), 7.63 (2H, d, J=8 Hz), 7.36 (2H, d, J=8 Hz), 7.25 (2H, d, J=9 Hz), 7.16 (1H, d, J=47 Hz), 6.87 (2H, d, J=9 Hz), 5.88-5.79 (1H, m), 4.91-4.76 (2H, m), 4.81 (1H, d, J=11 Hz), 4.64-4.57 (1H, m), 4.39 (1H, d, J=11 Hz), 3.79 (3H, s), 3.22-3.10 (1H, m), 2.97 (3H, d, J=5 Hz), 2.89-2.59 (4H, m), 2.32-1.49 (14H, m), 1.19 (3H, s), 1.03 (3H, s), 0.73-0.64 (1H, m).

Reference Example 26

2-Chloro-5-(4,4,4-trifluorobutyl)pyrimidine

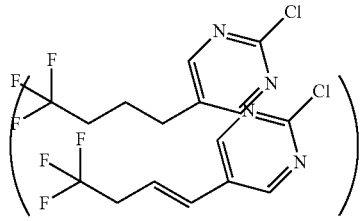

A solution of 1.2 g (2.4 mmol) of (3,3,3-trifluoropropyl)triphenylphosphonium iodide, which was synthesized by the method described in M. Zhang et al., Bioorganic and Medicinal Chemistry Letters, 2007, Vol. 17, pp. 2401-2403, in 16 ml of tetrahydrofuran was cooled to 0° C. and 1.6 ml (2.6 mmol) of 1.7 N n-butyl lithium/n-hexane solution was added thereto, and the reaction solution was stirred at room temperature for 30 minutes. The reaction solution was cooled to 0° C. again and then a solution of 0.31 g (2.2 mmol) of 2-chloropyrimidin-5-carbaldehyde in 4 ml of tetrahydrofuran was added to the reaction solution, and the reaction solution was stirred at room temperature for 30 minutes. After completion of the reaction, saturated ammonium chloride aqueous solution was added to the reaction solution and the reaction solution was extracted with ethyl acetate. The organic layer was washed with saturated sodium chloride aqueous solution and dried with anhydrous sodium sulfate, and then the solvent was distilled off under reduced pressure. The obtained residue was subjected to silica gel column chromatography [n-hexane/ethyl acetate=100/0-80/20 (V/V)] and the fraction including the desired compound was concentrated under reduced pressure to provide 0.17 g of 2-chloro-5-(4,4,4-trifluoro-1-buten-1-yl) pyrimidine.

To a solution of 0.17 g (0.78 mmol) of 2-chloro-5-(4,4,4-trifluoro-1-buten-1-yl)pyrimidine obtained above in 7 ml of ethanol, 35 mg of 10% palladium-carbon was added, and the reaction solution was stirred at room temperature for 45 minutes under a hydrogen gas atmosphere. The catalyst was removed by filtration and then the solvent was distilled off under reduced pressure to provide 0.14 g of the title compound as a colorless oil (yield: 30%).

$^1$H-NMR spectrum (400 MHz, CDCl$_3$) δ ppm: 8.49 (2H, s), 2.72 (2H, t, J=8 Hz), 2.23-2.09 (2H, m), 1.99-1.87 (2H, m).

Reference Example 27

4-(4,4-Difluorocyclohexyl)-3-{fluoro[4-(trifluoromethyl)phenyl]methyl}-2-{1-[5-(1-hydroxy-3-methylbutyl)pyrimidin-2-yl]piperidin-4-yl}-5-[(4-methoxybenzyl)oxy]-7,7-dimethyl-5,6,7,8-tetrahydroquinoline

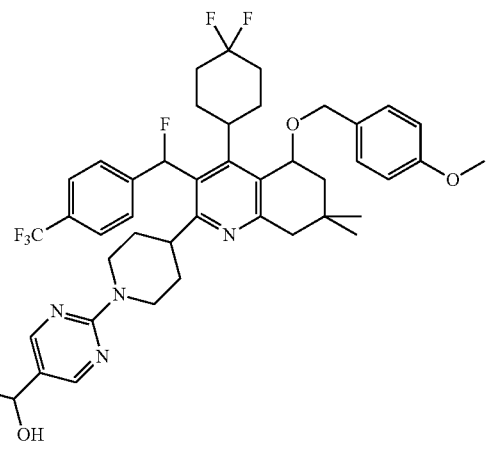

To a solution of 294 mg (0.377 mmol) of 4-(4,4-Difluorocyclohexyl)-3-{fluoro[4-(trifluoromethyl)phenyl]methyl}-2-[1-(5-formylpyrimidin-2-yl)piperidin-4-yl]-5-[(4-methoxybenzyl)oxy]-7,7-dimethyl-5,6,7,8-tetrahydroquinoline, which was prepared by a method similar to that of Reference Example 16, in 5 ml of tetrahydrofuran, 0.5 ml (0.5 mmol) of 1.0 mol/L isobutylmagnesium bromide-tetrahydrofuran solution was added under an argon gas atmosphere, and the reaction solution was stirred at room temperature for 0.17 hour. Then, 1.0 ml (1.0 mmol) of 1.0 mol/L isobutylmagnesium bromide-tetrahydrofuran solution was further added thereto and the reaction solution was stirred at room temperature for 0.33 hour. After completion of the reaction, the reaction solution was poured into saturated ammonium chloride aqueous solution and extracted with ethyl acetate. The organic layer was washed with saturated sodium chloride aqueous solution and then the solvent was distilled off under reduced pressure to provide 328 mg of the title compound as a foam (yield: quantitative).

$^1$H-NMR spectrum (300 MHz, CD$_2$Cl$_2$) δ ppm: 8.22 (2H, s), 7.64 (2H, d, J=8 Hz), 7.38 (2H, d, J=8 Hz), 7.26 (2H, d, J=9 Hz), 7.18 (1H, d, J=47 Hz), 6.86 (2H, d, J=9 Hz), 4.91-4.72 (1H, m), 4.85 (1H, t, J=5 Hz), 4.80 (1H, d, J=11 Hz), 4.61-4.43 (2H, m), 4.39 (1H, d, J=11 Hz), 3.77 (3H, s), 3.25-3.11 (1H, m), 2.89-2.57 (4H, m), 2.31-2.02 (4H, m), 1.99-1.42 (14H, m), 1.17 (3H, s), 1.04 (3H, s), 0.93 (6H, d, J=6 Hz), 0.73-0.63 (1H, m).

Mass spectrum (CI, m/z): 839 [(M+1)$^+$].

Reference Example 28

2-Chloro-5-[(1-methylpiperidin-4-yl)oxy]pyrimidine

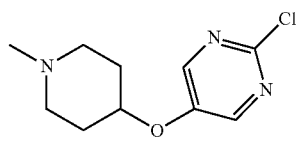

To a solution of 100 mg (0.766 mmol) of 4-hydroxy-1-methyl piperidine in 1.5 ml of tetrahydrofuran, 155 mg (1.53 mmol) of di-tert-butyl azocarboxylic acid, 402 mg (1.53 mmol) of triphenylphosphine and 0.170 ml (1.53 mmol) of 2-chloro-5-hydroxypyrimidine were added, and the reaction solution was stirred at room temperature for 1 hour. After completion of the reaction, ethyl acetate was added to the reaction solution and the reaction solution was extracted with 1 N hydrochloric acid. 1 N sodium hydroxide aqueous solution was added to the aqueous layer to make its pH 10 and then the aqueous layer was extracted with ethyl acetate. The organic layer was washed with saturated sodium chloride aqueous solution and dried with anhydrous sodium sulfate, and then the solvent was distilled off under reduced pressure to provide 152 mg of the title compound as a white solid (yield: 87%).

$^1$H-NMR spectrum (400 MHz, CDCl$_3$) δ ppm: 8.22 (2H, s), 4.33 (1H, tt, J=7.5, 3.8 Hz), 2.65-2.57 (2H, m), 2.30-2.22 (5H, m), 2.01-1.93 (2H, m), 1.85-1.75 (2H, m).

Reference Example 29

4-(4,4-Difluorocyclohexyl)-3-{fluoro[4-(trifluoromethyl)phenyl]methyl}-5-[(4-methoxybenzyl)oxy]-7,7-dimethyl-2-(1-{5-[(1-methylpiperidin-4-yl)oxy]pyrimidin-2-yl}piperidin-4-yl)-5,6,7,8-tetrahydroquinoline

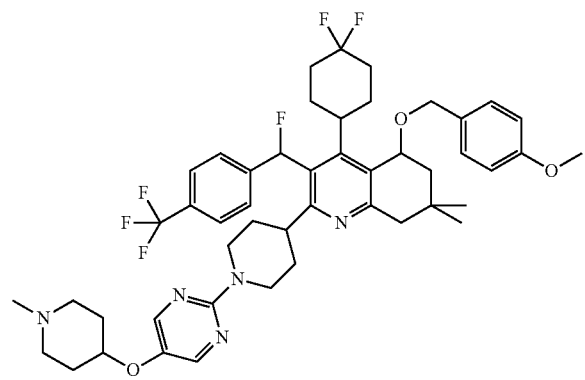

To a solution of 100 mg (0.155 mmol) of (−)-4-(4,4-Difluorocyclohexyl)-3-{fluoro[4-(trifluoromethyl)phenyl]methyl}-5-[(4-methoxybenzyl)oxy]-7,7-dimethyl-2-(piperidin-4-yl)-5,6,7,8-tetrahydroquinoline, which was prepared by a method similar to that of Reference Example 10, in 0.6 ml of isopropanol, 71 mg (0.31 mmol) of 2-chloro-5-[(1-methylpiperidin-4-yl)oxy]pyrimidine, which was prepared by a method similar to that of Reference Example 28, and 0.60 ml (0.33 mmol) of N,N-diisopropylethylamine were added, and the reaction solution was stirred at 160° C. for 30 minutes while microwave irradiating using a microwave reactor (product name: Initiator, manufactured by Biotage). After completion of the reaction, the solvent of the reaction solution was distilled off under reduced pressure. The obtained residue was subjected to silica gel column chromatography [n-hexane/ethyl acetate=100/0-20/80 (V/V)] and the fraction including the desired compound was concentrated under reduced pressure to provide 102 mg of the title compound as a colorless oil containing 16 mg of 2-chloro-5-[(1-methylpiperidin-4-yl)oxy]pyrimidine as impurities (yield: 64%).

$^1$H-NMR spectrum (400 MHz, CDCl$_3$) δ ppm: 8.03 (2H, s), 7.62 (2H, d, J=8 Hz), 7.37 (2H, d, J=8 Hz), 7.26 (2H, d, J=9 Hz), 7.16 (1H, d, J=47 Hz), 6.88 (2H, d, J=9 Hz), 4.88-4.77 (2H, m), 4.73-4.62 (1H, m), 4.45-4.32 (2H, m), 4.05-3.95 (1H, m), 3.79 (3H, s), 3.22-3.10 (1H, m), 2.93-2.57 (6H, m), 2.37-1.52 (23H, m), 1.20 (3H, s), 1.04 (3H, s), 0.73-0.60 (1H, m).

Reference Example 30

2-Chloro-5-{[(3R)-1-methylpyrrolidin-3-yl]oxy}pyrimidine

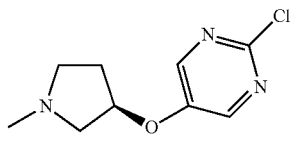

Reactions similar to those of Reference Example 28 were performed except for using (3S)-1-methyl-3-pyrrolidinol instead of 1-methyl-4-piperidinol, and from 100 mg (0.766 mmol) of 2-chloro-5-hydroxypyrimidine, 164 mg of the title compound was obtained as a white solid (yield: quantitative).

$^1$H-NMR spectrum (400 MHz, CDCl$_3$) δ ppm: 8.25 (2H, s), 4.89-4.84 (1H, m), 2.93-2.86 (2H, m), 2.78 (1H, dd, J=11.0, 5.9 Hz), 2.45-2.34 (5H, m), 2.05-1.97 (1H, m).

Reference Example 31

2-Chloro-5-(3,3,3-trifluoropropoxyl)pyrimidine

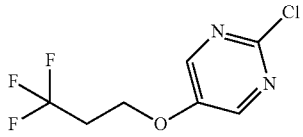 [SMILES: FC(F)(F)CCOc1cnc(Cl)nc1]

Reactions similar to those of Reference Example 28 were performed except for using 3,3,3-trifluoro-1-propanol instead of 1-methyl-4-piperidinol, and from 100 mg (0.693 mmol) of 2-chloro-5-hydroxypyrimidine, 144 mg of the title compound as a colorless oil (yield: 92%).

$^1$H-NMR spectrum (500 MHz, CDCl$_3$) δ ppm: 8.33 (2H, s), 4.30 (2H, t, J=6.5 Hz), 2.74-2.64 (2H, m).

Reference Example 32

2-Chloro-5-(difluoromethoxy)pyrimidine

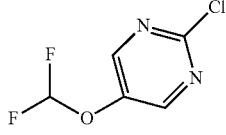 [SMILES: FC(F)Oc1cnc(Cl)nc1]

To a solution of 93 mg (0.71 mmol) of 4-hydroxy-1-methyl piperidine in 1.0 ml of N,N-dimethylformamide, 0.28 g (0.86 mmol) of cesium carbonate and 0.32 mg (2.2 mmol) of methyl chlorodifluoroacetate were added, and the reaction solution was stirred at 100° C. for 1 hour. After completion of the reaction, the reaction solution was poured into water and extracted with ethyl acetate. The organic layer was washed with saturated sodium chloride aqueous solution and dried with anhydrous magnesium sulfate, and then the solvent was distilled off under reduced pressure. The obtained residue was purified by preparative thin layer chromatography [n-hexane/ethyl acetate=75/25 (V/V)] to provide 55 mg of the title compound as a colorless oil (yield: 43%).

$^1$H-NMR spectrum (500 MHz, CDCl$_3$) δ ppm: 8.53 (2H, s), 6.62 (1H, t, J=71 Hz).

Reference Example 33

2-Chloro-5-[(2,2,5-trimethyl-1,3-dioxan-5-yl)methoxy]pyrimidine

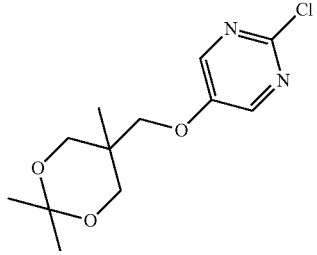 [SMILES: CC1(COc2cnc(Cl)nc2)COC(C)(C)OC1]

To a solution of 9.50 g (72.8 mmol) of 2-chloro-5-hydroxypyrimidine in 100 ml of N,N-dimethylformamide, 26.1 g (80.1 mmol) of cesium carbonate and 24.3 g (102 mmol) of 5-(methanesulfonyloxymethyl)-2,2,5-trimethyl-1,3-dioxane, which was synthesized by the method described in V. W. Gash, Journal of Organic Chemistry, 1972, Vol. 37, pp. 2197-2201, were added, and the reaction solution was stirred at 90° C. for 24 hours. After completion of the reaction, the insoluble material was filtered off and washed with ethyl acetate, and then 0.5 N sodium hydroxide aqueous solution was added to the filtrate and separation was performed. The obtained aqueous layer was further extracted with ethyl acetate. The obtained organic layers were combined, washed with water and saturated sodium chloride aqueous solution in order and dried with anhydrous magnesium sulfate, and then the solvent was distilled off under reduced pressure. Toluene was added to the obtained residue, and the precipitate was obtained by filtration and washed with toluene and n-heptane to provide 6.00 g of the title compound as a white solid (yield: 30%).

$^1$H-NMR spectrum (300 MHz, CDCl$_3$) δ ppm: 8.34 (2H, s), 4.16 (2H, s), 3.73 (4H, s), 1.47 (3H, s), 1.41 (3H, s), 0.94 (3H, s).

Reference Example 34

4-(4,4-Difluorocyclohexyl)-3-{fluoro[4-(trifluoromethyl)phenyl]methyl}-5-[(4-methoxybenzyl)oxy]-7,7-dimethyl-2-(1-{5-[(2,2,5-trimethyl-1,3-dioxan-5-yl)methoxy]pyrimidin-2-yl}piperidin-4-yl)-5,6,7,8-tetrahydroquinoline

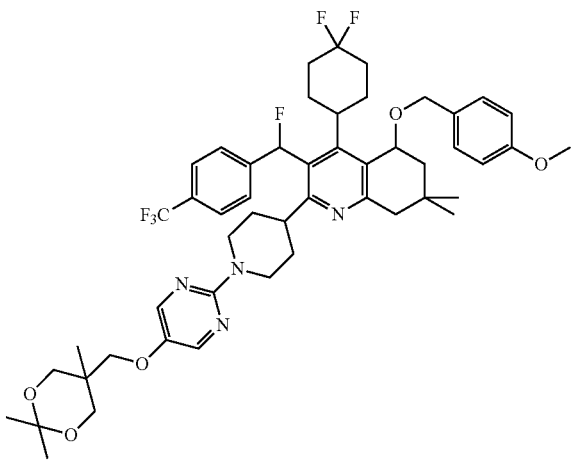

To a solution of 599 mg (0.887 mmol) of (−)-4-(4,4-Difluorocyclohexyl)-3-{fluoro[4-(trifluoromethyl)phenyl]methyl}-5-[(4-methoxybenzyl)oxy]-7,7-dimethyl-2-(piperidin-4-yl)-5,6,7,8-tetrahydroquinoline, which was prepared by a method similar to that of Reference Example 10, in 8 ml of toluene, 242 mg (0.887 mmol) of 2-chloro-5-[(2,2,5-trimethyl-1,3-dioxan-5-yl)methoxy]pyrimidine, which was prepared by a method similar to that of Reference Example 33, 128 mg (1.33 mmol) of tert-butoxy sodium, 26 mg (0.044 mmol) of bis(dibenzylideneacetone)palladium (0) and 63 mg (0.089 mmol) of 1,2,3,4,5-pentaphenyl-1'-(di-tert-butylphosphino)ferrocene were added, and the reaction solution was stirred at 90° C. for 21 hours under an argon gas atmosphere. After completion of the reaction, water and saturated sodium chloride aqueous solution were poured into the reaction solution and the reaction solution was extracted with ethyl acetate. The organic layer was washed with saturated sodium chloride aqueous solution and dried with anhydrous magnesium sulfate, and then the solvent was distilled off under reduced pressure. The obtained residue was subjected to silica gel column chromatography [n-hexane/ethyl acetate=4/1 (V/V)] and the fraction including the desired compound was concentrated under reduced pressure to provide 120 mg of the title compound as a brown oil (yield: 15%).

$^1$H-NMR spectrum (300 MHz, CDCl$_3$) δ ppm: 8.04 (2H, s), 7.61 (2H, d, J=8 Hz), 7.35 (2H, d, J=8 Hz), 7.25 (2H, d, J=9 Hz), 7.14 (1H, d, J=47 Hz), 6.87 (2H, d, J=9 Hz), 4.82 (1H, t, J=4 Hz), 4.81 (1H, d, J=11 Hz), 4.70-4.60 (1H, m), 4.43-4.33 (1H, m), 4.38 (1H, d, J=11 Hz), 3.95 (2H, s), 3.79 (3H, s), 3.76 (2H, d, J=12 Hz), 3.65 (2H, d, J=12 Hz), 3.23-3.08 (1H, m), 2.91-2.61 (4H, m), 2.32-1.50 (14H, m), 1.45 (3H, s), 1.40 (3H, s), 1.19 (3H, s), 1.03 (3H, s), 0.93 (3H, s), 0.70-0.60 (1H, m).

Mass spectrum (EI, m/z): 910 [M+].

Reference Example 35

2-Chloro-5-[3-(methoxycarbonyl)phenyl]pyrimidine

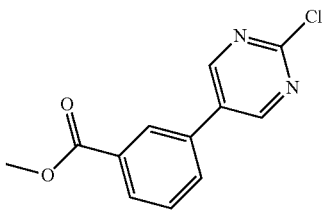 [SMILES: COC(=O)c1cccc(-c2cnc(Cl)nc2)c1]

To a solution of 1.93 g (10.0 mmol) of 2-chloro-5-bromopyrimidine in 30 ml of toluene, 4.12 g (30.0 mmol) of potassium carbonate, 1.89 g (10.5 mmol) of 3-(methoxycarbonyl)phenylboronic acid and 1.0 g (0.87 mmol) of tetrakis(triphenyl phosphine)palladium (0) were added, and the reaction solution was stirred at 110° C. for 10.5 hours. After completion of the reaction, the reaction solution was poured into water and extracted with ethyl acetate. The organic layer was washed with water and saturated sodium chloride aqueous solution in order and dried with anhydrous magnesium sulfate, and then the solvent was distilled off under reduced pressure. The obtained residue was subjected to silica gel column chromatography [n-hexane/ethyl acetate=95/5-0/100 (V/V)] and the fraction including the desired compound was concentrated under reduced pressure to provide 0.37 g of the title compound as a yellow solid (yield: 14%).

$^1$H-NMR spectrum (300 MHz, CDCl$_3$) δ ppm: 8.87 (2H, s), 8.25 (1H, t, J=2 Hz), 8.16 (1H, dt, J=8, 2 Hz), 7.75 (1H, ddd, J=8, 2, 1 Hz), 7.62 (1H, t, J=8 Hz), 3.98 (3H, s).

Mass spectrum (CI, m/z): 249 [(M+1)+].

Reference Example 36

2-Chloro-5-methylthiopyrimidine

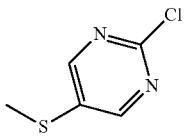

A solution of 1.00 g (5.17 mmol) of 5-bromo-2-chloropyrimidine and 551 µl (6.20 mmol) of dimethyl disulfide in 26 ml of tetrahydrofuran was cooled to −78° C. and 1.89 ml (5.17 mmol) of 2.73 N n-butyl lithium/n-hexane solution was added thereto, and the reaction solution was stirred for 2 hours. After completion of the reaction, saturated ammonium chloride aqueous solution was added to the reaction solution and the reaction solution was extracted with ethyl acetate. The organic layer was washed with saturated sodium chloride aqueous solution and dried with anhydrous sodium sulfate, and then the solvent was distilled off under reduced pressure. The obtained residue was subjected to silica gel column chromatography [n-hexane/ethyl acetate=90/10 (V/V)] and the fraction including the desired compound was concentrated under reduced pressure to provide 149 mg of the title compound as a white solid (yield: 18%).

$^1$H-NMR spectrum (500 MHz, CDCl$_3$) δ ppm: 8.49 (2H, s), 2.54 (3H, s).

Reference Example 37

(5S)-4-(4,4-Difluorocyclohexyl)-3-{(S)-fluoro[4-(trifluoromethyl)phenyl]methyl}-2-[1-((R)-2-hydroxy-2-phenylacetyl)piperidin-4-yl]-5-[(4-methoxybenzyl)oxy]-7,7-dimethyl-5,6,7,8-tetrahydroquinoline

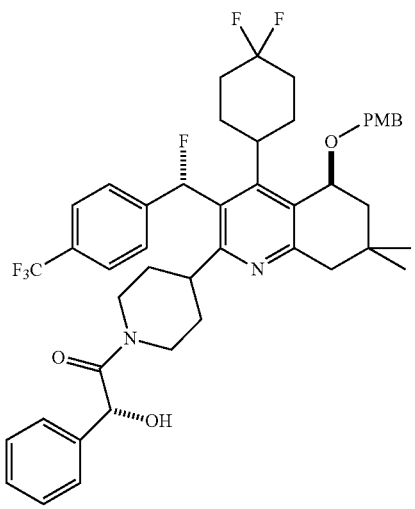

(37-1) Preparation of Title Compound

To 501 mg (0.742 mmol) of (−)-4-(4,4-Difluorocyclohexyl)-3-{fluoro[4-(trifluoromethyl)phenyl]methyl}-5-[(4-methoxybenzyl)oxy]-7,7-dimethyl-2-(piperidin-4-yl)-5,6,7,8-tetrahydroquinoline, which was obtained by a method similar to that of Reference Example 10, 113 mg (0.743 mmol) of (R)-D-(−)-mandelic acid, 255 µl (1.46 mmol) of diisopropylethylamine and 5 ml of methylene chloride were added. Then, 143 mg (0.746 mmol) of 1-(3-dimethylaminopropyl)-3-ethylcarbodiimide hydrochloride was added to the reaction solution and the reaction solution was stirred at room temperature for 20 hours. Furthermore, 143 mg (0.746 mmol) of 1-(3-dimethylaminopropyl)-3-ethylcarbodiimide hydrochloride and 133 mg (1.09 mmol) of 4-dimethylaminopyridine were added to the reaction solution and the reaction solution was stirred at room temperature for 4 days. Water was added to the reaction solution and the reaction solution was extracted with methylene chloride three times. After drying with anhydrous magnesium sulfate, the solvent was distilled off under reduced pressure. The obtained residue was subjected to silica gel column chromatography [n-hexane/ethyl acetate=80/20 (V/V)] to provide 156 mg of the title compound as a white solid (yield: 26%).

$^1$H-NMR spectrum (300 MHz, CD$_2$Cl$_2$) δ ppm: 7.61, 7.54 (total 2H, each d, J=8 Hz), 7.42-6.98 (10H, m), 6.85 (2H, d, J=8 Hz), 5.11 (1H, d, J=6 Hz), 4.88-4.28 (2H, m), 4.80, 4.78 (total 1H, each d, J=10, 11 Hz), 4.71, 4.66 (total 1H, each d, J=6, 7 Hz), 4.38, 4.37 (total 1H, each d, J=11 Hz), 3.76 (3H, s), 3.63-3.53, 3.45-3.34 (total 1H, each m), 3.24-3.05 (1H, m), 2.91-2.39 (4H, m), 2.29-2.06 (3H, m), 2.01-1.43 (11H, m), 1.19 (3H, s), 1.06, 1.05 (total 3H, each s), 0.76-0.58 (1H, m).

Mass spectrum (APCI POSITIVE, m/z): 809 [(M+1)$^+$].

(37-2) Determination of Absolute Configuration of Title Compound

800 µl of methanol was added to 3.5 mg of the title compound obtained in Reference Example (37-1) and it was dissolved and then methanol was slowly and naturally evaporated to provide a needle-shaped monocrystal. X ray crystalline structure analysis was performed for the obtained monocrystal.

The diffraction intensity data were collected under extremely low temperature air current (−150° C.) using an apparatus for analyzing monocrystalline X ray structure, Rigaku R-AXIS RAPID. After determination of the structure with the direct method using software CrystalStructure, structure refinement was performed with full-matrix least-squares method, wherein the temperature factor of non-hydrogen atoms was anisotropic and the temperature factor of a hydrogen atom was isotropic. The obtained crystallographic data were C$_{46}$H$_{50}$F$_6$N$_2$O$_4$, M$_w$=808.90, monoclinic system, space group P2$_1$, a=6.24540 (19) Å, b=22.2621 (7) Å, c=14.9460 (4) Å, β=90.3970 (19)°, V=2077.97 (11) Å$^3$, Z=2 and D$_{calc}$=1.293 g/cm$^3$. Final R value 0.0599 was obtained for 24045 reflections.

From the fact that the absolute configuration of the asymmetric carbon of the mandelic acid part introduced into the compound was the configuration R, the absolute configurations of the other asymmetric carbons of the title compound were determined. The absolute configuration of the carbon at the 5-position of 5,6,7,8-tetrahydroquinoline was the configuration S and the absolute configuration of the carbon at the 1-position of the fluoro[4-(trifluoromethyl)phenyl]methyl group was the configuration S, and the chemical structural formula including the absolute configurations of the title compound was as shown above.

The compound name and the chemical structural formula including the absolute configurations of each compound of the Examples and the Reference Examples are as shown in Table 1 (Tables 1-1 to 1-18) described below. The absolute configurations in the chemical structural formula described below are the same as those shown in general formula (I-1) described above.

TABLE 1-1

| Example/Reference Example No. | Name of Compound | Structural Formula |
|---|---|---|
| Example 1 | (5S)-4-(4,4-Difluorocyclohexyl)-3-{(S)-fluoro[4-(trifluoromethyl)phenyl]methyl}-7,7-dimethyl-2-[1-(pyrimidin-2-yl)piperidin-4-yl]-5,6,7,8-tetrahydroquinolin-5-ol | 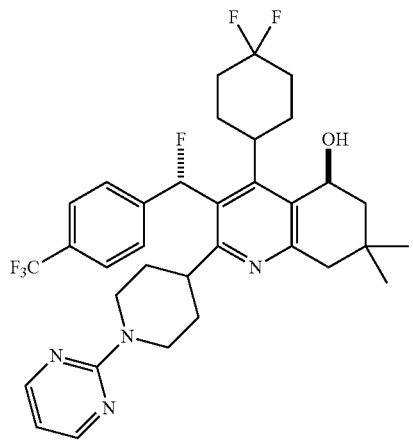 [SMILES: CC1(C)Cc2nc(C3CCN(c4ncccn4)CC3)c([C@@H](F)c3ccc(C(F)(F)F)cc3)c(C3CCC(F)(F)CC3)c2[C@@H](O)C1] |
| Example 2 | (5S)-2-[1-(5-Bromopyrimidin-2-yl)piperidin-4-yl]-4-(4,4-difluorocyclohexyl)-3-{(S)-fluoro[4-(trifluoromethyl)phenyl]methyl}-7,7-dimethyl-5,6,7,8-tetrahydroquinolin-5-ol | 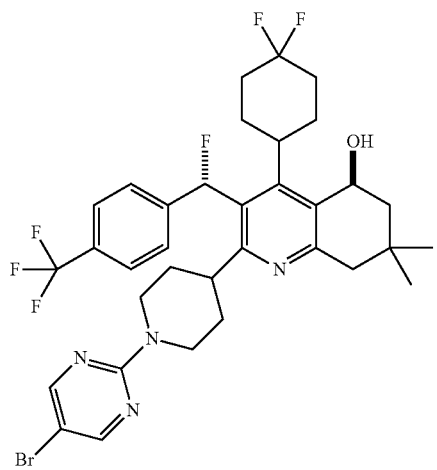 [SMILES: CC1(C)Cc2nc(C3CCN(c4ncc(Br)cn4)CC3)c([C@@H](F)c3ccc(C(F)(F)F)cc3)c(C3CCC(F)(F)CC3)c2[C@@H](O)C1] |
| Example 3 | (5S)-4-(4,4-Difluorocyclohexyl)-3-{(S)-fluoro[4-(trifluoromethyl)phenyl]methyl}-2-[1-(5-methoxypyrimidin-2-yl)piperidin-4-yl]-7,7-dimethyl-5,6,7,8-tetrahydroquinolin-5-ol | 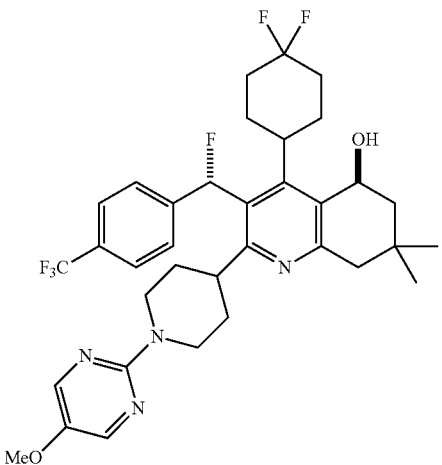 [SMILES: COc1cnc(N2CCC(c3nc4c(c(C5CCC(F)(F)CC5)c3[C@@H](F)c3ccc(C(F)(F)F)cc3)[C@@H](O)CC(C)(C)C4)CC2)nc1] |

TABLE 1-1-continued

| Example/Reference Example No. | Name of Compound | Structural Formula |
|---|---|---|
| Example 4 | (5S)-4-(4,4-Difluorocyclohexyl)-3-{(S)-fluoro[4-(trifluoromethyl)phenyl]methyl}-2-[1-(5-hydroxypyrimidin-2-yl)piperidin-4-yl]-7,7-dimethyl-5,6,7,8-tetrahydroquinolin-5-ol | |
| Example 5 | (5S)-4-(4,4-Difluorocyclohexyl)-3-{(S)-fluoro[4-(trifluoromethyl)phenyl]methyl}-7,7-dimethyl-2-{1-[5-(morpholin-4-yl)pyrimidin-2-yl]piperidin-4-yl}-5,6,7,8-tetrahydroquinolin-5-ol | |

TABLE 1-2

| Example | Name of Compound | Structural Formula |
|---|---|---|
| Example 6 | (5S)-4-(4,4-Difluorocyclohexyl)-3-{(S)-fluoro[4-(trifluoromethyl)phenyl]methyl}-7,7-dimethyl-2-{1-[5-(piperidin-1-yl)pyrimidin-2-yl]piperidin-4-yl}-5,6,7,8-tetrahydroquinolin-5-ol | |

TABLE 1-2-continued

| Example 7 | (5S)-4-(4,4-Difluorocyclohexyl)-2-(1-{5-[4-(ethoxycarbonyl)piperidin-1-yl]pyrimidin-2-yl}piperidin-4-yl)-3-{(S)-fluoro[4-(trifluoromethyl)phenyl]methyl}-7,7-dimethyl-5,6,7,8-tetrahydroquinolin-5-ol | 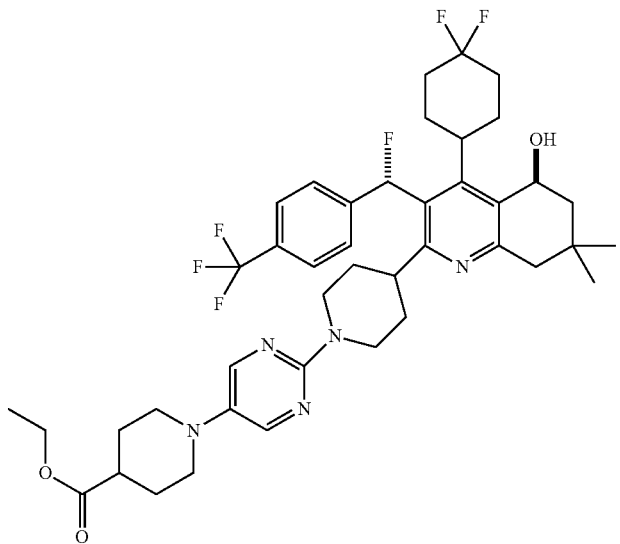 [SMILES: CCOC(=O)C1CCN(c2cnc(N3CCC(c4nc5c(c(C6CCC(F)(F)CC6)c4[C@@H](F)c4ccc(C(F)(F)F)cc4)[C@@H](O)CC(C)(C)C5)CC3)nc2)CC1] |
|---|---|---|
| Example 8 | (5S)-4-(4,4-Difluorocyclohexyl)-3-{(S)-fluoro[4-(trifluoromethyl)phenyl]methyl}-7,7-dimethyl-2-{1-[5-(4-methylpiperazin-1-yl)pyrimidin-2-yl]piperidin-4-yl}-5,6,7,8-tetrahydroquinolin-5-ol | 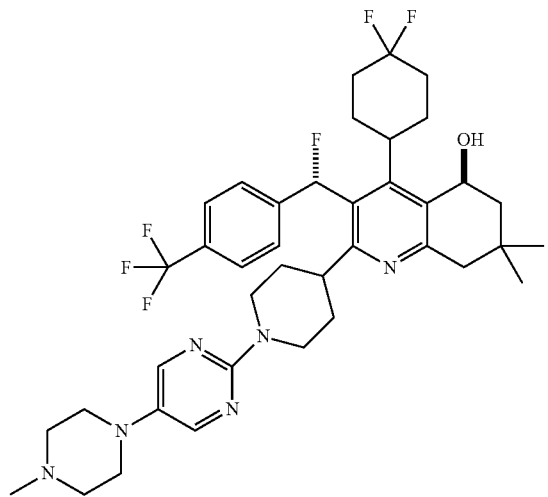 |
| Example 9 | (5S)-4-(4,4-Difluorocyclohexyl)-3-{(S)-fluoro[4-(trifluoromethyl)phenyl]methyl}-7,7-dimethyl-2-{1-[5-(thiomorpholin-4-yl)pyrimidin-2-yl]piperidin-4-yl}-5,6,7,8-tetrahydroquinolin-5-ol | 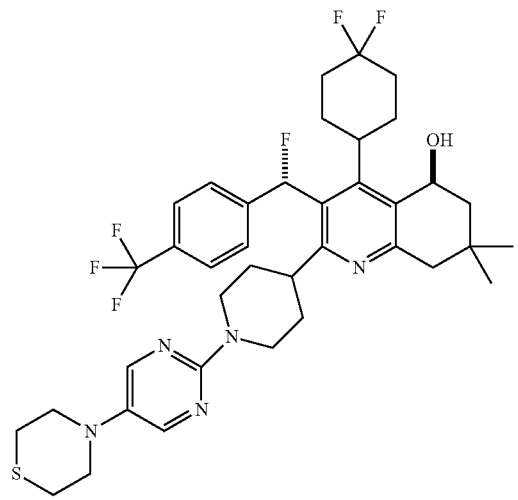 [SMILES: CC1(C)Cc2nc(C3CCN(c4ncc(N5CCSCC5)cn4)CC3)c([C@@H](F)c3ccc(C(F)(F)F)cc3)c(C3CCC(F)(F)CC3)c2[C@@H](O)C1] |

| | | |
|---|---|---|
| Example 10 | (5S)-4-(4,4-Difluorocyclohexyl)-2-{1-[5-(1,1-dioxidethiomorpholin-4-yl)pyrimidin-2-yl]piperidin-4-yl}-3-{(S)-fluoro[4-(trifluoromethyl)phenyl]methyl}-7,7-dimethyl-5,6,7,8-tetrahydroquinolin-5-ol | 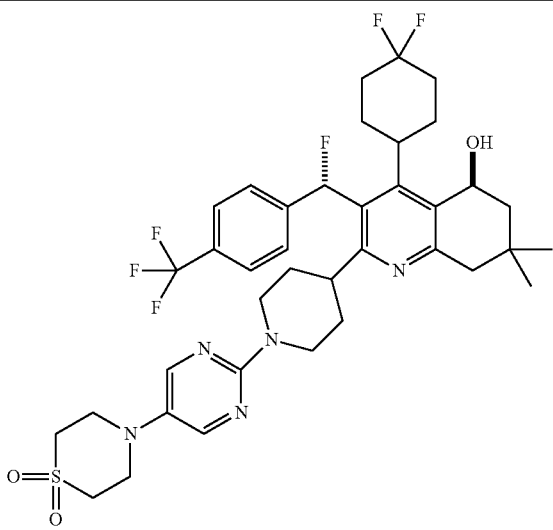 |

TABLE 1-3

| | | |
|---|---|---|
| Example 11 | (5S)-4-(4,4-Difluorocyclohexyl)-3-{(S)-fluoro[4-(trifluoromethyl)phenyl]methyl}-2-{1-[5-(4-hydroxypiperidin-1-yl)pyrimidin-2-yl]piperidin-4-yl}-7,7-dimethyl-5,6,7,8-tetrahydroquinolin-5-ol | 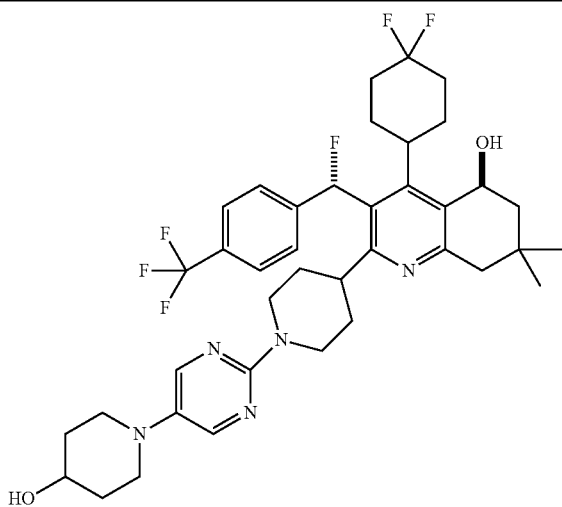 |
| Example 12 | (5S)-4-(4,4-Difluorocyclohexyl)-3-{(S)-fluoro[4-(trifluoromethyl)phenyl]methyl}-7,7-dimethyl-2-{1-[5-(propan-2-yl)pyrimidin-2-yl]piperidin-4-yl}-5,6,7,8-tetrahydroquinolin-5-ol | 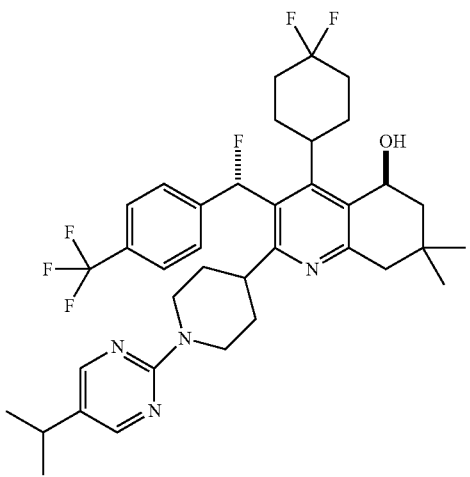 [SMILES: CC(C)c1cnc(N2CCC(c3nc4c(c(C5CCC(F)(F)CC5)c3[C@@H](F)c3ccc(C(F)(F)F)cc3)[C@@H](O)CC(C)(C)C4)CC2)nc1] |

TABLE 1-3-continued

| Example 13 | (5S)-4-(4,4-Difluorocyclohexyl)-2-[1-(5-ethoxypyrimidin-2-yl)piperidin-4-yl]-3-{(S)-fluoro[4-(trifluoromethyl)phenyl]methyl}-7,7-dimethyl-5,6,7,8-tetrahydroquinolin-5-ol | 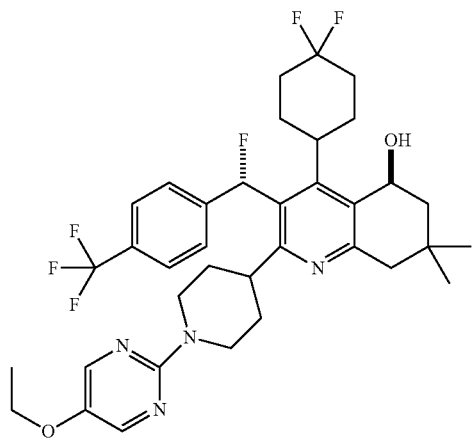 [SMILES: CCOc1cnc(N2CCC(c3nc4c(c(C5CCC(F)(F)CC5)c3[C@@H](F)c3ccc(C(F)(F)F)cc3)[C@@H](O)CC(C)(C)C4)CC2)nc1] |
| --- | --- | --- |
| Example 14 | (5S)-4-(4,4-Difluorocyclohexyl)-3-{(S)-fluoro[4-(trifluoromethyl)phenyl]methyl}-7,7-dimethyl-2-{1-[5-(propan-2-yloxy)pyrimidin-2-yl]piperidin-4-yl}-5,6,7,8-tetrahydroquinolin-5-ol | 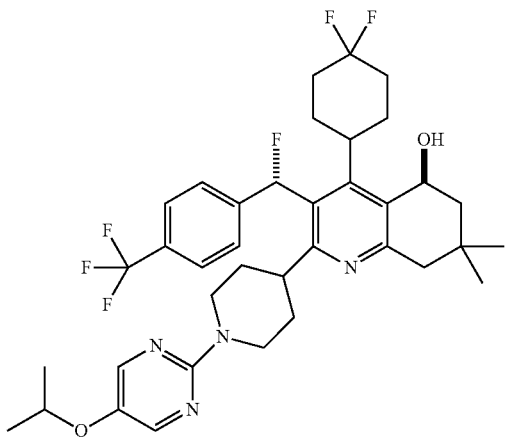 [SMILES: CC(C)Oc1cnc(N2CCC(c3nc4c(c(C5CCC(F)(F)CC5)c3[C@@H](F)c3ccc(C(F)(F)F)cc3)[C@@H](O)CC(C)(C)C4)CC2)nc1] |
| Example 15 | (5S)-4-(4,4-Difluorocyclohexyl)-3-{(S)-fluoro[4-(trifluoromethyl)phenyl]methyl}-2-{1-[5-(2-hydroxyethoxy)pyrimidin-2-yl]piperidin-4-yl}-7,7-dimethyl-5,6,7,8-tetrahydroquinolin-5-ol | 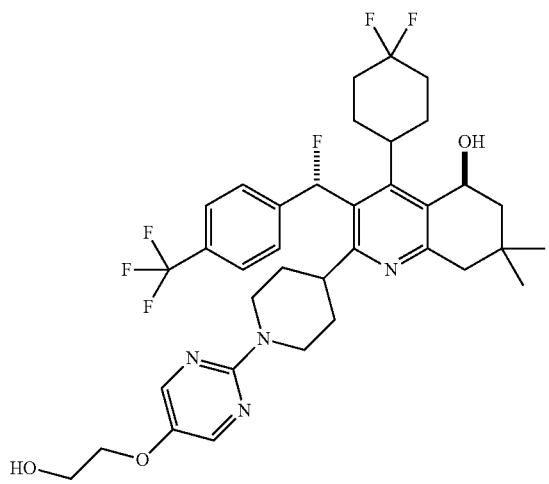 [SMILES: CC1(C)Cc2nc(C3CCN(c4ncc(OCCO)cn4)CC3)c([C@@H](F)c3ccc(C(F)(F)F)cc3)c(C3CCC(F)(F)CC3)c2[C@@H](O)C1] |

TABLE 1-4

| Example 15 Intermediate | (5S)-2-{1-[5-(2-{[tert-Butyl(dimethyl) silyl]oxy}ethoxypyrimidin-2-yl]piperidin-4-yl}-4-(4,4-difluorocyclohexyl)-3-{(S)-fluoro[4-(trifluoromethyl)phenyl]methyl}-7,7-dimethyl-5,6,7,8-tetrahydroquinolin 5-ol | 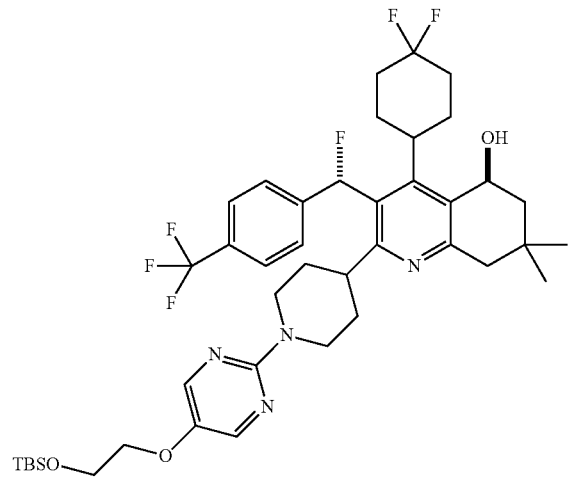 [SMILES: CC1(C)Cc2nc(C3CCN(c4ncc(OCCO[Si](C)(C)C(C)(C)C)cn4)CC3)c([C@@H](F)c3ccc(C(F)(F)F)cc3)c(C3CCC(F)(F)CC3)c2[C@@H](O)C1] |
|---|---|---|
| Example 16 | (5S)-4-(4,4-Difluorocyclohexyl)-3-{(S)-fluoro[4-(trifluoromethyl)phenyl]methyl}-7,7-dimethyl-2-[1-(5-pentylpyrimidin-2-yl)piperidin-4-yl]-5,6,7,8-tetrahydro-quinolin-5-ol | 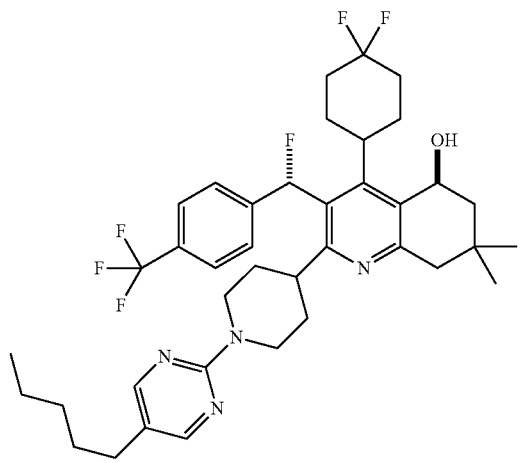 |
| Example 17 | (5S)-2-[1-(5-Cyanopyrimidin-2-yl)piperidin-4-yl]-(4,4-difluorocyclohexyl)-3-{(S)-fluoro[4-(trifluoromethyl)phenyl]methyl}-7,7-dimethyl-5,6,7,8-tetrahydro-quinolin-5-ol | 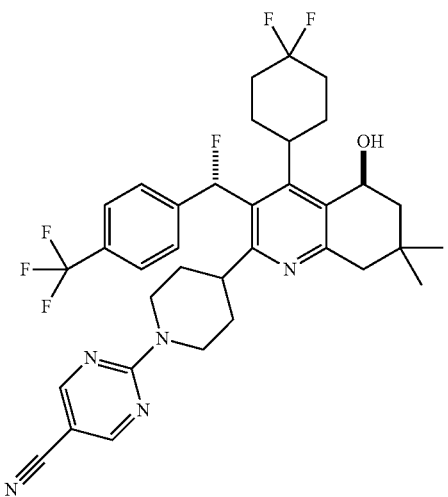 [SMILES: CC1(C)Cc2nc(C3CCN(c4ncc(C#N)cn4)CC3)c([C@@H](F)c3ccc(C(F)(F)F)cc3)c(C3CCC(F)(F)CC3)c2[C@@H](O)C1] |

TABLE 1-4-continued

| Example 18 | (5S)-2-{1-[5-(Cyclohex-1-en-1-yl)pyrimidin-2-yl]piperidin-4-yl}-4-(4,4-difluorocyclohexyl)-3-{(S)-fluoro[4-(trifluoromethyl)phenyl]methyl}-7,7-dimethyl-5,6,7,8-tetrahydroquinolin-5-ol | 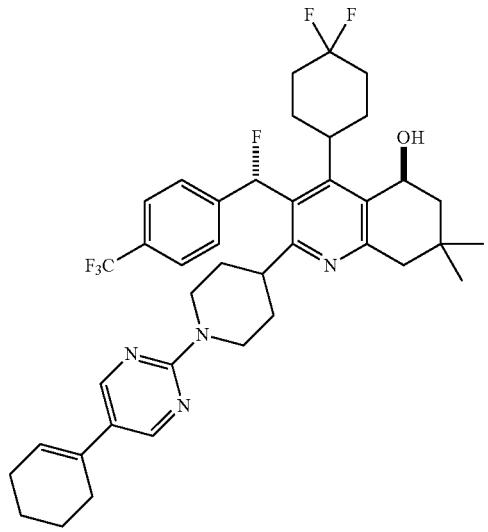 [SMILES: CC1(C)Cc2nc(C3CCN(c4ncc(C5=CCCCC5)cn4)CC3)c([C@@H](F)c3ccc(C(F)(F)F)cc3)c(C3CCC(F)(F)CC3)c2[C@@H](O)C1] |
|---|---|---|
| Example 19 | (5S)-2-[1-(5-Cyclopropylpyrimidin-2-yl)piperidin-4-yl]-4-(4,4-difluorocyclohexyl)-3-{(S)-fluoro[4-(trifluoromethyl)phenyl]methyl}-7,7-dimethyl-5,6,7,8-tetrahydroquinolin-5-ol | 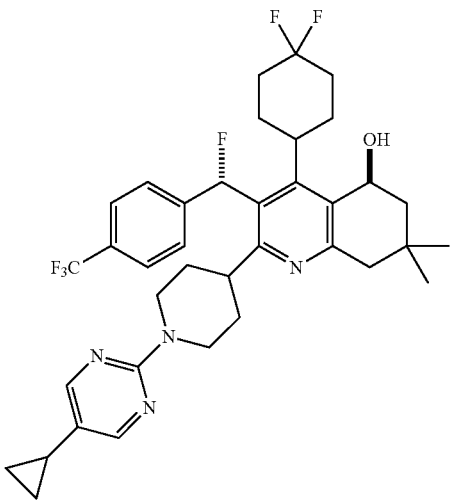 |

TABLE 1-5

| Example 20 | (5S)-4-(4,4-Difluorocyclohexyl)-3-{(S)-fluoro[4-(trifluoromethyl)phenyl]methyl}-2-[1-[5-(hydroxymethyl)pyrimidin-2-yl]piperidin-4-yl]-7,7-dimethyl-5,6,7,8-tetrahydroquinolin-5-ol | 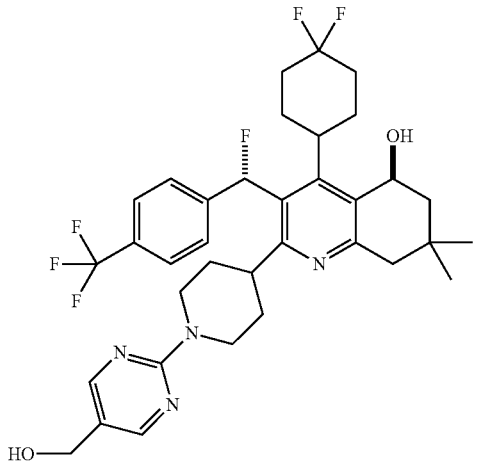 [SMILES: CC1(C)Cc2nc(C3CCN(c4ncc(CO)cn4)CC3)c([C@@H](F)c3ccc(C(F)(F)F)cc3)c(C3CCC(F)(F)CC3)c2[C@@H](O)C1] |

TABLE 1-5-continued

| Example 20 Intermediate | (5S)-4-(4,4-Difluorocyclohexyl)-3-{(S)-fluoro[4-(trifluoromethyl)phenyl]methyl}-2-[1-[5-(hydroxymethyl)pyrimidin-2-yl]piperidin-4-yl]-5-[(4-methoxybenzyl)oxy]-7,7-dimethyl-5,6,7,8-tetrahydroquinoline | 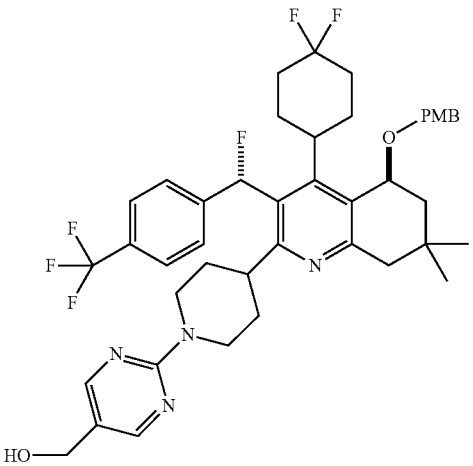 |
| --- | --- | --- |
| Example 21 | (5S)-4-(4,4-Difluorocyclohexyl)-3-{(S)-fluoro[4-(trifluoromethyl)phenyl]methyl}-7,7-dimethyl-2-{1-[5-(2-methylpropoxy)pyrimidin-2-yl]piperidin-4-yl}-5,6,7,8-tetrahydroquinolin-5-ol | 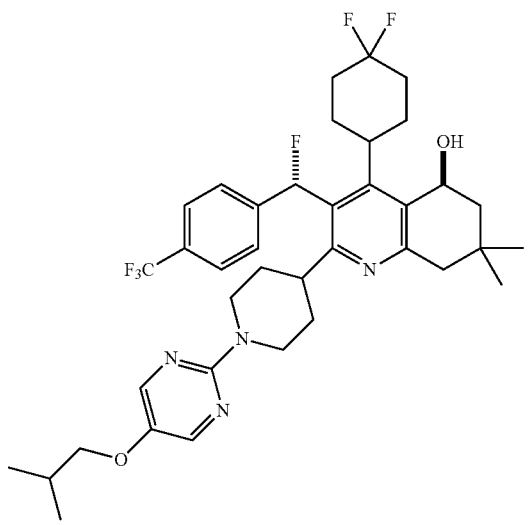 [SMILES: CC(C)COc1cnc(N2CCC(c3nc4c(c(C5CCC(F)(F)CC5)c3[C@@H](F)c3ccc(C(F)(F)F)cc3)[C@@H](O)CC(C)(C)C4)CC2)nc1] |
| Example 22 | (5S)-4-(4,4-Difluorocyclohexyl)-3-{(S)-fluoro[4-(trifluoromethyl)phenyl]methyl}-7,7-dimethyl-2-{1-[5-(3-methylbutoxy)pyrimidin-2-yl]piperidin-4-yl}-5,6,7,8-tetrahydroquinolin-5-ol | 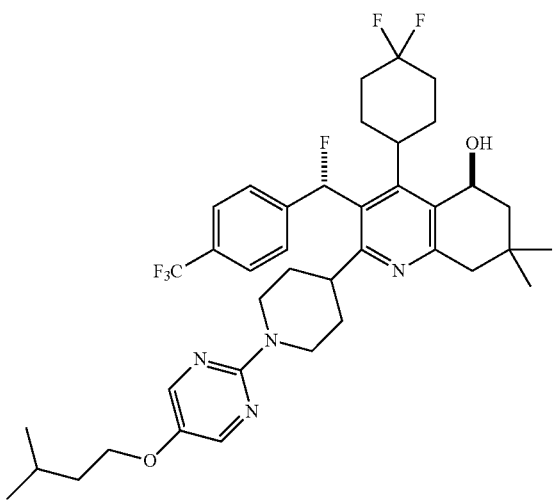 [SMILES: CC(C)CCOc1cnc(N2CCC(c3nc4c(c(C5CCC(F)(F)CC5)c3[C@@H](F)c3ccc(C(F)(F)F)cc3)[C@@H](O)CC(C)(C)C4)CC2)nc1] |

TABLE 1-5-continued

| Example 23 | (5S)-2-{1-[5-(4-Carboxybutoxy)pyrimidin-2-yl]piperidin-4-yl}-4-(4,4-difluoro cyclohexyl)-3-{(S)-fluoro[4-(trifluoromethyl) phenyl]methyl}-7,7-dimethyl-5,6,7,8-tetrahydroquinolin-5-ol | 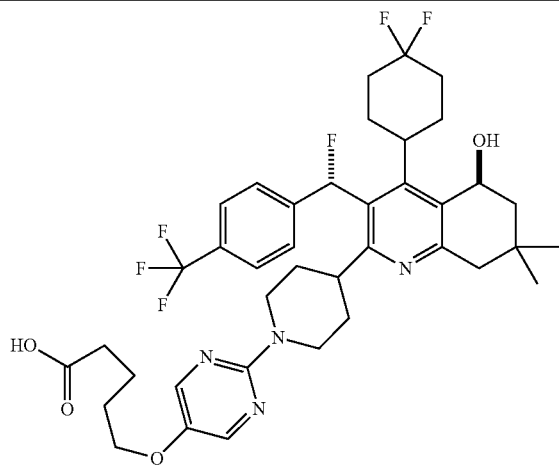 |

TABLE 1-6

| Example (23-1) | (5S)-2-{1-[5-(4-Ethoxycarbonylbutoxy) pyrimidin-2-yl]piperidin-4-yl}-4-(4,4-difluorocyclohexyl)-3-{(S)-fluoro[4-(trifluoromethyl)phenyl]methyl}-7,7-dimethyl-5,6,7,8-tetrahydroquinolin-5-ol | 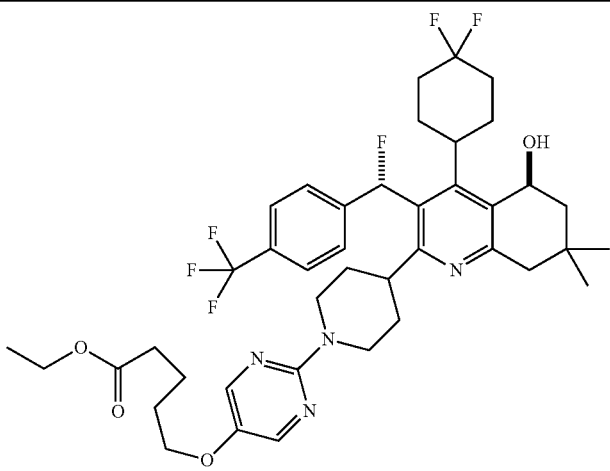 |
| Example 24 | (5S)-4-(4,4-Difluorocyclohexyl)-3-{(S)-fluoro[4-(trifluoromethyl)phenyl]methyl}-7,7-dimethyl-2-{1-[5-(2-methylpropyl) pyrimidin-2-yl]piperidin-4-yl}-5,6,7,8-tetrahydroquinolin-5-ol | 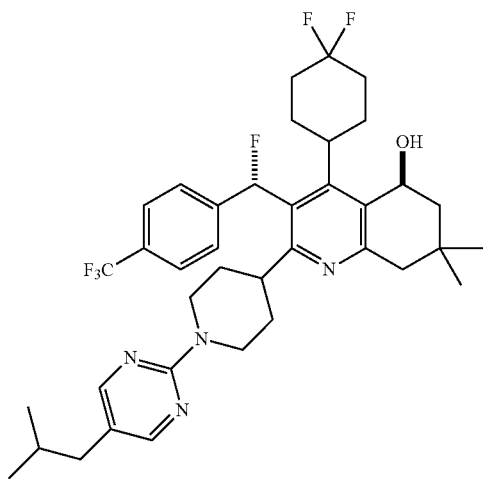 [SMILES: CC(C)Cc1cnc(N2CCC(c3nc4c(c(C5CCC(F)(F)CC5)c3[C@@H](F)c3ccc(C(F)(F)F)cc3)[C@@H](O)CC(C)(C)C4)CC2)nc1] |

TABLE 1-6-continued

| Example 25 | (5S)-2-{1-[5-(4-Carboxybutyl)pyrimidin-2-yl]piperidin-4-yl}-4-(4,4-difluorocyclohexyl)-3-{(S)-fluoro[4-(trifluoromethyl)phenyl]methyl}-7,7-dimethyl-5,6,7,8-tetrahydroquinolin-5-ol | 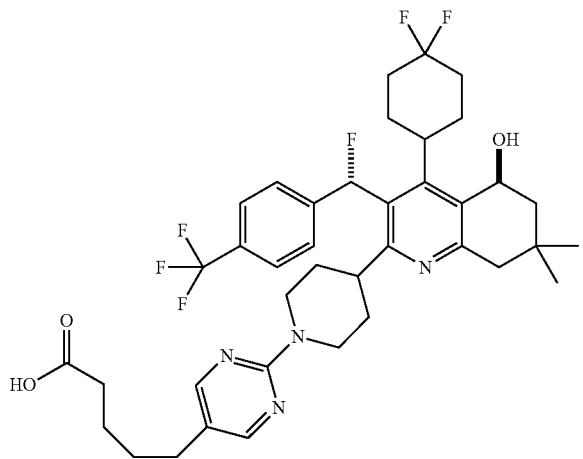 [SMILES: CC1(C)Cc2nc(C3CCN(c4ncc(CCCCC(=O)O)cn4)CC3)c([C@@H](F)c3ccc(C(F)(F)F)cc3)c(C3CCC(F)(F)CC3)c2[C@@H](O)C1] |
| --- | --- | --- |
| Example 26 | (5S)-4-(4,4-Difluorocyclohexyl)-2-{1-[5-(ethoxymethyl)pyrimidin-2-yl]piperidin-4-yl}-3-{(S)-fluoro[4-(trifluoromethyl)phenyl]methyl}-7,7-dimethyl-5,6,7,8-tetrahydroquinolin-5-ol | 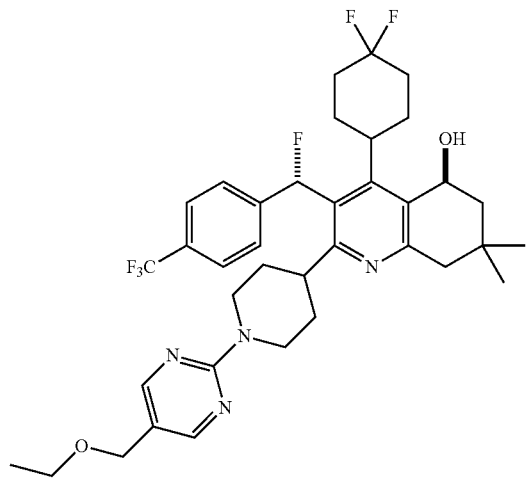 |
| Example 27 | (5S)-4-(4,4-Difluorocyclohexyl)-3-{(S)-fluoro[4-(trifluoromethyl)phenyl]methyl}-2-{1-[5-(methoxymethyl)pyrimidin-2-yl]piperidin-4-yl}-7,7-dimethyl-5,6,7,8-tetrahydroquinolin-5-ol | 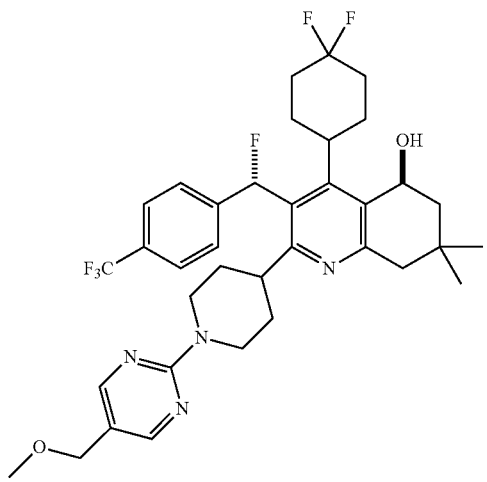 |

TABLE 1-7

| Example 28 | (5S)-4-(4,4-Difluorocyclohexyl)-3-{(S)-fluoro[4-(trifluoromethyl)phenyl]methyl}-7,7-dimethyl-2-(1-{5-[(propan-2-yloxy)methyl]pyrimidin-2-yl}piperidin-4-yl)-5,6,7,8-tetrahydroquinolin-5-ol | 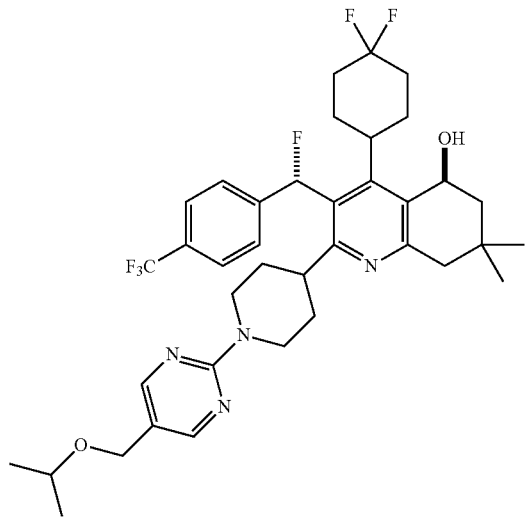 |
| --- | --- | --- |
| Example 29 | (5S)-4-(4,4-Difluorocyclohexyl)-3-{(S)-fluoro[4-(trifluoromethyl)phenyl]methyl}-7,7-dimethyl-2-(1-{5-[(2-methylpropoxy)methyl]pyrimidin-2-yl}piperidin-4-yl)-5,6,7,8-tetrahydroquinolin-5-ol | 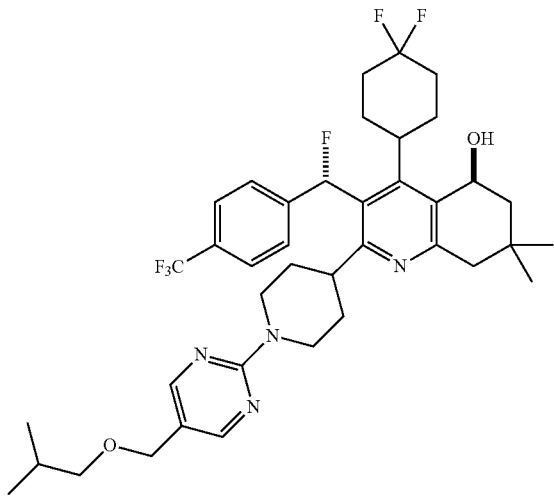 [SMILES: CC(C)COCc1cnc(N2CCC(c3nc4c(c(C5CCC(F)(F)CC5)c3[C@@H](F)c3ccc(C(F)(F)F)cc3)[C@@H](O)CC(C)(C)C4)CC2)nc1] |
| Example 30 | (5S)-4-(4,4-Difluorocyclohexyl)-3-{(S)-fluoro[4-(trifluoromethyl)phenyl]methyl}-7,7-dimethyl-2-{1-[5-(methylcarbamoyl)pyrimidin-2-yl]piperidin-4-yl}-5,6,7,8-tetrahydroquinolin-5-ol | 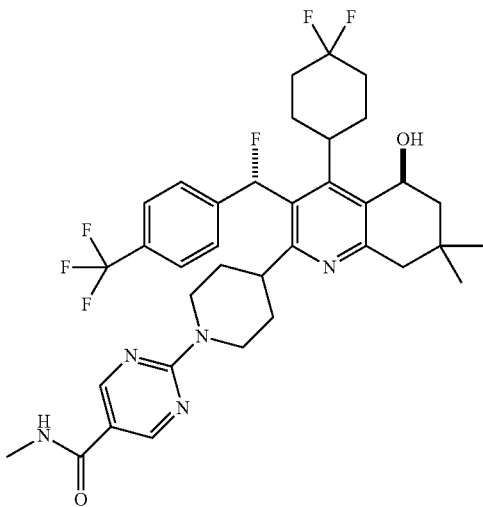 |

TABLE 1-7-continued

| Example 31 | (5S)-4-(4,4-Difluorocyclohexyl)-2-{1-[5-(dimethylcarbamoyl)pyrimidin-2-yl]piperidin-4-yl}-3-{(S)-fluoro[4-(trifluoromethyl)phenyl]methyl}-7,7-dimethyl-5,6,7,8-tetrahydroquinolin-5-ol | 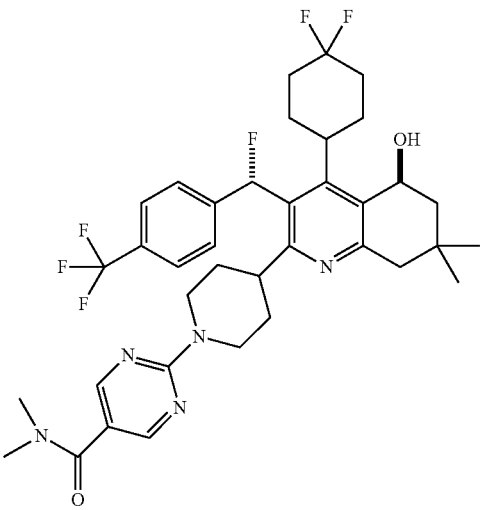 |
|---|---|---|
| Example 32 | (5S)-4-(4,4-Difluorocyclohexyl)-3-{(S)-fluoro[4-(trifluoromethyl)phenyl]methyl}-7,7-dimethyl-2-{1-[5-(morpholin-4-ylcarbonyl)pyrimidin-2-yl]piperidin-4-yl}-5,6,7,8-tetrahydroquinolin-5-ol | 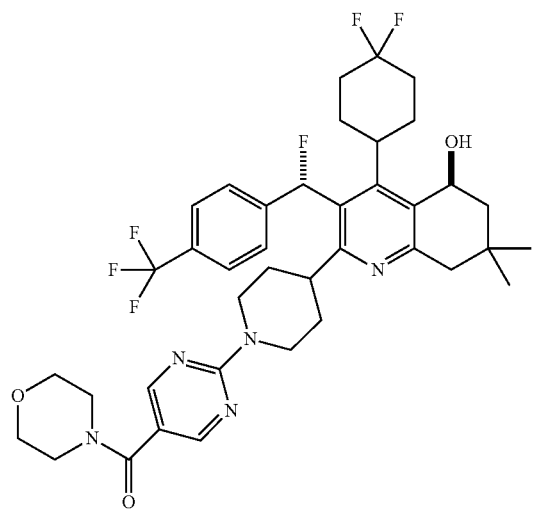 [SMILES: CC1(C)Cc2nc(C3CCN(c4ncc(C(=O)N5CCOCC5)cn4)CC3)c([C@@H](F)c3ccc(C(F)(F)F)cc3)c(C3CCC(F)(F)CC3)c2[C@@H](O)C1] |

TABLE 1-8

| Example 33 | (5S)-4-(4,4-Difluorocyclohexyl)-3-{(S)-fluoro[4-(trifluoromethyl)phenyl]methyl}-7,7-dimethyl-2-{1-[5-(4,4,4-trifluorobutyl)pyrimidin-2-yl]piperidin-4-yl}-5,6,7,8-tetrahydroquinolin-5-ol | 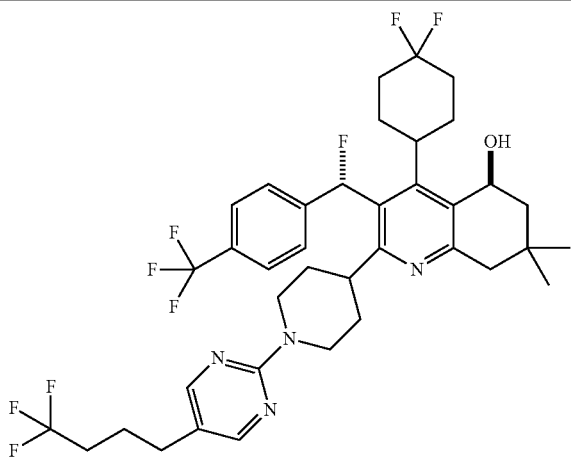 |

TABLE 1-8-continued

| Example 34 | (5S)-4-(4,4-Difluorocyclohexyl)-3-{(S)-fluoro[4-(trifluoromethyl)phenyl]methyl}-7,7-dimethyl-2-(1-{5-[(1E)-3-methylbutyl-en-1-yl]pyrimidin-2-yl}piperidin-4-yl)-5,6,7,8-tetrahydroquinolin-5-ol | 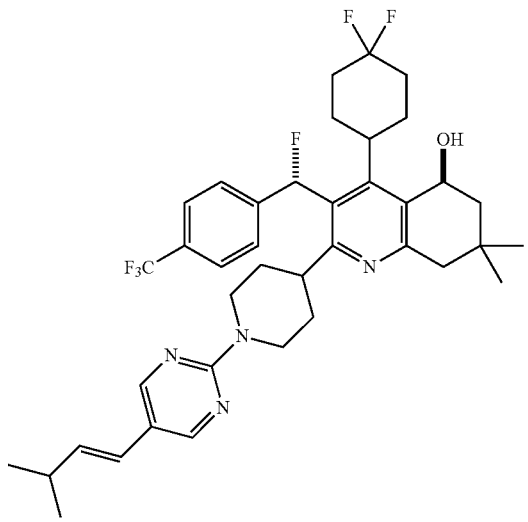 [SMILES: CC(C)/C=C/c1cnc(N2CCC(c3nc4c(c(C5CCC(F)(F)CC5)c3[C@@H](F)c3ccc(C(F)(F)F)cc3)[C@@H](O)CC(C)(C)C4)CC2)nc1] |
|---|---|---|
| Example 35 | (5S)-4-(4,4-Difluorocyclohexyl)-3-{(S)-fluoro[4-(trifluoromethyl)phenyl]methyl}-7,7-dimethyl-2-{1-[5-(3-methyl-1,2,4-oxa diazol-5-yl)pyrimidin-2-yl]piperidin-4-yl}-5,6,7,8-tetrahydroquinolin-5-ol | 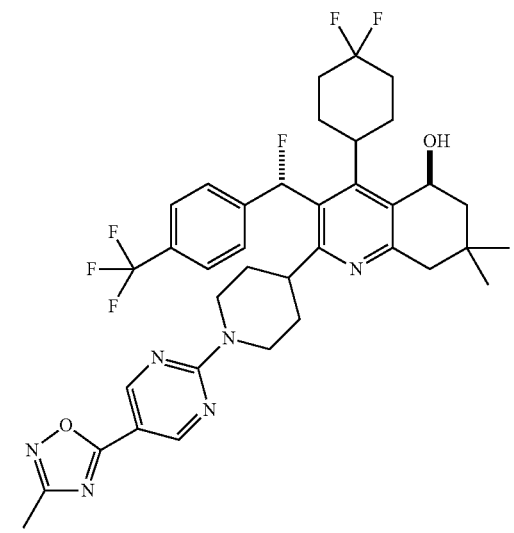 |
| Example 36 | (5S)-4-(4,4-Difluorocyclohexyl)-3-{(S)-fluoro[4-(trifluoromethyl)phenyl]methyl}-2-{1-(5-{[(2-hydroxyethyl)(methyl)amino]methyl}pyrimidin-2-yl)piperidin-4-yl}-7,7-dimethyl-5,6,7,8-tetrahydroquinolin-5-ol | 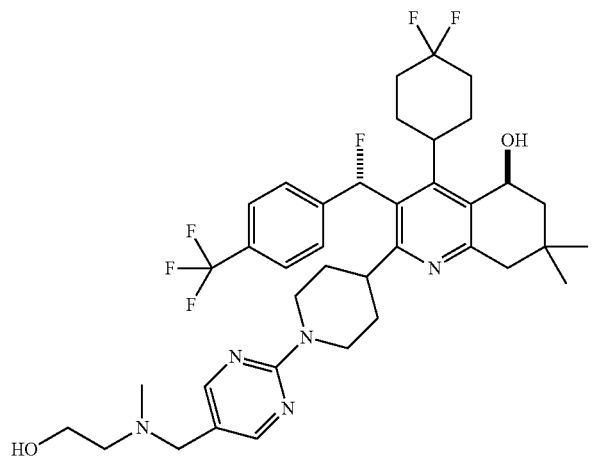 [SMILES: CN(CCO)Cc1cnc(N2CCC(c3nc4c(c(C5CCC(F)(F)CC5)c3[C@@H](F)c3ccc(C(F)(F)F)cc3)[C@@H](O)CC(C)(C)C4)CC2)nc1] |

TABLE 1-8-continued

| Example (36-1) | (5S)-4-(4,4-Difluorocyclohexyl)-3-{(S)-fluoro[4-(trifluoromethyl)phenyl]methyl}-2-[1-(5-formylpyrimidin-2-yl)piperidin-4-yl]-7,7-dimethyl-5,6,7,8-tetrahydro-quinolin-5-ol | 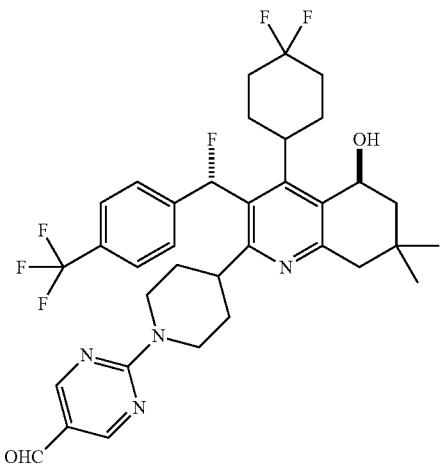 [SMILES: CC1(C)Cc2nc(C3CCN(c4ncc(C=O)cn4)CC3)c([C@@H](F)c3ccc(C(F)(F)F)cc3)c(C3CCC(F)(F)CC3)c2[C@@H](O)C1] |

TABLE 1-9

| Example 37 | (5S)-4-(4,4-Difluorocyclohexyl)-3-{(S)-fluoro[4-(trifluoromethyl)phenyl]methyl}-2-[1-(5-{[(2S)-2-hydroxypropyl]oxy}pyrimidin-2-yl)piperidin-4-yl]-7,7-dimethyl-5,6,7,8-tetrahydroquinolin-5-ol | 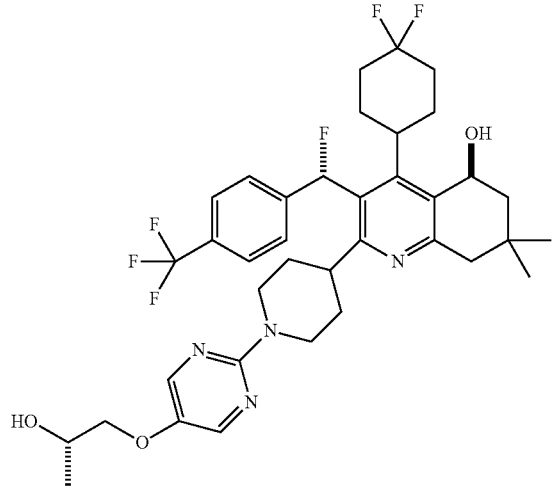 [SMILES: C[C@H](O)COc1cnc(N2CCC(c3nc4c(c(C5CCC(F)(F)CC5)c3[C@@H](F)c3ccc(C(F)(F)F)cc3)[C@@H](O)CC(C)(C)C4)CC2)nc1] |
| Example 37 Intermediate | (5S)-4-(4,4-Difluorocyclohexyl)-3-{(S)-fluoro[4-(trifluoromethyl)phenyl]methyl}-7,7-dimethyl-2-[1-(5-{[(2S)-2-(tetrahydro-2H-pyran-2-yloxy)propyl]oxy}pyrimidin-2-yl)piperidin-4-yl]-5,6,7,8-tetrahydroquinolin-5-ol | 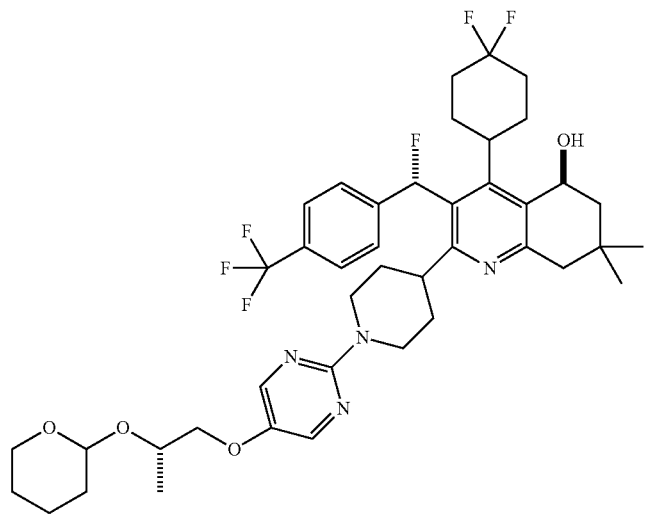 [SMILES: C[C@@H](COc1cnc(N2CCC(c3nc4c(c(C5CCC(F)(F)CC5)c3[C@@H](F)c3ccc(C(F)(F)F)cc3)[C@@H](O)CC(C)(C)C4)CC2)nc1)OC1CCCCO1] |

TABLE 1-9-continued

| Example 38 | (5S)-4-(4,4-Difluorocyclohexyl)-3-{(S)-fluoro[4-(trifluoromethyl)phenyl]methyl}-7,7-dimethyl-2-(1-{5-[(1-methyl piperidin-4-yl)oxy]pyrimidin-2-yl}piperidin-4-yl)-5,6,7,8-tetrahydroquinolin 5-ol | 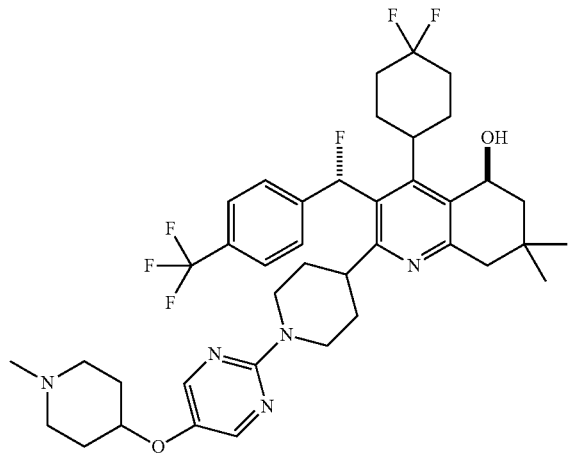 |
|---|---|---|
| Example 39 | (5S)-4-(4,4-Difluorocyclohexyl)-2-[1-(5-{[(2S)-2,3-dihydroxypropyl]oxy}pyrimidin-2-yl)piperidin-4-yl]-3-{(S)-fluoro[4-(trifluoromethyl)phenyl]methyl}-7,7-dimethyl-5,6,7,8-tetrahydroquinolin-5-ol | 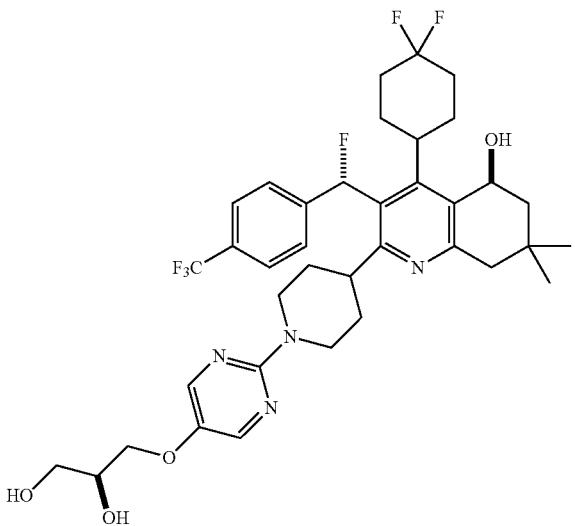 [SMILES: CC1(C)Cc2nc(C3CCN(c4ncc(OC[C@@H](O)CO)cn4)CC3)c([C@@H](F)c3ccc(C(F)(F)F)cc3)c(C3CCC(F)(F)CC3)c2[C@@H](O)C1] |
| Example 39 Intermediate | (5S)-4-(4,4-Difluorocyclohexyl)-2-[1-(5-{[(4)-2,2-dimethyl-1,3-dioxolan-4-yl]methoxy}pyrimidin-2-ylpiperidin-4-yl]-3-{(S)-fluoro[4-(trifluoromethyl)phenyl]methyl}-7,7-dimethyl-5,6,7,8-tetrahydroquinolin-5-ol | 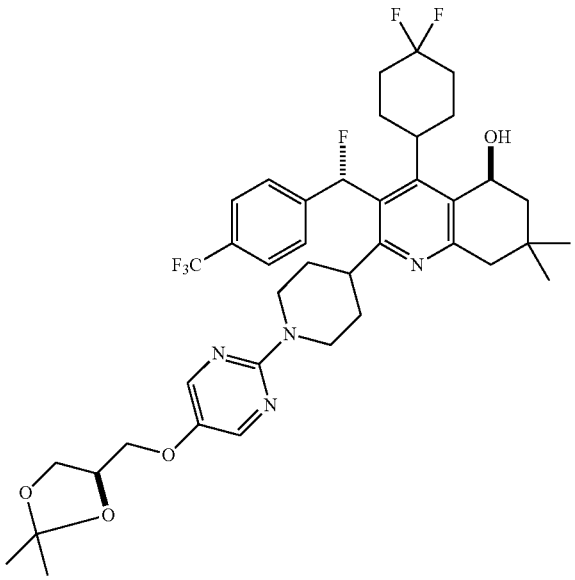 |

TABLE 1-10

| Example 40 | (5S)-4-(4,4-Difluorocyclohexyl)-2-[1-(5-{[(2R)-2,3-dihydroxypropyl]oxy}pyrimidin-2-yl)piperidin-4-yl]-3-{(S)-fluoro[4-(trifluoromethyl)phenyl]methyl}-7,7-dimethyl-5,6,7,8-tetrahydroquinolin-5-ol | 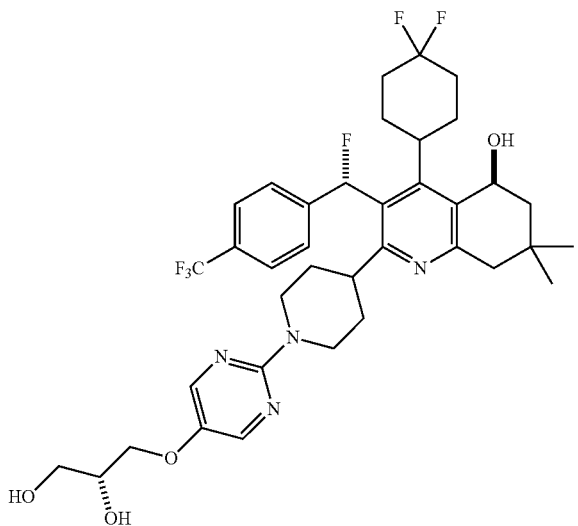 [SMILES: CC1(C)Cc2nc(C3CCN(c4ncc(OC[C@H](O)CO)cn4)CC3)c([C@@H](F)c3ccc(C(F)(F)F)cc3)c(C3CCC(F)(F)CC3)c2[C@@H](O)C1] |
| --- | --- | --- |
| Example 41 | (5S)-4-(4,4-Difluorocyclohexyl)-3-{(S)-fluoro[4-(trifluoromethyl)phenyl]methyl}-7,7-dimethyl-2-[1-(5-{[(3R)-1-methyl-pyrrolidin-3-yl]oxy}pyrimidin-2-yl)piperidine-4-yl]-5,6,7,8-tetrahydroquinolin-5-ol | 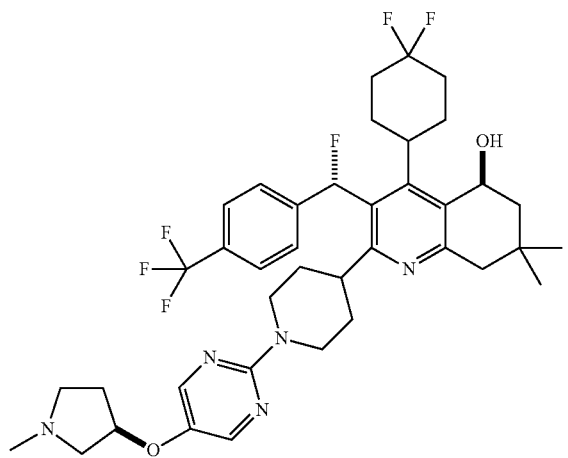 |
| Example 42 | (5S)-4-(4,4-Difluorocyclohexyl)-3-{(S)-fluoro[4-(trifluoromethyl)phenyl]methyl}-2-[1-(5-{[(2R)-2-hydroxypropyl]oxy}pyrimidin-2-yl)piperidin-4-yl]-7,7-dimethyl-5,6,7,8-tetrahydroquinolin-5-ol | 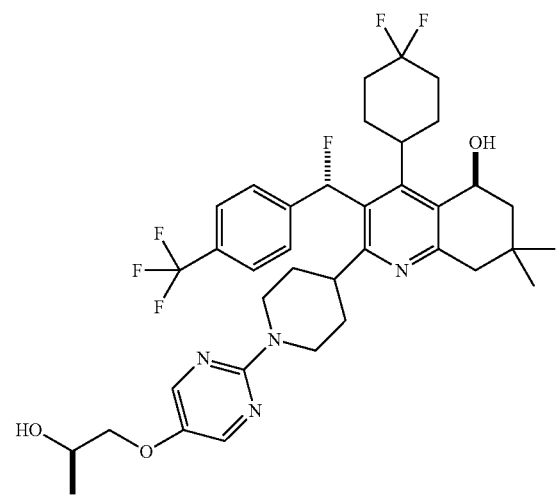 [SMILES: C[C@@H](O)COc1cnc(N2CCC(c3nc4c(c(C5CCC(F)(F)CC5)c3[C@@H](F)c3ccc(C(F)(F)F)cc3)[C@@H](O)CC(C)(C)C4)CC2)nc1] |

TABLE 1-10-continued

| Example 43 | (5S)-4-(4,4-Difluorocyclohexyl)-3-{(S)-fluoro[4-(trifluoromethyl)phenyl]methyl}-2-{1-[5-(3-hydroxy-3-methylbutoxy)pyrimidin-2-yl]piperidin-4-yl}-7,7-dimethyl-5,6,7,8-tetrahydroquinolin-5-ol | 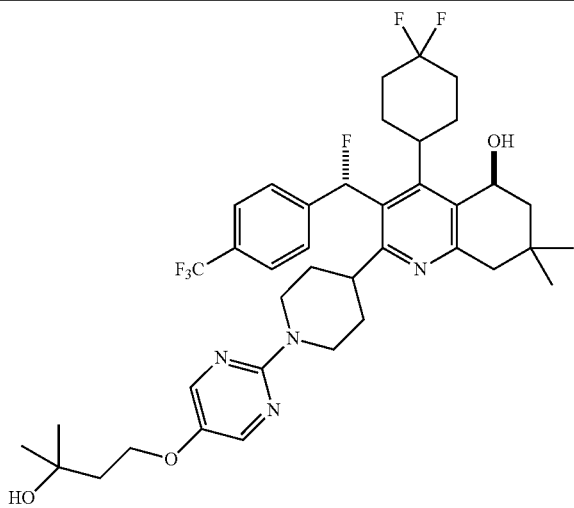 |
| --- | --- | --- |
| Example 44 | (5S)-4-(4,4-Difluorocyclohexyl)-3-{(S)-fluoro[4-(trifluoromethyl)phenyl]methyl}-2-{1-[5-(2-hydroxy-2-methylpropoxy)pyrimidin-2-yl]piperidin-4-yl}-7,7-dimethyl-5,6,7,8-tetrahydroquinolin-5-ol | 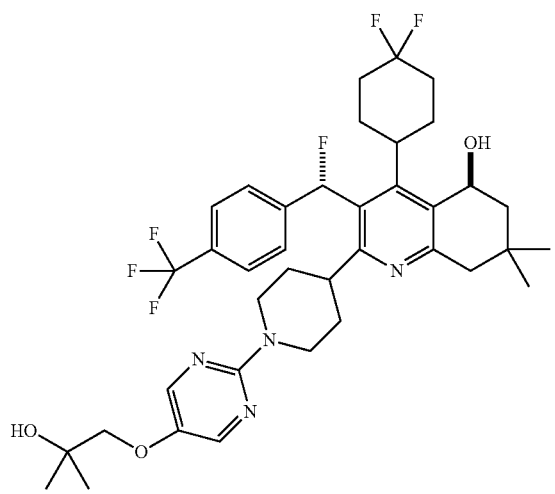 [SMILES: CC(C)(O)COc1cnc(N2CCC(c3nc4c(c(C5CCC(F)(F)CC5)c3[C@@H](F)c3ccc(C(F)(F)F)cc3)[C@@H](O)CC(C)(C)C4)CC2)nc1] |

TABLE 1-11

| Example 44 Intermediate | (5S)-4-(4,4-Difluorocyclohexyl)-2-{1-[5-(2-ethoxy-2-oxoethoxy)pyrimidin-2-yl]piperidin-4-yl}-3-{(S)-fluoro[4-(trifluoromethyl)phenyl]methyl}-7,7-dimethyl-5,6,7,8-tetrahydroquinolin-5-ol | 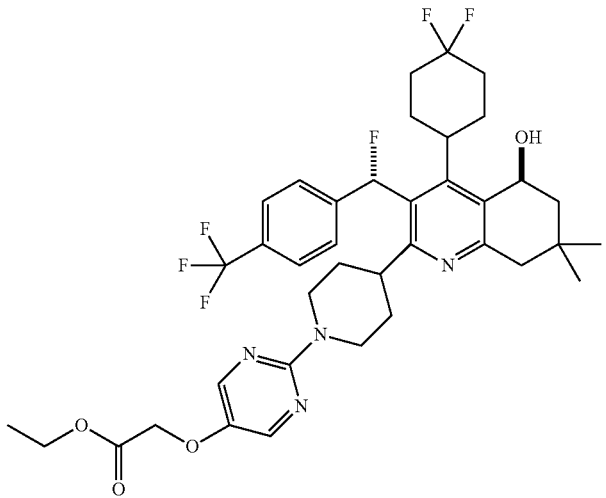 [SMILES: CCOC(=O)COc1cnc(N2CCC(c3nc4c(c(C5CCC(F)(F)CC5)c3[C@@H](F)c3ccc(C(F)(F)F)cc3)[C@@H](O)CC(C)(C)C4)CC2)nc1] |
| --- | --- | --- |

TABLE 1-11-continued

| Example 45 | (5S)-4-(4,4-Difluorocyclohexyl)-3-{(S)-fluoro[4-(trifluoromethyl)phenyl]methyl}-7,7-dimethyl-2-(1-{5-[3-(methylsulfonyl)propoxy]pyrimidin-2-yl}piperidin-4-yl)-5,6,7,8-tetrahydroquinolin-5-ol | 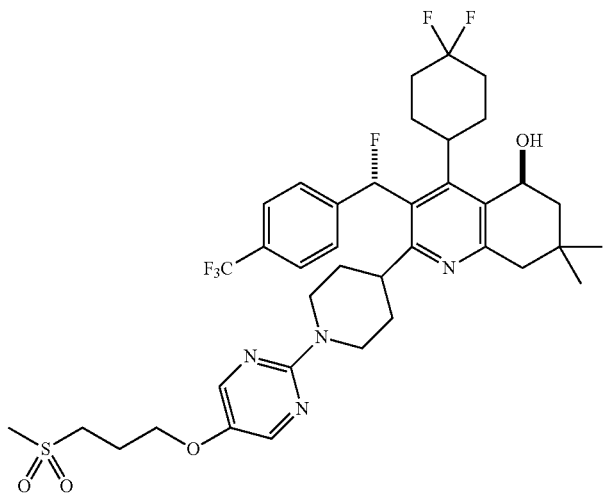 |
| --- | --- | --- |
| Example 46 | (5S)-4-(4,4-Difluorocyclohexyl)-3-{(S)-fluoro[4-(trifluoromethyl)phenyl]methyl}-2-{1-[5-(3-hydroxypropoxy)pyrimidin-2-yl]piperidin-4-yl}-7,7-dimethyl-5,6,7,8-tetrahydroquinolin-5-ol | 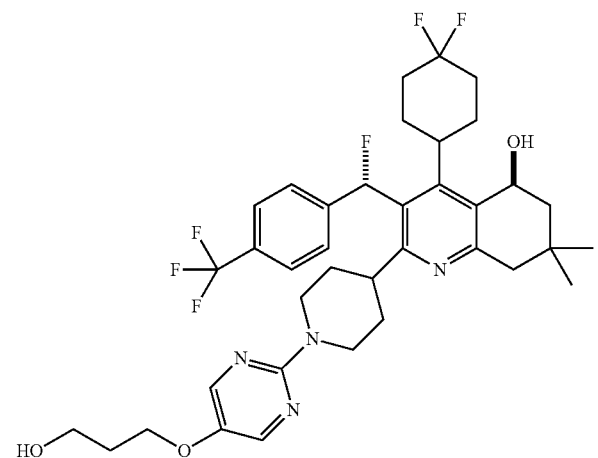 [SMILES: CC1(C)Cc2nc(C3CCN(c4ncc(OCCCO)cn4)CC3)c([C@@H](F)c3ccc(C(F)(F)F)cc3)c(C3CCC(F)(F)CC3)c2[C@@H](O)C1] |
| Example 46 Intermediate | (5S)-2-{1-[5-(3-{[tert-Butyl)(dimethyl)silyl]oxy}propoxy)pyrimidin-2-yl]piperidin-4-yl}-4-(4,4-difluorocyclohexyl)-3-{(S)-fluoro[4-(trifluoromethyl)phenyl]methyl}-7,7-dimethyl-5,6,7,8-tetrahydroquinolin-5-ol | 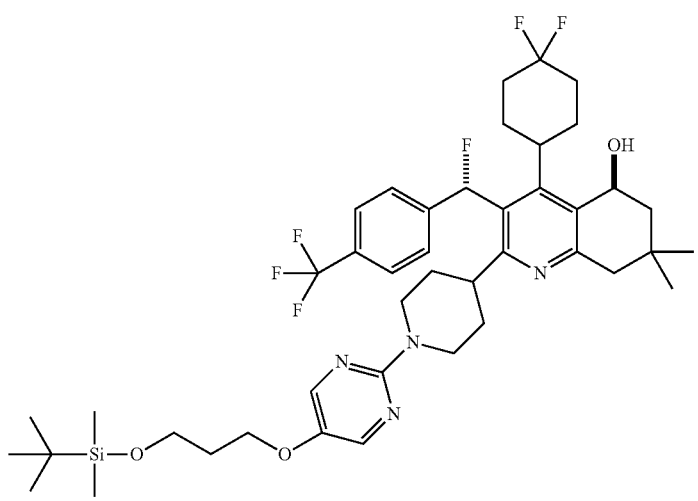 [SMILES: CC1(C)Cc2nc(C3CCN(c4ncc(OCCCO[Si](C)(C)C(C)(C)C)cn4)CC3)c([C@@H](F)c3ccc(C(F)(F)F)cc3)c(C3CCC(F)(F)CC3)c2[C@@H](O)C1] |

TABLE 1-11-continued

| Example 47 | (5S)-4-(4,4-Difluorocyclohexyl)-3-{(S)-fluoro[4-(trifluoromethyl)phenyl]methyl}-7,7-dimethyl-2-{1-[5-(3,3,3-trifluoropropoxy)pyrimidin-2-yl]piperidin-4-yl}-5,6,7,8-tetrahydroquinolin-5-ol | 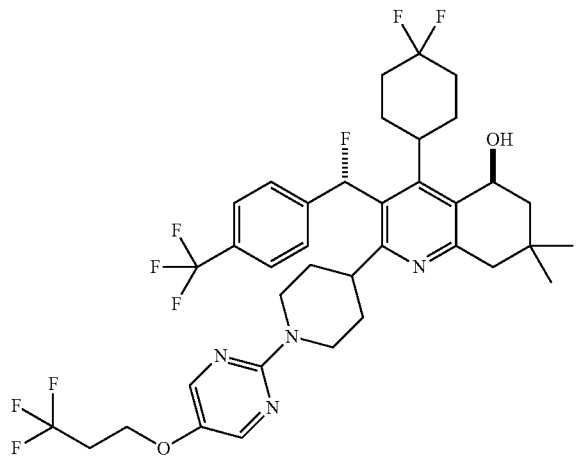 |

TABLE 1-12

| Example 48 | (5S)-4-(4,4-Difluorocyclohexyl)-2-{1-[5-(difluoromethoxy)pyrimidin-2-yl]piperidin-4-yl}-3-{(S)-fluoro[4-(trifluoromethyl)phenyl]methyl}-7,7-dimethyl-5,6,7,8-tetrahydroquinolin-5-ol | 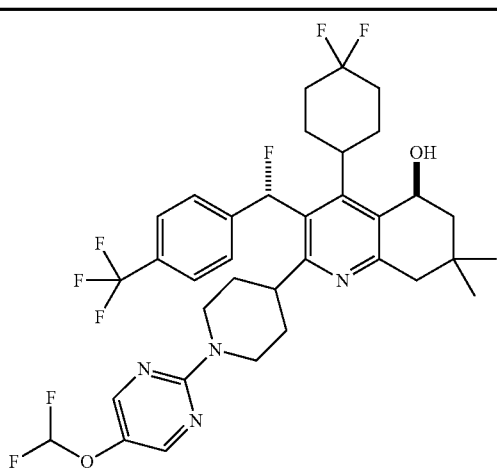 |
| Example 49 | (5S)-4-(4,4-Difluorocyclohexyl)-3-{(S)-fluoro[4-(trifluoromethyl)phenyl]methyl}-2-(1-{5-[3-hydroxy-2-(hydroxymethyl)propoxy]pyrimidin-2-yl}piperidin-4-yl)-7,7-dimethyl-5,6,7,8-tetrahydroquinolin-5-ol | 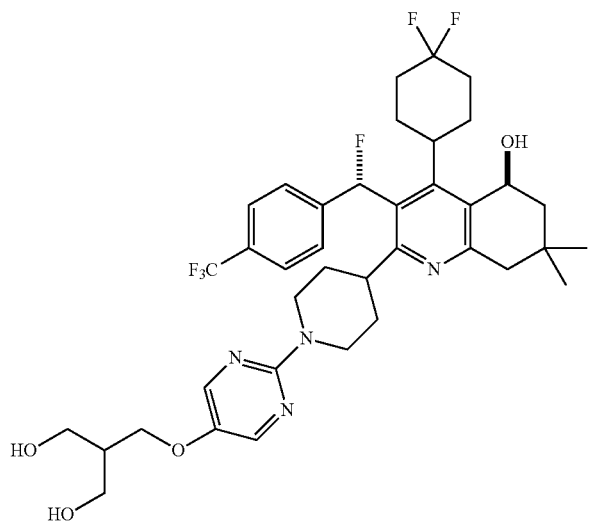 [SMILES: CC1(C)Cc2nc(C3CCN(c4ncc(OCC(CO)CO)cn4)CC3)c([C@@H](F)c3ccc(C(F)(F)F)cc3)c(C3CCC(F)(F)CC3)c2[C@@H](O)C1] |

TABLE 1-12-continued

| Example 50 | (5S)-4-(4,4-Difluorocyclohexyl)-3-{(S)-fluoro[4-(trifluoromethyl)phenyl]methyl}-2-(1-{5-[3-hydroxy-2-(hydroxymethyl)-2-methylpropoxy]pyrimidin-2-yl}piperidin-4-yl)-7,7-dimethyl-5,6,7,8-tetrahydroquinolin-5-ol | 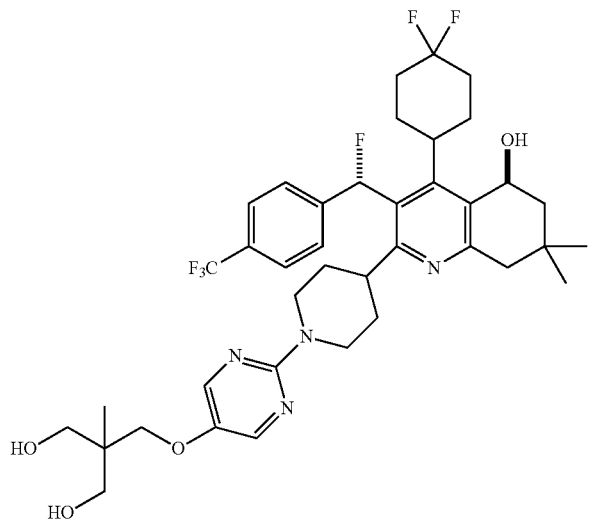 [SMILES: CC1(C)Cc2nc(C3CCN(c4ncc(OCC(C)(CO)CO)cn4)CC3)c([C@@H](F)c3ccc(C(F)(F)F)cc3)c(C3CCC(F)(F)CC3)c2[C@@H](O)C1] |
|---|---|---|
| Example 51 | (5S)-4-(4,4-Difluorocyclohexyl)-3-{(S)-fluoro[4-(trifluoromethyl)phenyl]methyl}-7,7-dimethyl-2-[1-(5-{[methyl(methylsulfonyl)amino]methyl}pyrimidin-2-yl)piperidin-4-yl]-5,6,7,8-tetrahydroquinolin-5-ol | 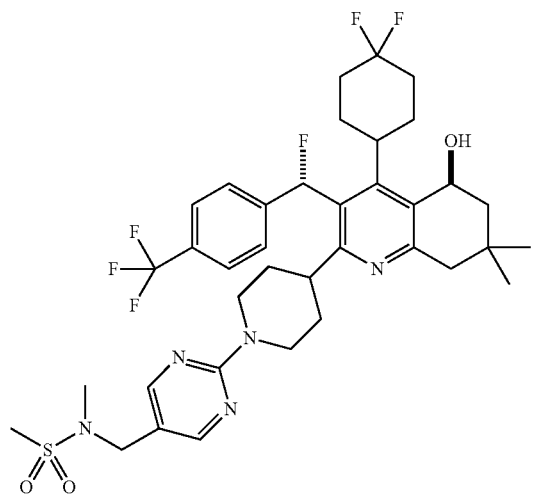 |
| Example 52 | (5S)-4-(4,4-Difluorocyclohexyl)-3-{(S)-fluoro[4-(trifluoromethyl)phenyl]methyl}-7,7-dimethyl-2-[1-(5-{[methyl(propane-2-ylsulfonyl)amino]methyl}pyrimidin-2-yl)piperidin-4-yl]-5,6,7,8-tetrahydroquinolin-5-ol | 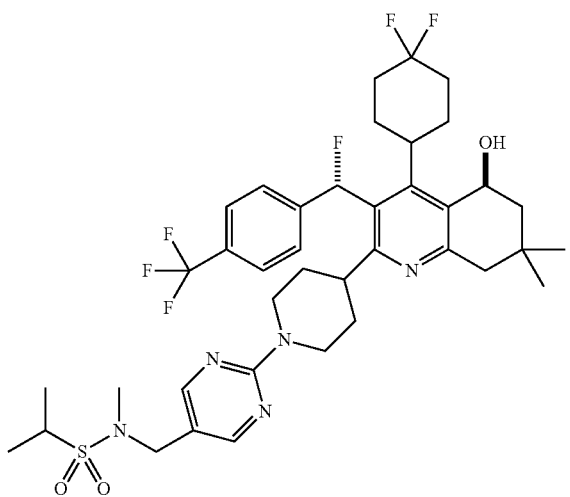 [SMILES: CC(C)S(=O)(=O)N(C)Cc1cnc(N2CCC(c3nc4c(c(C5CCC(F)(F)CC5)c3[C@@H](F)c3ccc(C(F)(F)F)cc3)[C@@H](O)CC(C)(C)C4)CC2)nc1] |

TABLE 1-13

| Example 53 | (5S)-4-(4,4-Difluorocyclohexyl)-3-{(S)-fluoro[4-(trifluoromethyl)phenyl]methyl}-7,7-dimethyl-2-[1-(5-methylthiopyrimidin-2-yl)piperidin-4-yl]-5,6,7,8-tetrahydroquinolin-5-ol | 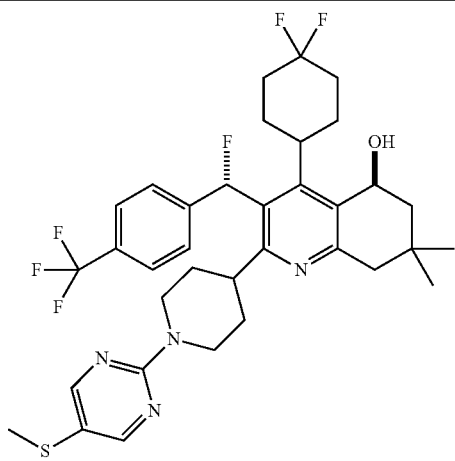 |
|---|---|---|
| Example 54 | (5S)-4-(4,4-Difluorocyclohexyl)-3-{(S)-fluoro[4-(trifluoromethyl)phenyl]methyl}-7,7-dimethyl-2-{1-[5-(methylsulfonyl)pyrimidin-2-yl]piperidin-4-yl}-5,6,7,8-tetrahydroquinolin-5-ol | 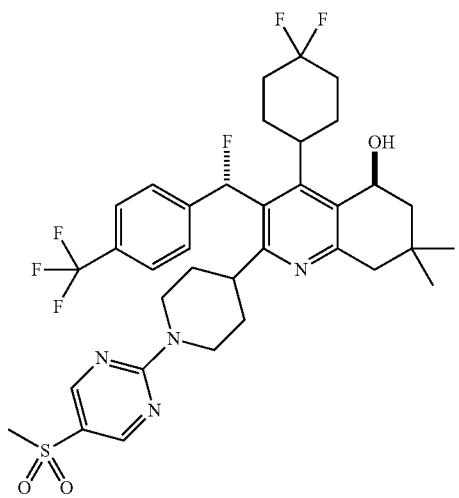 |
| Example 55 | (5S)-2-{1-[5-(3-Carboxyphenyl)pyrimidin-2-yl]piperidin-4-yl}-4-(4,4-difluorocyclohexyl)-3-{(S)-fluoro[4-(trifluoromethyl)phenyl]methyl}-7,7-dimethyl-5,6,7,8-tetrahydroquinolin 5-ol | 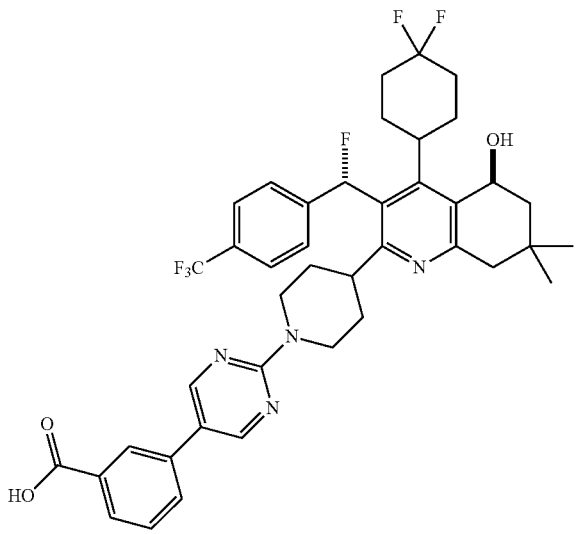 [SMILES: CC1(C)Cc2nc(C3CCN(c4ncc(-c5cccc(C(=O)O)c5)cn4)CC3)c([C@@H](F)c3ccc(C(F)(F)F)cc3)c(C3CCC(F)(F)CC3)c2[C@@H](O)C1] |

TABLE 1-13-continued

| Example 55 Intermediate 1 | (5S)-4-(4,4-Difluorocyclohexyl)-3-{(S)-fluoro[4-(trifluoromethyl)phenyl]methyl}-5-[(4-methoxybenzyl)oxy]-2-(1-{5-[3-(methoxycarbonyl)phenyl]pyrimidin-2-yl}piperidin-4-yl)-7,7-dimethyl-5,6,7,8-tetrahydroquinoline | 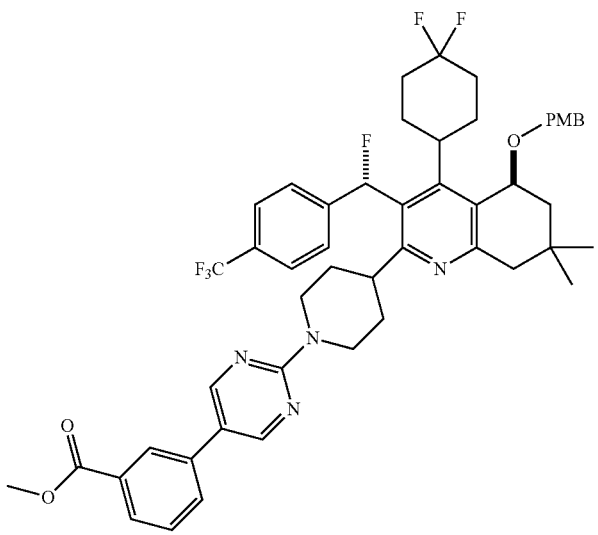 |
|---|---|---|
| The example 55 Intermediate 2 | (5S)-4-(4,4-Difluorocyclohexyl)-3-{(S)-fluoro[4-(trifluoromethyl)phenyl]methyl}-2-(1-{5-[3-(methoxycarbonyl)phenyl]pyrimidin-2-yl}piperidin-4-yl)-7,7-dimethyl-5,6,7,8-tetrahydroquinolin-5-ol | 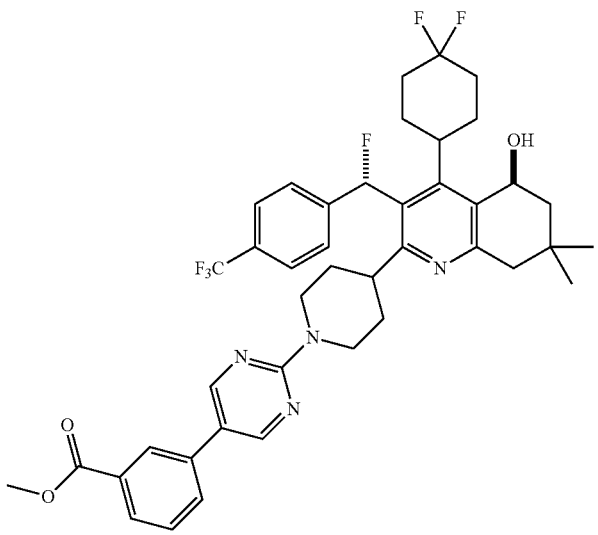 |

TABLE 1-14

| Example 56 | (5S)-4-(4,4-Difluorocyclohexyl)-3-{(S)-fluoro[4-(trifluoromethyl)phenyl]methyl}-2-(1-{5-[(2-hydroxyethyl)(methyl)amino]pyrimidin-2-yl}piperidin-4-yl)-7,7-dimethyl-5,6,7,8-tetrahydroquinolin-5-ol | 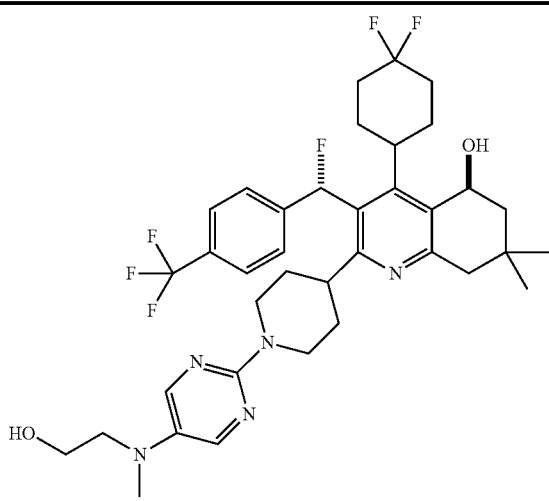 |
|---|---|---|

TABLE 1-14-continued

| Example 56 Intermediate 1 | (5S)-4-(4,4-Difluorocyclohexyl)-3-{(S)-fluoro[4-(trifluoromethyl)phenyl]methyl}-2-(1-{5-[(2-hydroxyethyl)(methyl)amino]pyrimidin-2-yl}piperidin-4-yl)-5-[(4-methoxybenzyl)oxy]-7,7-dimethyl-5,6,7,8-tetrahydroquinoline | 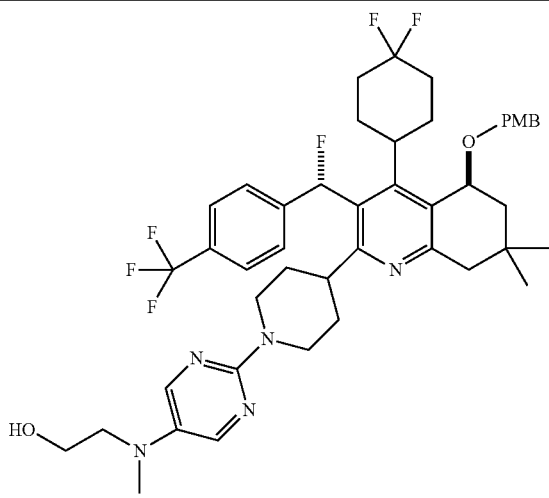 |
| --- | --- | --- |
| Example 56 Intermediate 2 | (5S)-2-(1-{5-[(2-Acetoxyethyl)(methyl)amino]pyrimidin-2-yl}piperidin-4-yl-4-(4,4-difluorocyclohexyl)-3-{(S)-fluoro[4-(trifluoromethyl)phenyl]methyl}-5-[(4-methoxybenzyl)oxy]-7,7-dimethyl-5,6,7,8-tetrahydroquinoline | 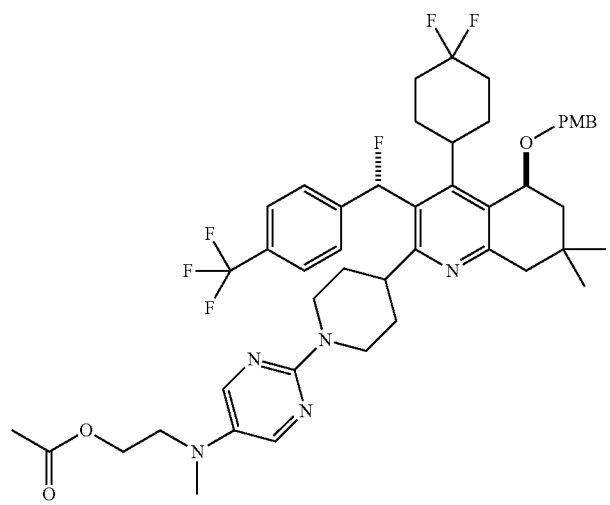 |
| Example 57 | (5S)-4-(4,4-Difluorocyclohexyl)-3-{(S)-fluoro[4-(trifluoromethyl)phenyl]methyl}-2-(1-{5-[(3S)-3-hydroxypyrrolidin-1-yl]pyrimidin-2-yl}piperidin-4-yl)-7,7-dimethyl-5,6,7,8-tetrahydroquinolin-5-ol | 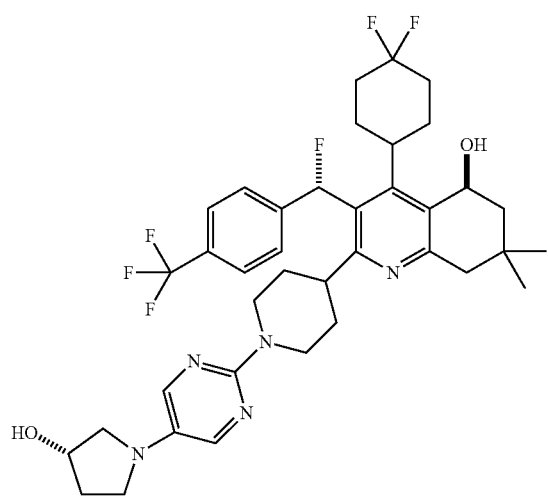 [SMILES: CC1(C)Cc2nc(C3CCN(c4ncc(N5CC[C@H](O)C5)cn4)CC3)c([C@@H](F)c3ccc(C(F)(F)F)cc3)c(C3CCC(F)(F)CC3)c2[C@@H](O)C1] |

TABLE 1-14-continued

| Example 58 | (5S)-4-(4,4-Difluorocyclohexyl)-3-{(S)-fluoro[4-(trifluoromethyl)phenyl]methyl}-7,7-dimethyl-2-(1-{5-[(methylamino)methyl]pyrimidin-2-yl}piperidin-4-yl)-5,6,7,8-tetrahydroquinolin-5-ol | 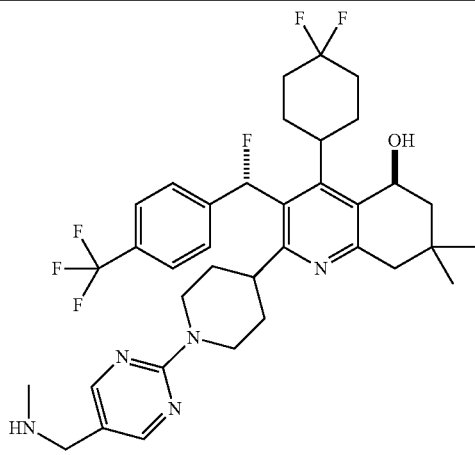 |

TABLE 1-15

| Reference Example 10 | (5S)-4-(4,4-Difluorocyclohexyl)-3-{(S)-fluoro[4-(trifluoromethyl)phenyl]methyl}-5-[(4-methoxybenzyl)oxy]-7,7-dimethyl-2-(piperidin-4-yl)-5,6,7,8-tetrahydroquinoline | 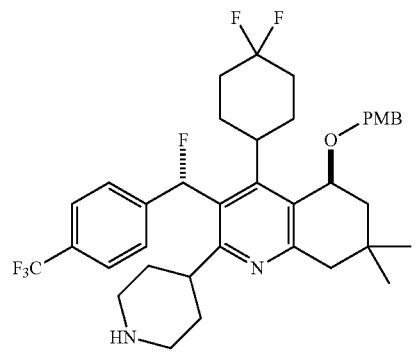 |
| Reference Example 11 | (5S)-2-[1-(5-Bromopyrimidin-2-yl)piperidin-4-yl]-4-(4,4-difluorocyclohexyl)-3-{(S)-fluoro[4-(trifluoromethyl)phenyl]methyl}-5-[(4-methoxybenzyl)oxy]-7,7-dimethyl-5,6,7,8-tetrahydroquinoline | 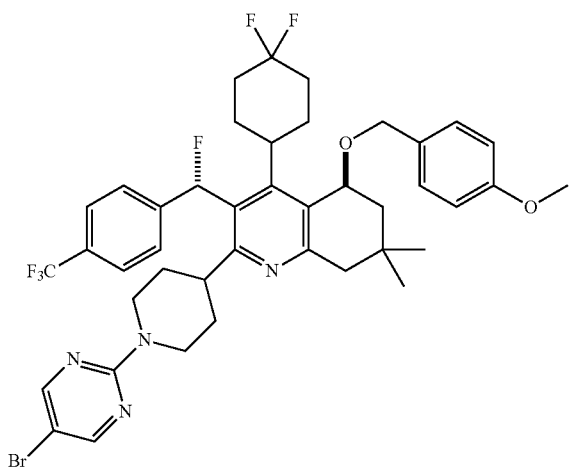 [SMILES: COc1ccc(CO[C@H]2CC(C)(C)Cc3nc(C4CCN(c5ncc(Br)cn5)CC4)c([C@@H](F)c4ccc(C(F)(F)F)cc4)c(C4CCC(F)(F)CC4)c32)cc1] |

TABLE 1-15-continued

| Reference Example 12 | (5S)-4-(4,4-Difluorocyclohexyl)-3-{(S)-fluoro[4-(trifluoromethyl)phenyl]methyl}-5-[(4-methoxybenzyl)oxy]-7,7-dimethyl-2-{1-[5-(morpholin-4-yl)pyrimidin-2-yl]piperidin-4-yl}-5,6,7,8-tetrahydroquinoline | 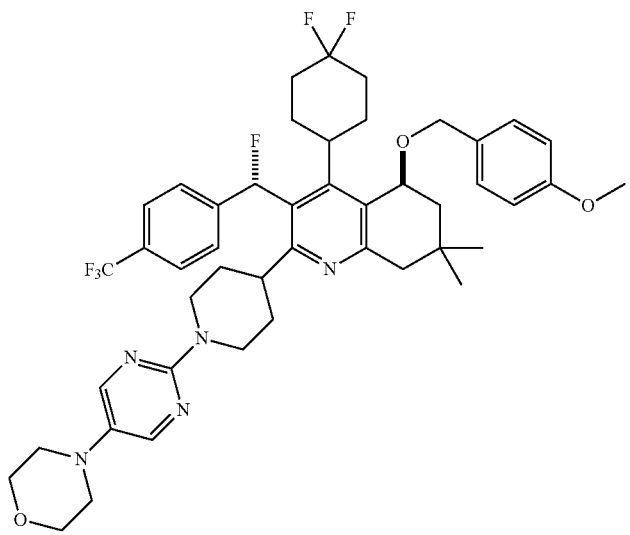 [SMILES: COc1ccc(CO[C@H]2CC(C)(C)Cc3nc(C4CCN(c5ncc(N6CCOCC6)cn5)CC4)c([C@@H](F)c4ccc(C(F)(F)F)cc4)c(C4CCC(F)(F)CC4)c32)cc1] |
| --- | --- | --- |
| Reference Example 13 | (5S)-4-(4,4-Difluorocyclohexyl)-2-(1-{5-[4-(ethoxycarbonyl)piperidin-1-yl]pyrimidin-2-yl}piperidin-4-yl-3-{(S)-fluoro[4-(trifluoromethyl)phenyl]methyl}-5-[(4-methoxybenzyl)oxy]-7,7-dimethyl-5,6,7,8-tetrahydroquinoline | 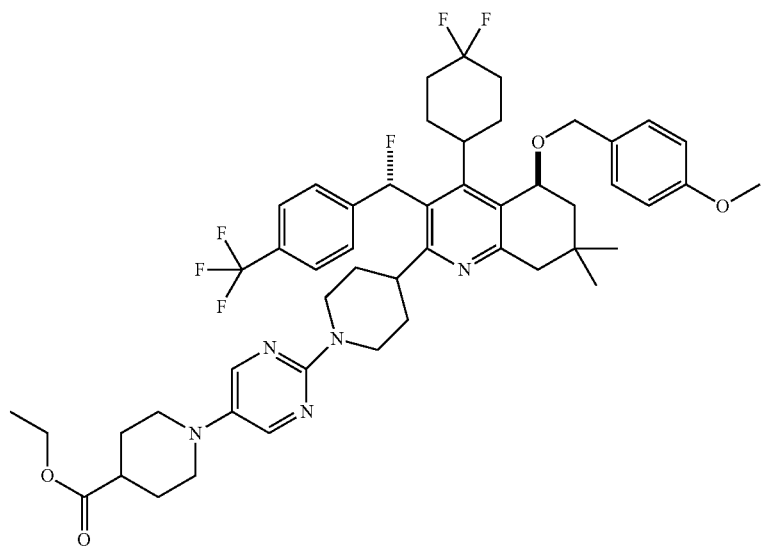 [SMILES: CCOC(=O)C1CCN(c2cnc(N3CCC(c4nc5c(c(C6CCC(F)(F)CC6)c4[C@@H](F)c4ccc(C(F)(F)F)cc4)[C@@H](OCc4ccc(OC)cc4)CC(C)(C)C5)CC3)nc2)CC1] |
| Reference Example 15 | (5S)-4-(4,4-Difluorocyclohexyl)-3-{(S)-fluoro[4-(trifluoromethyl)phenyl]methyl}-5-[(4-methoxybenzyl)oxy]-7,7-dimethyl-2-[1-(pyrimidin-2-yl)piperidin-4-yl]-5,6,7,8-tetrahydroquinoline | 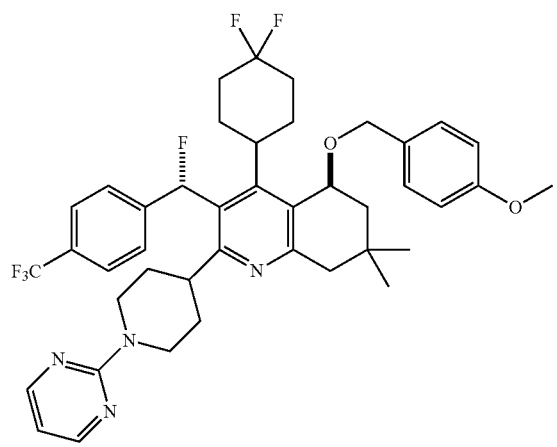 [SMILES: COc1ccc(CO[C@H]2CC(C)(C)Cc3nc(C4CCN(c5ncccn5)CC4)c([C@@H](F)c4ccc(C(F)(F)F)cc4)c(C4CCC(F)(F)CC4)c32)cc1] |

TABLE 1-16

| Reference Example 16 | (5S)-4-(4,4-Difluorocyclohexyl)-3-{(S)-fluoro[4-(trifluoromethyl)phenyl]methyl}-2-[1-(5-formylpyrimidin-2-yl)piperidin-4-yl]-5-[(4-methoxybenzyl)oxy]-7,7-dimethyl-5,6,7,8-tetrahydroquinoline | 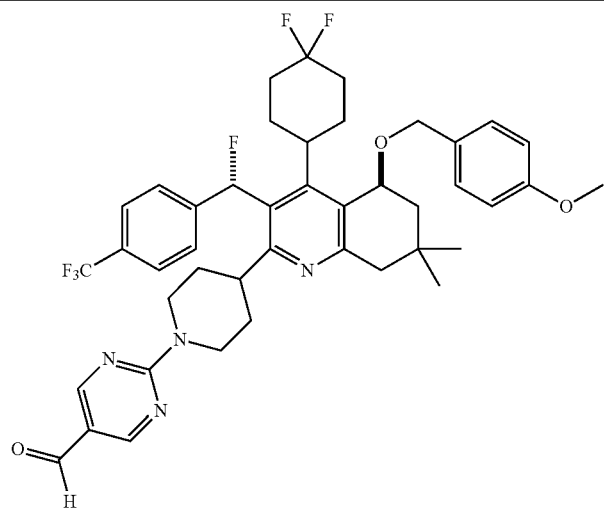 |
| --- | --- | --- |
| Reference Example 17 | (5S)-4-(4,4-Difluorocyclohexyl)-3-{(S)-fluoro[4-(trifluoromethyl)phenyl]methyl}-2-[1-[5-(hydroxymethyl)pyrimidin-2-yl]piperidin-4-yl]-5-[(4-methoxybenzyl)oxy]-7,7-dimethyl-5,6,7,8-tetrahydroquinoline | 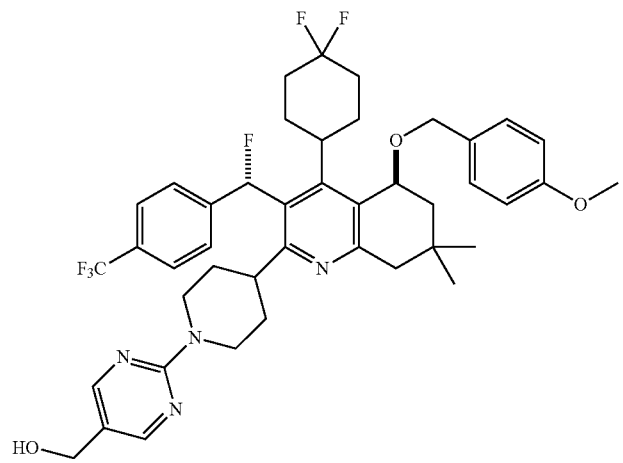 [SMILES: COc1ccc(CO[C@H]2CC(C)(C)Cc3nc(C4CCN(c5ncc(CO)cn5)CC4)c([C@@H](F)c4ccc(C(F)(F)F)cc4)c(C4CCC(F)(F)CC4)c32)cc1] |
| Reference Example 18 | (5S)-2-{1-[5-(Cyclohex-1-en-1-yl)pyrimidin-2-yl]piperidin-4-yl}-4-(4,4-difluorocyclohexyl)-3-{(S)-fluoro[4-(trifluoromethyl)phenyl]methyl}-5-[(4-methoxybenzyl)oxy]-7,7-dimethyl-5,6,7,8-tetrahydroquinoline | 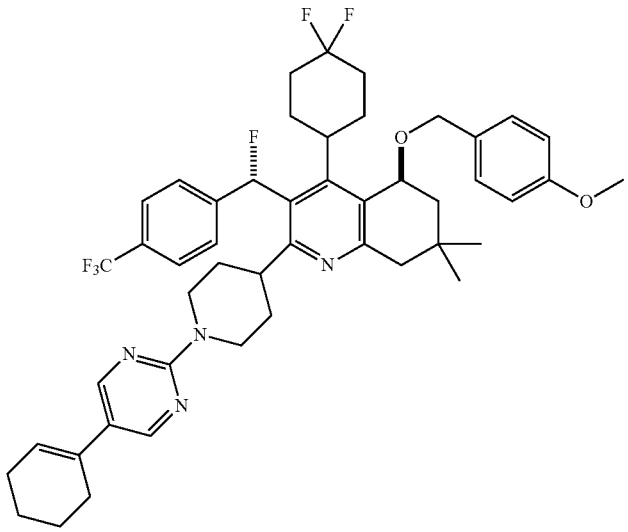 [SMILES: COc1ccc(CO[C@H]2CC(C)(C)Cc3nc(C4CCN(c5ncc(C6=CCCCC6)cn5)CC4)c([C@@H](F)c4ccc(C(F)(F)F)cc4)c(C4CCC(F)(F)CC4)c32)cc1] |

TABLE 1-16-continued

| Reference Example 19 | (5S)-4-(4,4-Difluorocyclohexyl)-3-{(S)-fluoro[4-(trifluoromethyl)phenyl]methyl}-2-{1-[5-(1-hydroxy-2-methylpropyl)pyrimidin-2-yl]piperidin-4-yl}-5-[(4-methoxybenzyl)oxy]-7,7-dimethyl-5,6,7,8-tetrahydroquinoline | 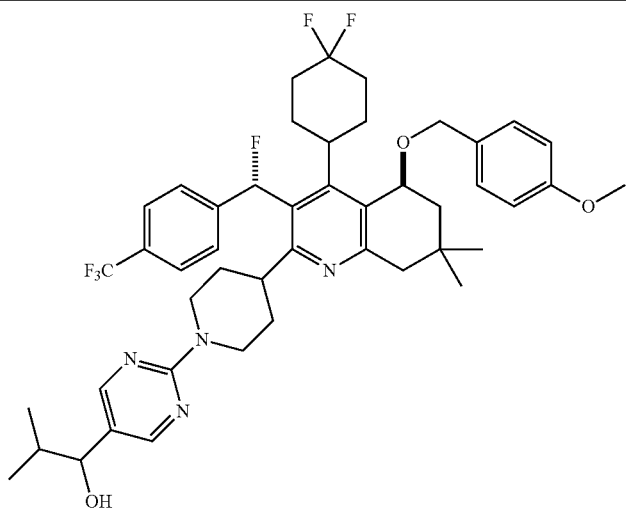 |
|---|---|---|
| Reference Example 21 | (5S)-4-(4,4-Difluorocyclohexyl)-2-{1-[5-(ethoxymethyl)pyrimidin-2-yl]piperidin-4-yl}-3-{(S)-fluoro[4-(trifluoromethyl)phenyl]methyl}-5-[(4-methoxybenzyl)oxy]-7,7-dimethyl-5,6,7,8-tetrahydroquinoline | 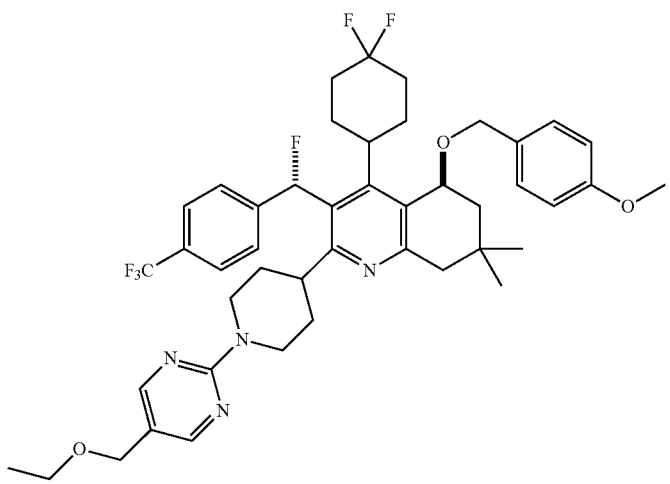 [SMILES: CCOCc1cnc(N2CCC(c3nc4c(c(C5CCC(F)(F)CC5)c3[C@@H](F)c3ccc(C(F)(F)F)cc3)[C@@H](OCc3ccc(OC)cc3)CC(C)(C)C4)CC2)nc1] |

TABLE 1-17

| Reference Example 22 | (5S)-4-(4,4-Difluorocyclohexyl)-3-{(S)-fluoro[4-(trifluoromethyl)phenyl]methyl}-5-[(4-methoxybenzyl)oxy]-2-{1-[5-(methoxymethyl)pyrimidin-2-yl]piperidin-4-yl}-7,7-dimethyl-5,6,7,8-tetrahydroquinoline | 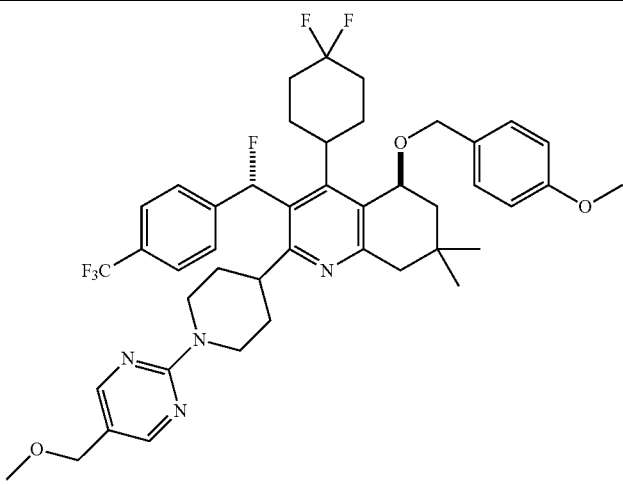 |

TABLE 1-17-continued

| Reference Example 23 | (5S)-4-(4,4-Difluorocyclohexyl)-3-{(S)-fluoro[4-(trifluoromethyl)phenyl]methyl}-5-[(4-methoxybenzyl)oxy]-7,7-dimethyl-2-(1-{5-[(propan-2-yloxy)methyl]pyrimidin-2-yl}piperidin-4-yl)-5,6,7,8-tetrahydroquinoline | 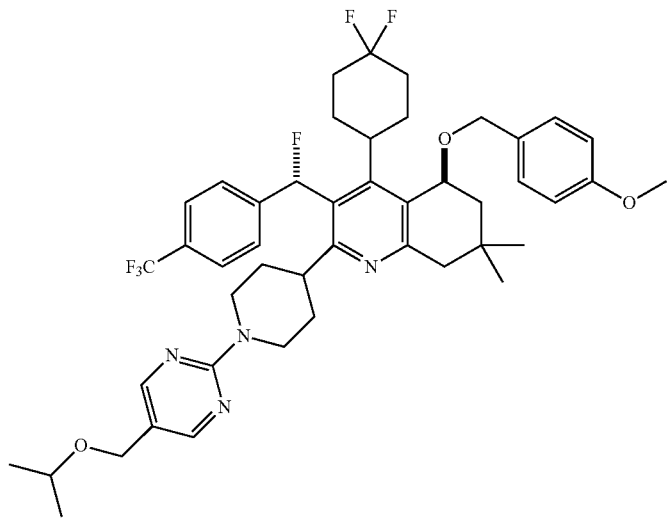 [SMILES: COc1ccc(CO[C@H]2CC(C)(C)Cc3nc(C4CCN(c5ncc(COC(C)C)cn5)CC4)c([C@@H](F)c4ccc(C(F)(F)F)cc4)c(C4CCC(F)(F)CC4)c32)cc1] |
|---|---|---|
| Reference Example 24 | (5S)-4-(4,4-Difluorocyclohexyl)-3-{(S)-fluoro[4-(trifluoromethyl)phenyl]methyl}-5-[(4-methoxybenzyl)oxy]-7,7-dimethyl-2-(1-{5-[(2-methylpropoxy)methyl]pyrimidin-2-yl}piperidin-4-yl)-5,6,7,8-tetrahydroquinoline | 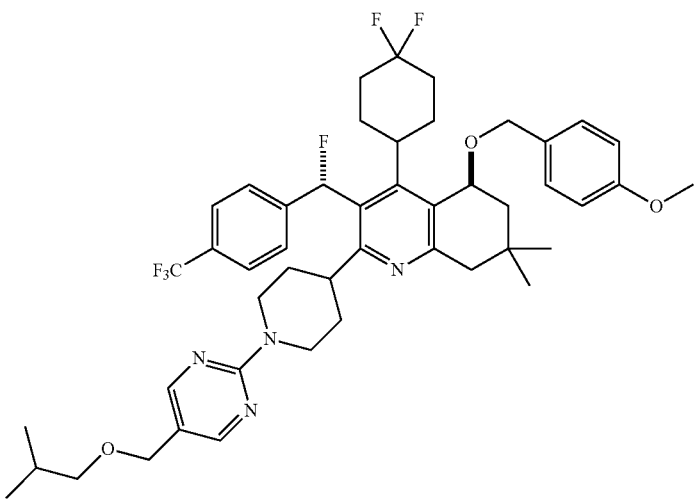 [SMILES: COc1ccc(CO[C@H]2CC(C)(C)Cc3nc(C4CCN(c5ncc(COCC(C)C)cn5)CC4)c([C@@H](F)c4ccc(C(F)(F)F)cc4)c(C4CCC(F)(F)CC4)c32)cc1] |
| Reference Example 25 | (5S)-4-(4,4-Difluorocyclohexyl)-3-{(S)-fluoro[4-(trifluoromethyl)phenyl]methyl}-5-[(4-methoxybenzyl)oxy]-7,7-dimethyl-2-{1-[5-(methylcarbamoyl)pyrimidin-2-yl]piperidin-4-yl}-5,6,7,8-tetrahydroquinoline | 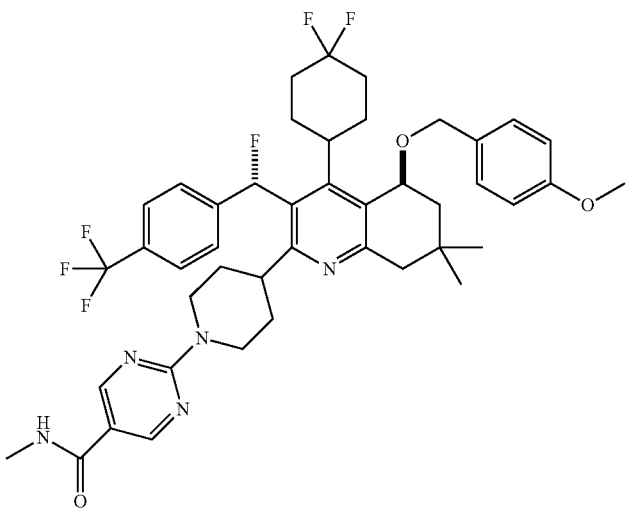 |

TABLE 1-17-continued

| | | |
|---|---|---|
| Reference Example 25 Intermediate | (5S)-2-[1-(5-Carboxypyrimidin-2-yl)piperidin-4-yl]-4-(4,4-difluorocyclohexyl)-3-{(S)-fluoro[4-(trifluoromethyl)phenyl]methyl}-5-[(4-methoxybenzyl)oxy]-7,7-dimethyl-5,6,7,8-tetrahydroquinoline | 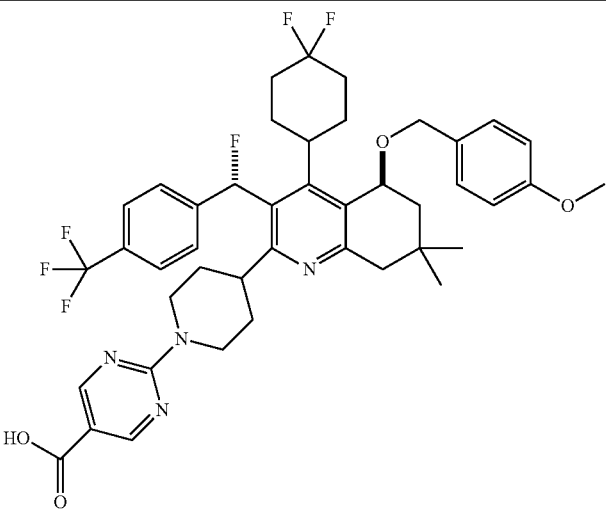 |

TABLE 1-18

| | | |
|---|---|---|
| Reference Example 27 | (5S)-4-(4,4-Difluorocyclohexyl)-3-{(S)-fluoro[4-(trifluoromethyl)phenyl]methyl}-2-{1-[5-(1-hydroxy-3-methylbutyl)pyrimidin-2-yl]piperidin-4-yl}-5-[(4-methoxybenzyl)oxy]-7,7-dimethyl-5,6,7,8-tetrahydroquinoline | 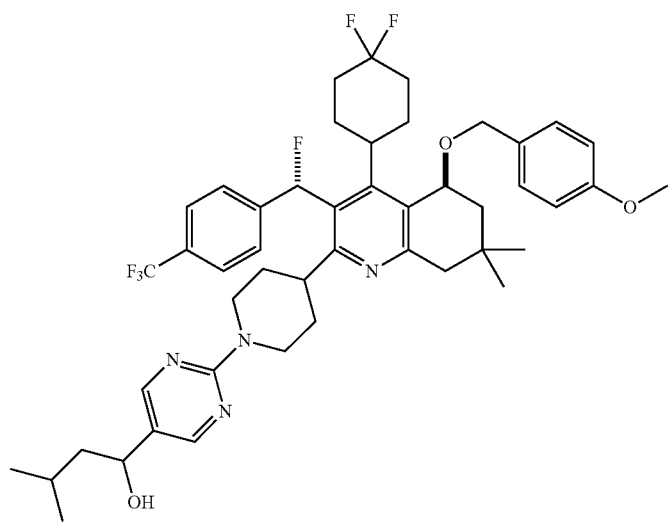 [SMILES: COc1ccc(CO[C@H]2CC(C)(C)Cc3nc(C4CCN(c5ncc(C(O)CC(C)C)cn5)CC4)c([C@@H](F)c4ccc(C(F)(F)F)cc4)c(C4CCC(F)(F)CC4)c32)cc1] |
| Reference Example 29 | (5S)-4-(4,4-Difluorocyclohexyl)-3-{(S)-fluoro[4-(trifluoromethyl)phenyl]methyl}-5-[(4-methoxybenzyl)oxy]-7,7-dimethyl-2-(1-{5-[(1-methylpiperidin-4-yl)oxy]pyrimidin-2-yl}piperidin-4-yl)-5,6,7,8-tetrahydroquinoline | 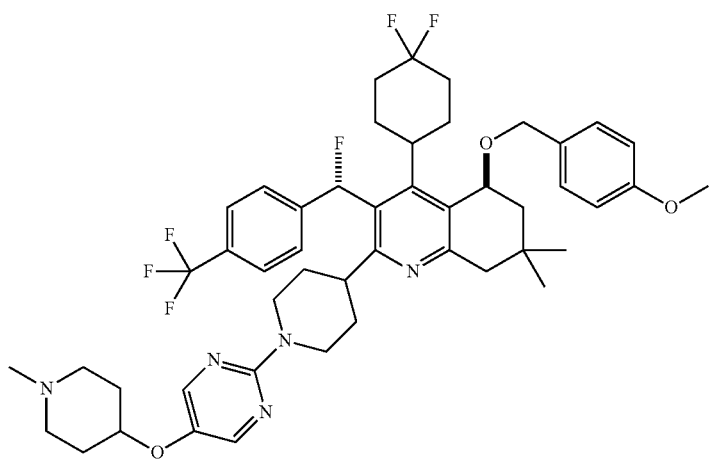 |

TABLE 1-18-continued

| Reference Example 34 | (5S)-4-(4,4-Difluoro-cyclohexyl)-3-{(S)-fluoro[4-(trifluoromethyl)phenyl]methyl}-5-[(4-methoxybenzyl)oxy]-7,7-dimethyl-2-(1-{5-[(2,2,5-trimethyl-1,3-dioxan-5-yl)methoxy]pyrimidin-2-yl}piperidin-4-yl)-5,6,7,8-tetrahydroquinoline | 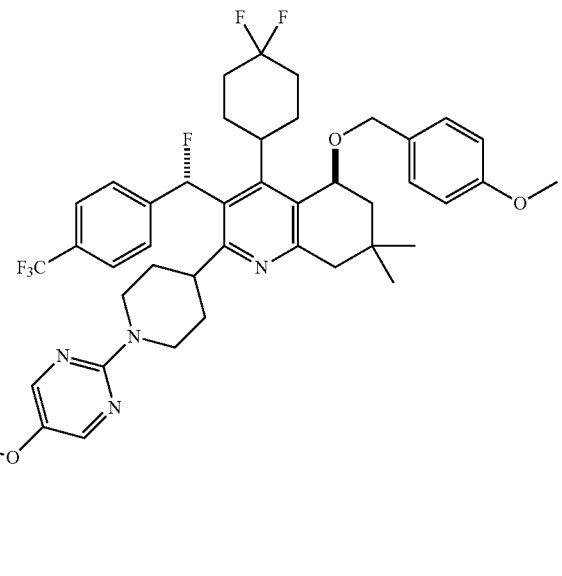 |

Test Example 1

Test of CETP Inhibition Activity (In Vitro, Buffer-Based)

(1) Preparation of Reconstituted HDL

Cholesterol (1.125 μmol), phosphatidyl choline (4.5 μmol) and [$^{14}$C]-labeled cholesteryl ester (2.0 μCi; 40 μl) were taken in a glass test tube and well mixed with a vortex, and dried under a nitrogen gas current so that it formed a thin film. The obtained mixture was dissolved in ethanol (200 μl), which was designated as Solution A. A PBS solution [a mixed solution of $Na_2HPO_4$ (30 mM), $KH_2PO_4$ (8.8 mM), NaCl (60 mM) and EDTA (pH 7.4; 0.67 mM); 4 ml] was taken in a tube and the reaction solution was vigorously stirred with a vortex under a nitrogen current. The above-described Solution A was gently injected into this mixture with a syringe and the reaction solution was vigorously stirred with a vortex for 5 minutes under a nitrogen current. Sodium cholate (200 1M; 0.38 ml) was added to the obtained mixture and the reaction solution was stirred for 2 minutes. ApoA-I protein (3 mg) was added to the obtained mixture and the reaction solution was stirred for 2 minutes. The obtained mixture was adjusted to 5 ml with the PBS solution and then dialyzed with the PBS solution. The obtained mixture was designated as the reconstituted HDL.

(2) Preparation of Acceptor Lipoprotein

NaBr was added to the plasma of a healthy person and the density of the mixture was adjusted to 1.019, and the mixture was subjected to density gradient centrifugation (40000 rpm, for 16 hours) to remove the fraction having a density of less than 1.019. NaBr was added to the obtained mixture and the density of the solution was adjusted to 1.063, and the solution was subjected to density gradient centrifugation (40000 rpm, 18 hours) to provide the fraction consisting of IDL (intermediate density lipoprotein) and LDL (1.019<density<1.063). The obtained fraction was dialyzed with the PBS solution. The obtained mixture was designated as the acceptor lipoprotein.

(3) Measurement of CETP Inhibition Activity

A recombinant human CETP protein (manufactured by Roar Biomedical Inc.; 4.5 ng), the acceptor lipoprotein described in (2) above (32.5 μg) and 5,5'-dithio-bis-(2-nitrobenzoic acid) (7 mM, 15 μl) were taken in a 96 well plate and the total amount of the mixture was adjusted to 48.5 μl with the PBS solution. The test compound [DMSO solution (concentration: 0.15, 0.5, 1.5, 5, 15, 50, 150 and 500 μM; 1.5 μl] was added to each well and the mixture was incubated in a thermostatic bath at 37° C. for 60 minutes. The reconstituted HDL (50 μl) described in (1) above was added to each well and the mixture was reacted in a thermostatic bath at 37° C. for 60 minutes. The 96 well plate was moved onto ice and a precipitation reagent [a mixed solution of magnesium chloride (60 mM) and 0.1% dextran sulfate [1/1 (v/v)]; 15 μl] was added to each well, and then the mixture was allowed to stand on ice for 15 minutes. The reaction solution (80 μl) in each well was moved to a filter plate and centrifuged at 1500 rpm for 1 minute, and the filtrate which passed through the filter was designated as the HDL fraction and the radioactivity thereof was measured with a scintillation counter. The percentage decrease in radioactivity in the case where the test compound was added in comparison with that in case where the test compound was not added was designated as the percentage CETP inhibition. The $IC_{50}$ value was calculated from the percentage CETP inhibition.

(4) Results

The test results of the compound of the present invention are shown in Table 2.

TABLE 2

| Example No. | $IC_{50}$ (nM) |
|---|---|
| 1 | 83 |
| 2 | 150 |
| 3 | 51 |
| 4 | 73 |
| 5 | 250 |
| 6 | 66 |
| 8 | 19 |
| 9 | 122 |

TABLE 2-continued

| Example No. | IC$_{50}$ (nM) |
|---|---|
| 10 | 49 |
| 11 | 46 |
| 12 | 103 |
| 13 | 92 |
| 14 | 97 |
| 15 | 37 |
| 16 | 243 |
| 17 | 217 |
| 18 | 177 |
| 19 | 198 |
| 20 | 255 |
| 21 | 99 |
| 22 | 111 |
| 23 | 37 |
| 24 | 54 |
| 25 | 19 |
| 26 | 45 |
| 27 | 40 |
| 28 | 78 |
| 29 | 62 |
| 30 | 32 |
| 31 | 29 |
| 32 | 19 |
| 33 | 48 |
| 34 | 54 |
| 35 | 88 |
| 36 | 35 |
| 37 | 25 |
| 38 | 10 |
| 39 | 32 |
| 40 | 11 |
| 41 | 16 |
| 42 | 22 |
| 43 | 9 |
| 44 | 21 |
| 45 | 13 |
| 46 | 16 |
| 47 | 31 |
| 48 | 42 |
| 49 | 8 |
| 50 | 13 |
| 51 | 6 |
| 52 | 6 |
| 53 | 34 |
| 54 | 32 |
| 55 | 59 |
| 56 | 28 |
| 57 | 33 |

The compound of the present invention has excellent CETP inhibition activity in the present test and is useful as a medicament for treatment or prophylaxis of dyslipidemia, hypercholesterolemia, low HDL cholesterolemia, high LDL cholesterolemia, arteriosclerosis, arteriosclerotic heart disease, coronary heart disease or the like.

Test Example 2

Test of CETP Inhibition Activity (In Vitro, Plasma-Based)

(1) Preparation of Donor Lipoprotein

NaBr was added to the human plasma and the density of the mixture was adjusted to 1.125, and the mixture was subjected to density gradient centrifugation (40000 rpm, 40 hours) to remove the fraction having a density of less than 1.125. NaBr was added to the obtained mixture and the density of the mixture was adjusted to 1.21, and the mixture was subjected to density gradient centrifugation (40000 rpm, 40 hours) to provide the fraction having the following density: 1.125<density<1.21. The obtained fraction was dialyzed with the PBS solution. The obtained mixture was designated as the HDL$_3$ fraction. Phosphatidyl choline (5 mg) and [$^3$H]-labeled cholesteryl ester (0.5 mCi; 0.5 ml) were taken in a glass test tube and dried under a nitrogen current. PBS solution (500 µl) was added to the obtained mixture and the mixture was mixed for 30 minutes under ultrasonic wave irradiation. The HDL$_3$ fraction (1.75 mg) and the lipoprotein-depleted human serum (LPDS; 12 mg) were added to the obtained mixture and the total amount of the mixture was adjusted to 3.5 ml with the PBS solution. The obtained mixture was incubated at 37° C. for 48 hours. NaBr was added to the obtained mixture and the density of the mixture was adjusted to 1.063, and the mixture was subjected to density gradient centrifugation (40000 rpm, 18 hours) to remove the fraction having a density of less than 1.063. NaBr was added to the obtained fraction and the density of the mixture was adjusted to 1.21, and the mixture was subjected to density gradient centrifugation (40000 rpm, 40 hours) to provide the fraction having the following density: 1.063<density<1.21. The obtained fraction was dialyzed with the PBS solution and the mixture was designated as the donor lipoprotein.

(2) Measurement of CETP Inhibition Activity

The donor lipoprotein described in (1) above (2 µL) and the test compound [DMSO solution (concentration: 0.15, 0.5, 1.5, 5, 15, 50, 150 and 500 µM; 1 µL] were mixed with the human plasma or the plasma (37 µL) collected from double-transgenic mice into which human Apo B and human CETP gene were introduced (hereinafter, CETP/apoB Tg mice; J. Lipid Res., 1995, Vol. 36, pp. 1082-1091) and the mixture was added to a 96-well V bottom plate (total 40 µL). The mixture was lightly mixed and then reacted at 37° C. for 2 hours. The 96-well V bottom plate was moved onto ice and a precipitation reagent [a mixed solution of magnesium chloride (200 mM) and 0.2% dextran sulfate [1/1 (v/v)]; 10 µl] was added to each well, and then the mixture was allowed to stand on ice for 15 minutes. The reaction solution (40 µl) in each well was moved to a filter plate and centrifuged at 1500 rpm for 1 minute. The filtrate which passed through the filter was designated as the HDL fraction and the fraction which remained on the filter was designated as the LDL fraction, and the radioactivity of each fraction was measured with a scintillation counter, respectively. The percentage transfer of cholesteryl ester was calculated from the radioactivities of the HDL fraction and the LDL fraction before and after the reaction at 37° C. according to the formula described below.

Percentage transfer of cholesteryl ester (%)=[[Radioactivity of LDL fraction (after reaction)−Radioactivity of LDL fraction (before reaction)]/[Radioactivity of LDL fraction (after reaction)+Radioactivity of HDL fraction (after reaction)]]×100

The percentage decrease in the percentage transfer of cholesteryl ester in the case where the test compound was added in comparison with that in the case where the test compound was not added was designated as the percentage CETP inhibition. The IC$_{50}$ value was calculated from the percentage CETP inhibition.

The compound of the present invention has excellent CETP inhibition activity in the present test and is useful as a medicament for treatment or prophylaxis of dyslipidemia, hypercholesterolemia, low HDL cholesterolemia, high LDL cholesterolemia, arteriosclerosis, arteriosclerotic heart disease, coronary heart disease or the like.

Test Example 3

Test of CETP Inhibition Activity (In Vitro, Fluorescence, Plasma-Based)

Reagent A (73 µl) of Ex vivo CETP Activity Assay (RB-EVAK) manufactured by Roar Biomedical Inc. was mixed with Reagent B (311 µl) of the same to prepare Reagent C. 2.5

µl of Reagent C was mixed with the human plasma or the plasma collected from CETP/ApoB Tg mice (46.5 µl) and the mixture was added to a 96 well black plate (Half Area, No. 3694 manufactured by Corning). The test compound [DMSO solution (concentration: 0.15, 0.5, 1.5, 5, 15, 50, 150 and 500 µM; 1 µl] was added to each well and the mixture was lightly mixed. The mixture was reacted for 90 minutes in a thermostatic bath at 37° C. and the fluorescence intensity of the sample in each well was measured (excitation wavelength: 485 nm; fluorescence wavelength: 530 nm) with a fluorescence plate reader (manufactured by LJL Biosystems; Analyst HT). The fluorescence intensity in the reaction using the plasma of the wild-type mice was deducted as a blank and the percentage decrease in the fluorescence intensity in the case where the test compound was added in comparison with that in the case where the test compound was not added was designated as the percentage CETP inhibition. The $IC_{50}$ value was calculated from the percentage CETP inhibition.

The compound of the present invention has excellent CETP inhibition activity in the present test and is useful as a medicament for treatment or prophylaxis of dyslipidemia, hypercholesterolemia, low HDL cholesterolemia, high LDL cholesterolemia, arteriosclerosis, arteriosclerotic heart disease, coronary heart disease or the like.

Test Example 4

Test of Pharmacological Effect in Mice (Mice In Vivo and Mice Ex Vivo)

(1) Administration of Compound

The test compound was dissolved in a mixed solvent of propylene glycol-Tween 80 (trade name) [4/1 (v/v)] and orally administered to CETP/apoB Tg mice for 2 or 7 days. The blood was collected before the administration and 14 or 24 hours after the administration on the 2nd or 7th day.

(2) Measurement of Cholesterol Content in Plasma

The cholesterol content in plasma was measured using a commercially available measurement kit (cholesterol-E Wako, manufactured by Wako Junyaku Inc.).

(3) Measurement of the Contents of HDL Cholesterol and Non-HDL Cholesterol

The lipoprotein profile was analyzed by HPLC (column: Lipopropack XL, manufactured by Tosoh Corp.). The contents of HDL cholesterol and non-HDL cholesterol were calculated according to the calculation formula described below.

HDL cholesterol content=Cholesterol content in plasma×(peak area of HDL cholesterol/sum of each peak area)

Non-HDL cholesterol content=Cholesterol content in plasma×(peak area of non-HDL cholesterol/sum of each peak area)

(4) Preparation of Donor Lipoprotein

NaBr was added to the human plasma and the density of the mixture was adjusted to 1.125, and the mixture was subjected to density gradient centrifugation (40000 rpm, 40 hours) to remove the fraction having a density of less than 1.125. NaBr was added to the obtained mixture and the density of the mixture was adjusted to 1.21, and the mixture was subjected to density gradient centrifugation (40000 rpm, 40 hours) to provide the fraction having the following density: $1.125 < \text{density} < 1.21$. The obtained fraction was dialyzed with the PBS solution. The obtained mixture was designated as the $HDL_3$ fraction. Phosphatidyl choline (5 mg) and tritium-labeled cholesteryl ester (0.5 mCi; 0.5 ml) were taken in a glass test tube and dried under a nitrogen current. The PBS solution (500 µl) was added to the obtained mixture and the mixture was mixed under ultrasonic wave irradiation for 30 minutes. The $HDL_3$ fraction (1.75 mg) and the lipoprotein-depleted human serum (12 mg) was added to the obtained mixture and the total amount of the mixture was adjusted to 3.5 ml with the PBS solution. The obtained mixture was incubated at 37° C. for 48 hours. NaBr was added to the obtained mixture and the density of the mixture was adjusted to 1.063, and the mixture was subjected to density gradient centrifugation (40000 rpm, 18 hours) to remove the fraction having a density of less than 1.063. NaBr was added to the obtained fraction and the density of the mixture was adjusted to 1.21, and the mixture was subjected to density gradient centrifugation (40000 rpm, 40 hours) to provide the fraction having the following density: $1.063 < \text{density} < 1.21$. The obtained fraction was dialyzed with the PBS solution. The obtained mixture was designated as the donor lipoprotein.

(5) Measurement of CETP Inhibition Activity (Fluorescence, Ex Vivo)

Reagent A (73 µl) and Reagent B (311 µl) of Ex vivo CETP Activity Assay (RB-EVAK) of Roar Biomedical Inc. were mixed to prepare Reagent C. 1 µl of Reagent C and the plasma (19 µl) collected from the test animal were added to a black 384 well round-bottom plate (No. 3676 manufactured by Corning). The mixture was reacted in a thermostatic bath at 37° C. for 90 minutes and the fluorescence intensity of the sample in each well was measured (excitation wavelength: 485 nm, fluorescence wavelength: 530 nm) with a fluorescence plate reader (manufactured by LJL Biosystems: Analyst HT). The fluorescence intensity in the reaction using the plasma of the wild-type mice was deducted as a blank and the percentage decrease in the fluorescence intensity in the case where the test compound was added in comparison with that in case where the test compound was not added was designated as the percentage CETP inhibition.

The compound of the present invention has excellent CETP inhibition activity, increasing action on the concentration of HDL cholesterol or decreasing action on the concentration of LDL cholesterol in the present test and is useful as a medicament for treatment or prophylaxis of dyslipidemia, hypercholesterolemia, low HDL cholesterolemia, high LDL cholesterolemia, arteriosclerosis, arteriosclerotic heart disease, coronary heart disease or the like.

Formulation Example 1

Hard Capsule

Powdered compound of Example 1 (100 mg), lactose (150 mg), cellulose (50 mg) and magnesium stearate (6 mg) are filled into a standard two-split hard gelatin capsule to prepare a hard capsule and the hard capsule is washed and then dried.

Formulation Example 2

Soft Capsule

A mixture of a digestible oil material such as soybean oil and olive oil and the compound of Example 2 are injected into gelatin so as to contain 100 mg of active ingredient to prepare a soft capsule and the soft capsule is washed and then dried.

Formulation Example 3

Tablet

A tablet is prepared according to a method which is well known in the field of formulation science using the compound of Example 3 (100 mg), colloidal silicon dioxide (0.2 mg), magnesium stearate (0.2 mg), microcrystalline cellulose (0.2 mg), starch (0.2 mg) and lactose (98.8 mg). The obtained tablet may be coated as necessary.

INDUSTRIAL APPLICABILITY

The compound represented by general formula (I) or a pharmacologically acceptable salt thereof of the present invention has excellent properties in terms of CETP inhibition activity, increasing action on the concentration of HDL cholesterol, decreasing action on the concentration of LDL cholesterol, rapid onset of pharmacological effect, prolonged pharmacological effect, physical stability, solubility, oral absorbability, blood concentration, cell membrane permeability, metabolic stability, tissue migration, bioavailability (BA), drug-drug interaction, toxicity or the like, and is useful as a medicament for a warm-blooded animal (particularly, for a human). The above-described medicament is a medicament for treatment or prophylaxis of, preferably dyslipidemia, hypercholesterolemia, low HDL cholesterolemia, high LDL cholesterolemia, hypertriglyceridemia, arteriosclerosis, arteriosclerotic heart disease, coronary heart disease (including heart failure, myocardial infarction, angina pectoris, cardiac ischemia, cardiovascular disorder and angioplasty-related restenosis), cerebrovascular disease (including stroke and cerebral infarction), peripheral vascular disease (including diabetic vascular complications) or obesity, more preferably dyslipidemia, hypercholesterolemia, low HDL cholesterolemia, high LDL cholesterolemia, arteriosclerosis, arteriosclerotic heart disease or coronary heart disease, further preferably dyslipidemia, low HDL cholesterolemia, arteriosclerosis or coronary heart disease, and even more preferably low HDL cholesterolemia or arteriosclerosis.

The invention claimed is:

1. A compound of general formula (I):

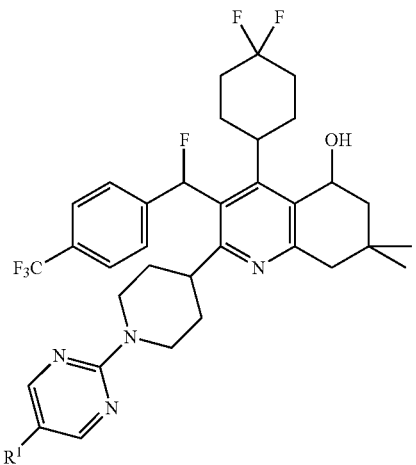

(I)

or a pharmacologically acceptable salt thereof, wherein
$R^1$ represents a hydrogen atom, a $C_1$-$C_6$ alkyl group, a hydroxy($C_1$-$C_6$ alkyl) group, a ($C_1$-$C_6$ alkoxy)-($C_1$-$C_6$ alkyl) group, a hydroxy($C_1$-$C_6$ alkoxy)-($C_1$-$C_6$ alkyl) group, a ($C_1$-$C_6$ alkyl)amino-($C_1$-$C_6$ alkyl) group, a hydroxy($C_1$-$C_6$ alkyl)amino-($C_1$-$C_6$ alkyl) group, a [N—($C_1$-$C_6$ alkyl)-N-hydroxy($C_1$-$C_6$ alkyl)amino]-($C_1$-$C_6$ alkyl) group, a ($C_1$-$C_6$ alkyl)sulfonylamino-($C_1$-$C_6$ alkyl) group, a [N—($C_1$-$C_6$ alkyl)-N—($C_1$-$C_6$ alkyl)sulfonylamino]-($C_1$-$C_6$ alkyl) group, a carboxy($C_1$-$C_6$ alkyl) group, a halogeno($C_1$-$C_6$ alkyl) group, a ($C_3$-$C_8$ cycloalkyl)-($C_1$-$C_6$ alkyl) group, a $C_2$-$C_6$ alkenyl group, a $C_2$-$C_6$ alkynyl group, a $C_3$-$C_8$ cycloalkyl group, a $C_3$-$C_8$ cycloalkenyl group, a hydroxy group, a $C_1$-$C_6$ alkoxy group, a hydroxy($C_1$-$C_6$ alkoxy) group, a ($C_1$-$C_6$ alkoxy)-($C_1$-$C_6$ alkoxy) group, a ($C_1$-$C_6$ alkyl)sulfonyl-($C_1$-$C_6$ alkoxy) group, a carboxy($C_1$-$C_6$ alkoxy) group, a halogeno($C_1$-$C_6$ alkoxy) group, a $C_1$-$C_6$ alkylthio group, a $C_1$-$C_6$ alkylsulfinyl group, a $C_1$-$C_6$ alkylsulfonyl group, an amino group, a $C_1$-$C_6$ alkylamino group, a di($C_1$-$C_6$ alkyl)amino group, a hydroxy($C_1$-$C_6$ alkyl) amino group, a N—($C_1$-$C_6$ alkyl)-N-hydroxy($C_1$-$C_6$ alkyl)amino group, a formylamino group, a ($C_1$-$C_6$ alkyl)carbonylamino group, a carboxy group, a ($C_1$-$C_6$ alkoxy)carbonyl group, a carbamoyl group, a ($C_1$-$C_6$ alkylamino)carbonyl group, a di($C_1$-$C_6$ alkyl)aminocarbonyl group, a cyano group, a halogeno group, a phenyl group, a substituted phenyl group in which the substituent(s) represent 1 to 4 groups independently selected from Substituent Group α, a 5- or 6-membered aromatic heterocyclyl group, a substituted 5- or 6-membered aromatic heterocyclyl group in which the substituent(s) represent 1 to 4 groups independently selected from Substituent Group α, a 5- or 6-membered saturated heterocyclyl group, a substituted 5- or 6-membered saturated heterocyclyl group in which the substituent(s) represent 1 to 4 groups independently selected from Substituent Group α, a 5- or 6-membered saturated heterocyclyl-($C_1$-$C_6$ alkyl) group, a substituted 5- or 6-membered saturated heterocyclyl-($C_1$-$C_6$ alkyl) group in which the substituent(s) represent 1 to 4 groups independently selected from Substituent Group α, a 5- or 6-membered saturated heterocyclyloxy group, a substituted 5- or 6-membered saturated heterocyclyloxy group in which the substituent(s) represent 1 to 4 groups independently selected from Substituent Group α, a 5- or 6-membered saturated heterocyclylcarbonyl group or a substituted 5- or 6-membered saturated heterocyclylcarbonyl group in which the substituent(s) represent 1 to 4 groups independently selected from Substituent Group α, and Substituent Group α represents the group consisting of a $C_1$-$C_6$ alkyl group, a hydroxy($C_1$-$C_6$ alkyl) group, a halogeno($C_1$-$C_6$ alkyl) group, a ($C_3$-$C_8$ cycloalkyl)-($C_1$-$C_6$ alkyl) group, a $C_3$-$C_8$ cycloalkyl group, a hydroxy group, a $C_1$-$C_6$ alkoxy group, a halogeno($C_1$-$C_6$ alkoxy) group, a $C_1$-$C_6$ alkylamino group, a di($C_1$-$C_6$ alkyl) amino group, a carboxy group, a ($C_1$-$C_6$ alkoxy)carbonyl group, a carbamoyl group, a ($C_1$-$C_6$ alkylamino) carbonyl group, a di($C_1$-$C_6$ alkyl)aminocarbonyl group, a cyano group, a halogeno group and an oxo group.

2. The compound of claim 1 represented by general formula (I-1):

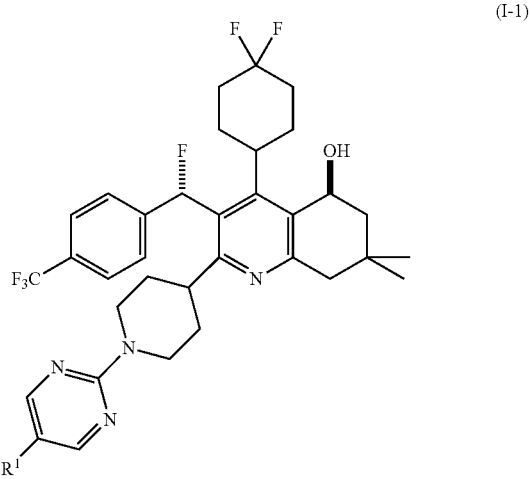

(I-1)

or a pharmacologically acceptable salt thereof.

3. The compound of claim 2 or a pharmacologically acceptable salt thereof, wherein $R^1$ is a hydrogen atom, a $C_1$-$C_6$ alkyl group, a hydroxy($C_1$-$C_6$ alkyl) group, a ($C_1$-$C_6$ alkoxy)-($C_1$-$C_6$ alkyl) group, a ($C_1$-$C_6$ alkyl)amino-($C_1$-$C_6$ alkyl) group, a [N—($C_1$-$C_6$ alkyl)-N-hydroxy($C_1$-$C_6$ alkyl) amino]-($C_1$-$C_6$ alkyl) group, a [N—($C_1$-$C_6$ alkyl)-N—($C_1$-$C_6$ alkyl)sulfonylamino]-($C_1$-$C_6$ alkyl) group, a carboxy($C_1$-$C_6$ alkyl) group, a halogeno($C_1$-$C_6$ alkyl) group, a $C_2$-$C_6$ alkenyl group, a $C_3$-$C_8$ cycloalkyl group, a $C_3$-$C_8$ cycloalkenyl group, a hydroxy group, a $C_1$-$C_6$ alkoxy group, a hydroxy($C_1$-$C_6$ alkoxy) group, a ($C_1$-$C_6$ alkyl)sulfonyl-($C_1$-$C_6$ alkoxy) group, a carboxy($C_1$-$C_6$ alkoxy) group, a halogeno($C_1$-$C_6$ alkoxy) group, a $C_1$-$C_6$ alkylthio group, a $C_1$-$C_6$ alkylsulfonyl group, a N—($C_1$-$C_6$ alkyl)-N-hydroxy($C_1$-$C_6$ alkyl)amino group, a ($C_1$-$C_6$ alkylamino)carbonyl group, a di($C_1$-$C_6$ alkyl)aminocarbonyl group, a cyano group or a halogeno group.

4. The compound of claim 2 or a pharmacologically acceptable salt thereof, wherein $R^1$ is a hydrogen atom, a $C_1$-$C_4$ alkyl group, a hydroxy($C_1$-$C_4$ alkyl) group, a ($C_1$-$C_4$ alkoxy)-($C_1$-$C_4$ alkyl) group, a halogeno($C_1$-$C_4$ alkyl) group, a $C_1$-$C_4$ alkoxy group, a hydroxy($C_1$-$C_6$ alkoxy) group or a ($C_1$-$C_4$ alkyl)sulfonyl-($C_1$-$C_4$ alkoxy) group.

5. The compound of claim 2 or a pharmacologically acceptable salt thereof, wherein $R^1$ is a $C_1$-$C_4$ alkyl group, a halogeno($C_1$-$C_4$ alkyl) group, a $C_1$-$C_4$ alkoxy group or a hydroxy($C_1$-$C_6$ alkoxy) group.

6. The compound of claim 2 or a pharmacologically acceptable salt thereof, wherein $R^1$ is a $C_1$-$C_4$ alkyl group.

7. The compound of claim 2 or a pharmacologically acceptable salt thereof, wherein $R^1$ is a halogeno($C_1$-$C_4$ alkyl) group.

8. The compound of claim 2 or a pharmacologically acceptable salt thereof, wherein $R^1$ is a $C_1$-$C_4$ alkoxy group.

9. The compound of claim 2 or a pharmacologically acceptable salt thereof, wherein $R^1$ is a hydroxy($C_1$-$C_6$ alkoxy) group.

10. The compound of claim 2 or a pharmacologically acceptable salt thereof, wherein $R^1$ is a ($C_1$-$C_4$ alkyl)sulfonyl-($C_1$-$C_4$ alkoxy) group.

11. The compound of claim 2 or a pharmacologically acceptable salt thereof, wherein
   $R^1$ is a substituted phenyl group in which the substituent(s) represent 1 to 4 groups independently selected from Substituent Group α1, a substituted 5- or 6-membered aromatic heterocyclyl group in which the substituent(s) represent 1 to 4 groups independently selected from Substituent Group α1, a 5- or 6-membered saturated heterocyclyl group, a substituted 5- or 6-membered saturated heterocyclyl group in which the substituent(s) represent 1 to 4 groups independently selected from Substituent Group α1, a substituted 5- or 6-membered saturated heterocyclyloxy group in which the substituent(s) represent 1 to 4 groups independently selected from Substituent Group α1 or a 5- or 6-membered saturated heterocyclylcarbonyl group, and
   Substituent Group α1 represents the group consisting of a $C_1$-$C_6$ alkyl group, a hydroxy group, a carboxy group and an oxo group.

12. The compound of claim 2 or a pharmacologically acceptable salt thereof, wherein
   $R^1$ is a 5- or 6-membered nitrogen-containing saturated heterocyclyl group, a substituted 5- or 6-membered nitrogen-containing saturated heterocyclyl group in which the substituent(s) represent 1 to 4 groups independently selected from Substituent Group α2, a substituted 5- or 6-membered nitrogen-containing saturated heterocyclyloxy group in which the substituent(s) represent 1 to 4 groups independently selected from Substituent Group α2, or a 5- or 6-membered nitrogen-containing saturated heterocyclylcarbonyl group, and Substituent Group α2 represents the group consisting of a $C_1$-$C_4$ alkyl group and a hydroxy group.

13. The compound of claim 2 or a pharmacologically acceptable salt thereof, wherein
   $R^1$ is a substituted pyrrolidinyl group, a substituted piperazyl group, a substituted pyrrolidinyloxy group or a substituted piperidyloxy group in which the substituent(s) of the pyrrolidinyl group, piperazyl group, pyrrolidinyloxy group and piperidyloxy group represent 1 to 2 groups independently selected from Substituent Group α3, or a morpholinylcarbonyl group, and
   Substituent Group α3 represents the group consisting of a methyl group and a hydroxy group.

14. The compound of claim 11 or a pharmacologically acceptable salt thereof, wherein $R^1$ is a substituted phenyl group in which the substituent(s) represent 1 to 2 groups independently selected from Substituent Group α1.

15. The compound of claim 2 or a pharmacologically acceptable salt thereof, selected from the group consisting of
   (5S)-4-(4,4-Difluorocyclohexyl)-3-{(S)-fluoro[4-(trifluoromethyl)phenyl]methyl}-7,7-dimethyl-2-{1-[5-(4-methylpiperazin-1-yl)pyrimidin-2-yl]piperidin-4-yl}-5,6,7,8-tetrahydroquinolin-5-ol,
   (5S)-4-(4,4-Difluorocyclohexyl)-3-{(S)-fluoro[4-(trifluoromethyl)phenyl]methyl}-2-{1-[5-(2-hydroxyethoxy)pyrimidin-2-yl]piperidin-4-yl}-7,7-dimethyl-5,6,7,8-tetrahydroquinolin-5-ol,
   (5S)-2-{1-[5-(4-Carboxybutoxy)pyrimidin-2-yl]piperidin-4-yl}-4-(4,4-difluorocyclohexyl)-3-{(S)-fluoro[4-(trifluoromethyl)phenyl]methyl}-7,7-dimethyl-5,6,7,8-tetrahydroquinolin-5-ol,
   (5S)-2-{1-[5-(4-Carboxybutyl)pyrimidin-2-yl]piperidin-4-yl}-4-(4,4-difluorocyclohexyl)-3-{(S)-fluoro[4-(trifluoromethyl)phenyl]methyl}-7,7-dimethyl-5,6,7,8-tetrahydroquinolin-5-ol,
   (5S)-4-(4,4-Difluorocyclohexyl)-3-{(S)-fluoro[4-(trifluoromethyl)phenyl]methyl}-7,7-dimethyl-2-{1-[5-(methylcarbamoyl)pyrimidin-2-yl]piperidin-4-yl}-5,6,7,8-tetrahydroquinolin-5-ol,
   (5S)-4-(4,4-Difluorocyclohexyl)-2-{1-[5-(dimethylcarbamoyl)pyrimidin-2-yl]piperidin-4-yl}-3-{(S)-fluoro[4-(trifluoromethyl)phenyl]methyl}-7,7-dimethyl-5,6,7,8-tetrahydroquinolin-5-ol,
   (5S)-4-(4,4-Difluorocyclohexyl)-3-{(S)-fluoro[4-(trifluoromethyl)phenyl]methyl}-7,7-dimethyl-2-{1-[5-(morpholin-4-ylcarbonyl)pyrimidin-2-yl]piperidin-4-yl}-5,6,7,8-tetrahydroquinolin-5-ol,
   (5S)-4-(4,4-Difluorocyclohexyl)-3-{(S)-fluoro[4-(trifluoromethyl)phenyl]methyl}-2-{1-(5-{[(2-hydroxyethyl)(methyl)amino]methyl}pyrimidin-2-yl)piperidin-4-yl}-7,7-dimethyl-5,6,7,8-tetrahydroquinolin-5-ol,
   (5S)-4-(4,4-Difluorocyclohexyl)-3-{(S)-fluoro[4-(trifluoromethyl)phenyl]methyl}-2-[1-(5-{[(2S)-2-hydroxypropyl]oxy}pyrimidin-2-yl)piperidin-4-yl]-7,7-dimethyl-5,6,7,8-tetrahydroquinolin-5-ol,
   (5S)-4-(4,4-Difluorocyclohexyl)-3-{(S)-fluoro[4-(trifluoromethyl)phenyl]methyl}-7,7-dimethyl-2-(1-{5-[(1-methylpiperidin-4-yl)oxy]pyrimidin-2-yl}piperidin-4-yl)-5,6,7,8-tetrahydroquinolin-5-ol,
   (5S)-4-(4,4-Difluorocyclohexyl)-2-[1-(5-{[(2S)-2,3-dihydroxypropyl]oxy}pyrimidin-2-yl)piperidin-4-yl]-3-{(S)-fluoro[4-(trifluoromethyl)phenyl]methyl}-7,7-dimethyl-5,6,7,8-tetrahydroquinolin-5-ol,
   (5S)-4-(4,4-Difluorocyclohexyl)-2-[1-(5-{[(2R)-2,3-dihydroxypropyl]oxy}pyrimidin-2-yl)piperidin-4-yl]-3-{(S)-fluoro[4-(trifluoromethyl)phenyl]methyl}-7,7-dimethyl-5,6,7,8-tetrahydroquinolin-5-ol, (5S)-4-(4,4-Difluorocyclohexyl)-3-{(S)-fluoro[4-(trifluoromethyl)phenyl]methyl}-7,7-dimethyl-2-[1-(5-{[(3R)-1-methylpyrrolidin-3-yl]oxy}pyrimidin-2-yl)piperidin-4-yl]-5,6,7,8-tetrahydroquinolin-5-ol, (5S)-4-(4,4-Difluorocyclohexyl)-3-{(S)-fluoro[4-(trifluoromethyl)phenyl]methyl}-2-[1-(5-{[(2R)-2-hydroxypropyl]oxy}pyrimidin-2-yl)piperidin-4-yl]-7,7-dimethyl-5,6,7,8-tetrahydroquinolin-5-ol, (5S)-4-(4,4-Difluorocyclohexyl)-3-{(S)-fluoro[4-(trifluoromethyl)phenyl]methyl}-2-{1-[5-(3-hydroxy-3-methylbutoxy)pyrimidin-2-yl]piperidin-4-yl}-7,7-dimethyl-5,6,7,8-tetrahydroquinolin-5-ol, (5S)-4-(4,4-Difluorocyclohexyl)-3-{(S)-fluoro[4-(trifluoromethyl)phenyl]methyl}-2-{1-[5-(2-hydroxy-2-methylpropoxy)pyrimidin-2-yl]piperidin-4-yl}-7,7-dimethyl-5,6,7,8-tetrahydroquinolin-5-ol, (5S)-4-(4,4-Difluorocyclohexyl)-3-{(S)-fluoro[4-(trifluoromethyl)phenyl]methyl}-7,7-dimethyl-2-(1-{5-[3-(methylsulphonyl)propoxy]pyrimidin-2-yl}piperidin-4-yl)-5,6,7,8-tetrahydroquinolin-5-ol, (5S)-4-(4,4-Difluorocyclohexyl)-3-{(S)-fluoro[4-(trifluoromethyl)phenyl]methyl}-2-{1-[5-(3-hydroxypropoxy)pyrimidin-2-yl]piperidin-4-yl}-7,7-dimethyl-5,6,7,8-tetrahydroquinolin-5-ol, (5S)-4-(4,4-Difluorocyclohexyl)-3-{(S)-fluoro[4-(trifluoromethyl)phenyl]methyl}-7,7-dimethyl-2-{1-[5-(3,3,3-trifluoropropoxy)pyrimidin-2-yl]piperidin-4-yl}-5,6,7,8-tetrahydroquinolin-5-ol, (5S)-4-(4,4-Difluorocyclohexyl)-3-{(S)-fluoro[4-(trifluoromethyl)phenyl]methyl}-2-(1-{5-[3-hydroxy-2-(hydroxymethyl)propoxy]pyrimidin-2-yl}piperidin-4-yl)-7,7-dimethyl-5,6,7,8-tetrahydroquinolin-5-ol, (5S)-4-(4,4-Difluorocyclohexyl)-3-{(S)-fluoro[4-(trifluoromethyl)phenyl]methyl}-2-(1-{5-[3-hydroxy-2-(hydroxymethyl)-2-methylpropoxy]pyrimidin-2-yl}piperidin-4-yl)-7,7-dimethyl-5,6,7,8-tetrahydroquinolin-5-ol, (5S)-4-(4,4-Difluorocyclohexyl)-3-{(S)-fluoro[4-(trifluoromethyl)phenyl]methyl}-7,7-dimethyl-2-[1-(5-{[methyl(methylsulphonyl)amino]methyl}pyrimidin-2-yl)piperidin-4-yl]-5,6,7,8-tetrahydroquinolin-5-ol, (5S)-4-(4,4-Difluorocyclohexyl)-3-{(S)-fluoro[4-(trifluoromethyl)phenyl]methyl}-7,7-dimethyl-2-[1-(5-{[methyl(propan-2-ylsulfonyl)amino]methyl}pyrimidin-2-yl)piperidin-4-yl]-5,6,7,8-tetrahydroquinolin-5-ol, (5S)-4-(4,4-Difluorocyclohexyl)-3-{(S)-fluoro[4-(trifluoromethyl)phenyl]methyl}-7,7-dimethyl-2-[1-(5-methylthiopyrimidin-2-yl)piperidin-4-yl]-5,6,7,8-tetrahydroquinolin-5-ol, (5S)-4-(4,4-Difluorocyclohexyl)-3-{(S)-fluoro[4-(trifluoromethyl)phenyl]methyl}-7,7-dimethyl-2-{1-[5-(methylsulphonyl)pyrimidin-2-yl]piperidin-4-yl}-5,6,7,8-tetrahydroquinolin-5-ol, (5S)-2-{1-[5-(3-Carboxyphenyl)pyrimidin-2-yl]piperidin-4-yl}-4-(4,4-difluorocyclohexyl)-3-{(S)-fluoro[4-(trifluoromethyl)phenyl]methyl}-7,7-dimethyl-5,6,7,8-tetrahydroquinolin-5-ol, (5S)-4-(4,4-Difluorocyclohexyl)-3-{(S)-fluoro[4-(trifluoromethyl)phenyl]methyl}-2-(1-{5-[(2-hydroxyethyl)(methyl)amino]pyrimidin-2-yl}piperidin-4-yl)-7,7-dimethyl-5,6,7,8-tetrahydroquinolin-5-ol, and (5S)-4-(4,4-Difluorocyclohexyl)-3-{(S)-fluoro[4-(trifluoromethyl)phenyl]methyl}-2-(1-{5-[(3S)-3-hydroxypyrrolidin-1-yl]pyrimidin-2-yl}piperidin-4-yl)-7,7-dimethyl-5,6,7,8-tetrahydroquinolin-5-ol.

16. A pharmaceutical composition comprising a compound of claim 2 or a pharmacologically acceptable salt thereof.

17. The compound of claim 2 or a pharmacologically acceptable salt thereof, wherein the compound is (5S)-4-(4,4-Difluorocyclohexyl)-2-[1-(5-{[(2S)-2,3-dihydroxypropyl]oxy}pyrimidin-2-yl)piperidin-4-yl]-3-{(S)-fluoro[4-(trifluoromethyl)phenyl]methyl}-7,7-dimethyl-5,6,7,8-tetrahydroquinolin-5-ol.

18. The compound of claim 2 or a pharmacologically acceptable salt thereof, wherein the compound is (5S)-4-(4,4-Difluorocyclohexyl)-2-[1-(5-{[(2R)-2,3-dihydroxypropyl]oxy}pyrimidin-2-yl)piperidin-4-yl]-3-{(S)-fluoro[4-(trifluoromethyl)phenyl]methyl}-7,7-dimethyl-5,6,7,8-tetrahydroquinolin-5-ol.

19. The compound of claim 2 or a pharmacologically acceptable salt thereof, wherein the compound is (5S)-4-(4,4-Difluorocyclohexyl)-3-{(S)-fluoro[4-(trifluoromethyl)phenyl]methyl}-2-{1-[5-(3-hydroxy-3-methylbutoxy)pyrimidin-2-yl]piperidin-4-yl}-7,7-dimethyl-5,6,7,8-tetrahydroquinolin-5-ol.

20. The compound of claim 2 or a pharmacologically acceptable salt thereof, wherein the compound is (5S)-4-(4,4-Difluorocyclohexyl)-3-{(S)-fluoro[4-(trifluoromethyl)phenyl]methyl}-7,7-dimethyl-2-(1-{5-[3-(methylsulphonyl)propoxy]pyrimidin-2-yl}piperidin-4-yl)-5,6,7,8-tetrahydroquinolin-5-ol.

21. The compound of claim 2 or a pharmacologically acceptable salt thereof, wherein the compound is (5S)-4-(4,4-Difluorocyclohexyl)-3-{(S)-fluoro[4-(trifluoromethyl)phenyl]methyl}-2-(1-{5-[3-hydroxy-2-(hydroxymethyl)propoxy]pyrimidin-2-yl}piperidin-4-yl)-7,7-dimethyl-5,6,7,8-tetrahydroquinolin-5-ol.

22. The compound of claim 2 or a pharmacologically acceptable salt thereof, wherein the compound is (5S)-4-(4,4-Difluorocyclohexyl)-3-{(S)-fluoro[4-(trifluoromethyl)phenyl]methyl}-2-(1-{5-[3-hydroxy-2-(hydroxymethyl)-2-methylpropoxy]pyrimidin-2-yl}piperidin-4-yl)-7,7-dimethyl-5,6,7,8-tetrahydroquinolin-5-ol.

23. The compound of claim 2 or a pharmacologically acceptable salt thereof, wherein the compound is (5S)-2-{1-[5-(3-Carboxyphenyl)pyrimidin-2-yl]piperidin-4-yl}-4-(4,4-difluorocyclohexyl)-3-{(S)-fluoro[4-(trifluoromethyl)phenyl]methyl}-7,7-dimethyl-5,6,7,8-tetrahydroquinolin-5-ol.

24. A method for treatment of a disease selected from the group consisting of dyslipidemia, low HDL cholesterolemia, arteriosclerosis, arteriosclerotic heart disease, and obesity comprising administering to a warm-blooded animal a pharmacologically effective amount of a compound according to claim 2 or a pharmacologically acceptable salt thereof.

25. The method of claim 24, wherein the dyslipidemia is selected from the group consisting of hypercholesterolemia, high LDL cholesterolemia, and hypertriglyceridemia.

26. The method of claim 24, wherein the disease is dyslipidemia, low HDL cholesterolemia, or arteriosclerosis.

27. The method of claim 24, wherein the disease is low HDL cholesterolemia.

28. The method of claim 24, wherein the disease is arteriosclerosis.

29. The method of claim 24, wherein the warm-blooded animal is human.

30. The method of claim 24, wherein the disease is caused by a decrease in the blood concentration of HDL cholesterol.

31. The method of claim 24, wherein the disease is caused by an increase in the blood concentration of LDL cholesterol.

32. A method of inhibiting cholesteryl ester transfer protein comprising administering to a warm-blooded animal a pharmacologically effective amount of a compound according to claim 2, or a pharmacologically acceptable salt thereof.

33. A method of increasing the concentration of HDL cholesterol comprising administering to a warm-blooded animal a pharmacologically effective amount of a compound according to claim 2, or a pharmacologically acceptable salt thereof.

34. A method of decreasing the concentration of LDL cholesterol comprising administering to a warm-blooded animal a pharmacologically effective amount of a compound according to claim 2, or a pharmacologically acceptable salt thereof.

35. The method of claim 24, wherein the disease is dyslipidemia.

* * * * *

UNITED STATES PATENT AND TRADEMARK OFFICE
CERTIFICATE OF CORRECTION

PATENT NO. : 9,187,450 B2
APPLICATION NO. : 13/809115
DATED : November 17, 2015
INVENTOR(S) : Tsuyoshi Nakamura et al.

It is certified that error appears in the above-identified patent and that said Letters Patent is hereby corrected as shown below:

In the Claims

In claim 15, in column 198, at line 25, delete "romethyl)phenyl]methyl}-2-{1-[5-(2-hydroxyethoxyl)" and insert therefor -- romethyl)phenyl]methyl}-2-{1-[5-(2-hydroxyethoxy) --.

In claim 15, in column 199, at line 26, delete "3-trifluoropropoxyl)pyrimidin-2-yl]piperidin-4-yl}-5," and insert therefor -- 3-trifluoropropoxy)pyrimidin-2-yl]piperidin-4-yl}-5, --.

Signed and Sealed this
Fifth Day of July, 2016

Michelle K. Lee
*Director of the United States Patent and Trademark Office*